US008962580B2

(12) United States Patent
Manoharan et al.

(10) Patent No.: US 8,962,580 B2
(45) Date of Patent: Feb. 24, 2015

(54) CHEMICAL MODIFICATIONS OF MONOMERS AND OLIGONUCLEOTIDES WITH CYCLOADDITION

(75) Inventors: Muthiah Manoharan, Cambridge, MA (US); Kallanthottathil G. Rajeev, Cambridge, MA (US); Takeshi Yamada, Cambridge, MA (US); David Butler, Cambridge, MA (US); Narayanannair K. Jayaprakash, Cambridge, MA (US); Muthusamy Jayaraman, Cambridge, MA (US); Shigeo Matsuda, Cambridge, MA (US); Rajendra K. Pandey, Cambridge, MA (US); Chang Geng Peng, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 836 days.

(21) Appl. No.: 13/120,389

(22) PCT Filed: Sep. 23, 2009

(86) PCT No.: PCT/US2009/058084
§ 371 (c)(1),
(2), (4) Date: Oct. 17, 2011

(87) PCT Pub. No.: WO2010/039548
PCT Pub. Date: Apr. 8, 2010

(65) Prior Publication Data
US 2012/0035115 A1  Feb. 9, 2012

Related U.S. Application Data

(60) Provisional application No. 61/099,497, filed on Sep. 23, 2008.

(51) Int. Cl.
*A61K 48/00* (2006.01)
*H04L 29/06* (2006.01)
*C07H 21/00* (2006.01)
*H04L 29/08* (2006.01)

(52) U.S. Cl.
CPC .............. *H04L 65/602* (2013.01); *C07H 21/00* (2013.01); *H04L 67/36* (2013.01)
USPC ..................... 514/44 R; 514/252.06; 514/381; 514/359; 514/365; 514/372; 514/374; 514/378; 514/255.05; 544/238; 544/349; 548/254; 548/255; 536/22.1; 536/23.1; 536/23.2; 536/26.1

(58) Field of Classification Search
CPC .................................................. C07D 249/04
USPC ........ 548/255, 254; 514/255.05, 252.05, 381, 514/359, 365, 372, 374, 378, 44 R; 544/238, 544/249; 536/22.1, 23.1, 26.1
See application file for complete search history.

(56) References Cited

U.S. PATENT DOCUMENTS

| 2006/0147963 | A1 | 7/2006 | Barone et al. |
| 2009/0068738 | A1 | 3/2009 | Bertozzi et al. |
| 2012/0165542 | A1* | 6/2012 | Sharpless et al. ............. 548/255 |

FOREIGN PATENT DOCUMENTS

| WO | 2006116629 A2 | 11/2006 |
| WO | 2006117161 A2 | 11/2006 |
| WO | WO 2007081031 A1 * | 7/2007 |
| WO | 2008052775 A2 | 5/2008 |
| WO | 2009/067663 A1 | 5/2009 |

OTHER PUBLICATIONS

A. Matsuda et al., 34 Journal of Medicinal Chemistry, 2917-2919 (1991).*
K.N. Jayaprakash et al., 12 Organic Letters, 5410-5413 (2010).*
G. Godeau et al., 51 Journal of Medicinal Chemistry, 4374-4376 (2008).*
T. Yamada et al., 76 Journal of Organic Chemistry, 1198-1211 (2011).*
Oxford Dictionary of Chemistry 169 (John Daintith ed., 6th ed., 2008).*
S. Mirozoeva et al. J. Med. Chem. 45, 563-566 (2002).*
B Testa et al., Prodrug Design in, 5 Encyclopedia of Pharmaceutical Technology, 3008-3014 (J. Swarbrick ed., 3rd ed., 2007).*
Hawley'S Condensed Chemical Dictionary 1186 (Richard J. Lewis, Sr. ed., 15th ed., 2007).*
See e.g., Dictionary of Food Science and Technology 254 (2nd ed., 2009).*

(Continued)

*Primary Examiner* — James O Wilson
*Assistant Examiner* — Alexander R Pagano
(74) *Attorney, Agent, or Firm* — Jeffrey N. Townes; LeClairRyan

(57) ABSTRACT

The invention features compounds of formula I or II:

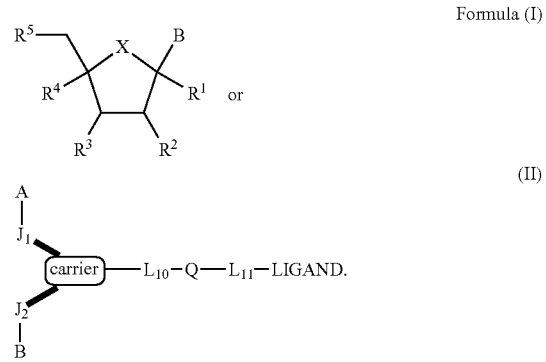

In one embodiment, the invention relates compounds and processes for conjugating ligand to oligonucleotide. The invention further relates to methods for treating various disorders and diseases such as viral infections, bacterial infections, parasitic infections, cancers, allergies, autoimmune diseases, immunodeficiencies and immunosuppression.

11 Claims, 25 Drawing Sheets

(56) References Cited

OTHER PUBLICATIONS

T Ami et al., Nucleic Acids Symposium Series No. 52 (Sep. 8, 2008).*
L. Zhou et al., 14 Bioorganic & Medicinal Chemistry, 7862-7874 (2006).*
Toxicological Profile for Naphthalene Dec. 1990 (Agency for Toxic Substances and Disease Registry U.S. Dept. of Health and Human Services).*
C. Cleveland, et al., (2009). Dictionary of Energy, 339 (2009).*
C.S. Thakur et al., A Convenient and Sensitive Fluorescence Resonance Energy Transfer Assay for RNase L and 2',5' Oligoadenylates, in Interferon Methods and Protocols 103-113 (D.J. Carr ed., 2005).*
Codelli, Julian A. et al., "Second-Generation Difluorinated Cyclooctynes for Copper-Free Click Chemistry", J. Am. Chem. Soc. 130(34):11486-11493 (2008).
Gutsmiedl, Katrin et al., "Copper-Free "Click" Modification of DNA via Nitrile Oxide-Norbornene 1,3-Dipolar Cycloaddition", Org. Lett. 11(11):2405-2408 (2009).
Laughlin, Scott T. et al., "In Vivo Imaging of Membrane-Associated Glycans in Developing Zebrafish", Science 320:664-667 (2008).
Ning, Xinghai et al., "Visualizing Metabolically Labeled Glycoconjugates of Living Cells by Copper-Free and Fast Huisgen Cycloadditions", Angew. Chem. Int. Ed. 47:2253-2255 (2008).
Singh, Ishwar et al., "Metal-Free "Click" Chemistry: Efficient Polymer Modification via 1,3-Dipolar Cycloaddition of Nitrile Oxides and Alkynes", Macromolecules 42(15): 5411-5413 (2009).
Sletten, Ellen M. et al., "A Hydrophilic Azacyclooctyne for Cu-Free Click Chemistry", Org. Lett. 10(14):3097-3099 (2008).
Van Berkel, Sander S. et al., "Metal-Free Triazole Formation as a Tool for Bioconjugation", ChemBioChem 8:1504-1508 (2007).
Van Dijk, Maarten et al., "Synthesis and Applications of Biomedical and Pharmaceutical Polymers via Click Chemistry Methodologies", Bioconjugate Chem. 20(11):2001-2016 (2009).
Burley et al., "Directed DNA Metallization" J. Am. Chem. Soc. 128:1398-99 (2006).
Gierlich et al., "Click Chemistry as a Reliable Method for the High-Density Postsynthetic Functionalization of Alkyne-Modified DNA" Org. Lett. 8(17):3639-42 (2006).
Godeau et al., "Lipid-Conjugated Oligonucleotides via "Click Chemistry" Efficiently Inhibit Hepatitis C Virus Translation" J. Med. Chem. 51:4374-76 (2008).
Grotli et al., "2'-O-Propargyl Oligoribonucleotides: Synthesis and Hybridisation" Tetrahedron 54:5899-5914 (1998).
Korshun et al., "Novel Uridin-2'-yl Carbamates: Synthesis, Incorporation into Oligodeoxyribonucleotides, and Remarkable Fluorescence Properties of 2'-pyren-1-ylmethylcarbamate" J. Chem. Soc., Perkin Trans. 1:1092-1104 (2002).
Seo et al., "Click Chemistry to Construct Fluorescent Oligonucleotides for DNA Sequencing" J. Org. Chem. 68:609-12 (2003).
Shchepinov et al., "A Facile Route to 3'-Modified Oligonucleotides" Bioorg. Med. Chem. Lett. 7(9):1181-84 (1997).
Ustinov et al., "Oligonucleotides Containing Arylacetylene Residues: Synthesis and Post-Synthetic Modification via [3+2] Cycloaddition" Russ. Chem. Bull. Int. Ed. 55(7):1268-74 (2006).

* cited by examiner

Figure 1. Schematics of representative click-conjugate of single stranded oligonucleotides.
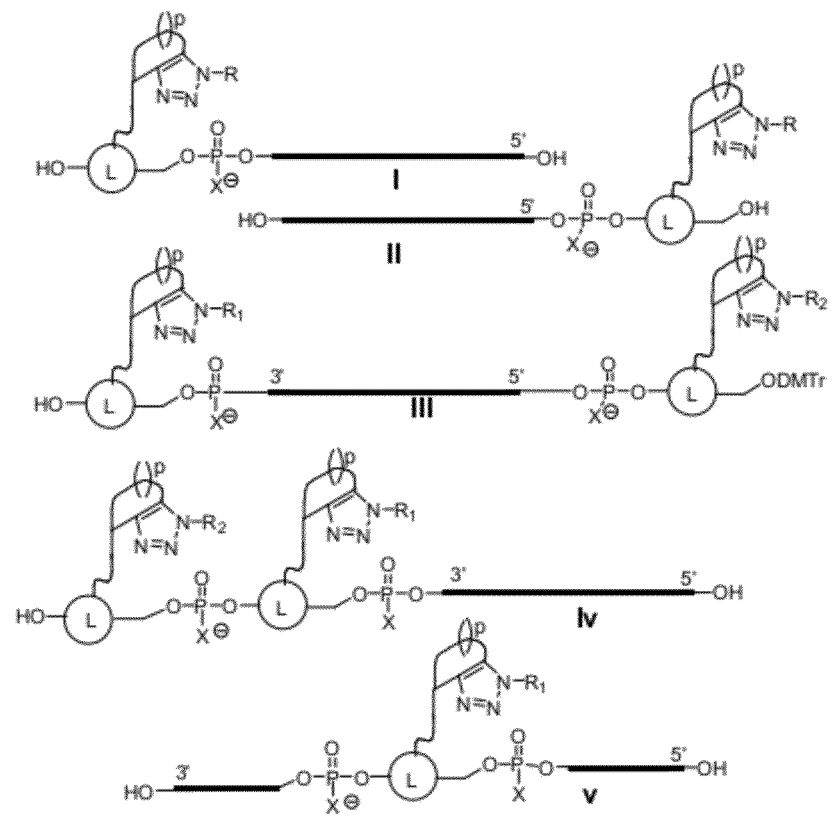

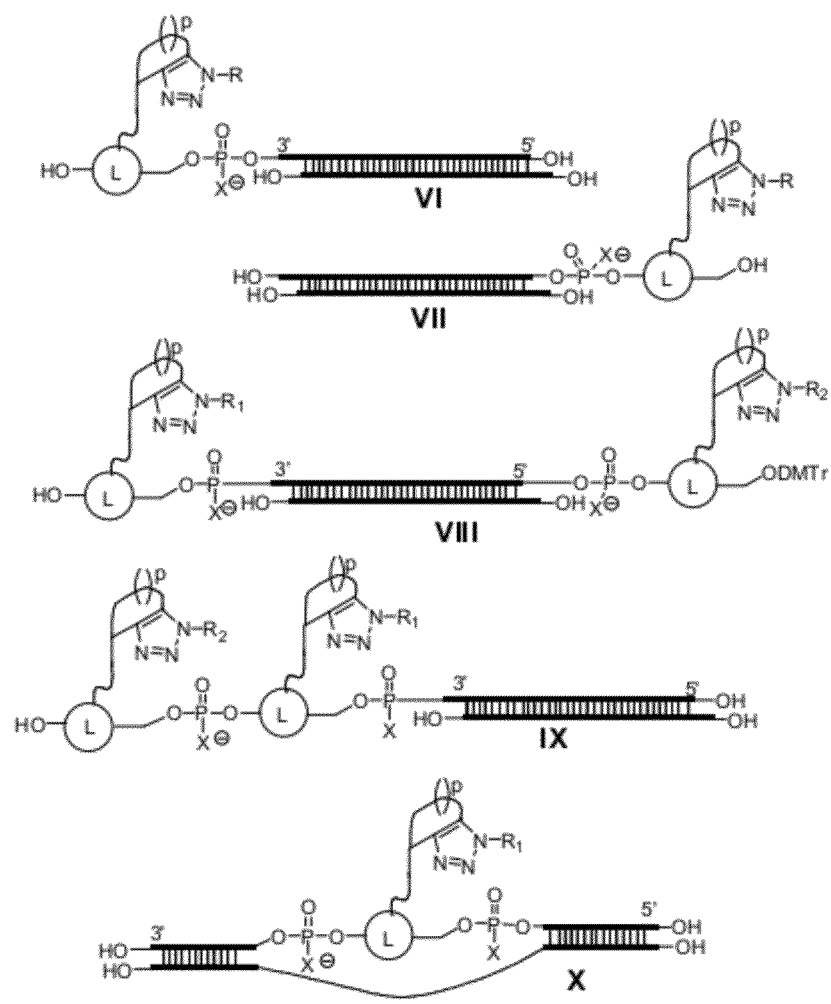
Figure 2. Schematics of representative click-conjugate of double stranded oligonucleotides.

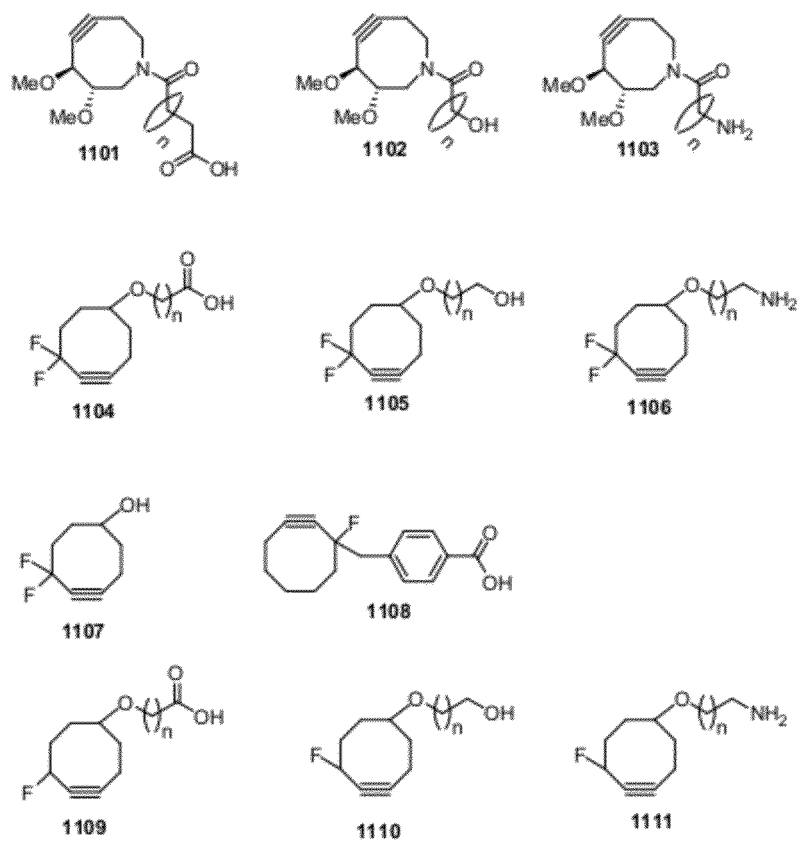
Figure 3. Ring strained alkynes for copper-free click chemistry

Figure 4. 3'-Conjugation of ligand to antagomirs, antisense oligonucleotides and siRNAs using Click Chemistry.
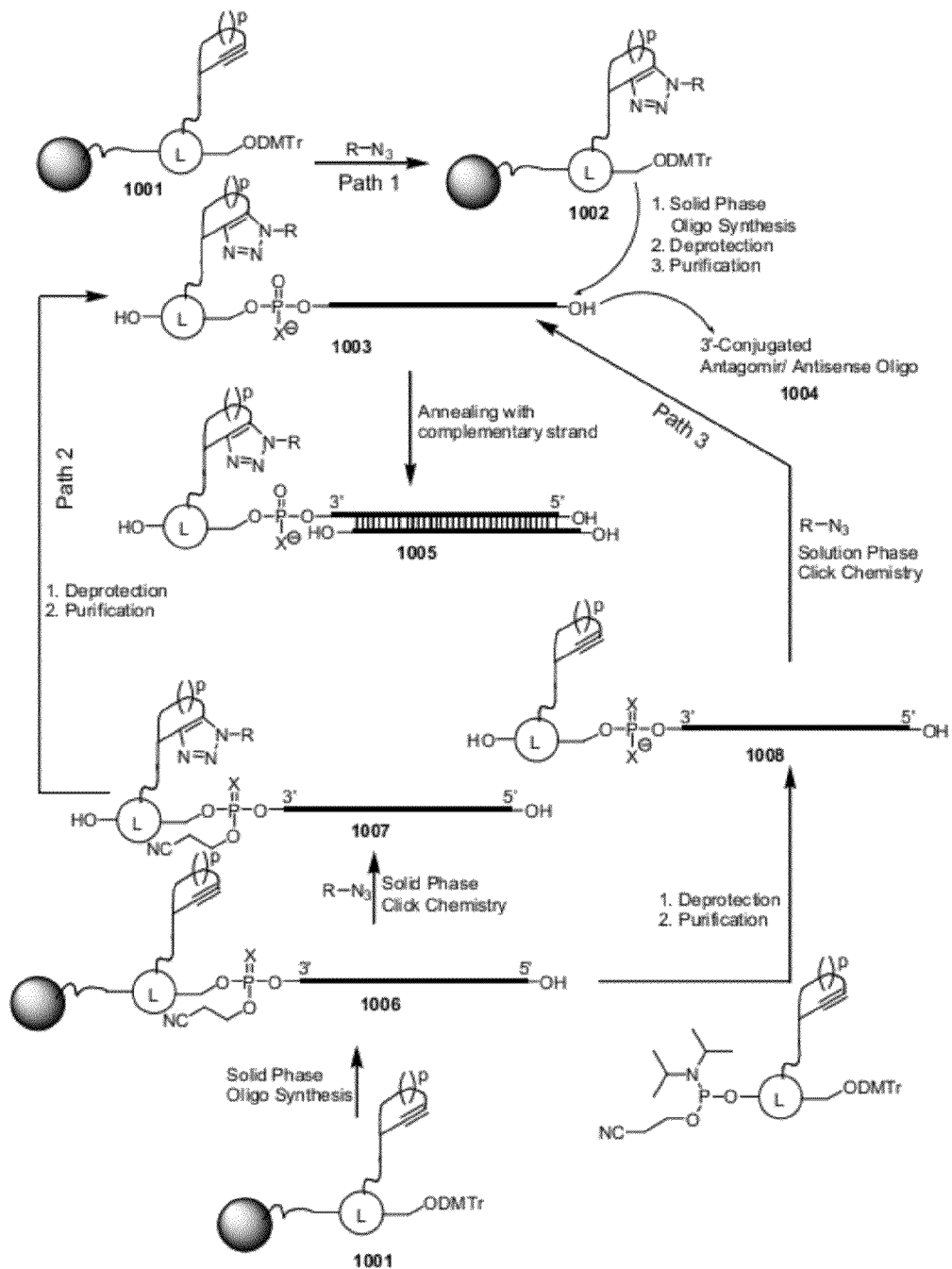

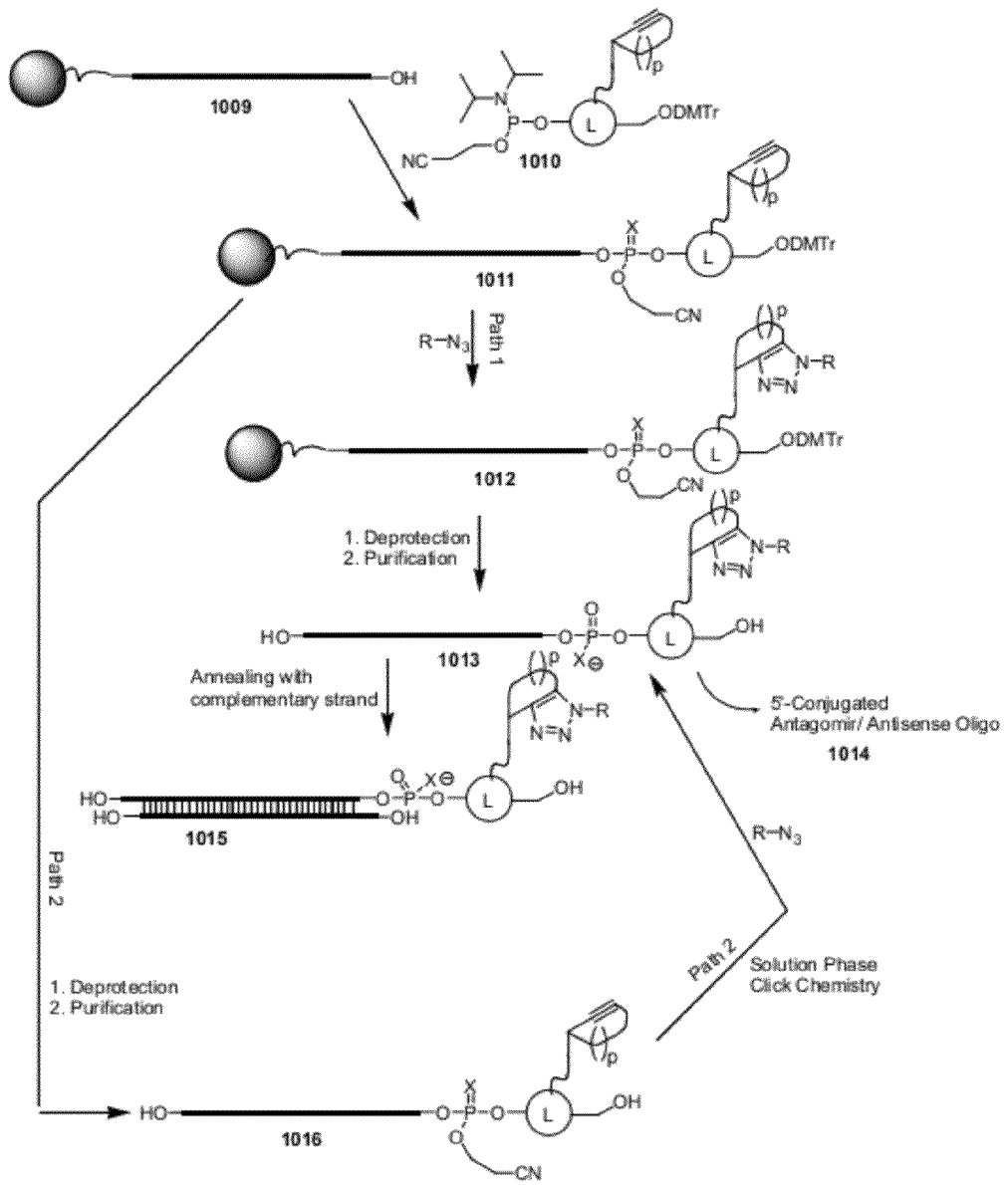
Figure 5. 5'- Conjugation of ligand to antagomirs, antisense oligonucleotides and siRNAs using Click Chemistry.

Figure 6. Conjugation of ligand to antagomirs, antisense oligonucleotides and siRNAs using abasic linker and click chemistry.
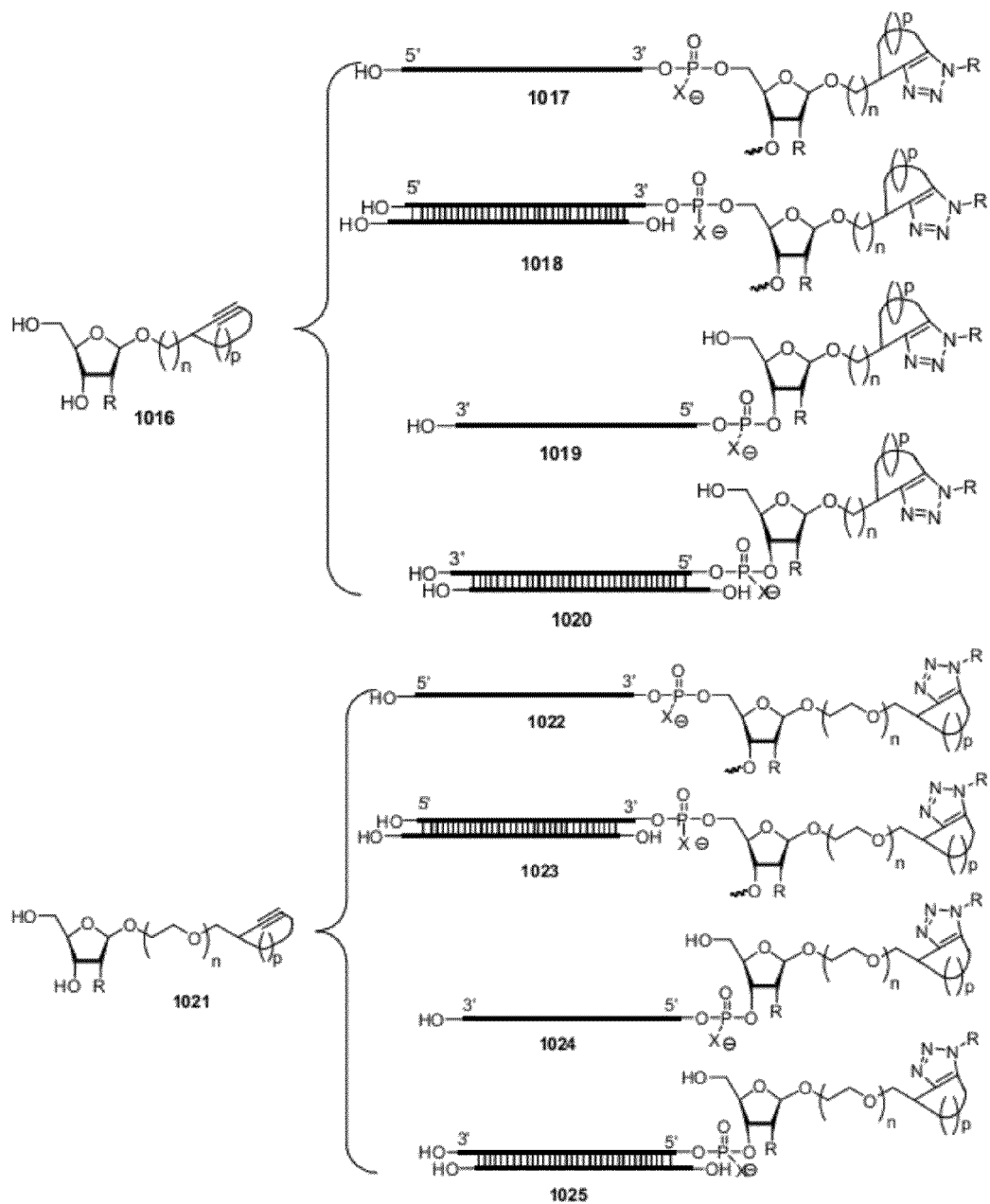

Figure 7: Ligand attachment points on siRNAs
Ligand Sites of siRNA
1. 3'-terminal of sense strand
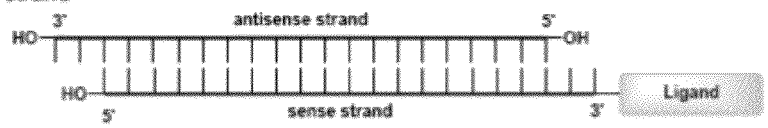
2. 5'-terminal of sense strand
3. Internal position of sense strand
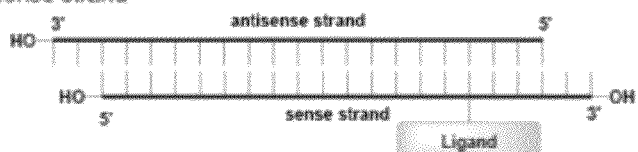
4. 3'-position of antisense strand if needed.
 = Lipid, Cholesterol, Carbohydrate, Folate, Polyamines , Peptides and so on.

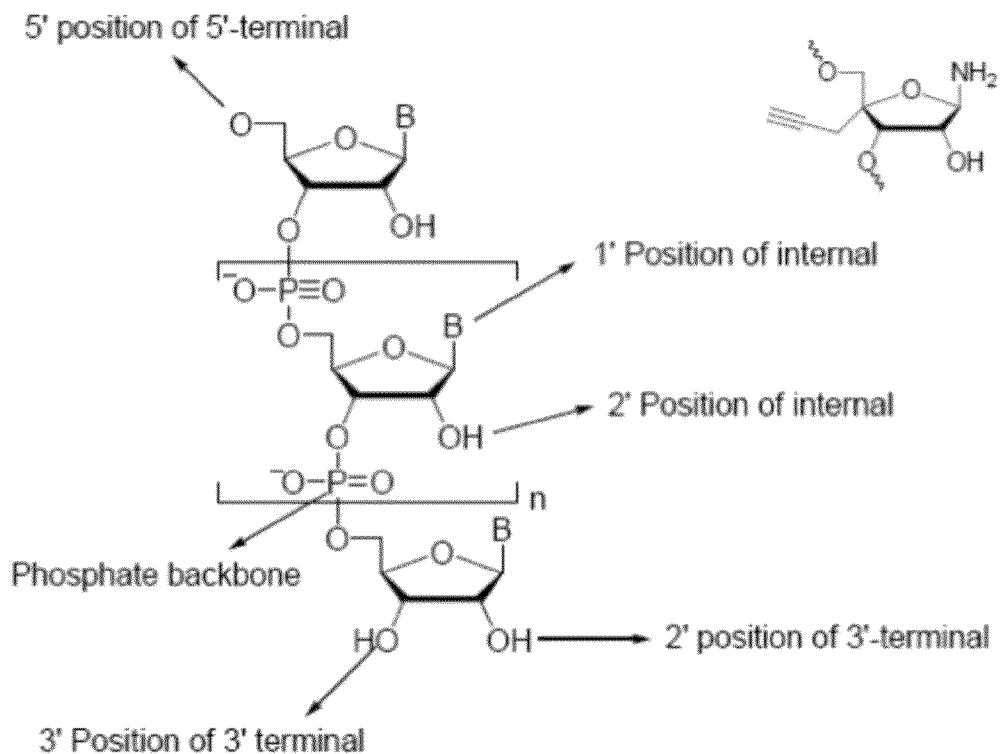
Figure 8: Ligand attachment points on oligonucleotides

Figure 9: Ligand conjugation to oligonucleotides by Click Chemistry

Strategies for Conjugation of Ligands to RNA by Click Chemistry

1. Making Building Blocks by Click Chemistry

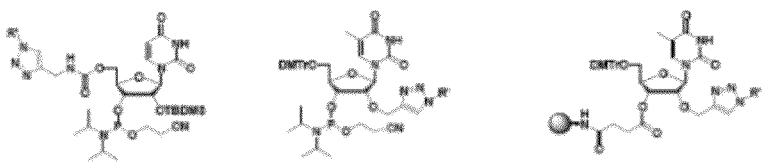

2. On Solid Support: Post-Synthetic Click chemistry after Solid Phase RNA Synthesis

Various ligands can be incorporated easily.

3. In Solution: Post-Synthetic Click Chemistry after treating with ammonia

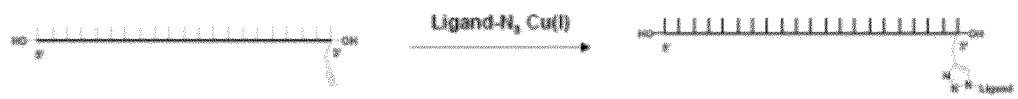

Base labile ligands can be incorporated.

Figure 12: HPLC analysis of Click chemistry conjugation

Figure 13: HPLC analysis of purified Click chemistry conjugation 33561 was purified by RP HPLC (Gradient: 0-90% buffer B in 30min)

Figure 14: An Azido-labeled oligonucleotide

Figure 15: 6-Carboxyfluorescein-propargylamide conjugated with an azido-labeled oligonucleotide by Click chemistry Figure 16: LC-MS analysis of crude product of Click chemistry reaction between 6-Carboxyfluorescein-propargylamide and azide-labeled oligonucleotide n, Fluorescein-conjugated oligomer, MWcalc: 7684, MWfound: 7682.3
b, unconj. starting material (azido), MWcalc: 7269, MWfound: 7277

Figure 18
a)
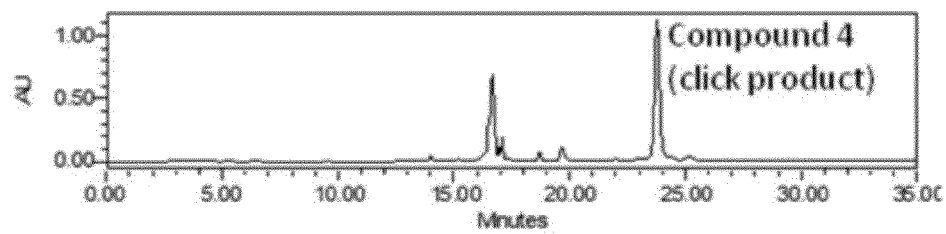
b)
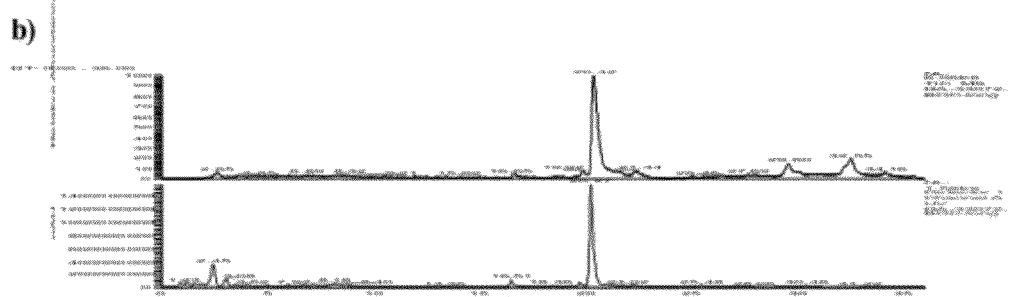

Figure 21
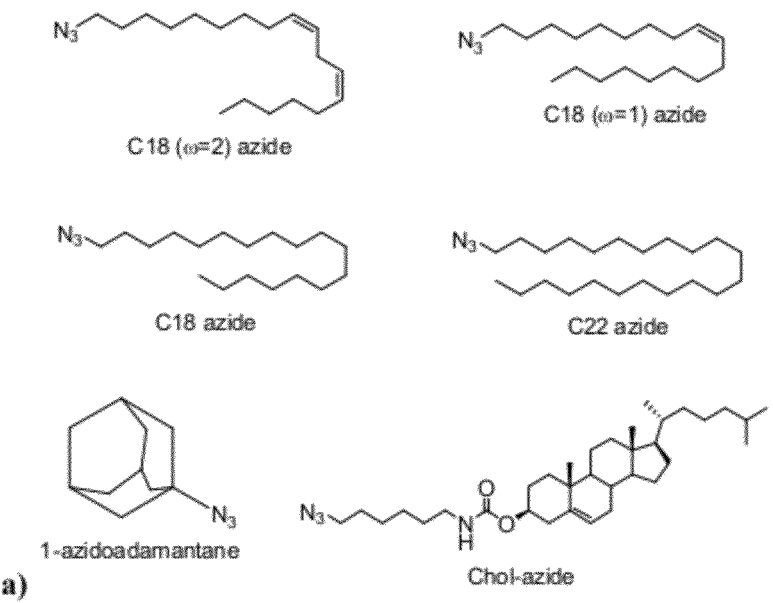
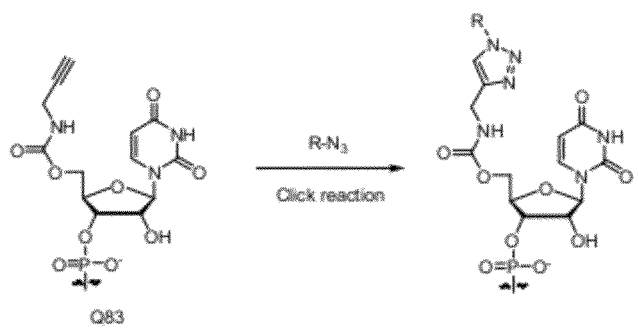
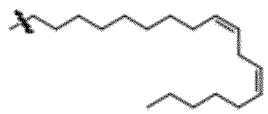
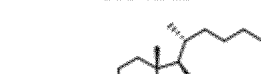
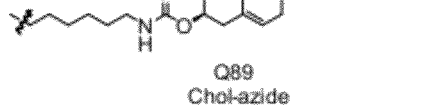

Figure 23
a)
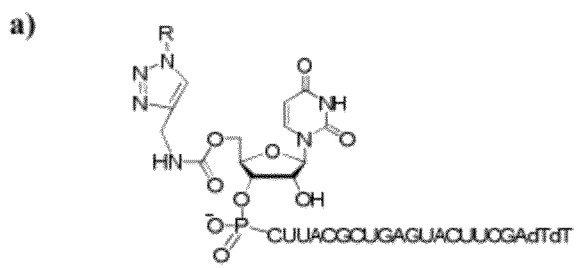
b)
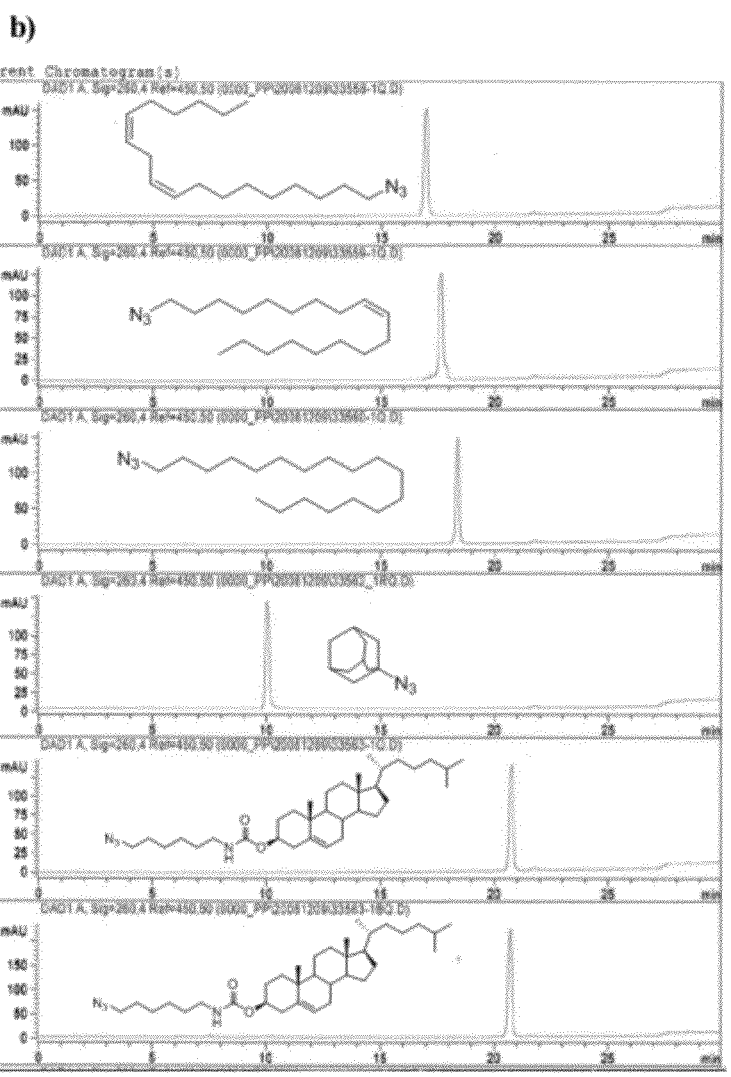

c)

CHEMICAL MODIFICATIONS OF MONOMERS AND OLIGONUCLEOTIDES WITH CYCLOADDITION

PRIORITY

This application claims benefit of priority to PCT Application No. PCT/US2009/058084, filed Sep. 23, 2009, which claims priority to U.S. Application No. 61/099,497, filed on Sep. 23, 2008, both of which are herein incorporated by reference in their entirety.

FIELD OF INVENTION

The present invention relates to the field of conjugation of ligands to oligonucleotides with "click" chemistry.

BACKGROUND

Oligonucleotide compounds have important therapeutic applications in medicine. Oligonucleotides can be used to silence genes that are responsible for a particular disease. Gene-silencing prevents formation of a protein by inhibiting translation. Importantly, gene-silencing agents are a promising alternative to traditional small, organic compounds that inhibit the function of the protein linked to the disease. siRNA, antisense RNA, and micro-RNA are oligonucleotides that prevent the formation of proteins by gene-silencing.

RNA interference or "RNAi" is a term initially coined by Fire and co-workers to describe the observation that double-stranded RNA (dsRNA) can block gene expression (Fire et al. (1998) *Nature* 391, 806-811; Elbashir et al. (2001) *Genes Dev.* 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

siRNA compounds are promising agents for a variety of diagnostic and therapeutic purposes. siRNA compounds can be used to identify the function of a gene. In addition, siRNA compounds offer enormous potential as a new type of pharmaceutical agent which acts by silencing disease-causing genes. Research is currently underway to develop interference RNA therapeutic agents for the treatment of many diseases including central-nervous-system diseases, inflammatory diseases, metabolic disorders, oncology, infectious diseases, and ocular disease.

Many diseases (e.g., cancers, hematopoietic disorders, endocrine disorders, and immune disorders) arise from the abnormal or otherwise unwanted expression or activity of a particular gene or group of genes. For example, disease can result through misregulated gene expression, expression of a mutant form of a protein, or expression of viral, bacterial or other pathogen-derived genes. The RNAi pathway can be used to inhibit or decrease the unwanted expression of such genes (Agrawal et al., *Microbiol Mol Biol Rev.*, 2003, 67, 657-685; Alisky & Davidson, *Am. J. Pharmacogenomics*, 2004, 4, 45-51).

In yet a further aspect, the invention relates to a method for treating a disease or disorder in a subject. The method includes identifying a subject having or at risk for developing the disease, administering a pharmaceutical composition containing an immunoselective iRNA agent having one or more of the modified nucleotides or linkages described above, and a pharmaceutically acceptable carrier. The subject may be monitored for an effect on the immune system, e.g., an immunostimulatory or immunoinhibitory response, such as by monitoring for increased expression of a growth factor, such as a cytokine or a cell-surface receptor (e.g., a Toll-like receptor) as described above. Cytokines of interest can be those expressed from T cells, B cells, monocytes, macrophages, dendritic cells, or natural killer cells of the subject. The assays can be performed using blood or serum samples from the subject. The disease or disorder can be one where it is particularly undesirable to stimulate the immune system, e.g., in a patient that has received organ, tissue or bone marrow transplants. In another alternative, the disease or disorder can be one where it is particularly desirable to stimulate the immune system, e.g., in patients with cancer or viral diseases. In one embodiment, the subject is immunocompromised, and an iRNA agent that includes nucleotide modifications stimulates an immune response in a cell to a greater extent than an iRNA agent that does not include nucleotide modifications. The subject may be a mammal, such as a human.

In a preferred embodiment, administration of an immunoselective iRNA agent is for treatment of a disease or disorder present in the subject. In another preferred embodiment, administration of the iRNA agent is for prophylactic treatment.

It is therefore an object of the present invention to provide polynucleotides/oligonucleotides which are capable of stimulating an anti-viral response, in particular, a type I IFN response. It is another object of the present invention to provide a pharmaceutical composition capable of inducing an anti-viral response, in particular, type I IFN production, in a patient for the prevention and treatment of diseases and disorders such as viral infection. It is also an object of the present invention to provide a pharmaceutical composition for treating tumor.

The disease and/or disorder include, but are not limited to infections, tumor, allergy, multiple sclerosis, and immune disorders.

Infections include, but are not limited to, viral infections, bacterial infections, anthrax, parasitic infections, fungal infections and prion infection. Viral infections include, but are not limited to, infection by hepatitis C, hepatitis B, herpes simplex virus (HSV), HIV-AIDS, poliovirus, encephalomyocarditis virus (EMCV) and smallpox virus. Examples of (+) strand RNA viruses which can be targeted for inhibition include, without limitation, picornaviruses, caliciviruses, nodaviruses, coronaviruses, arteriviruses, flaviviruses, and togaviruses. Examples of picornaviruses include enterovirus (poliovirus 1), rhinovirus (human rhinovirus 1A), hepatovirus (hepatitis A virus), cardiovirus (encephalomyocarditis virus), aphthovirus (foot-and-mouth disease virus O), and parechovirus (human echovirus 22). Examples of caliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is the representative nodavirus. Coronaviruses include coronavirus (avian infections bronchitis virus) and torovirus (Berne virus). Arterivirus (equine arteritis virus) is the representative arteriviridus. Togaviruses include alphavirus (Sindbis virus) and rubivirus (Rubella virus). Finally, the flaviviruses include flavivirus (Yellow fever virus), pestivirus (bovine diarrhea virus), and hepacivirus (hepatitis C virus).

In certain embodiments, the viral infections are selected from chronic hepatitis B, chronic hepatitis C, HIV infection, RSV infection, HSV infection, VSV infection, CMV infection, and influenza infection.

In one embodiment, the infection to be prevented and/or treated is upper respiratory tract infections caused by viruses and/or bacteria. In another embodiment, the infection to be prevented and/or treated is bird flu.

Bacterial infections include, but are not limited to, *streptococci, staphylococci, E. coli, pseudomonas*.

In one embodiment, bacterial infection is intracellular bacterial infection. Intracellular bacterial infection refers to infection by intracellular bacteria such as mycobacteria (tuberculosis), *chlamydia, mycoplasma, listeria*, and facultative intracellular bacteria such as *staphylococcus aureus*.

Parasitic infections include, but are not limited to, worm infections, in particular, intestinal worm infection.

Tumors include both benign and malignant tumors (i.e., cancer).

Cancers include, but are not limited to biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer and renal cancer.

In certain embodiments, cancers are selected from hairy cell leukemia, chronic myelogenous leukemia, cutaneous T-cell leukemia, chronic myeloid leukemia, non-Hodgkin's lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basaliom, colon carcinoma, cervical dysplasia, and Kaposi's sarcoma (AIDS-related and non-AIDS related).

Allergies include, but are not limited to, respiratory allergies, contact allergies and food allergies.

Immune disorders include, but are not limited to, autoimmune diseases, immunodeficiency, and immunosuppression.

Autoimmune diseases include, but are not limited to, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, automimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis. Immunodeficiencies include, but are not limited to, spontaneous immunodeficiency, acquired immunodeficiency (including AIDS), drug-induced immunodeficiency (such as that induced by immunosuppressants used in transplantation and chemotherapeutic agents used for treating cancer), immunosuppression caused by chronic hemodialysis, trauma or surgical procedures.

Immunosuppression includes, but is not limited to, bone marrow suppression by cytotoxic chemotherapy.

siRNA has been shown to be extremely effective as a potential anti-viral therapeutic with numerous published examples appearing recently. siRNA molecules directed against targets in the viral genome dramatically reduce viral titers by orders of magnitude in animal models of influenza (Ge et al., (2004) *Proc. Natl. Acd. Sci. USA*, 101, 8676-8681; Tompkins et al. (2004) *Proc. Natl. Acd. Sci. USA*, 101, 8682-8686; Thomas et al. (2005) *Expert Opin. Biol. Ther.* 5, 495-505), respiratory synctial virus (RSV) (Bitko et al. (2005) *Nat. Med.* 11, 50-55), hepatitis B virus (HBV) (Morrissey et al. (2005) *Nat. Biotechnol.* 23, 1002-1007), hepatitis C virus (Kapadia et al. (2003) *Proc. Natl. Acad. Sci. USA*, 100, 2014-2018; Wilson et al. (2003) *Proc. Natl. Acad. Sci. USA*, 100, 2783-2788) and SARS coronavirus (Li et al. (2005) *Nat. Med.* 11, 944-951).

The opportunity to use these and other nucleic acid based therapies holds significant promise, providing solutions to medical problems that could not be addressed with current, traditional medicines. The location and sequences of an increasing number of disease-related genes are being identified, and clinical testing of nucleic acid-based therapeutics for a variety of diseases is now underway.

Despite the different synthetic strategies developed for conjugation of various ligands to the oligonucleotides, the synthesis of ligand-oligonucleotide conjugates is anything but trivial and requires extensive expertise in organic chemistry and solid-phase synthesis. A real advance would be to use a coupling reaction that can be utilized for a large variety of ligands and oligonucleotides. The Huisgen 1,3-dipolar cycloaddition of alkynes and azides, the "click" reaction, is especially attractive for irreversible coupling of two molecules under mild conditions. The "click" chemistry has recently emerged as an efficient strategy to conjugate carbohydrates, peptides and proteins, fluorescent labels and lipids to oligonucleotides. Therefore, there is a clear need for new reagents that can be utilize for "click" chemistry for conjugation of ligands to oligonucleotides. The present invention is directed to this very important end.

SUMMARY

The invention relates to compounds that can be used as a ribose replacement or can be used as universal base to conjugate various ligands to oligonucleotides, e.g. iRNA agents, through "click" chemistry. These compounds are also referred to as the "click-carrier" herein.

For instance, the invention features a compound having the structure shown in formula (I)

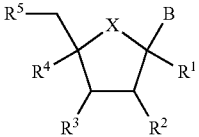

Formula (I)

wherein:
X is O, S, $NR^N$ or $CR^P_2$;
B is independently for each occurrence hydrogen, optionally substituted natural or non-natural nucleobase, optionally substituted triazole or optionally substituted tetrazole; NH—C(O)—O—C($CH_2B_1)_3$, NH—C(O)—NH—C $(CH_2B_1)_3$; where $B_1$ is halogen, mesylate, $N_3$, CN, optionally substituted triazole or optionally substituted tetrazole;

$R^1$, $R^2$, $R^3$, $R^4$ and $R^5$ are each independently for each occurrence H, $OR^6$, F, $N(R^N)_2$, $N_3$, CN, -J-linker-$N_3$, -J-linker-CN, -J-linker-C≡$R^8$, -J-linker-cycloalkyne, -J-linker-$R_L$, or -J-linker-Q-linker-$R^L$;

J is absent, O, S, $NR^N$, OC(O)NH, NHC(O)O, C(O)NH, NHC(O), NHSO, $NHSO_2$, $NHSO_2NH$, OC(O), C(O)O, OC(O)O, NHC(O)NH, NHC(S)NH, OC(S)NH, $OP(N(R^P)_2)$O, or $OP(N(R^P)_2)$;

$R^6$ is independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothio late, a phosphorodithioate, a phosphorothiolothionate, a phosphodiester, a phosphotriester, an activated phosphate group, an activated phosphite group, a phosphoramidite, a solid support, —$P(Z^1)(Z^2)$—O-nucleoside, —$P(Z^1)(Z^2)$—O-oligonucleotide, —$P(Z^1)(Z^2)$-formula (I), —$P(Z^1)$(O-linker-Q-linker-$R^L$)—O-nucleoside, $P(Z^1)$(O-linker-$R^L$)—O-nucleoside, —$P(Z')$(O-linker-$N_3$)—O-nucleoside, $P(Z^1)$(O-linker-CN)—O-nucleoside, $P(Z^1)$(O-linker-C≡$R^8$)—O-nucleoside, $P(Z^1)$(O-linker-cycloalkyne)-O-nucleoside, —$P(Z^1)$(O-linker-Q-linker-$R^L$)—O-oligonucleotide, $P(Z^1)$(O-linker-$R^L$)—O-oligonucleotide, $P(Z^1)$(O-linker-$N_3$)—O-oligonucleotide, —$P(Z^1)$(O-linker-CN)—O-oligonucleotide, $P(Z^1)$(O-linker-C≡$R^8$)—O-oligonucleotide, $P(Z^1)$(O-linker-cycloalkyne)-O-oligonucleotide, —$P(Z^1)$(-linker-Q-linker-$R^L$)—O-nucleoside, —$P(Z^1)$(-linker-Q-$R^L$)—O-nucleoside, —$P(Z^1)$(-linker-$N_3$)—O-nucleoside, $P(Z^1)$(-linker-CN)—O-nucleoside, $P(Z^1)$(-linker-C≡$R^8$)—O-nucleoside, $P(Z^1)$(-linker-cycloalkyne)-O-nucleoside, —$P(Z^1)$(-linker-Q-linker-$R^L$)—O-oligonucleotide, —$P(Z^1)$(-linker-$R^L$)—O-oligonucleotide, $P(Z^1)$(-linker-$N_3$)—O-oligonucleotide, —$P(Z^1)$(-linker-CN)—O-oligonucleotide, $P(Z^1)$(-linker-C≡$R^8$)—O-oligonucleotide or $P(Z^1)$(-linker-cycloalkyne)-O-oligonucleotide;

$R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

$R^P$ is independently for each occurrence H, optionally substituted alkyl, optionally substituted alkenyl, optionally substituted alkynyl, optionally substituted aryl, optionally substituted cycloalkyl or optionally substituted heteroaryl;

Q is absent or independently for each occurrence

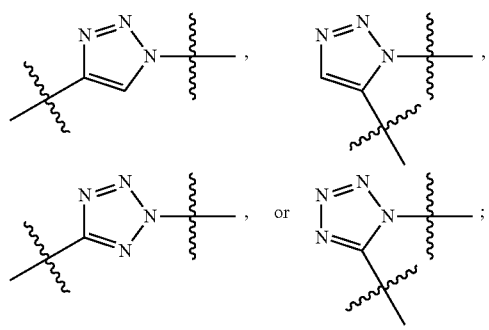

$R^L$ is hydrogen or a ligand;
$R^8$ is N or $CR^9$;
$R^9$ is H, optionally substituted alkyl or silyl;
$Z^1$ and $Z^2$ are each independently for each occurrence O, S or optionally substituted alkyl;

provided that at least one of $R^1$, $R^2$, $R^3$, $R^4$ and $R^5$ is -J-Linker-Q-Linker-$R^L$ or -Linker-Q-$R^L$ when B is an unsubstituted natural base.

In one aspect, the invention features, a compound having the structure shown in formula (Ia)

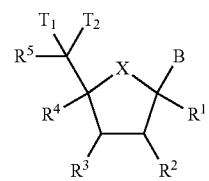

Formula (Ia)

wherein $T_1$ and $T_2$ are each independently H, $C_1$-$C_9$ alkyl, $C_2$-$C_9$ alkenyl, $C_2$-$C_9$ alkynyl, substituted $C_1$-$C_9$ alkyl, substituted $C_1$-$C_9$ alkenyl and substituted $C_2$-$C_9$ alkynyl; and R1, R2, R3, R4R5, X and B are as previously defined.

In one embodiment, the invention features, a compound having the structure shown in formula (II)

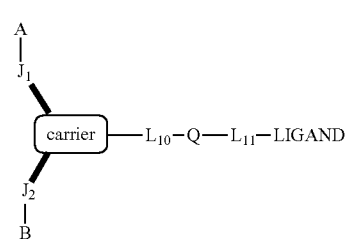

(II)

A and B are independently for each occurrence hydrogen, protecting group, optionally substituted aliphatic, optionally substituted aryl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothio late, a phosphorodithioate, a phosphorothiolothionate, a phosphodiester, a phosphotriester, an activated phosphate group, an activated phosphite group, a phosphoramidite, a solid support, —$P(Z^1)(Z^2)$—O-nucleoside, or —$P(Z^1)(Z^2)$—O-oligonucleotide; wherein $Z^1$ and $Z^2$ are each independently for each occurrence O, S or optionally substituted alkyl;

$J_1$ and $J_2$ are independently O, S, $NR^N$, optionally substituted alkyl, OC(O)NH, NHC(O)O, C(O)NH, NHC(O), OC(O), C(O)O, OC(O)O, NHC(O)NH, NHC(S)NH, OC(S)NH, $OP(N(R^P)_2)$O, or $OP(N(R^P)_2)$;

carrier is cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone;

Q is independently for each occurrence

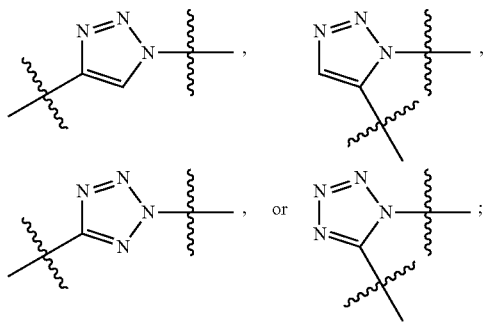

and $L_{10}$ and $L_{11}$ are independently absent or a linker

In another embodiment of the present invention there are disclosed pharmaceutical compositions comprising a therapeutically effective amount of an iRNA agent of the invention in combination with a pharmaceutically acceptable carrier or excipient. In yet another embodiment of the invention describes process for preparing said compounds

BRIEF DESCRIPTION OF THE DRAWINGS

FIG. 1. Schematics of representative click-conjugate of single stranded oligonucleotides. Multiple conjugation to the 5'-end and all combinations of multiples are possible with the linker scaffold design and thus conjugation of ligand. By choosing chemistry and order of conjugation hetero-ligand (separate ligands or hybrid ligand) conjugation are done.

FIG. 2. Schematics of representative click-conjugate of double stranded oligonucleotides. Multiple conjugation to the 5'-end and all combinations of multiples are possible with the linker scaffold design and thus conjugation of ligand. By choosing chemistry and order of conjugation hetero-ligand (separate ligands or hybrid ligand) conjugation are done.

FIG. 3. Ring strained alkynes for copper-free click chemistry.

FIG. 4. 3'-Conjugation of ligand to antagomirs, antisense oligonucleotides and siRNAs using Click Chemistry. The alkyne used is open chain or cyclic constrained. Cyclic constrained used for click reaction in the absence of copper. Path 1. Conjugation of ligand-azide to solid support followed by solid phase synthesis, deprotection and purification of oligonucleotide. Path 2. Conjugation of ligand-azide to solid-bound oligonucleotide, followed by deprotection and purification. Path 3. Post-synthetic conjugation of ligand-azide to an alkyne bearing oligonucleotide Annealing with complementary strand gives the siRNA. Direct use of the conjugated single strand enable antagomir and antisense application of the conjugates. L is linker scaffold X is O or S, R is ligand and p is zero or 3-8 with or without substitution on the ring carbon. The ring also can have hetero atoms such as N, S, O, SO, $SO_2$. Substitution on the ring carbon are: single or geminal disubstitution with F, OMe, COQ where Q is OH, $NH_2$, NHMe, $NMe_2$, COOMe, NH(Alkyl), perfluorosubstitution. The site tethering of the cylic alkyne could be a nitrogen atom as described by Sletten and Bertoszzi in *Organic Letters*, 2008, 10, 3097-99. Reverse conjugation of Alkyne to solid bound azide is another approach or reverse conjugation can be achieved via post-synthesis. In some instance the other regeo isomer is expected as the major or sole products depends on the nature of the incoming azide and nature of the alkyne. In another instance the product could be an equimolar mixture of the two regeoselective products that could form from the same reaction. Relevant reference for using ring strained cyclic alkynes for copper-free click chemistry include: Johnson et al., Copper-free click chemistry for the in situ cross-linking of photodegradable star polymers. *Chemical Communications*, 2008, (26), 3064-3066; Sletten and Bertoszzi in *Organic Letters*, A hydrophilic azacyclooctyne for Cu-free click chemistry, 2008, 10, 3097-99; Baskin et al., Copper-free chlick chemistry for dynamic in vivo imaging. *Proc. Natl. Acad. Sci. USA*, 2007, 104(43), 16793; Agard et al., A comparative study of bioorthogonal reactions with azides., *ACS Chem. Biol.*, 2006, 1, 644 and Chen, Fish 'n clicks, *Nature Chemical Biology*, 2008, 4(7), 391-92.

FIG. 5. 5'—Conjugation of ligand to antagomirs, antisense oligonucleotides and siRNAs using Click Chemistry. The alkyne used is open chain of cyclic constrained. Cyclic constrained used for click reaction in the absence of copper. Path 1. Conjugation of ligand-azide to solid support bound oligonucleotide followed by deprotection and purification of oligonucleotide. Path 2. Post-synthetic conjugation of ligand-azide to an alkyne bearing oligonucleotide. Annealing with complementary strand gives the siRNA. Direct use of the conjugated single strand enable antagomir and antisense application of the conjugates. See FIG. 4 for detailed description.

FIG. 6. Conjugation of ligand to antagomirs, antisense oligonucleotides and siRNAs using abasic linker and click chemistry. Conjugation of ligand to antagomirs, antisense oligonucleotides and siRNAs using abasic linker and click chemistry. R is the ligand, the alkyne used is open chain of cyclic constrained. Cyclic constrained used for click reaction in the absence of copper. See legend for FIG. 4 for details.

FIG. 7: Schematic representation of ligand attachment points on siRNAs.

FIG. 8: Schematic representation of ligand attachment points on oligonucleotides.

FIG. 9: Conjugation strategies for conjugation of ligands to oligonucleotides by Click Chemistry.

FIG. 18: Reverse-phase HPLC (a) and LC-MS analysis of crude reaction mixture of conjugation of Boc-protected spermine-azide with RNA alkyne.

FIG. 21: FIG. 21 (a) is a schematic representation of exemplary azides used for click reaction to make the modified RNA sequences of Tables 8 and 9, and (b) is a schematic representation of monomers after click reaction.

DETAILED DESCRIPTION

Figure 10:
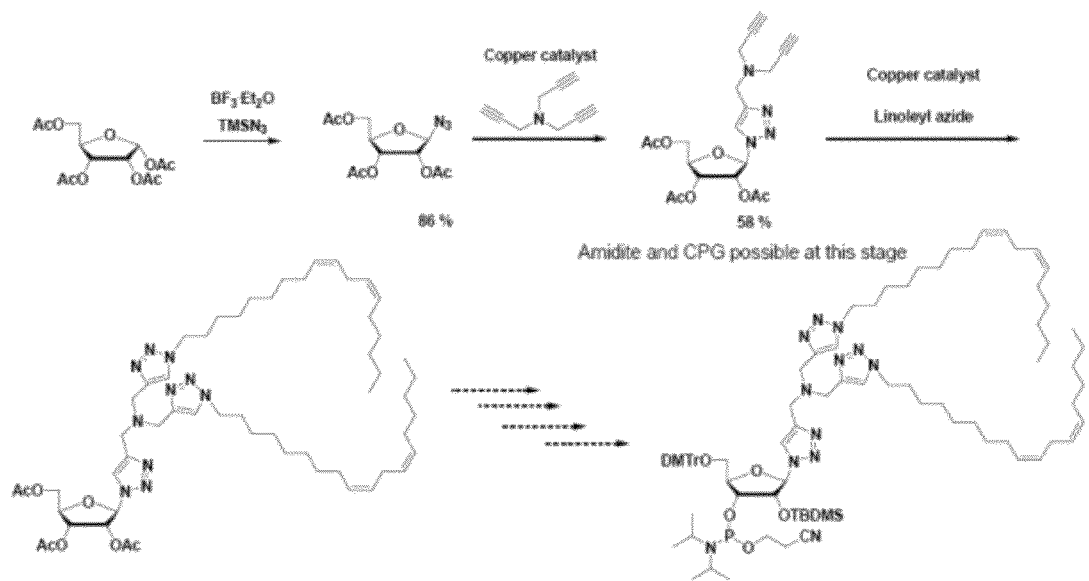
FIG. 10: An abasic linker for Click chemistry.
Figure 11:
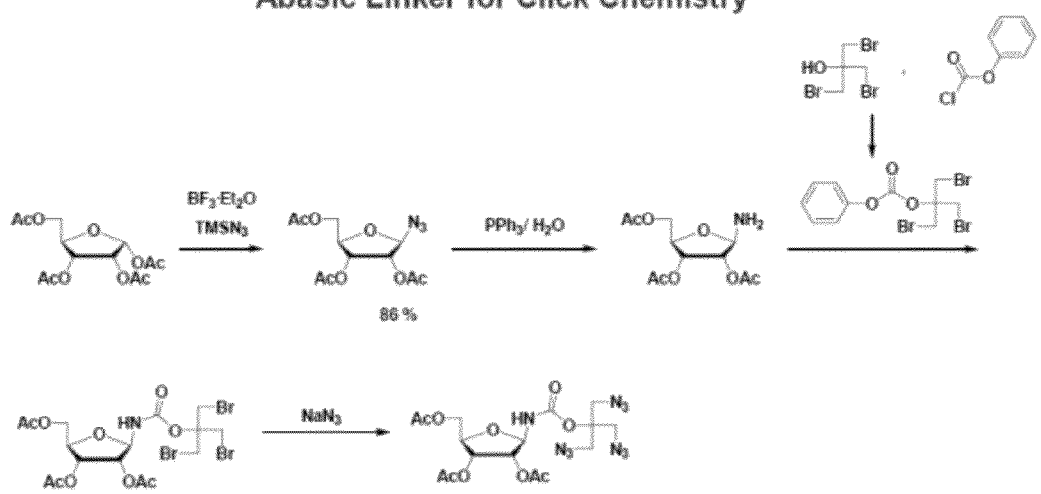
FIG. 11: An abasic linker for Click chemistry.

In one embodiment of the compounds of the present invention are compounds represented by formula I or II as illustrated above, or a pharmaceutically acceptable salt, ester or prodrug thereof.

Alternatively, formula I, or pharmaceutically acceptable salts or prodrugs thereof, may be represented as:

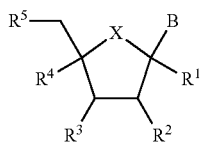

Formula (I)

In one embodiment, X is O, S, $NR^N$ or $CR^P_2$.

In one embodiment, B is hydrogen, optionally substituted natural or non-natural nucleobase, optionally substituted triazole, or optionally substituted tetrazole, NH—C(O)—O—C(CH$_2$B$_1$)$_3$, NH—C(O)—NH—C(CH$_2$B$_1$)$_3$; where B$_1$ is independently halogen, mesylate, N$_3$, CN, optionally substituted triazole or optionally substituted tetrazole, and where the nucleobase may further be substituted by -J-linker-N$_3$, -J-linker-CN, 4-linker-C≡R$^8$, -J-linker-cycloalkyne, -J-linker-R$^L$, -Linker-Q-R$^L$, or J-linker-Q-linker-R$^L$. B$_1$ can also be hydrogen.

In one embodiment, $R^1$, $R^2$, $R^3$, $R^4$ and $R^5$ are each independently H, $OR^6$, F, $N(R^N)_2$, $N_3$, CN, -J-linker-N$_3$, -J-linker-CN, 4-linker-C≡R$^8$, -J-linker-cycloalkyne, -J-linker-R$^L$, -Linker-Q-R$^L$, or -J-linker-Q-linker-R$^L$. $R^1$, $R^2$, $R^3$, $R^4$ and $R^5$ can each also be independently $R^6$.

In one embodiment, J is absent, O, S, $NR^N$, OC(O)NH, NHC(O)O, C(O)NH, NHC(O), NHSO, NHSO$_2$, NHSO$_2$NH, OC(O), C(O)O, OC(O)O, NHC(O)NH, NHC(S)NH, OC(S)NH, OP(N($R^P$)$_2$)O, or OP(N($R^P$)$_2$).

In one embodiment, $R^6$ is hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)—O-nucleoside, —P($Z^1$)($Z^2$)—O-oligonucleotide, —P($Z^1$)($Z^2$)-formula (I), —P($Z^1$)(O-linker-Q-linker-$R^L$)—O-nucleoside, P($Z^1$)(O-linker-$R^L$)—O-nucleoside, —P($Z^1$)(O-linker-N$_3$)—O-nucleoside, P($Z^1$)(O-linker-CN)—O-nucleoside, P($Z^1$)(O-linker-C≡$R^8$)—O-nucleoside, P($Z^1$)(O-linker-cycloalkyne)-O-nucleoside, —P($Z^1$)(O-linker-Q-linker-$R^L$)—O-oligonucleotide, P($Z^1$)(O-linker-$R^L$)—O-oligonucleotide, P($Z^1$)(O-linker-N$_3$)—O-oligonucleotide, —P($Z^1$)(O-linker-CN)—O-oligonucleotide, P($Z^1$)(O-linker-C≡$R^8$)—O-oligonucleotide, P($Z^1$)(O-linker-cycloalkyne)-O-oligonucleotide, —P($Z^1$)(-linker-Q-linker-$R^L$)—O-nucleoside, —P($Z^1$)(-linker-Q-$R^L$)—O-nucleoside, —P($Z^1$)(-linker-N$_3$)—O-nucleoside, P($Z^1$)(-linker-CN)—O-nucleoside, P($Z^1$)(-linker-C≡$R^8$)—O-nucleoside, P($Z^1$)(-linker-cycloalkyne)-O-nucleoside, —P($Z^1$)(-linker-Q-linker-$R^L$)—O-oligonucleotide, —P($Z^1$)(-linker-$R^L$)—O-oligonucleotide, P($Z^1$)(-linker-N$_3$)—O-oligonucleotide, —P($Z^1$)(-linker-CN)—O-oligonucleotide, P($Z^1$)(-linker-C≡$R^8$)—O-oligonucleotide or P($Z^1$)(-linker-cycloalkyne)-O-oligonucleotide.

In one embodiment, $R^N$ is H, optionally substituted alkyl, optionally substituted alkenyl, optionally substituted alkynyl, optionally substituted aryl, optionally substituted cycloalkyl, optionally substituted aralkyl, optionally substituted heteroaryl, or an amino protecting group.

In one embodiment, $R^P$ is independently H, optionally substituted alkyl, optionally substituted alkenyl, optionally substituted alkynyl, optionally substituted aryl, optionally substituted cycloalkyl, or optionally substituted heteroaryl.

In one embodiment, Q is

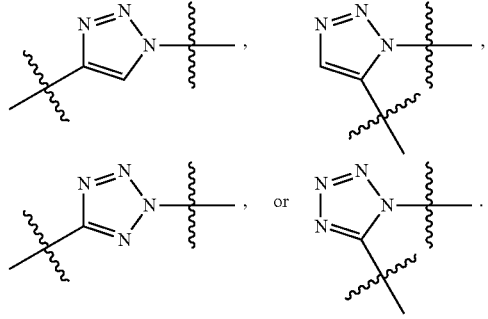

In one embodiment, $R^L$ is hydrogen or a ligand.

In one embodiment, $R^8$ is N or $CR^9$.

In one embodiment, $R^9$ is H, optionally substituted alkyl, or silyl.

In one embodiment, $Z^1$ and $Z^2$ are each independently O, S, or optionally substituted alkyl.

In this embodiment of formula I, Q, —N$_3$, —CN, —C≡$R^8$, an optionally substituted triazole, or an optionally substituted tetrazole must be present at least once in the compound. For instance, $R^1$ is, in at least one instance, N$_3$, CN, -J-linker-N$_3$, -J-linker-CN, -J-linker-C≡$R^8$, -Linker-Q-$R^L$, or -J-linker-Q-linker-$R^L$; $R^2$ is, in at least one instance, N$_3$, CN, -J-linker-N$_3$, -J-linker-CN, -J-linker-C≡$R^8$, -Linker-Q-$R^L$, or -J-linker-Q-linker-$R^L$; $R^3$ is, in at least one instance, N$_3$, CN, -J-linker-N$_3$, -J-linker-CN, -J-linker-C≡$R^8$, -Linker-Q-$R^L$, or -J-linker-Q-linker-$R^L$; $R^4$ is, in at least one instance, N$_3$, CN, -J-linker-N$_3$, -J-linker-CN, -J-linker-C≡$R^8$, -Linker-Q-$R^L$, or -J-linker-Q-linker-$R^L$; $R^5$ is, in at least one instance, N$_3$, CN, -J-linker-N$_3$, -J-linker-CN, -J-linker-C≡$R^8$, -Linker-Q-$R^L$, or -J-linker-Q-linker-$R^L$; B is, in at least one instance, optionally substituted triazole, or optionally substituted tetrazole, NH—C(O)—O—C(CH$_2$B$_1$)$_3$, NH—C(O)—NH—C(CH$_2$B$_1$)$_3$, where B$_1$ is N$_3$, CN, optionally substituted triazole or optionally substituted tetrazole, and where the nucleobase is further substituted by -J-linker-N$_3$, -J-linker-CN, -J-linker-C≡$R^8$, -Linker-Q-$R^L$, or -J-linker-Q-linker-$R^L$; or a combination of the above. In one embodiment, $R^1$ is -J-Linker-Q-Linker-$R^L$ or -Linker-Q-$R^L$. Thus, in one embodiment, $R^2$ is -J-Linker-Q-Linker-$R^L$ or -Linker-Q-$R^L$; in one embodiment, $R^3$ is -J-Linker-Q-Linker-$R^L$ or -Linker-Q-$R^L$; in one embodiment, $R^4$ is -J-Linker-Q-Linker-$R^L$ or -Linker-Q-$R^L$; in one embodiment, $R^5$ is -J-Linker-Q-Linker-$R^L$ or -Linker-Q-$R^L$; and in one embodiment, B comprises -J-Linker-Q-Linker-$R^L$ or -Linker-Q-$R^L$.

In another embodiment, the carrier is a ribose sugar as shown in formula (III). In this embodiment, the compound, e.g., a click-carrier compound is a nucleoside/nucleotide or a nucleoside/nucleotide analog.

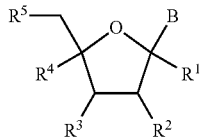

Formula (III)

In one embodiment, the $R^2$ and $R^4$ of the same compound are connected together to form a "locked" compound similar to a locked nucleic acid (LNA).

In one embodiment, $R^1$ and $R^4$ are H.

In one embodiment, $R^1$ is —O-Linker-Q-Linker-$R^L$, —OC(O)N($R^N$)-Linker-Q-Linker-$R^L$ or -Linker-Q-Linker-$R^L$, B is H.

In one embodiment, the $R^2$ and $R^4$ of the same compound are connected together to form a "locked" compound similar to a locked nucleic acid (LNA).

In one embodiment, when B is hydrogen, $R^1$ is —O-Linker-Q-Linker-$R^L$, —OC(O)N($R^7$)-Linker-Q-Linker-$R^L$ or -Linker-Q-Linker-$R^L$.

In one embodiment, B is H.

In one embodiment, B is pyrimidine substituted at C5 position.

In one embodiment, $R^2$ is $OR^6$ and $R^3$ is —O-Linker-Q-Linker-$R^L$, —OC(O)N($R^N$)— Linker-Q-Linker-$R^L$ or -Linker-Q-Linker-$R^L$ and $R^L$ is present.

In one embodiment, $R^3$ is $OR^6$ and $R^2$ is —O-Linker-Q-Linker-$R^L$, —OC(O)N($R^N$)— Linker-Q-Linker-$R^L$ or -Linker-Q-Linker-$R^L$ and $R^L$ is present.

In one embodiment, $R^2$ is OH.

In one embodiment, $R^9$ is H.

In one embodiment, $R^5$ is —O-Linker-Q-Linker-$R^L$, —OC(O)N($R^N$)-Linker-Q-Linker-$R^L$ or -Linker-Q-Linker-$R^L$ and $R^L$ is present.

In one embodiment, $R^5$ is —OC(O)NH(CH$_2$)$_f$C≡$CR^9$, and f is 1-20.

In one embodiment, $R^4$ is —OC(O)NH(CH$_2$)$_f$C≡$CR^9$, and f is 1-20.

In one embodiment, $R^3$ is —OC(O)NH(CH$_2$)$_f$C≡$CR^9$, and f is 1-20.

In one embodiment, $R^2$ is —OC(O)NH(CH$_2$)$_f$C≡$CR^9$, and f is 1-20.

In one embodiment, $R^1$ is —OC(O)NH(CH$_2$)$_f$C≡$CR^9$, and f is 1-20.

In one embodiment, B is a nucleobase substituted with —OC(O)NH(CH$_2$)$_f$C≡CH, and f is 1-20.

In one embodiment, $R^5$ is

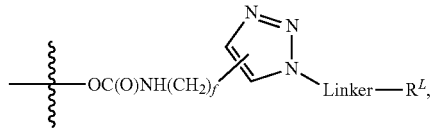

and f is 1-20.

In one embodiment, $R^4$ is

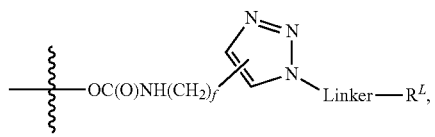

and f is 1-20.

In one embodiment, $R^3$ is

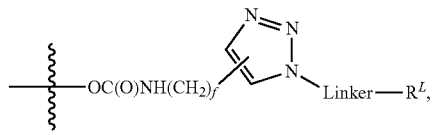

and f is 1-20.

In one embodiment, $R^2$ is

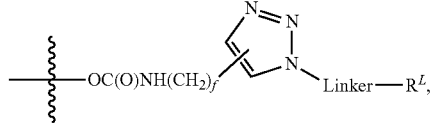

and f is 1-20.

In one embodiment, $R^1$ is

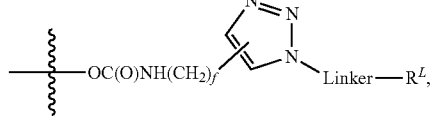

and f is 1-20.

In one embodiment, B is a nucleobase substituted with

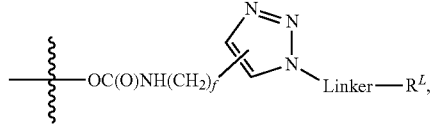

and f is 1-20.

In one embodiment, B is a nucleobase substituted with

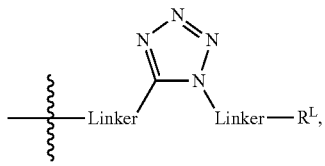

In one embodiment, B is a nucleobase substituted with

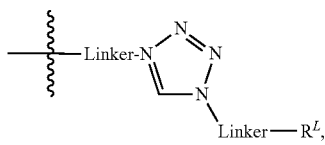

In one embodiment, $R^5$ is —O—$(CH_2)_f$C≡$CR^9$, and f is 1-20.

In one embodiment, $R^4$ is —O—$(CH_2)_f$C≡$CR^9$, and f is 1-20.

In one embodiment, $R^3$ is —O—$(CH_2)_f$C≡$CR^9$, and f is 1-20.

In one embodiment, $R^2$ is —O—$(CH_2)_f$C≡$CR^9$, and f is 1-20.

In one embodiment, $R^1$ is —O—$(CH_2)_f$C≡$CR^9$, and f is 1-20.

In one embodiment, B is a nucleobase substituted with —O—$(CH_2)_f$C≡CH, and f is 1-20

In one embodiment, $R^5$ is

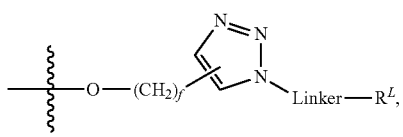

and f is 1-20.

In one embodiment, $R^4$ is

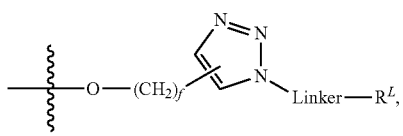

and f is 1-20.

In one embodiment, $R^3$ is

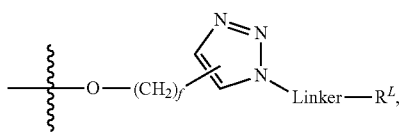

and f is 1-20.

In one embodiment, $R^2$ is

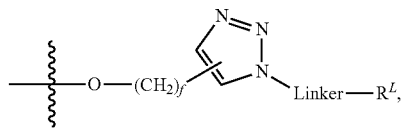

and f is 1-20.

In one embodiment, $R^1$ is

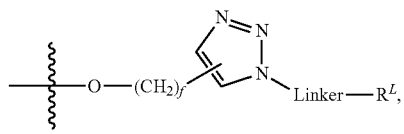

and f is 1-20.

In one embodiment, B is nucleobase substituted with

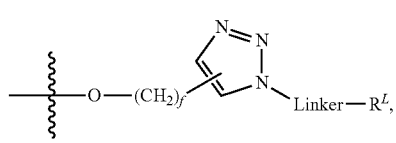

and f is 1-20.

In one embodiment, f is 1, 2, 3, 4 or 5. In a preferred embodiment, f is 1.

In one embodiment Q is

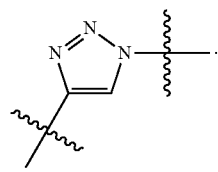 [SMILES: *c1cn(*)nn1]

In one embodiment, Q is

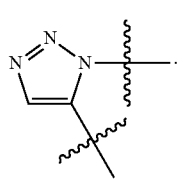 [SMILES: *c1cnnn1*]

In one embodiment, Q is

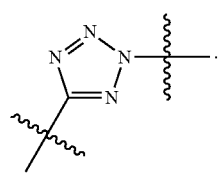 [SMILES: *c1nnn(*)n1]

In one embodiment, Q is

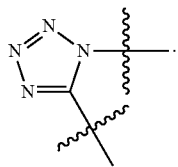 [SMILES: *c1nnnn1*]

In one embodiment, the ribose sugar of formula (I) has the structure shown in formula (I').

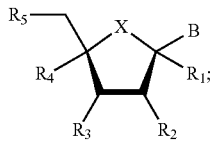
Formula (I')

wherein variable are as defined above for formula (I).
In one embodiment, the ribose sugar of formula (I) has the structure shown in formula (I' a).

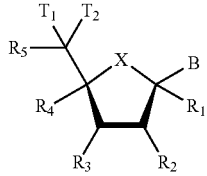
Formula (I'a)

wherein $T_1$ and $T_2$ are each independently H, $C_1$-$C_9$ aryl, $C_2$-$C_9$ alkenyl, $C_2$-$C_9$ alkynyl, substituted $C_1$-$C_9$ alkyl, substituted $C_1$-$C_9$ alkenyl and substituted $C_2$-$C_9$ alkynyl; and R1, R2, R3, R4R5, X and B are as previously defined.
In one embodiment, the ribose sugar of formula (I) has the structure shown in formula (I").

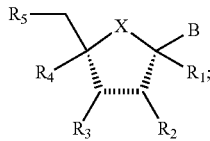
Formula (I")

wherein variable are as defined above for formula (I).
In one embodiment, the ribose sugar of formula (I) has the structure shown in formula (II'a).

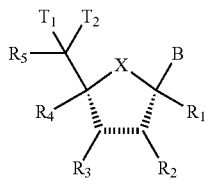
Formula (I")

wherein and $T_1$ and $T_2$ are each independently H, $C_1$-$C_9$ alkyl, $C_2$-$C_9$ alkenyl, $C_1$-$C_9$ alkynyl, substituted $C_1$-$C_9$ alkyl, substituted $C_1$-$C_9$ alkenyl and substituted $C_2$-$C_9$ alkynyl; and R1, R2, R3, R4R5, X and B are as previously defined.

In one embodiment, when click-carrier compound of formula (I) is at the 5'-terminal end of an oligonucleotide, the oligonucleotides is linked at the $R^5$ position of the click-carrier compound.

In one embodiment, when click-carrier compound of formula (I) is at the 3'-terminal end of an oligonucleotide, the oligonucleotides is linked at the $R^3$ or $R^2$ position of the click-carrier compound.

In one embodiment, when the click-carrier compound of formula (I) is not at a terminal position in an oligonucleotide, the $R^5$ position of the compound is linked to the 3'- or 2'-position of an oligonucleotide on one side and the $R^2$ or $R^3$ position of the compound is linked to the 5'-position of an oligonucleotide on the other side.

In one embodiment, the two different click-carrier compounds comprise complementary functional groups and are clicked together to each other. In one embodiment, complementary functional groups are at $R^5$ position of one click-compound and $R^2$ or $R^3$ position of the second compound. In one embodiment, the complementary functional groups are at $R^5$ position of one click-compound and $R^5$ position of the second compound. In one embodiment, complementary functional groups are at $R^2$ or $R^3$ position of one click-compound and $R^2$ or $R^3$ position of the second compound.

In some embodiments, B can form part of the click-carrier that connects the linker to the carrier. For example, the -linker-Q-linker-$R^L$ can be present at the C2, C6, C7 or C8 position of a purine nucleobase or at the C2, C5 or C6 position of a pyrimidine nucleobase. The linker can be directly attached to the nucleobase or indirectly through one or more intervening groups such as O, N, S, C(O), C(O)O C(O)NH. In certain embodiments, B, in the click-carrier described above, is uracilyl or a universal base, e.g., an aryl moiety, e.g., phenyl, optionally having additional substituents, e.g., one or more fluoro groups.

In one embodiment, the invention features, a compound having the structure shown in formula (IV)

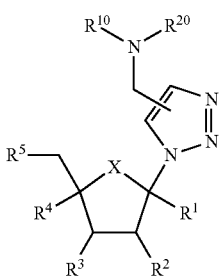
Formula (IV)

wherein $R^{10}$ and $R^{20}$ are independently for each occurrence hydrogen, optionally substituted aliphatic, optionally substituted aryl, or optionally substituted heteroaryl; $R^1$, $R^2$, $R^3$, $R^4$, $R^5$, and X are as defined in the first embodiment.

In one embodiment, the invention features, a compound having the structure shown in formula (IVa)

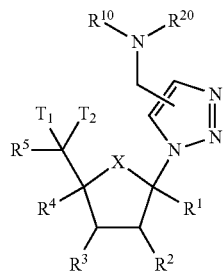

Formula (IVa)

wherein $T_1$ and $T_2$ are each independently H, $C_1$-$C_9$ alkyl, $C_2$-$C_9$ alkenyl, $C_2$-$C_9$ alkynyl, substituted $C_1$-$C_9$ alkyl, substituted $C_1$-$C_9$ alkenyl and substituted $C_2$-$C_9$ alkynyl; and R1, R2, R3, R4R5, R10, R20 and X are as previously defined.

In one embodiment, the invention features, a compound having the structure shown in formula (V)

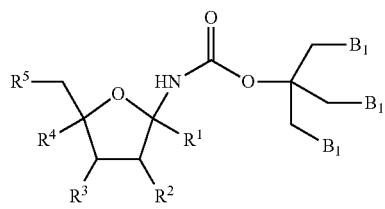

Formula (V)

wherein $B_1$ is halogen, $N_3$, CN, optionally substituted triazole or optionally substituted tetrazole. $B_1$ can also be mesylate. $R^1$, $R^2$, $R^3$, $R^4$, and $R^5$ are as defined in the first embodiment.

In one embodiment, the invention features, a compound having the structure shown in formula (Va)

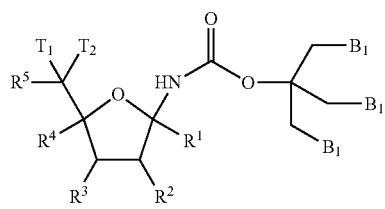

Formula (Va)

wherein $B_1$ is halogen, $N_3$, CN, optionally substituted triazole or optionally substituted tetrazole; $T_1$ and $T_2$ are each independently H, $C_1$-$C_9$ alkyl, $C_2$-$C_9$ alkenyl, $C_2$-$C_9$ alkynyl, substituted $C_1$-$C_9$ alkyl, substituted $C_1$-$C_9$ alkenyl and substituted $C_7$-$C_9$ alkyrryl; and R1, R2, R3, R4 and R5 are as previously defined.

In one embodiment, the carrier may be based on the pyrroline ring system as shown in formula (VI).

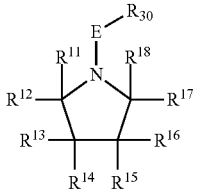

Formula (VI)

wherein E is absent or C(O), C(O)O, C(O)NH, C(S), C(S)NH, SO, $SO_2$, or $SO_2NH$;

$R^{11}$, $R^{12}$, $R^{13}$, $R^{14}$, $R^{15}$, $R^{16}$ $R^{17}$, and $R^{18}$ are each independently for each occurrence H, —$CH_2OR^a$, or $OR^b$, $R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —$P(Z^1)(Z^2)$—O-nucleoside, —$P(Z^1)(Z^2)$—O-oligonucleotide, —$P(Z^1)(Z^2)$-formula (I), —$P(Z^1)$(O-linker-Q-linker-$R^L$)—O-nucleoside, —$P(Z^1)$(O-linker-$N_3$)—O-nucleoside, $P(Z^1)$(O-linker-CN)—O-nucleoside, $P(Z^1)$(O-linker-C≡$R^8$)—O-nucleoside, $P(Z^1)$(O-linker-cycloalkyne)-O-nucleoside, —$P(Z^1)$(O— linker-$R^L$)—O-oligonucleotide, —$P(Z^1)$(O-linker-Q-linker-$R^L$)—O-oligonucleotide, —$P(Z^1)$(O-linker-$R^L$)—O-oligonucleotide, $P(Z^1)$(O-linker-$N_3$)—O-oligonucleotide, —$P(Z^1)$(O-linker-CN)—O-oligonucleotide, $P(Z^1)$(O-linker-C≡$R^8$)—O-oligonucleotide, $P(Z^1)$(O-linker-cycloalkyne)-O-oligonucleotide, —$P(Z^1)$(-linker-Q-linker-$R^L$)—O-nucleoside, $P(Z^1)$(-linker-$R^L$)—O-nucleoside, —$P(Z^1)$(-linker-$N_3$)—O-nucleoside, $P(Z^1)$(-linker-CN)—O-nucleoside, $P(Z^1)$(-linker-C≡$R^8$)—O-nucleoside, $P(Z^1)$(-linker-cycloalkyne)-O-nucleoside, —$P(Z^1)$(-linker-Q-linker-$R^L$)—O-oligonucleotide, $(Z^1)$(-linker-$R^L$)—O-oligonucleotide, $P(Z^1)$(-linker-$N_3$)—O-oligonucleotide, —$P(Z^1)$(-linker-CN)—O-oligonucleotide, $P(Z^1)$(-linker-C≡$R^8$)—O-oligonucleotide or $P(Z^1)$(-linker-cycloalkyne)-O-oligonucleotide;

$R^{30}$ is independently for each occurrence -linker-Q-linker-$R^L$, -linker-$R^L$ or $R^{31}$;

Q is absent or independently for each occurrence

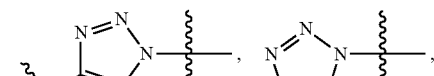

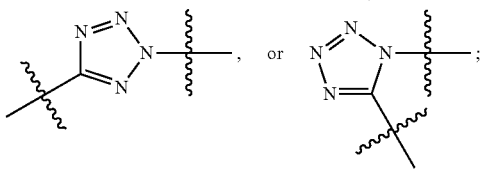

$R^L$ is hydrogen or a ligand;
$R^8$ is N or $CR^9$;

$R^9$ is H, optionally substituted alkyl or silyl;

$R^{31}$ is —C(O)CH(N($R^{32}$)$_2$)(CH$_2$)$_h$N($R^{32}$)$_2$;

$R^{32}$ is independently for each occurrence H, -linker-Q-linker-$R^L$, -linker-$R^L$ or $R^{31}$;

f and h are independently for each occurrence 1-20; and $Z^1$ and $Z^2$ are each independently for each occurrence O, S or optionally substituted alkyl.

For the pyrroline-based click-carriers, $R^{11}$ is —CH$_2$O$R^a$ and $R^3$ is O$R^b$; or $R^{11}$ is —CH$_2$O$R^a$ and $R^9$ is O$R^b$; or $R^{11}$ is —CH$_2$O$R^a$ and $R^{17}$ is O$R^b$; or $R^{13}$ is —CH$_2$O$R^a$ and $R^{11}$ is O$R^b$; or $R^{13}$ is —CH$_2$O$R^a$ and $R^{15}$ is O$R^b$; or $R^{13}$ is —CH$_2$O$R^a$ and $R^{17}$ is O$R^b$. In certain embodiments, CH$_2$O$R^a$ and O$R^b$ may be geminally substituted. For the 4-hydroxyproline-based carriers, $R^{11}$ is —CH$_2$O$R^a$ and $R^{17}$ is O$R^b$. The pyrroline- and 4-hydroxyproline-based compounds may therefore contain linkages (e.g., carbon-carbon bonds) wherein bond rotation is restricted about that particular linkage, e.g. restriction resulting from the presence of a ring. Thus, CH$_2$O$R^a$ and O$R^b$ may be cis or trans with respect to one another in any of the pairings delineated above Accordingly, all cis/trans isomers are expressly included. The compounds may also contain one or more asymmetric centers and thus occur as racemates and racemic mixtures, single enantiomers, individual diastereomers and diastereomeric mixtures. All such isomeric forms of the compounds are expressly included (e.g., the centers bearing CH$_2$O$R^a$ and O$R^b$ can both have the R configuration; or both have the S configuration; or one center can have the R configuration and the other center can have the S configuration and vice versa).

In one embodiment, $R^{11}$ is CH$_2$O$R^a$ and $R^9$ is O$R^b$.

In one embodiment, $R^b$ is a solid support.

In one embodiment, $R^{30}$ is —C(O)(CH$_2$)$_f$NHC(O)(CH$_2$)$_g$C≡C$R^9$; wherein f and g are independently 1-20.

In one embodiment, $R^{30}$ is

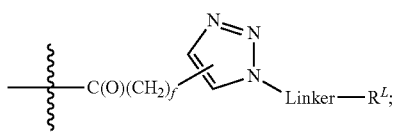

wherein f is 1-20.

In one embodiment, $R^{30}$ is

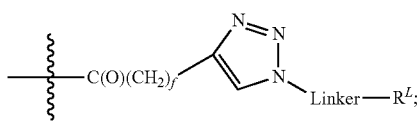

wherein f is 1-20.

In one embodiment, $R^{30}$ is

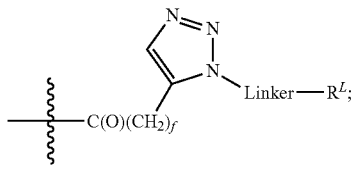

wherein f is 1-20.

In one embodiment, $R^{30}$ is

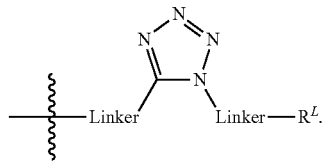

In one embodiment, $R^{30}$ is

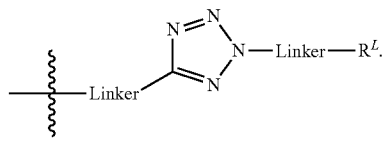

In one preferred embodiment, $R^{30}$ is $R^{31}$.

In one preferred embodiment, $R^{31}$ is —C(O)CH(N($R^{32}$)$_2$)(CH$_2$)$_4$N($R^{32}$)$_2$ and at least one $R^{32}$ is —C(O)(CH$_2$)$_f$C≡$R^8$ or -linker-Q-linker-$R^L$ and $R^L$ is present.

In one preferred embodiment, $R^{31}$ is —C(O)CH(N($R^{32}$)$_2$)(CH$_2$)$_4$NH$_2$ and at least one $R^{32}$ is —C(O)(CH$_2$)$_f$C≡$R^8$ or -linker-Q-linker-$R^L$ and $R^L$ is present.

In one embodiment, $R^{32}$ is —C(O)(CH$_2$)$_f$C≡$R^8$.

In one embodiment, $R^{32}$ is —C(O)(CH$_2$)$_3$C≡H.

In one embodiment, $R^{31}$ is —C(O) (NH$_2$)(CH$_2$)$_4$NH$_2$.

In one embodiment features acyclic sugar replacement-based compounds, e.g., sugar replacement based click-carrier compounds, are also referred to herein as ribose replacement compound subunit (RRMS) compound compounds. Preferred acyclic carriers can have the structure shown in formula (III) or formula (IV) below.

In one aspect, the invention features, an acyclic click-carrier compound having the structure shown in formula (VII)

Formula (VII)

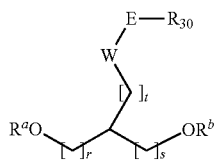

wherein:

W is absent, O, S and N($R^N$), where $R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

E is absent or C(O), C(O)O, C(O)NH, C(S), C(S)NH, SO, SO$_2$, or SO$_2$NH;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P(Z$^1$)(Z$^2$)—O-nucleoside, —P(Z$^1$)(Z$^2$)—O-oligonucleotide, —P(Z$^1$)(Z$^2$)-formula (I), —P(Z$^1$)(O-linker-Q-linker-R$^L$)—O-nucleoside, —P(Z$^1$)(O-linker-N$_3$)—O-nucleoside, P(Z$^1$)(O-linker-CN)—O-nucleoside, P(Z$^1$)(O-linker-C≡R$^8$)—O-nucleoside, P(Z$^1$)(O-linker-cycloalkyne)-O-nucleoside, —P(Z$^1$)(O— linker-R$^L$)—O-oligonucleotide, —P(Z$^1$)(O-linker-Q-linker-R$^L$)—O-oligonucleotide, —P(Z$^1$)(O-linker-R$^L$)—O-oligonucleotide, P(Z$^1$)(O-linker-N$_3$)—O-oligonucleotide, —P(Z$^1$)(O-linker-CN)—O-oligonucleotide, P(Z$^1$)(O-linker-C≡R$^8$)—O-oligonucleotide, P(Z$^1$)(O-linker-cycloalkyne)-O-oligonucleotide, —P(Z$^1$)(-linker-Q-linker-R$^L$)—O-nucleoside, P(Z$^1$)(-linker-R$^L$)—O-nucleoside, —P(Z$^1$)(-linker-N$_3$)—O-nucleoside, P(Z$^1$)(-linker-CN)—O-nucleoside, P(Z$^1$)(-linker-C≡R$^8$)—O-nucleoside, P(Z$^1$)(-linker-cycloalkyne)-O-nucleoside, —P(Z$^1$)(-linker-Q-linker-R$^L$)—O-oligonucleotide, (Z$^1$)(-linker-R$^L$)—O-oligonucleotide, P(Z$^1$)(-linker-N$_3$)—O-oligonucleotide, —P(Z$^1$)(-linker-CN)—O-oligonucleotide, P(Z$^1$)(-linker-C≡R$^8$)—O-oligonucleotide or P(Z$^1$)(-linker-cycloalkyne)-O-oligonucleotide;

R$^{30}$ is independently for each occurrence -linker-Q-linker-R$^L$, -linker-R$^L$ or R$^{31}$;

Q is absent or independently for each occurrence

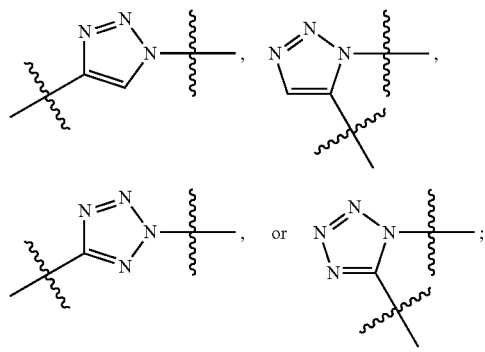

R$^L$ is hydrogen or a ligand;
R$^8$ is N or CR$^9$
R$^9$ is H, optionally substituted alkyl or silyl;
R$^{31}$ is —C(O)CH(N(R$^{32}$)$_2$)(CH$_2$)$_h$N(R$^{32}$)$_2$;
R$^{32}$ is independently for each occurrence H, -linker-Q-linker-R$^L$ or R$^{31}$;

f and h are independently for each occurrence 1-20;

Z$^1$ and Z$^2$ are each independently for each occurrence O, S or optionally substituted alkyl; and r, s and t are each independently for each occurrence 0, 1, 2 or 3.

When r and s are different, then the tertiary carbon can be either the R or S configuration. In preferred embodiments, x and y are one and z is zero (e.g. carrier is based on serinol). The acyclic carriers can optionally be substituted, e.g. with hydroxy, alkoxy, perhaloalky.

In another aspect, the invention features, an acyclic click-carrier compound having the structure shown in formula (VIII)

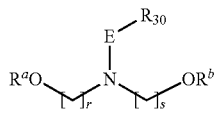

Formula (VIII)

wherein E is absent or C(O), C(O)O, C(O)NH, C(S), C(S)NH, SO, SO$_2$, or SO$_2$NH;

R$^a$ and R$^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P(Z$^1$)(Z$^2$)—O-nucleoside, —P(Z$^1$)(Z$^2$)—O-oligonucleotide, —P(Z$^1$)(Z$^2$)-formula (I), —P(Z$^1$)(O-linker-Q-linker-R$^L$)—O-nucleoside, —P(Z$^1$)(O-linker-N$_3$)—O-nucleoside, P(Z$^1$)(O-linker-CN)—O-nucleoside, P(Z$^1$)(O-linker-C≡R$^8$)—O-nucleoside, P(Z$^1$)(O-linker-cycloalkyne)-O-nucleoside, —P(Z$^1$)(O— linker-R$^L$)—O-oligonucleotide, —P(Z$^1$)(O-linker-Q-linker-R$^L$)—O-oligonucleotide, —P(Z$^1$)(O-linker-R$^L$)—O-oligonucleotide, P(Z$^1$)(O-linker-N$_3$)—O-oligonucleotide, —P(Z$^1$)(O-linker-CN)-β-oligonucleotide, P(Z$^1$)(O-linker-C≡R$^8$)—O-oligonucleotide, P(Z$^1$)(O-linker-cycloalkyne)-O-oligonucleotide, —P(Z$^1$)(-linker-Q-linker-R$^L$)—O-nucleoside, P(Z$^1$)(-linker-R$^L$)—O-nucleoside, —P(Z$^1$)(-linker-N$_3$)—O-nucleoside, P(Z$^1$)(-linker-CN)—O-nucleoside, P(Z$^1$)(-linker-C≡R$^8$)—O-nucleoside, P(Z$^1$)(-linker-cycloalkyne)-O-nucleoside, —P(Z$^1$)(-linker-Q-linker-R$^L$)—O-oligonucleotide, (Z$^1$)(-linker-R$^L$)—O-oligonucleotide, P(Z$^1$)(-linker-N$_3$)—O-oligonucleotide, —P(Z$^1$)(-linker-CN)—O-oligonucleotide, P(Z$^1$)(-linker-C≡R$^8$)—O-oligonucleotide or P(Z$^1$)(-linker-cycloalkyne)-O-oligonucleotide;

R$^{30}$ is independently for each occurrence -linker-Q-linker-R$^L$, -linker-R$^L$ or R$^{31}$;

Q is absent or independently for each occurrence

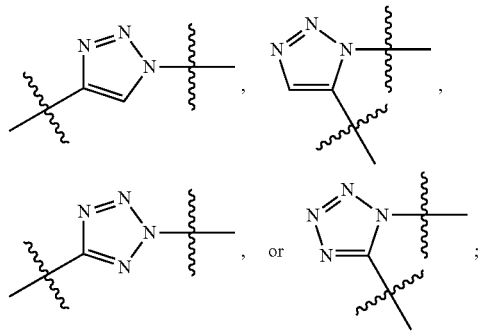

R$^L$ is hydrogen or a ligand;
R$^8$ is N or CR$^9$;
R$^9$ is H, optionally substituted alkyl or silyl;
R$^{31}$ is —C(O)CH(N(R$^{32}$)$_2$)(CH$_2$)$_h$N(R$^{32}$)$_2$;
R$^{32}$ is independently for each occurrence H, -linker-Q-linker-R$^L$ or R$^{31}$;

f and h are independently for each occurrence 1-20;

$Z^1$ and $Z^2$ are each independently for each occurrence O, S or optionally substituted alkyl; and r and s are each independently for each occurrence 0, 1, 2 or 3.

Preferably, Q, —$N_3$, —CN, or —C≡$R^8$ is present at least once in the compounds of formulas (VI), (VII), and (VIII).

Other carrier compounds amenable to the invention are described in copending applications U.S. Ser. No. 10/916,185, filed Aug. 10, 2004; U.S. Ser. No. 10/946,873, filed Sep. 21, 2004; U.S. Ser. No. 10/985,426, filed Nov. 9, 2004; U.S. Ser. No. 10/833,934, filed Aug. 3, 2007; U.S. Ser. No. 11/115,989 filed Apr. 27, 2005 and U.S. Ser. No. 11/119,533, filed Apr. 29, 2005, which are incorporated by reference in their entireties for all purposes.

Linkers

The term "linker" means an organic moiety that connects two parts of a compound. Linkers typically comprise a direct bond or an atom such as oxygen or sulfur, a unit such as $NR^1$, C(O), C(O)NH, SO, $SO_2$, $SO_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R^1)_2$, C(O), substituted or unsubstituted aryl, substituted or unsubstituted heteroaryl, substituted or unsubstituted heterocyclic; where $R^1$ is hydrogen, acyl, aliphatic or substituted aliphatic.

In one embodiment, the linker is represented by structure

—[P-$Q_1$-R]$_q$-T-, wherein:

P, R and T are each independently for each occurrence absent, CO, NH, O, S, OC(O), NHC(O), $CH_2$, $CH_2$NH, $CH_2$O; NHCH($R^a$)C(O), —C(O)—CH($R^a$)—NH—, —C(O)—

(optionally substituted alkyl)-NH—, CH=N—O, $Q_1$ is independently for each occurrence absent, —$(CH_2)_n$—, —C($R^{100}$)($R^{200}$)$(CH_2)_n$—, —$(CH_2)_n$C($R^{100}$)($R^{200}$)—, —$(CH_2CH_2O)_m CH_2CH_2$—, or —$(CH_2CH_2O)_m CH_2CH_2NH$—;

$R^a$ is H or an amino acid side chain;

$R^{100}$ and $R^{200}$ are each independently for each occurrence H, $CH_3$, OH, SH or $N(R^X)_2$;

$R^X$ is independently for each occurrence H, methyl, ethyl, propyl, isopropyl, butyl or benzyl;

q is independently for each occurrence 0-20;

n is independently for each occurrence 1-20; and m is independently for each occurrence 0-50.

In one embodiment, the linker has the structure —[(P-$Q_1$-R)$_q$—X—(P'-$Q_1$'-R')$_{q'}$]$_{q''}$-T, wherein:

P, R, T, P', $R^1$ and T' are each independently for each occurrence absent, CO, NH, O, S, OC(O), NHC(O), $CH_2$, $CH_2$NH, $CH_2$O; NHCH($R^a$)C(O), —C(O)—CH($R^a$)—NH—, —C(O)-(optionally substituted alkyl)-NH—, CH=N—O, $Q_1$ and $Q_1$' are each independently for each occurrence absent, —$(CH_2)_n$—, —C($R^{100}$)($R^{200}$)$(CH_2)_n$—, —$(CH_2)_n$C($R^{100}$)($R^{200}$)—, —$(CH_2CH_2O)_m CH_2CH_2$—, or —$(CH_2CH_2O)_m CH_2CH_2NH$—;

X is a cleavable linking group;

$R^a$ is H or an amino acid side chain;

$R^{100}$ and $R^{200}$ are each independently for each occurrence H, $CH_3$, OH, SH or $N(R^X)_2$;

$R^X$ is independently for each occurrence H, methyl, ethyl, propyl, isopropyl, butyl or benzyl;

q, q' and q' are each independently for each occurrence 0-20;

n is independently for each occurrence 1-20; and m is independently for each occurrence 0-50.

In one embodiment, the linker comprises at least one cleavable linking group.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some spacers will have a linkage group that is cleaved at a preferred pH, thereby releasing the iRNA agent from the carrier oligomer inside the cell, or into the desired compartment of the cell.

A spacer can include a linking group that is cleavable by a particular enzyme. The type of linking group incorporated into a spacer can depend on the cell to be targeted by the iRNA agent. For example, an iRNA agent that targets an mRNA in liver cells can be linked to the carrier oligomer through a spacer that includes an ester group. Liver cells are rich in esterases, and therefore the tether will be cleaved more efficiently in liver cells than in cell types that are not esterase-rich. Cleavage of the spacer releases the iRNA agent from the carrier oligomer, thereby potentially enhancing silencing activity of the iRNA agent. Other cell-types rich in esterases include cells of the lung, renal cortex, and testis.

Spacers that contain peptide bonds can be used when the iRNA agents are targeting cell types rich in peptidases, such as liver cells and synoviocytes. For example, an iRNA agent targeted to synoviocytes, such as for the treatment of an inflammatory disease (e.g., rheumatoid arthritis), can be linked to a carrier oligomer through spacer that comprises a peptide bond.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue, e.g., tissue the iRNA agent would be exposed to when administered to a subject. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)—O—, —O—P(S)(ORk)—O—, —O—P(S)(SRk)—O—, —S—P(O)(ORk)—O—, —O—P(O)(ORk)-S—, —S—P(O)(ORk)-S—, —O—P(S)(ORk)-S—, —S—P(S)(ORk)—O—, —O—P(O)(Rk)—O—, —O—P(S)(Rk)—O—, —S—P(O)(Rk)—O—, —S—P(S)(Rk)—O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide cleavable linking groups have the general formula —NHCHR$^1$C(O)NHCHR$^2$C(O)—, where R$^1$ and R$^2$ are the R groups of the two adjacent amino acids. These candidates can be evaluated using methods analogous to those described above.

"Click" Reaction

The synthesis methods of the present invention utilize click chemistry to conjugate the ligand to the click-carrier compound. Click chemistry techniques are described, for example, in the following references, which are incorporated herein by reference in their entirety:

Kolb, H. C.; Finn, M. G. and Sharpless, K. B. *Angew. Chem., Int. Ed.* (2001) 40: 2004-2021.

Kolb, H. C. and Shrapless, K. B. *Drug Disc. Today* (2003) 8: 112-1137.

Rostovtsev, V. V.; Green L. G.; Fokin, V. V. and Shrapless, K. B. *Angew. Chem., Int. Ed.* (2002) 41: 2596-2599.

Tornøe, C. W.; Christensen, C. and Meldal, M. *J. Org. Chem.* (2002) 67: 3057-3064.

Wang, Q. et al., *J. Am. Chem. Soc.* (2003) 125: 3192-3193.

Lee, L. V. et al., *J. Am. Chem. Soc.* (2003) 125: 9588-9589.

Lewis, W. G. et al., *Angew. Chem., Int. Ed.* (2002) 41: 1053-1057.

Manetsch, R. et al., *J. Am. Chem. Soc.* (2004) 126: 12809-12818.

Mocharla, V. P. et al., *Angew. Chem., Int. Ed.* (2005) 44: 116-120.

Although other click chemistry functional groups can be utilized, such as those described in the above references, the use of cycloaddition reactions is preferred, particularly the reaction of azides with alkynyl groups. In the presence of Cu(I) salts, terminal alkynes and azides undergo 1,3-dipolar cycloaddition forming 1,4-disubstituted 1,2,3-triazoles. In the presence of Ru(II) salts (e.g. Cu*RuCl(PPh$_3$)$_2$), terminal alkynes and azides under go 1,3-dipolar cycloaddition forming 1,5-disubstituted 1,2,3-triazoles (Folkin, V. V. et al., *Org. Lett.* (2005) 127: 15998-15999). Alternatively, a 1,5-disubstituted 1,2,3-triazole can be formed using azide and alkynyl reagents (Kraniski, A.; Fokin, V. V. and Sharpless, K. B. *Org. Lett.* (2004) 6: 1237-1240. Hetero-Diels-Alder reactions or 1,3-dipolar cycloaddition reaction could also be used (see for example Padwa, A. 1,3-*Dipolar Cycloaddition Chemistry: Volume* 1, John Wiley, New York, (1984) 1-176; Jørgensen, K. A. *Angew. Chem., Int. Ed.* (2000) 39: 3558-3588 and Tietze, L. F. and Kettschau, G. *Top. Curr. Chem.* (1997) 189: 1-120)

The choice of azides and alkynes as coupling partners is particularly advantageous as they are essentially non-reactive towards each other (in the absence of copper) and are extremely tolerant of other functional groups and reaction conditions. This chemical compatibility helps ensure that many different types of azides and alkynes may be coupled with each other with a minimal amount of side reactions.

The required copper(I) species are added directly as cuprous salts, for example CuI, CuOTf.C$_6$H$_6$ or [Cu(CH$_3$CN)$_4$][PF$_6$], usually with stabilizing ligands (see for example Tornøe, C. W.; Christensen, C. and Meldal, M. *J. Org. Chem.* (2002) 67: 3057-3064; Chan, T. R. et al., *Org. Lett.* (2004) 6: 2853-2855; Lewis, W. G. et al., *J. Am. Chem. Soc.* (2004) 126: 9152-9153; Mantovani, G. et al., *Chem. Comm.* (2005) 2089-2091; Diez-Gonzalez, S. et al., *Chem. Eur. J.* (2006) 12: 7558-7564 and Candelon, N. et al., *Chem. Comm.* (2008) 741-743), or more often generated from copper (II) salts with reducing agents (Rostovtsev, V. V. et al., *Angew. Chem.* (2002) 114: 2708-2711 and *Angew. Chem., Int. Ed.* (2002) 41: 2596-2599). Metallic copper (for example see Himo, F. et al., *J. Am. Chem. Soc.* (2005) 127: 210-216) or clusters (for example see Pachon, L. D. et al., *Adv. Synth. Catal.* (2005) 347: 811-815 and Molteni, G. et al., *New J. Chem* (2006) 30: 1137-1139) can also be employed. Chassaing et al., recently reported copper(I) zeolites as catalysts for the azide-alkyne cycloaddition (*Chem. Eur. J.* (2008) 14: 6713-6721). As copper(I) salts are prone to redox process, nitrogen- or phosphorous-based ligands must be added to protect and stabilize the active copper catalyst during the cycloaddition reaction.

The reaction is extremely straightforward. The azide and alkyne are usually mixed together in water and a co-solvent such as tert-butanol, THF, DMSO, toluene or DMF. The water/co-solvent are usually in a 1:1 to 1:9 ratio. The reactions are usually run overnight although mild heating shortens reaction times (Sharpless, W. D.; Wu, P.; Hansen, T. V.; and Li, J. G. *J. Chem. Ed.* (2005) 82: 1833). Aqueous systems can also use copper(I) species directly such that a reducing agent is not needed. The reactions conditions then usually require acetonitrile as a co-solvent (although not essential (Chan, T. R.; Hilgraf, R.; Shrapless, K. B. and Fokin, V. V. *Org. Lett.* (2004) 6: 2853)) and a nitrogen base, such as triethylamine, 2,6-lutidine, pyridine and diisopropylamine. In this case copper(I) species is supplied as CuI, CuOTf.C$_6$H$_6$ or [Cu(CH$_3$CN)$_4$][PF$_6$] (Rostoctsev, V. V.; Green L. G.; Fokin, V. V. and Shrapless, K. B. *Angew. Chem., Int. Ed.* (2002) 41: 2596-2599).

Although the water-based methods are attractive for many applications, solvent based azide-alkyne cycloaddition methods have found utility in situations when solubility and/or other problems arise, for example see:

Malkoch, M. et al., *Macromolecules* (2005) 38: 3663.

Gujadhur, R.; Venkataraman, D. and J. T. Kintigh. J. T. *Tet. Lett.* (2001) 42: 4791.

Laurent, B. A. and Grayson, S. M. *J. Am. Chem. Soc.* (2006) 128: 4238.

Opsteen, J. A.; van Hest, J. C. M. *Chem. Commun.* (2005) 57.

Tsarevsky, N. V.; Sumerlin, B. S, and Matyjaszewski, K. *Macromolecules* (2005) 38: 3558.

Johnson, J. A. et al., *J. Am. Chem. Soc.* (2006) 128: 6564.

Sumerlin, B. S. et al., *Macromolecules* (2005) 38: 7540.

Gao, H. F. and Matyjaszewski, K. *Macromolecules* (2006) 39: 4960.

Gao, H. et al, *Macromolecules* (2005) 38: 8979.

Vogt, A. P. and Sumerlin, B. S. *Macromolecules* (2006) 39: 5286.

Lutz, J. F.; Borner, H. G. and Weichenhan, K. *Macromol. Rapid Comm.* (2005) 26: 514.

Mantovani, G.; Ladmiral, V.; Tao, L. and Haddleton, D. M. *Chem. Comm.* (2005) 2089.

The click reaction may be performed thermally. In one aspect, the click reaction is performed at slightly elevated temperatures between 25° C. and 100° C. In one aspect, the reaction may be performed between 25° C. and 75° C., or between 25° C. and 65° C., or between 25° C. and 50° C. In one embodiment, the reaction is performed at room temperature. In another aspect, the click reaction may also be performed using a microwave oven. The microwave assisted click reaction may be carried out in the presence or absence of copper.

In one aspect, the invention provides a method for coupling a click-carrier compound to a ligand through a click reaction. In a preferred embodiment, the click reaction is a cycloaddition reaction of azide with alkynyl group and catalyzed by copper. In one embodiment the equal molar amount of alkyne and azide are mixed together in DCM/MeOH (10:1 to 1:1 ratio v/v) and 0.05-0.5 mol % each of $[Cu(CH_3CN)_4][PF_6]$ and copper are added the reaction. In one embodiment DCM/MeOH ratio is 5:1 to 1:1. In a preferred embodiment, DCM/MeOH ratio is 4:1. In one embodiment, equal molar amounts of $[Cu(CH_3CN)_4][PF_6]$ and copper are added. In a preferred embodiment, 0.05-0.25 mol % each of $[Cu(CH_3CN)_4][PF_6]$ and copper are added to the reaction. In a more preferred embodiment, 0.05 mol %, 0.1 mol %, 0.15 mol %, 0.2 mol % or 0.25 mol % each of $[Cu(CH_3CN)_4][PF_6]$ and copper are added to the reaction.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the oligomeric compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

Ligands

A wide variety of entities can be coupled to the oligonucleotide, e.g. the iRNA agent, using the "click" reaction. Preferred entities can be coupled to the oligonucleotide at various places, for example, 3'-end, 5'-end, and/or at internal positions.

In preferred embodiments, the ligand is attached to the iRNA agent via an intervening linker. The ligand may be present on a compound when said compound is incorporated into the growing strand. In some embodiments, the ligand may be incorporated via coupling to a "precursor" compound after said "precursor" compound has been incorporated into the growing strand. For example, a compound having, e.g., an azide terminated linker (i.e., having no associated ligand), e.g., -linker-$N_3$ may be incorporated into a growing sense or antisense strand. In a subsequent operation, i.e., after incorporation of the precursor compound into the strand, a ligand having an alkyne, e.g. terminal acetylene, e.g. ligand-C≡CH, can subsequently be attached to the precursor compound by the "click" reaction. Alternatively, the compound linker comprises an alkyne, e.g. terminal acetylene; and the ligand comprises an azide functionality for the "click" reaction to take place. The azide or alkyne functionalities can be incorporated into the ligand by methods known in the art. For example, moieties carrying azide or alkyne functionalities can be linked to the ligand or a functional group on the ligand can be transformed into an azide or alkyne. In one embodiment, the conjugation of the ligand to the precursor compound takes place while the oligonucleotide is still attached to the solid support. In one embodiment, the precursor carrying oligonucleotide is first deprotected but not purified before the ligand conjugation takes place. In one embodiment, the precursor compound carrying oligonucleotide is first deprotected and purified before the ligand conjugation takes place. In certain embodiments, the "click" reaction is carried out under microwave.

In preferred embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Preferred ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In certain embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GAL4 peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component may contain a chemical group (e.g., an amino acid) which will undergo a change in charge or protonation in response to a change in pH. The endosomolytic component may be linear or branched. Exemplary primary sequences of peptide based endosomolytic ligands are shown in table 1.

TABLE 1

List of peptides with endosomolytic activity.

| Name | Sequence (N to C) | Ref. |
|---|---|---|
| GALA | AALEALAEALEALAEALEALAEAAAAGGC | 1 |
| EALA | AALAEALAEALAEALAEALAEALAAAAGGC | 2 |
|  | ALEALAEALEALAEA | 3 |
| INF-7 | GLFEAIEGFIENGWEGMIWDYG | 4 |
| Inf HA-2 | GLFGAIAGFIENGWEGMIDGWYG | 5 |
| diINF-7 | GLF EAI EGFI ENGW EGMI DGWYGC<br>GLF EAI EGFI ENGW EGMI DGWYGC | 5 |
| diINF3 | GLF EAI EGFI ENGW EGMI DGGC<br>GLF EAI EGFI ENGW EGMI DGGC | 6 |
| GLF | GLFGALAEALAEALAEHLAEALAEALEALAAGG<br>SC | 6 |
| GALA-INF3 | GLFEAIEGFIENGWEGLAEALAEALEALAAGGS<br>C | 6 |

TABLE 1-continued

List of peptides with endosomolytic activity.

| Name | Sequence (N to C) | Ref. |
|---|---|---|
| INF-5 | GLF EAI EGFI ENGW EGnI DG K GLF EAI EGFI ENGW EGnI DG | 4 | n, norleucine
References
1. Subbarao et al. (1987) *Biochemistry* 26: 2964-2972.
2. Vogel, et al. (1996) *J. Am. Chem. Soc.* 118: 1581-1586
3. Turk, et al. (2002) *Biochim. Biophys. Acta* 1559: 56-68.
4. Plank, et al. (1994) *J. Biol. Chem.* 269: 12918-12924.
5. Mastrobattista, et al. (2002) *J. Biol. Chem.* 277:27135-43.
6. Oberhauser, et al. (1995) *Deliv. Strategies Antisense Oligonucleotide Ther.* 247-66.

Preferred ligands can improve transport, hybridization, and specificity properties and may also improve nuclease resistance of the resultant natural or modified oligoribonucleotide, or a polymeric molecule comprising any combination of compounds described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 2 shows some examples of targeting ligands and their associated receptors.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

TABLE 2

Liver targeting Ligands and their associated receptors

| Liver Cells | Ligand | Receptor |
|---|---|---|
| 3) Kupffer Cell (KC) | Mannose | Mannose receptors |
| | Fucose | Fucose receptors |
| 1) Parenchymal Cell | Galactose | ASGP-R |
| | Albumins | Non-specific |
| (PC) (Hepatocytes) | Mannose-albumin conjugates | (Asiologlycoprotein receptor) |
| | Gal NAc (n-acetyl-galactosamine) | ASPG-R (GalNAc Receptor) |
| | Lactose | |
| | Asialofetuin | ASPG-r |
| 2) Sinusoidal Endothelial Cell (SEC) | Hyaluronan | Hyaluronan receptor |
| | Procollagen | Procollagen receptor |
| | Negatively charged molecules | Scavenger receptors |
| | Mannose | Mannose receptors |
| | N-acetyl Glucosamine | Scavenger receptors |
| | Immunoglobulins | Fc Receptor |
| | LPS | CD14 Receptor |
| | Insulin | Receptor mediated transcytosis |
| | Transferrin | Receptor mediated transcytosis |
| | Albumins | Non-specific |
| | Sugar-Albumin conjugates | |
| | Mannose-6-phosphate | Mannose-6-phosphate receptor |

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the iRNA agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long (see Table 3, for example).

TABLE 3

Exemplary Cell Permeation Peptides

| Cell Permeation Peptide | Amino acid Sequence | Reference |
|---|---|---|
| Penetratin | RQIKIWFQNRRMKWKK | Derossi et al., J. Biol. Chem. 269:10444, 1994 |
| Tat fragment (48-60) | GRKKRRQRRRPPQC | Vives et al., J. Biol. Chem., 272:16010, 1997 |
| Signal Sequence-based peptide | GALFLGWLGAAGSTMGAWSQPKKKRKV | Chaloin et al., Biochem. Biophys. Res. Commun., 243:601, 1998 |
| PVEC | LLIILRRRIRKQAHAHSK | Elmquist et al., Exp. Cell Res., 269:237, 2001 |
| Transportan | GWTLNSAGYLLKINLKALAALAKKIL | Pooga et al., FASEB J., 12:67, 1998 |
| Amphiphilic model peptide | KLALKLALKALKAALKLA | Oehlke et al., Mol. Ther., 2:339, 2000 |
| Arg$_9$ | RRRRRRRRR | Mitchell et al., J. Pept. Res., 56:318, 2000 |

TABLE 3-continued

Exemplary Cell Permeation Peptides

| Cell Permeation Peptide | Amino acid Sequence | Reference |
|---|---|---|
| Bacterial cell wall permeating | KFFKFFKFFK | |
| LL-37 | LLGDFFRKSKEKIGKEFKRIVQRIKDFLRNL VPRTES | |
| Cecropin P1 | SWLSKTAKKLENSAKKRISEGIAIAIQGGPR | |
| α-defensin | ACYCRIPACIAGERRYGTCIYQGRLWAFCC | |
| b-defensin | DHYNCVSSGGQCLYSACPIFTKIQGTCYRG KAKCCK ) | |
| Bactenecin | RKCRIVVIRVCR | |
| PR-39 | RRRPRPPYLPRPRPPPFFPPRLPPRIPPGFPPR FPPRFPGKR-NH2 | |
| Indo licidin | ILPWKWPWWPWRR-NH2 | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP. An RFGF analogue (e.g., amino acid sequence AALLPVLLAAP) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ) and the *Drosophila* Antennapedia protein (RQIKIWFQNRRMKWKK) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated compound unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an $I_v\vartheta_{33}$ integrin. Thus, one could use RGD peptides, cyclic peptides containing RGD, RGD peptides that include D-amino acids, as well as synthetic RGD mimics. In addition to RGD, one can use other moieties that target the $I_v-\vartheta_{33}$ integrin ligand. Generally, such ligands can be used to control proliferating cells and angiogeneis. Preferred conjugates of this type ligands that targets PECAM-1, VEGF, or other cancer gene, e.g., a cancer gene described herein.

TABLE 4

Azide modified peptides.

| | |
|---|---|
| NB12675 | N3-(CH2)5-CO-Tyr-Gly-Arg-Lys-Lys-Arg-Arg-Gln-Arg-Arg-Arg-Pro-Pro-Gln-NH2 |
| NB12707 | N3-(CH2)15-CO-Tyr-Gly-Arg-Lys-Lys-Arg-Arg-Gln-Arg-Arg-Arg-Pro-Pro-Gln-NH2 |
| NB12676 | cyclo-[Phe-Arg-Gly-Asp-Lys(N3-(CH2)5-COOH)] |
| NB12708 | cyclo-[Phe-Arg-Gly-Asp-Lys(N3-(CH2)15-COOH)] |

TABLE 4-continued

Azide modified peptides.

NB12709 N3-(CH2)5-CO-Arg-Arg-Arg-Arg-Arg-Arg-Arg-Arg-NH2

NB12710 N3-(CH2)15-CO-Arg-Arg-Arg-Arg-Arg-Arg-Arg-Arg-NH2

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide tethered to an iRNA agent and/or the carrier oligomer can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic compoundic units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homoarginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, GalNAc$_3$, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polycations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligands amenable to the invention are described in copending applications U.S. Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

The compound comprising the ligand, e.g. the click-carrier compound, can be present in any position of an oligonucleotide, e.g. an iRNA agent. In some embodiments, click-carrier compound can be present at the terminus such as a 5' or 3' terminal of the iRNA agent. Click-carrier compounds can also present at an internal position of the iRNA agent. For double-stranded iRNA agents, click-carrier compounds can be incorporated into one or both strands. In some embodiments, the sense strand of the double-stranded iRNA agent comprises the click-carrier compound. In other embodiments, the antisense strand of the double-stranded iRNA agent comprises the click-carrier compound.

In some embodiments, ligands can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligomeric compounds. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative United States patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; each of which is herein incorporated by reference.

Oligonucleotide

The term "oligonucleotide" as used herein refers to an unmodified RNA, modified RNA, or nucleoside surrogate, all of which are defined herein. Although the modifications are described in context of an iRNA agent, it is understood that these modifications are also applicable to other oligonucleotides of the invention such as antisense, antagomir, aptamer, ribozyme and decoy oligonucleotides. While numerous modified RNAs and nucleoside surrogates are described, preferred examples include those which have greater resistance to nuclease degradation than do unmodified RNAs. Preferred examples include those which have a 2' sugar modification, a modification in a single strand overhang, preferably a 3' single strand overhang, or, particularly if single stranded, a 5' modification which includes one or more phosphate groups or one or more analogs of a phosphate group.

An "iRNA agent" as used herein, is an RNA agent which can, or which can be cleaved into an RNA agent which can, down regulate the expression of a target gene, preferably an endogenous or pathogen target RNA. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded iRNA agent. If the iRNA agent is a single strand it is particularly preferred that it include a 5' modification which includes one or more phosphate groups or one or more analogs of a phosphate group. If the iRNA agent is double stranded the double stranded region can include more than two or more strands, e.g., two strands, e.g. three strands, in the double stranded region.

The iRNA agent should include a region of sufficient homology to the target gene, and be of sufficient length in terms of nucleotides, such that the iRNA agent, or a fragment thereof, can mediate down regulation of the target gene. (For ease of exposition the term nucleotide or ribonucleotide is sometimes used herein in reference to one or more compoundic subunits of an RNA agent. It will be understood herein that the usage of the term "ribonucleotide" or "nucleotide", herein can, in the case of a modified RNA or nucleotide surrogate, also refer to a modified nucleotide, or surrogate replacement moiety at one or more positions.) Thus, the iRNA agent is or includes a region which is at least partially, and in some embodiments fully, complementary to the target RNA. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA.

An iRNA agent will often be modified or include nucleoside surrogates in addition to the click-carrier compound. Single stranded regions of an iRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an iRNA agent, e.g., against exonucleases, or to favor the antisense sRNA agent to enter into RISC are also favored. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents are preferably antisense with regard to the target molecule. In preferred embodiments single strand iRNA agents are 5'-phosphorylated or include a phosphoryl analog at the 5'-terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alphathiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)$_2$(O)P-5'-CH$_2$—), 5'-alkyletherphosphonates (R=alkylether=methoxymethyl (MeOCH2-), ethoxymethyl, etc., e.g. RP(OH)(O)—O-5'-). (These modifications can also be used with the antisense strand of a multi-strand iRNA agent.)

A "multi-strand iRNA agent" as used herein, is an iRNA agent which comprises two or more strands, for example a double-stranded iRNA agent. The strands form duplexed regions and may include a hairpin, pan-handle structure, loop or bulges. At least one strand of the iRNA agent is preferably antisense with regard to the target molecule.

It may be desirable to modify only one, only two or all strands of a multi-strand iRNA agent. In some cases they will have the same modification or the same class of modification but in other cases the different strand will have different modifications, e.g., in some cases it is desirable to modify only one strand. It may be desirable to modify only some strands, e.g., to inactivate them, e.g., strands can be modified in order to inactivate them and prevent formation of an active iRNA/protein or RISC. This can be accomplished by a modification which prevents 5'-phosphorylation of the strands, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage, though this may be less desirable as phosphodiesterases can cleave such a linkage and release a functional iRNA 5'-end. Antisense strand modifications include 5'-phosphorylation as well as any of the other 5' modifications discussed herein, particularly the 5' modifications discussed above in the section on single stranded iRNA molecules.

In some cases, the different strands will include different modifications. Multiple different modifications can be included on each of the strands. The modifications on a given strand may differ from each other, and may also differ from the various modifications on other strands. For example, one strand may have a modification, e.g., a modification described herein, and a different strand may have a different modification, e.g., a different modification described herein. In other cases, one strand may have two or more different modifications, and the another strand may include a modification that differs from the at least two modifications on the other strand.

It is preferred that the strands be chosen such that the iRNA agent includes a single strand or unpaired region at one or both ends of the molecule. Thus, an iRNA agent contains two or more strands, preferable paired to contain an overhang, e.g., one or two 5' or 3' overhangs but preferably a 3' overhang of 2-3 nucleotides. Most embodiments will have a 3' overhang. Preferred iRNA agents will have single-stranded overhangs, preferably 3' overhangs, of 1 or preferably 2 or 3 nucleotides in length at each end. The overhangs can be the result of one strand being longer than the other, or the result of two strands of the same length being staggered.

Preferred lengths for the duplexed regions between the strands are between 6 and 30 nucleotides in length. The preferred duplexed regions are between 15 and 30, most preferably 18, 19, 20, 21, 22, and 23 nucleotides in length. Other preferred duplexed regions are between 6 and 20 nucleotides, most preferably 6, 7, 8, 9, 10, 11 and 12 nucleotides in length. In multi-strand iRNA agents different duplexes formed may have different lengths, e.g. duplexed region formed between strand A and B may have a different length than duplexed region formed between strand A and C.

In iRNA agents comprising more than two strands duplexed agents can resemble in length and structure the natural Dicer processed products from long dsRNAs. Embodiments in which the two or more strands of the iRNA agent are linked, e.g., covalently linked are also included. Hairpins or other single strand structures which provide the required double stranded region, and preferably a 3' overhang are also within the invention.

As nucleic acids are polymers of subunits or compounds, many of the modifications described below occur at a position which is repeated within a nucleic acid, e.g., a modification of a base, or a phosphate moiety, or the non-bridging oxygen of a phosphate moiety. In some cases the modification will occur at all of the subject positions in the nucleic acid but in many, and in fact in most cases it will not. By way of example, a modification may only occur at a 3' or 5' terminal position, may only occur in the internal unpaired region, may only occur in a terminal regions, e.g. at a position on a terminal nucleotide or in the last 2, 3, 4, 5, or 10 nucleotides of a strand. A modification may occur in a double strand region, a single strand region, or in both. A modification may occur only in the double strand region of an RNA agent or may only occur in a single strand region of an RNA agent. E.g., a phosphorothioate modification at a non-bridging oxygen position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

In some embodiments it is particularly preferred, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

MicroRNAs

MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

MicroRNAs have also been implicated in modulation of pathogens in hosts. For example, see Jopling, C. L., et al., Science (2005) vol. 309, pp 1577-1581. Without wishing to be bound by theory, administration of a microRNA, microRNA mimic, and/or anti microRNA oligonucleotide, leads to modulation of pathogen viability, growth, development, and/or replication. In certain embodiments, the oligonucleotide is a microRNA, microRNA mimic, and/or anti microRNA, wherein microRNA is a host microRNA.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. N A R, 2006, 34, Database Issue, D140-D144; "*The microRNA Registry*" Griffiths-Jones S, N A R, 2004, 32, Database Issue, D109-D111; and also on the worldwide web at http://microrna.dot.sanger.dot.ac.dot.uk/sequences/.

Ribozymes

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Aptamers

Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000). Aptamers can be RNA or DNA based. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer can be prepared by any known method, including synthetic, recombinant, and purification methods, and can be used alone or in combination with other aptamers specific for the same target. Further, as described more fully herein, the term "aptamer" specifically includes "secondary aptamers" containing a consensus sequence derived from comparing two or more known aptamers to a given target.

Decoy Oligonucleotides

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides can be found in Mann et al., J. Clin. Invest., 2000, 106: 1071-1075, which is expressly incorporated by reference herein, in its entirety.

miRNA Mimics miRNA mimics represent a class of molecules that can be used to imitate the gene modulating activity of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs).

In one design, miRNA mimics are double stranded molecules (e.g., with a duplex region of between about 16 and about 31 nucleotides in length) and contain one or more sequences that have identity with the mature strand of a given miRNA. Double-stranded miRNA mimics have designs similar to as described above for double-stranded oligonucleotides.

In one embodiment, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Supermirs

A supermir refers to an oligonucleotide, e.g., single stranded, double stranded or partially double stranded, which has a nucleotide sequence that is substantially identical to an miRNA and that is antisense with respect to its target. This term includes oligonucleotides which comprise at least one non-naturally-occurring portion which functions similarly. In a preferred embodiment, the supermir does not include a sense strand, and in another preferred embodiment, the supermir does not self-hybridize to a significant extent. An supermir featured in the invention can have secondary structure, but it is substantially single-stranded under physiological conditions. A supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or 5 nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

Antimirs or miRNA Inhibitors

The terms "antimir" "microRNA inhibitor" or "miR inhibitor" are synonymous and refer to oligonucleotides or modified oligonucleotides that interfere with the activity of specific miRNAs. Inhibitors can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor can also comprise additional sequences located 5' and 3' to the sequence that is the reverse complement of the mature miRNA. The additional sequences can be the reverse complements of the sequences that are adjacent to the mature miRNA in the pri-miRNA from which the mature miRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, can include mismatches between nucleotides on opposite strands. Furthermore, microRNA inhibitors can be linked to conjugate moieties in order to facilitate uptake of the inhibitor into a cell.

MicroRNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. In a preferred embodiment, antagomir comprises a 2'-O-methylmodification at all nucleotides, a cholesterol moiety at 3'-end, two phosphorothioate backbone linkages at the first two positions at the 5'-end and four phosphorothioate linkages at the 3'-end of the molecule. Antagomirs can be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety.

U1 adaptors

U1 adaptors inhibit polyA sites and are bifunctional oligonucleotides with a target domain complementary to a site in the target gene's terminal exon and a 'U1 domain' that binds to the U1 smaller nuclear RNA component of the U1 snRNP (Goraczniak, et al., 2008, Nature Biotechnology, 27(3), 257-263, which is expressly incorporated by reference herein, in its entirety). U1 snRNP is a ribonucleoprotein complex that functions primarily to direct early steps in spliceosome formation by binding to the pre-mRNA exon-intron boundary (Brown and Simpson, 1998, Annu Rev Plant Physiol Plant Mol Biol 49:77-95). Nucleotides 2-11 of the 5'-end of U1 snRNA base pair with the 5'-end of single stranded region of the pre mRNA. In one embodiment, oligonucleotides of the invention are U1 adaptors. In one embodiment, the U1 adaptor can be administered in combination with at least one other RNAi agent.

Immunostimulatory Oligonucleotides

Nucleic acids of the present invention can be immunostimulatory, including immunostimulatory oligonucleotides (single- or double-stranded) capable of inducing an immune response when administered to a subject, which can be a mammal or other patient. The immune response can be an innate or an adaptive immune response. The immune system is divided into a more innate immune system, and acquired adaptive immune system of vertebrates, the latter of which is further divided into humoral cellular components. In particular embodiments, the immune response can be mucosal.

Immunostimulatory nucleic acids are considered to be non-sequence specific when it is not required that they specifically bind to and reduce the expression of a target polynucleotide in order to provoke an immune response. Thus, certain immunostimulatory nucleic acids can comprise a sequence corresponding to a region of a naturally occurring gene or mRNA, but they can still be considered non-sequence specific immunostimulatory nucleic acids.

In one embodiment, the immunostimulatory nucleic acid or oligonucleotide comprises at least one CpG dinucleotide. The oligonucleotide or CpG dinucleotide can be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated.

In another embodiment, the immunostimulatory oligonucleotide comprises a phosphate or a phosphate modification at the 5'-end. Without wishing to be bound by theory, oligonucleotides with modified or unmodified 5'-phosphates induce an anti-viral or an antibacterial response, in particular, the induction of type I IFN, IL-18 and/or IL-1β by modulating RIG-I.

RNA Activators

Recent studies have found that dsRNA can also activate gene expression, a mechanism that has been termed "small RNA-induced gene activation" or RNAa. See for example Li, L. C. et al. *Proc Natl Acad Sci USA*. (2006), 103(46):17337-42 and Li L.C. (2008). "Small RNA-Mediated Gene Activation". RNA and the Regulation of Gene Expression: A Hidden Layer of Complexity. Caister Academic Press. ISBN 978-1-904455-25-7. It has been shown that dsRNAs targeting gene promoters induce potent transcriptional activation of associated genes. Endogenous miRNA that cause RNAa has also been found in humans. Check E. Nature (2007). 448 (7156): 855-858.

Another surprising observation is that gene activation by RNAa is long-lasting. Induction of gene expression has been seen to last for over ten days. The prolonged effect of RNAa could be attributed to epigenetic changes at dsRNA target sites.

In certain embodiments, the oligonucleotide is an RNA activator, wherein oligonucleotide increases the expression of a gene. In one embodiment, increased gene expression inhibits its viability, growth development, and/or reproduction.

Triplex Forming Oligonucleotides

Recent studies have shown that triplex forming oligonucleotides (TFO) can be designed which can recognize and bind to polypurine/polypyrimidine regions in double-stranded helical DNA in a sequence-specific manner. These recognition rules are outline by Maher III, L. J., et al., *Science* (1989) vol. 245, pp 725-730; Moser, H. E., et al., *Science* (1987) vol. 238, pp 645-630; Beal, P. A., et al., *Science* (1992) vol. 251, pp 1360-1363; Conney, M., et al., *Science* (1988) vol. 241, pp 456-459 and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 1 12:487-94). In general, the triplex-forming oligonucleotide has the sequence correspondence:

```
oligo        3'-A G G T duplex       5'-A G C T duplex       3'-T C G A
```

However, it has been shown that the A-AT and G-GC triplets have the greatest triple helical stability (Reither and Jeltsch, BMC Biochem, 2002, Sept12, Epub). The same authors have demonstrated that TFOs designed according to the A-AT and G-GC rule do not form non-specific triplexes, indicating that the triplex formation is indeed sequence specific.

Thus for any given sequence a triplex forming sequence can be devised. Triplex-forming oligonucleotides preferably are at least 15, more preferably 25, still more preferably 30 or more nucleotides in length, up to 50 or 100 nucleotides.

Formation of the triple helical structure with the target DNA induces steric and functional changes, blocking transcription initiation and elongation, allowing the introduction of desired sequence changes in the endogenous DNA and resulting in the specific down-regulation of gene expression. Examples of such suppression of gene expression in cells treated with TFOs include knockout of episomal supFG1 and endogenous HPRT genes in mammalian cells (Vasquez et al., Nucl Acids Res. 1999; 27: 1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277: 32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both down-regulation and up-regulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn, contents of which are herein incorporated in their entireties.

Specific modifications are discussed in more detail below. Although, the modifications herein are described in context of an iRNA agent, these modifications are also amenable in modifying the carrier oligonucleotides of the invention.

The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-bridging oxygens replaced by sulfur. The phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both non-bridging oxygens, which eliminate the chiral center, e.g. phosphorodithioate formation, may be desirable in that they cannot produce diastereomer mixtures. Thus, the non-bridging oxygens can be independently any one of S, Se, B, C, H, N, or OR (R is alkyl or aryl). Replacement of the non-bridging oxygens with sulfur is preferred.

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon is preferred. When the bridging oxygen is the 5'-oxygen of a nucleoside, replacement with nitrogen is preferred.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Modified phosphate linkages where at least one of the oxygens linked to the phosphate has been replaced or the phosphate group has been replaced by a non-phosphorous group, are also referred to as "non phosphodiester backbone linkage."

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the mophilino, cyclobutyl, pyrrolidine and peptide nucleic acid (PNA) nucleoside surrogates. A preferred surrogate is a PNA surrogate.

Sugar Modifications

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O) R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C— allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

The modification can also entail the wholesale replacement of a ribose structure with another entity at one or more sites in the iRNA agent.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' 0, N, S or C group of the sugar. Alternatively, the spacer can connect to or replace the terminal atom of a nucleotide surrogate (e.g., PNAs). These spacers or linkers can include e.g., —$(CH_2)_n$—, —$(CH_2)_n$N—, —$(CH_2)_nO$—, —$(CH_2)_nS$—, $O(CH_2CH_2O)_n$ $CH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation.

Terminal modifications useful for modulating activity include modification of the 5' end with phosphate or phosphate analogs. E.g., in preferred embodiments iRNA agents, especially antisense strands, are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO) 2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5');
5'-adenosine cap (Appp), and any modified or unmodified nucleotide cap structure (N—O-5'-(HO)(O)P—O—(HO)(O) P—O—P(HO)(O)—O-5'); 5'-monothiophosphate (phosphorothioate; (HO)2(S)P—O-5); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Nucleobases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases", "modified bases", "non-natual bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are less preferred for promoting stability, but they can be useful for other reasons, e.g., some, e.g., 2,6-diaminopurine and 2 amino purine, are fluorescent. Modified bases can reduce target specificity. This should be taken into consideration in the design of iRNA agents.

Cationic Groups

Modifications can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., O($CH_2$)$_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid); or NH($CH_2CH_2NH$)$_n$$CH_2CH_2$-AMINE (AMINE=$NH_2$; alkylamino, dialkylamino, heterocyclyl, arylamino, diaryl amino, heteroaryl amino, or diheteroaryl amino).

Exemplary Modifications and Placement within an iRNA Agent

Some modifications may preferably be included on an iRNA agent at a particular location, e.g., at an internal position of a strand, or on the 5' or 3' end of a strand of an iRNA agent. A preferred location of a modification on an iRNA agent, may confer preferred properties on the agent. For example, preferred locations of particular modifications may confer optimum gene silencing properties, or increased resistance to endonuclease or exonuclease activity. A modification described herein and below may be the sole modification, or the sole type of modification included on multiple ribonucleotides, or a modification can be combined with one or more other modifications described herein and below. For example, a modification on one strand of a multi-strand iRNA agent can be different than a modification on another strand of the multi-strand iRNA agent. Similarly, two different modifications on one strand can differ from a modification on a different strand of the iRNA agent. Other additional unique modifications, without limitation, can be incorporates into strands of the iRNA agent.

An iRNA agent may include a backbone modification to any nucleotide on an iRNA strand. For example, an iRNA agent may include a phosphorothioate linkage or P-alkyl modification in the linkages between one or more nucleotides of an iRNA agent. The nucleotides can be terminal nucleotides, e.g., nucleotides at the last position of a sense or antisense strand, or internal nucleotides.

An iRNA agent can include a sugar modification, e.g., a 2' or 3' sugar modification. Exemplary sugar modifications include, for example, a 2'-O-methylated nucleotide, a 2'-deoxy nucleotide, (e.g., a 2'-deoxyfluoro nucleotide), a 2'-O-methoxyethyl nucleotide, a 2'-O-NMA, a 2'-DMAEOE, a 2'-aminopropyl, 2'-hydroxy, or a 2'-ara-fluoro or a locked nucleic acid (LNA), extended nucleic acid (ENA), hexose nucleic acid (HNA), or cyclohexene nucleic acid (CeNA). A 2' modification is preferably 2'-OMe, and more preferably, 2'-deoxyfluoro. When the modification is 2'-OMe, the modification is preferably on the sense strands. When the modification is a 2'-fluoro, and the modification may be on any strand of the iRNA agent. A 2'-ara-fluoro modification will preferably be on the sense strands of the iRNA agent. An iRNA agent may include a 3' sugar modification, e.g., a 3'-OMe modification. Preferably a 3'-OMe modification is on the sense strand of the iRNA agent.

An iRNA agent may include a 5'-methyl-pyrimidine (e.g., a 5'-methyl-uridine modification or a 5'-methyl-cytodine) modification.

The modifications described herein can be combined onto a single iRNA agent. For example, an iRNA agent may have a phosphorothioate linkage and a 2' sugar modification, e.g., a 2'-OMe or 2'-F modification. In another example, an iRNA agent may include at least one 5-Me-pyrimidine and a 2'-sugar modification, e.g., a 2'-F or 2'-OMe modification.

An iRNA agent may include a nucleobase modification, such as a cationic modification, such as a 3'-abasic cationic modification. The cationic modification can be e.g., an alkylamino-dT (e.g., a C6 amino-dT), an allylamino conjugate, a pyrrolidine conjugate, a pthalamido, a porphyrin, or a hydroxyprolinol conjugate, on one or more of the terminal nucleotides of the iRNA agent. When an alkylamino-dT conjugate is attached to the terminal nucleotide of an iRNA agent, the conjugate is preferably attached to the 3' end of the sense or antisense strand of an iRNA agent. When a pyrrolidine linker is attached to the terminal nucleotide of an iRNA agent, the linker is preferably attached to the 3'- or 5'-end of the sense strand, or the 3'-end of the antisense strand. When a pyrrolidine linker is attached to the terminal nucleotide of an iRNA agent, the linker is preferably on the 3'- or 5'-end of the sense strand, and not on the 5'-end of the antisense strand.

An iRNA agent may include at least one conjugate, such as a lipophile, a terpene, a protein binding agent, a vitamin, a carbohydrate, or a peptide. For example, the conjugate can be naproxen, nitroindole (or another conjugate that contributes to stacking interactions), folate, ibuprofen, or a C5 pyrimidine linker. The conjugate can also be a glyceride lipid conjugate (e.g., a dialkyl glyceride derivatives), vitamin E conjugate, or a thio-cholesterol. In generally, and except where noted to the contrary below, when a conjugate is on the terminal nucleotide of a sense or antisense strand, the conjugate is preferably on the 5' or 3' end of the sense strand or on the 5' end of the antisense strand, and preferably the conjugate is not on the 3' end of the antisense strand.

When the conjugate is naproxen, and the conjugate is on the terminal nucleotide of a sense or antisense strand, the conjugate is preferably on the 5' or 3' end of the sense or antisense strands. When the conjugate is cholesterol, and the conjugate is on the terminal nucleotide of a sense or antisense strand, the cholesterol conjugate is preferably on the 5' or 3' end of the sense strand and preferably not present on the antisense strand. Cholesterol may be conjugated to the iRNA agent by a pyrrolidine linker, serinol linker, hydroxyprolinol linker, or disulfide linkage. A dU-cholesterol conjugate may also be conjugated to the iRNA agent by a disulfide linkage. When the conjugate is cholanic acid, and the conjugate is on the terminal nucleotide of a sense or antisense strand, the cholanic acid is preferably attached to the 5' or 3' end of the sense strand, or the 3' end of the antisense strand. In one embodiment, the cholanic acid is attached to the 3' end of the sense strand and the 3' end of the antisense strand.

One or more nucleotides of an iRNA agent may have a 2'-5' linkage. Preferably, the 2'-5' linkage is on the sense strand. When the 2'-5' linkage is on the terminal nucleotide of an iRNA agent, the 2'-5' linkage occurs on the 5' end of the sense strand.

The iRNA agent may include an L-sugar, preferably on the sense strand, and not on the antisense strand.

The iRNA agent may include a methylphosphonate modification. When the methylphosphonate is on the terminal nucleotide of an iRNA agent, the methylphosphonate is at the 3' end of the sense or antisense strands of the iRNA agent.

An iRNA agent may be modified by replacing one or more ribonucleotides with deoxyribonucleotides. Preferably, adjacent deoxyribonucleotides are joined by phosphorothioate linkages, and the iRNA agent does not include more than four consecutive deoxyribonucleotides on the sense or the antisense strands.

An iRNA agent may include a difluorotoluoyl (DFT) modification, e.g., 2,4-difluorotoluoyl uracil, or a guanidine to inosine substitution.

The iRNA agent may include at least one 5'-uridine-adenine-3' (5'-UA-3') dinucleotide wherein the uridine is a 2'-modified nucleotide, or a terminal 5'-uridine-guanine-3' (5'-UG-3')dinucleotide, wherein the 5'-uridine is a 2'-modified nucleotide, or a terminal 5'-cytidine-adenine-3' (5'-CA-3')dinucleotide, wherein the 5'-cytidine is a 2'-modified nucleotide, or a terminal 5'-uridine-uridine-3' (5'-UU-3')dinucleotide, wherein the 5'-uridine is a 2'-modified nucleotide, or a terminal 5'-cytidine-cytidine-3' (5'-CC-3')dinucleotide, wherein the 5'-cytidine is a 2'-modified nucleotide, or a terminal 5'-cytidine-uridine-3' (5'-CU-3')dinucleotide, wherein the 5'-cytidine is a 2'-modified nucleotide, or a terminal 5'-uridine-cytidine-3' (5'-UC-3')dinucleotide, wherein the 5'-uridine is a 2'-modified nucleotide. The chemically modified nucleotide in the iRNA agent may be a 2'-O-methylated nucleotide. In some embodiments, the modified nucleotide can be a 2'-deoxy nucleotide, a 2'-deoxyfluoro nucleotide, a 2'-O-methoxyethyl nucleotide, a 2'-O-NMA, a 2'-DMAEOE, a 2'-aminopropyl, 2'-hydroxy, or a 2'-ara-fluoro, or a locked nucleic acid (LNA), extended nucleic acid (ENA), hexose nucleic acid (HNA), or cyclohexene nucleic acid (CeNA). The iRNA agents including these modifications are particularly stabilized against exonuclease activity, when the modified dinucleotide occurs on a terminal end of the sense or antisense strand of an iRNA agent, and are otherwise particularly stabilized against endonuclease activity.

An iRNA agent may have a single overhang, e.g., one end of the iRNA agent has a 3' or 5' overhang and the other end of the iRNA agent is a blunt end, or the iRNA agent may have a double overhang, e.g., both ends of the iRNA agent have a 3' or 5' overhang, such as a dinucleotide overhang. In another alternative, both ends of the iRNA agent may have blunt ends. The unpaired nucleotides may have at least one phosphorothioate dinucleotide linkage, and at least one of the unpaired nucleotides may be chemically modified in the 2'-position. The doublestrand region of the iRNA agent may include phosphorothioate dinucleotide linkages on one or both of the sense and antisense strands. Various strands of the multi-strand iRNA agent may be connected with a linker, e.g., a chemical linker such as hexaethylene glycol linker, a poly-(oxyphosphinico-oxy-1,3-propandiol) linker, an allyl linker, or a polyethylene glycol linker Nuclease Resistant Compounds An iRNA agent can include compounds which have been modified so as to inhibit degradation, e.g., by nucleases, e.g., endonucleases or exonucleases, found in the body of a subject. These compounds are referred to herein as NRMs, or nuclease resistance promoting compounds or modifications. In many cases these modifications will modulate other properties of the iRNA agent as well, e.g., the ability to interact with a protein, e.g., a transport protein, e.g., serum albumin, or a member of the RISC(RNA-induced Silencing Complex), or the ability of the first and second sequences to form a duplex with one another or to form a duplex with another sequence, e.g., a target molecule.

While not wishing to be bound by theory, it is believed that modifications of the sugar, base, and/or phosphate backbone in an iRNA agent can enhance endonuclease and exonuclease resistance, and can enhance interactions with transporter proteins and one or more of the functional components of the RISC complex. Preferred modifications are those that increase exonuclease and endonuclease resistance and thus prolong the half-life of the iRNA agent prior to interaction with the RISC complex, but at the same time do not render the iRNA agent resistant to endonuclease activity in the RISC complex. Again, while not wishing to be bound by any theory, it is believed that placement of the modifications at or near the 3' and/or 5' end of antisense strands can result in iRNA agents that meet the preferred nuclease resistance criteria delineated above. Again, still while not wishing to be bound by any theory, it is believed that placement of the modifications at e.g., the middle of a sense strand can result in iRNA agents that are relatively less likely to undergo off-targeting.

Modifications described herein can be incorporated into any RNA and RNA-like molecule described herein, e.g., an iRNA agent, a carrier oligonucleotide. An iRNA agent may include a duplex comprising a hybridized sense and antisense strand, in which the antisense strand and/or the sense strand may include one or more of the modifications described herein. The anti sense strand may include modifications at the 3' end and/or the 5' end and/or at one or more positions that occur 1-6 (e.g., 1-5, 1-4, 1-3, 1-2) nucleotides from either end of the strand. The sense strand may include modifications at the 3' end and/or the 5' end and/or at any one of the intervening positions between the two ends of the strand. The iRNA agent may also include a duplex comprising two hybridized antisense strands. The first and/or the second antisense strand may include one or more of the modifications described herein. Thus, one and/or both antisense strands may include modifications at the 3' end and/or the 5' end and/or at one or more positions that occur 1-6 (e.g., 1-5, 1-4, 1-3, 1-2) nucleotides from either end of the strand. Particular configurations are discussed below.

Modifications that can be useful for producing iRNA agents that meet the preferred nuclease resistance criteria delineated above can include one or more of the following chemical and/or stereochemical modifications of the sugar, base, and/or phosphate backbone:

(i) chiral ($S_P$) thioates. Thus, preferred NRMs include nucleotide dimers with an enriched or pure for a particular chiral form of a modified phosphate group containing a heteroatom at the nonbridging position, e.g., Sp or Rp, where this is the position normally occupied by the oxygen. The heteroatom can be S, Se, $Nr_2$, or $Br_3$. When the heteroatom is S, enriched or chirally pure Sp linkage is preferred. Enriched means at least 70, 80, 90, 95, or 99% of the preferred form. Such NRMs are discussed in more detail below;

(ii) attachment of one or more cationic groups to the sugar, base, and/or the phosphorus atom of a phosphate or modified phosphate backbone moiety. Thus, preferred NRMs include compounds at the terminal position derivatized at a cationic group. As the 5' end of an antisense sequence should have a terminal —OH or phosphate group this NRM is preferably not used at the 5' end of an anti-sense sequence. The group should be attached at a position on the base which minimizes interference with H bond formation and hybridization, e.g., away form the face which interacts with the complementary base on the other strand, e.g., at the 5' position of a pyrimidine or a 7-position of a purine. These are discussed in more detail below;

(iii) nonphosphate linkages at the termini. Thus, preferred NRMs include Non-phosphate linkages, e.g., a linkage of 4 atoms which confers greater resistance to cleavage than does a phosphate bond. Examples include 3' CH2-$NCH_3$—O—CH2-5' and 3' CH2-NH—(O=)—CH2-5';

(iv) 3'-bridging thiophosphates and 5'-bridging thiophosphates. Thus, preferred NRM's can included these structures;

(v) L-RNA, 2'-5' linkages, inverted linkages, a-nucleosides. Thus, other preferred NRM's include: L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; compounds having an alpha linkage at the 1' site on the sugar, e.g., the structures described herein having an alpha linkage;

(vi) conjugate groups. Thus, preferred NRM's can include e.g., a targeting moiety or a conjugated ligand described herein conjugated with the compound, e.g., through the sugar, base, or backbone;

(vii) abasic linkages. Thus, preferred NRM's can include an abasic compound, e.g., an abasic compound as described herein (e.g., a nucleobaseless compound); an aromatic or heterocyclic or polyheterocyclic aromatic compound as described herein; and (viii) 5'-phosphonates and 5'-phosphate prodrugs. Thus, preferred NRM's include compounds, preferably at the terminal position, e.g., the 5' position, in which one or more atoms of the phosphate group is derivatized with a protecting group, which protecting group or groups, are removed as a result of the action of a component in the subject's body, e.g., a carboxyesterase or an enzyme present in the subject's body. E.g., a phosphate prodrug in which a carboxy esterase cleaves the protected molecule resulting in the production of a thioate anion which attacks a carbon adjacent to the O of a phosphate and resulting in the production of an unprotected phosphate.

One or more different NRM modifications can be introduced into an iRNA agent or into a sequence of an iRNA agent. An NRM modification can be used more than once in a sequence or in an iRNA agent. As some NRM's interfere with hybridization the total number incorporated, should be such that acceptable levels of iRNA agent duplex formation are maintained.

In some embodiments NRM modifications are introduced into the terminal the cleavage site or in the cleavage region of a sequence (a sense strand or sequence) which does not target a desired sequence or gene in the subject. This can reduce off-target silencing.

References
General References

The oligoribonucleotides and oligoribonucleosides used in accordance with this invention may be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and, Chapter 7, Oligodeoxynucleotides containing modified bases. Other particularly useful synthetic procedures, reagents, blocking groups and reaction conditions are described in Martin, P., *Helv. Chim. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein.

Modification described in WO 00/44895, WO01/75164, or WO02/44321 can be used herein.

The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or U.S. Pat. No. 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Bases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references are disclosed in the above section on base modifications.

Oligonucleotide Production

The oligonucleotide compounds of the invention can be prepared using solution-phase or solid-phase organic synthesis. Organic synthesis offers the advantage that the oligonucleotide strands comprising non-natural or modified nucleotides can be easily prepared. Any other means for such synthesis known in the art may additionally or alternatively be employed. It is also known to use similar techniques to prepare other oligonucleotides, such as the phosphorothioates, phosphorodithioates and alkylated derivatives. The double-stranded oligonucleotide compounds of the invention may be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the iRNA preparation can be precipitated and redissolved in pure double-distilled water, and lyophilized. The dried iRNA can then be resuspended in a solution appropriate for the intended formulation process.

Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to compounds for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having .beta.-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No.

5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262, 241, and 5,459,255, drawn to, inter alia, methods of synthesizing 2'-fluoro-oligonucleotides.

It is not necessary for all positions in a given compound to be uniformly modified, and in fact more than one type of modification may be incorporated in a single oligonucleotide compound or even in a single nucleotide thereof.

Routes of Delivery

For ease of exposition the formulations, compositions and methods in this section are discussed largely with regard to unmodified iRNA agents. It should be understood, however, that these formulations, compositions and methods can be practiced with other oligonucleotide of the invention, e.g., modified iRNA agents, antisense, antagomirs, apatamers, ribozymes, and such practice is within the invention. A composition that includes an iRNA can be delivered to a subject by a variety of routes. Exemplary routes include: intravenous, topical, rectal, anal, vaginal, nasal, pulmonary, ocular.

The iRNA molecules of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water, syrups, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers.

Topical Delivery

For ease of exposition the formulations, compositions and methods in this section are discussed largely with regard to unmodified iRNA agents. It should be understood, however, that these formulations, compositions and methods can be practiced with other oligonucleotides of the invention, e.g., modified iRNA agents, antisense, apatamer, antagomir and ribozyme, and such practice is within the invention. In a preferred embodiment, an iRNA agent is delivered to a subject via topical administration. "Topical administration" refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

The term "skin," as used herein, refers to the epidermis and/or dermis of an animal. Mammalian skin consists of two major, distinct layers. The outer layer of the skin is called the epidermis. The epidermis is comprised of the stratum corneum, the stratum granulo sum, the stratum spinosum, and the stratum basale, with the stratum corneum being at the surface of the skin and the stratum basale being the deepest portion of the epidermis. The epidermis is between 50 µm and 0.2 mm thick, depending on its location on the body.

Beneath the epidermis is the dermis, which is significantly thicker than the epidermis. The dermis is primarily composed of collagen in the form of fibrous bundles. The collagenous bundles provide support for, inter alia, blood vessels, lymph capillaries, glands, nerve endings and immunologically active cells.

One of the major functions of the skin as an organ is to regulate the entry of substances into the body. The principal permeability barrier of the skin is provided by the stratum corneum, which is formed from many layers of cells in various states of differentiation. The spaces between cells in the stratum corneum is filled with different lipids arranged in lattice-like formations that provide seals to further enhance the skins permeability barrier.

The permeability barrier provided by the skin is such that it is largely impermeable to molecules having molecular weight greater than about 750 Da. For larger molecules to cross the skin's permeability barrier, mechanisms other than normal osmosis must be used.

Several factors determine the permeability of the skin to administered agents. These factors include the characteristics of the treated skin, the characteristics of the delivery agent, interactions between both the drug and delivery agent and the drug and skin, the dosage of the drug applied, the form of treatment, and the post treatment regimen. To selectively target the epidermis and dermis, it is sometimes possible to formulate a composition that comprises one or more penetration enhancers that will enable penetration of the drug to a preselected stratum.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy.

In addition, iontophoresis (transfer of ionic solutes through biological membranes under the influence of an electric field) (Lee et al., Critical Reviews in Therapeutic Drug Carrier Systems, 1991, p. 163), phonophoresis or sonophoresis (use of ultrasound to enhance the absorption of various therapeutic agents across biological membranes, notably the skin and the cornea) (Lee et al., Critical Reviews in Therapeutic Drug Carrier Systems, 1991, p. 166), and optimization of vehicle characteristics relative to dose position and retention at the site of administration (Lee et al., Critical Reviews in Therapeutic Drug Carrier Systems, 1991, p. 168) may be useful methods for enhancing the transport of topically applied compositions across skin and mucosal sites.

The compositions and methods provided may also be used to examine the function of various proteins and genes in vitro in cultured or preserved dermal tissues and in animals. The invention can be thus applied to examine the function of any gene. The methods of the invention can also be used therapeutically or prophylactically. For example, for the treatment of animals that are known or suspected to suffer from diseases such as psoriasis, lichen planus, toxic epidermal necrolysis, ertythema multiforme, basal cell carcinoma, squamous cell carcinoma, malignant melanoma, Paget's disease, Kaposi's sarcoma, pulmonary fibrosis, Lyme disease and viral, fungal and bacterial infections of the skin.

Pulmonary Delivery

For ease of exposition the formulations, compositions and methods in this section are discussed largely with regard to unmodified iRNA agents. It should be understood, however, that these formulations, compositions and methods can be practiced with other oligonucleotides of the invention, e.g., modified iRNA agents, antisense, apatamer, antagomir and ribozyme, and such practice is within the invention. A composition that includes an iRNA agent, e.g., a double-stranded iRNA agent, can be administered to a subject by pulmonary delivery. Pulmonary delivery compositions can be delivered by inhalation by the patient of a dispersion so that the composition, preferably iRNA, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. An iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 µm in diameter preferably with a relatively uniform spheroidal shape distribution. More preferably the diameter is less than about 7.5 µm and most preferably less than about 5.0 µm. Usually the particle size distribution is between about 0.1 µm and about 5 µm in diameter, particularly about 0.3 µm to about 5 µm.

The term "dry" means that the composition has a moisture content below about 10% by weight (% w) water, usually below about 5% w and preferably less it than about 3% w. A dry composition can be such that the particles are readily dispersible in an inhalation device to form an aerosol.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, trehalose, raffinose maltodextrins, and mannitol. Suitable polypeptides include aspartame. Amino acids include alanine and glycine, with glycine being preferred.

Additives, which are minor components of the composition of this invention, may be included for conformational stability during spray drying and for improving dispersibility of the powder. These additives include hydrophobic amino acids such as tryptophan, tyrosine, leucine, phenylalanine, and the like.

Suitable pH adjusters or buffers include organic salts prepared from organic acids and bases, such as sodium citrate, sodium ascorbate, and the like; sodium citrate is preferred.

Pulmonary administration of a micellar iRNA formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Oral or Nasal Delivery

For ease of exposition the formulations, compositions and methods in this section are discussed largely with regard to unmodified iRNA agents. It should be understood, however, that these formulations, compositions and methods can be practiced with other oligonucleotides of the invention, e.g., modified iRNA agents, antisense, apatamer, antagomir and ribozyme, and such practice is within the invention. Both the oral and nasal membranes offer advantages over other routes of administration. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many drugs. Further, the sublingual mucosa is convenient, acceptable and easily accessible.

The ability of molecules to permeate through the oral mucosa appears to be related to molecular size, lipid solubility and peptide protein ionization. Small molecules, less than 1000 daltons appear to cross mucosa rapidly. As molecular size increases, the permeability decreases rapidly. Lipid soluble compounds are more permeable than non-lipid soluble molecules. Maximum absorption occurs when molecules are un-ionized or neutral in electrical charges. Therefore charged molecules present the biggest challenges to absorption through the oral mucosae.

A pharmaceutical composition of iRNA may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Devices

For ease of exposition the devices, formulations, compositions and methods in this section are discussed largely with regard to unmodified iRNA agents. It should be understood, however, that these formulations, compositions and methods can be practiced with other oligonucleotides of the invention, e.g., modified iRNA agents, antisense, apatamer, antagomir and ribozyme, and such practice is within the invention. An iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) can be disposed on or in a device, e.g., a device which implanted or otherwise placed in a subject. Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a iRNA, e.g., a device can release insulin.

Other devices include artificial joints, e.g., hip joints, and other orthopedic implants.

In one embodiment, unit doses or measured doses of a composition that includes iRNA are dispensed by an implanted device. The device can include a sensor that monitors a parameter within a subject. For example, the device can include pump, e.g., and, optionally, associated electronics.

Tissue, e.g., cells or organs, such as the kidney, can be treated with an iRNA agent ex vivo and then administered or implanted in a subject.

The tissue can be autologous, allogeneic, or xenogeneic tissue. For example, tissue (e.g., kidney) can be treated to reduce graft v. host disease. In other embodiments, the tissue is allogeneic and the tissue is treated to treat a disorder characterized by unwanted gene expression in that tissue, such as in the kidney. In another example, tissue containing hematopoietic cells, e.g., bone marrow hematopoietic cells, can be treated to inhibit unwanted cell proliferation.

Introduction of treated tissue, whether autologous or transplant, can be combined with other therapies.

In some implementations, the iRNA treated cells are insulated from other cells, e.g., by a semi-permeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains an iRNA agent. Exemplary devices include condoms, diaphragms, IUD (implantable uterine devices, sponges, vaginal sheaths, and birth control devices. In one embodiment, the iRNA is chosen to inactive sperm or egg. In another embodiment, the iRNA is chosen to be complementary to a viral or pathogen RNA, e.g., an RNA of an STD. In some instances, the iRNA composition can include a spermicidal agent.

Formulations

The iRNA agents described herein can be formulated for administration to a subject. For ease of exposition the formulations, compositions and methods in this section are discussed largely with regard to unmodified iRNA agents. It should be understood, however, that these formulations, compositions and methods can be practiced with other oligonucleotides of the invention, e.g., modified iRNA agents, antisense, apatamer, antagomir and ribozyme, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An iRNA preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA preparation includes another iRNA agent, e.g., a second iRNA that can mediated RNAi with respect to a second gene, or with respect to the same gene. Still other preparation can include at least 3, 5, ten, twenty, fifty, or a hundred or more different iRNA species. Such iRNAs can mediated RNAi with respect to a similar number of different genes.

In one embodiment, the iRNA preparation includes at least a second therapeutic agent (e.g., an agent other than a RNA or a DNA). For example, an iRNA composition for the treatment of a viral disease, e.g. HIV, might include a known antiviral agent (e.g., a protease inhibitor or reverse transcriptase inhibitor). In another example, an iRNA composition for the treatment of a cancer might further comprise a chemotherapeutic agent.

Other formulations amenable to the present invention are described in U.S. provisional application Ser. Nos. 61/018, 616, filed Jan. 2, 2008; 61/018,611, filed Jan. 2, 2008; 61/039, 748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Pharmaceutical Compositions

In one embodiment, the invention relates to a pharmaceutical composition containing an oligonucleotide of the invention e.g. an iRNA agent, as described in the preceding sections, and a pharmaceutically acceptable carrier, as described below. A pharmaceutical composition including the modified iRNA agent is useful for treating a disease caused by expression of a target gene. In this aspect of the invention, the iRNA agent of the invention is formulated as described below. The pharmaceutical composition is administered in a dosage sufficient to inhibit expression of the target gene.

The pharmaceutical compositions of the present invention are administered in dosages sufficient to inhibit the expression or activity of the target gene. Compositions containing the iRNA agent of the invention can be administered at surprisingly low dosages. A maximum dosage of 5 mg iRNA agent per kilogram body weight per day may be sufficient to inhibit or completely suppress the expression or activity of the target gene.

In general, a suitable dose of modified iRNA agent will be in the range of 0.001 to 500 milligrams per kilogram body weight of the recipient per day (e.g., about 1 microgram per kilogram to about 500 milligrams per kilogram, about 100 micrograms per kilogram to about 100 milligrams per kilogram, about 1 milligrams per kilogram to about 75 milligrams per kilogram, about 10 micrograms per kilogram to about 50 milligrams per kilogram, or about 1 microgram per kilogram to about 50 micrograms per kilogram). The pharmaceutical composition may be administered once per day, or the iRNA agent may be administered as two, three, four, five, six or more sub-doses at appropriate intervals throughout the day. In that case, the iRNA agent contained in each sub-dose must be correspondingly smaller in order to achieve the total daily dosage. The dosage unit can also be compounded for delivery over several days, e.g., using a conventional sustained release formulation which provides sustained release of the iRNA agent over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the infection or disease, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNA agent encompassed by the invention can be made using conventional methodologies or on the basis of in vivo testing using an appropriate animal model, as described elsewhere herein.

Advances in mouse genetics have generated a number of mouse models for the study of various human diseases. For example, mouse repositories can be found at The Jackson Laboratory, Charles River Laboratories, Taconic, Harlan, Mutant Mouse Regional Resource Centers (MMRRC) National Network and at the European Mouse Mutant Archive. Such models may be used for in vivo testing of iRNA agent, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), ocular, rectal, vaginal and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

For oral administration, the iRNA agent useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of iRNA agent in the cells that harbor the target gene or virus. Such substances include, for example, micellar structures, such as liposomes or capsids, as described below. Although microinjection, lipofection, viruses, viroids, capsids, capsoids, or other auxiliary agents are required to introduce iRNA agent into cell cultures, surprisingly these methods and agents are not necessary for uptake of iRNA agent in vivo. The iRNA agent of the present invention are particularly advantageous in that they do not require the use of an auxiliary agent to mediate uptake of the iRNA agent into the cell, many of which agents are toxic or associated with deleterious side effects. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions can also include encapsulated formulations to protect the iRNA agent against rapid elimination from the body, such as a controlled release formulation, including implants and microencapsulated delivery systems. Biodegradable, bio compatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

Toxicity and therapeutic efficacy of iRNA agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. iRNA agents that exhibit high therapeutic indices are preferred.

The data obtained from cell culture assays and animal studies can be used in formulating a range of dosage for use in humans. The dosages of compositions of the invention are preferably within a range of circulating concentrations that include the ED50 with little or no toxicity. The dosage may vary within this range depending upon the dosage form employed and the route of administration utilized. For any iRNA agent used in the method of the invention, the therapeutically effective dose can be estimated initially from cell culture assays. A dose may be formulated in animal models to achieve a circulating plasma concentration range of the iRNA agent or, when appropriate, of the polypeptide product of a target sequence (e.g., achieving a decreased concentration of the polypeptide) that includes the IC50 (i.e., the concentration of the test iRNA agent which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, iRNA agents relating to the invention can be administered in combination with other known agents effective in treating viral infections and diseases. In any event, the administering physician can adjust the amount and timing of iRNA agent administration on the basis of results observed using standard measures of efficacy known in the art or described herein.

Combination Therapy

In one aspect, composition of the invention can be used in combination therapy. The term "combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g. IGFI-R); Eph (e.g. CEK5, CEK8, EBK, ECK, EEK, EHK-I, EHK-2, ELK, EPH, ERK, HEK, MDK2, MDK5, SEK); AxI (e.g. Mer/Nyk, Rse); RET; and platelet-derived growth factor receptor (PDGFR) (e.g. PDGF$\alpha$-R, PDGF$\beta$-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. $p43^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more agents that modulate non-kinase biological targets or processes. Such targets include histone deacetylases (HDAC), DNA methyltransferase (DNMT), heat shock proteins (e.g. HSP90), and proteosomes.

In one embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affmitak, Avastin, Herceptin, Erbitux, AG24322, PD325901, ZD6474, PD 184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cis-platin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplasties such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA). In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include steroids, such as corticosteroids (amcinonide, betamethasone, betamethasone dipropionate, betamethasone valerate, budesonide, clobetasol, clobetasol acetate, clobetasol butyrate, clobetasol 17-propionate, cortisone, deflazacort, desoximetasone, diflucortolone valerate, dexamethasone, dexamethasone sodium phosphate, desonide, furoate, fluocinonide, fluocino lone acetonide, halcinonide, hydrocortisone, hydrocortisone butyrate, hydrocortisone sodium succinate, hydrocortisone valerate, methyl predniso lone, mometasone, prednicarbate, predniso lone, triamcinolone, triamcinolone acetonide, and halobetasol proprionate); a 5HTi agonist, such as a triptan (e.g. sumatriptan or naratriptan); an adenosine Al agonist; an EP ligand; an NMDA modulator, such as a glycine antagonist; a sodium channel blocker (e.g. lamotrigine); a substance P antagonist (e.g. an NKi antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor α; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an H2-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazo line, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

Methods for Inhibiting Expression of a Target Gene

In yet another aspect, the invention relates to a method for inhibiting the expression of a target gene in a cell or organism. In one embodiment, the method includes administering the inventive oligonucleotide, e.g. antisense, aptamer, antagomir, or an iRNA agent; or a pharmaceutical composition containing the said oligonucleotide to a cell or an organism, such as a mammal, such that expression of the target gene is silenced. Compositions and methods for inhibiting the expression of a target gene using the inventive oligonucleotide, e.g. an iRNA agent, can be performed as described in the preceding sections.

In this embodiment, a pharmaceutical composition containing the inventive oligonucleotide may be administered by any means known in the art including, but not limited to oral or parenteral routes, including intravenous, intramuscular, intraperitoneal, subcutaneous, transdermal, airway (aerosol), ocular, rectal, vaginal, and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

The methods for inhibiting the expression of a target gene can be applied to any gene one wishes to silence, thereby specifically inhibiting its expression, provided the cell or organism in which the target gene is expressed includes the cellular machinery which effects RNA interference. Examples of genes which can be targeted for silencing include, without limitation, developmental genes including but not limited to adhesion molecules, cyclin kinase inhibitors, Wnt family members, Pax family members, Winged helix family members, Hox family members, cytokines/lymphokines and their receptors, growth/differentiation factors and their receptors, and neurotransmitters and their receptors; (2) oncogenes including but not limited to ABLI, BCL1, BCL2, BCL6, CBFA2, CBL, CSFIR, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES; (3) tumor suppresser genes including but not limited to APC, BRCA1, BRCA2, MADH4, MCC, NF1, NF2, RB1, TP53 and WT1; and (4) enzymes including but not limited to ACP desaturases and hydroxylases, ADP-glucose pyrophorylases, ATPases, alcohol dehydrogenases, amylases, amyloglucosidases, catalases, cellulases, cyclooxygenases, decarboxylases, dextrinases, DNA and RNA polymerases, galactosidases, glucanases, glucose oxidases, GTPases, helicases, hemicellulases, integrases, invertases, isomerases, kinases, lactases, lipases, lipoxygenases, lysozymes, pectinesterases, peroxidases, phosphatases, phospholipases, phosphorylases, polygalacturonases, proteinases and peptidases, pullanases, recombinases, reverse transcriptases, topoisomerases, and xylanases.

In addition to in vivo gene inhibition, the skilled artisan will appreciate that the inventive oligonucleotides, e.g. iRNA agent, of the present invention are useful in a wide variety of in vitro applications. Such in vitro applications, include, for example, scientific and commercial research (e.g., elucidation of physiological pathways, drug discovery and development), and medical and veterinary diagnostics. In general, the method involves the introduction of the oligonucleotide, e.g. an iRNA agent, into a cell using known techniques (e.g., absorption through cellular processes, or by auxiliary agents or devices, such as electroporation and lipofection), then maintaining the cell for a time sufficient to obtain degradation of an mRNA transcript of the target gene.

DEFINITIONS

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl) alkyl or (cycloalkyl)alkenyl. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines, for example. Aliphatic groups as used herein may optionally include further substitutent groups.

The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{20}$ indicates that the group may have from 1 to 20 (inclusive) carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino. The term "mercapto" refers to an —SH radical. The term "thioalkoxy" refers to an —S-alkyl radical.

The term "cyclic" as used herein includes a cycloalkyl group and a heterocyclic group. Any suitable ring position of the cyclic group may be covalently linked to the defined chemical structure.

The term "acyclic" may describe any carrier that is branched or unbranched, and does not form a closed ring.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, decalin, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocycloalkyl" and "heterocyclic" can be used interchangeably and refer to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "silyl" as used herein is represented by the formula —SiA$^1$A$^2$A$^3$, where A$^1$, A$^2$, and A$^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylamino carbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-aminoadenine, 2-fluoroadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl) uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

The term "non-natural" nucleobase refers any one of the following: 2-methyladeninyl, N6-methyladeninyl, 2-methylthio-N6-methyladeninyl, N6-isopentenyladeninyl, 2-methylthio-N6-isopentenyladeninyl, N6-(cis-hydroxyisopentenyl)adeninyl, 2-methylthio-N-6-(cis-hydroxyisopentenyl) adeninyl, N6-glycinylcarbamoyladeninyl, N6-threonylcarbamoyladeninyl, 2-methylthio-N6-threonyl carbamoyladeninyl, N6-methyl-N6-threonylcarbamoyladeninyl, N6-hydroxynorvalylcarbamoyladeninyl, 2-methylthio-N6-hydroxynorvalyl carbamoyladeninyl, N6,N6-dimethyladeninyl, 3-methylcytosinyl, 5-methylcytosinyl, 2-thiocytosinyl, 5-formylcytosinyl, N4-methylcytosinyl, 5-hydroxymethylcytosinyl, 1-methylguaninyl, N2-methylguaninyl, 7-methylguaninyl, N2,N2-dimethylguaninyl, N2,7-dimethylguaninyl, N2,N2,7-trimethylguaninyl, 1-methylguaninyl, 7-cyano-7-deazaguaninyl, 7-aminomethyl-7-deazaguaninyl, pseudouracilyl, dihydrouracilyl, 5-methyluracilyl, 1-methylpseudouracilyl, 2-thiouracilyl, 4-thiouracilyl, 2-thiothyminyl 5-methyl-2-thiouracilyl, 3-(3-amino-3-carboxypropyl)uracilyl, 5-hydroxyuracilyl, 5-methoxyuracilyl, uracilyl 5-oxyacetic acid, uracilyl 5-oxyacetic acid methyl ester, 5-(carboxyhydroxymethyl)uracilyl, 5-(carboxyhydroxymethyl)uracilyl methyl ester, 5-methoxycarbonylmethyluracilyl, 5-methoxycarbonylmethyl-2-thiouracilyl, 5-aminomethyl-2-thiouracilyl, 5-methylaminomethyluracilyl, 5-methylaminomethyl-2-thiouracilyl, 5-methylaminomethyl-2-selenouracilyl, 5-carbamoylmethyluracilyl, 5-carboxymethylaminomethyluracilyl, 5-carboxymethylaminomethyl-2-thiouracilyl, 3-methyluracilyl, 1-methyl-3-(3-amino-3-carboxypropyl)pseudouracilyl, 5-carboxymethyluracilyl, 5-methyldihydrouracilyl, 3-methylpseudouracilyl,

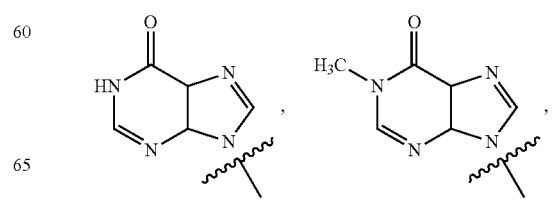

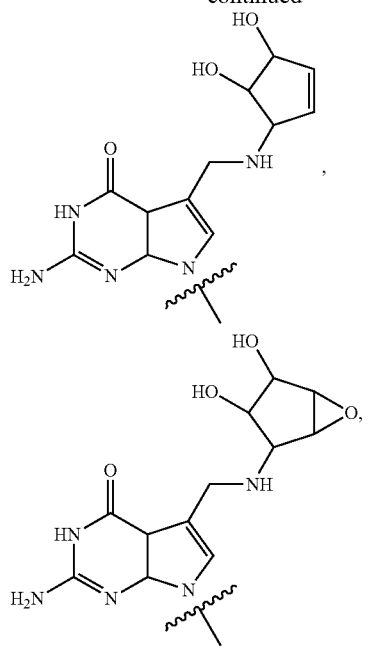
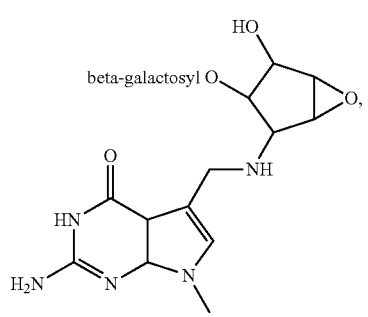
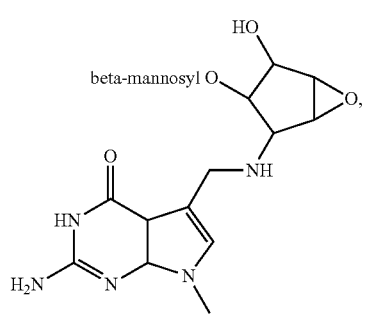
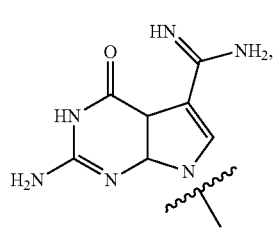
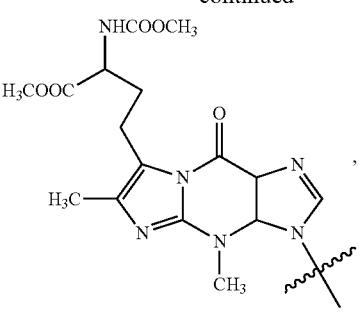
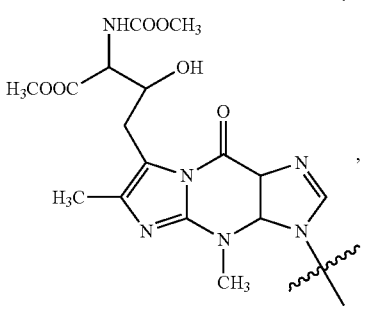
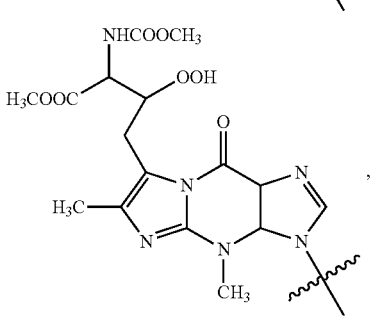
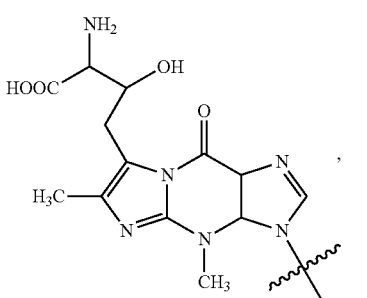
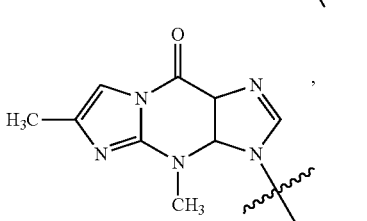
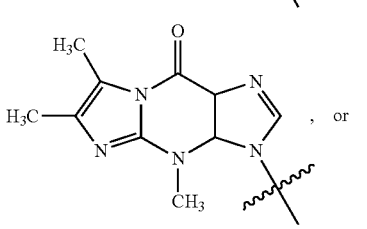

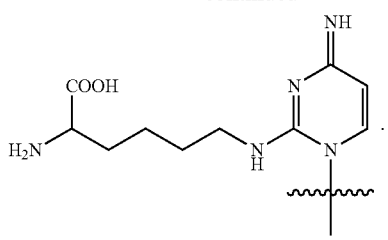

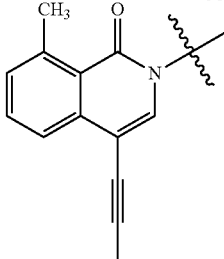

A universal base can form base pairs with each of the natural DNA/RNA bases, exhibiting relatively little discrimination between them. In general, the universal bases are non-hydrogen bonding, hydrophobic, aromatic moieties which can stabilize e.g., duplex RNA or RNA-like molecules, via stacking interactions. A universal base can also include hydrogen bonding substituents. As used herein, a "universal base" can include anthracenes, pyrenes or any one of the following:

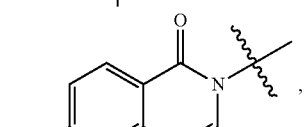

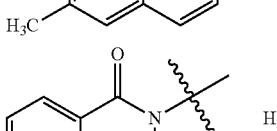

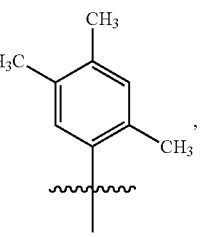

lp;1p

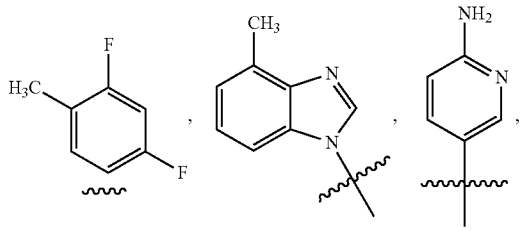

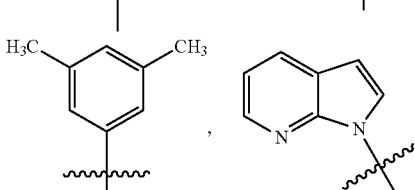

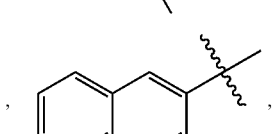

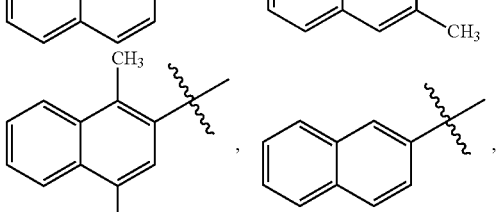

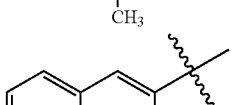

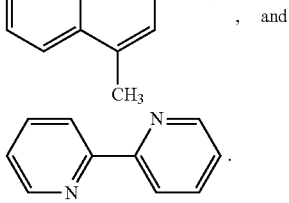

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein, in its entirety.

Decoy Oligonucleotides

Because transcription factors can recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in Mann et al., J. Clin. Invest., 2000, 106: 1071-1075, which is expressly incorporated by reference herein, in its entirety.

Antisense Oligonucleotides

Antisense oligonucleotides are single strands of DNA or RNA that are at least partially complementary to a chosen sequence. In the case of antisense RNA, they prevent translation of complementary RNA strands by binding to it. Antisense DNA can also be used to target a specific, complementary (coding or non-coding) RNA. If binding takes place, the DNA/RNA hybrid can be degraded by the enzyme RNase H. Examples of the utilization of antisense oligonucleotides may be found in Dias et al., Mol. Cancer. Ther., 2002, 1: 347-355, which is expressly incorporated by reference herein, in its entirety.

Aptamers

Aptamers are nucleic acid molecules that bind a specific target molecule or molecules. Aptamers may be RNA or DNA based, and may include a riboswitch. A riboswitch is a part of an mRNA molecule that can directly bind a small target molecule, and whose binding of the target affects the gene's activity. Thus, an mRNA that contains a riboswitch is directly involved in regulating its own activity, depending on the presence or absence of its target molecule.

REFERENCES

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

EXAMPLES

The invention now being generally described, it will be more readily understood by reference to the following examples, which are included merely for purposes of illustration of certain aspects and embodiments of the invention, and are not intended to limit the invention. Thus, the invention should in way be construed as being limited to the following examples, but rather, should be construed to encompass any and all variations which become evident as a result of the teaching provided herein.

Example 1

Synthesis of Lipidic Azides

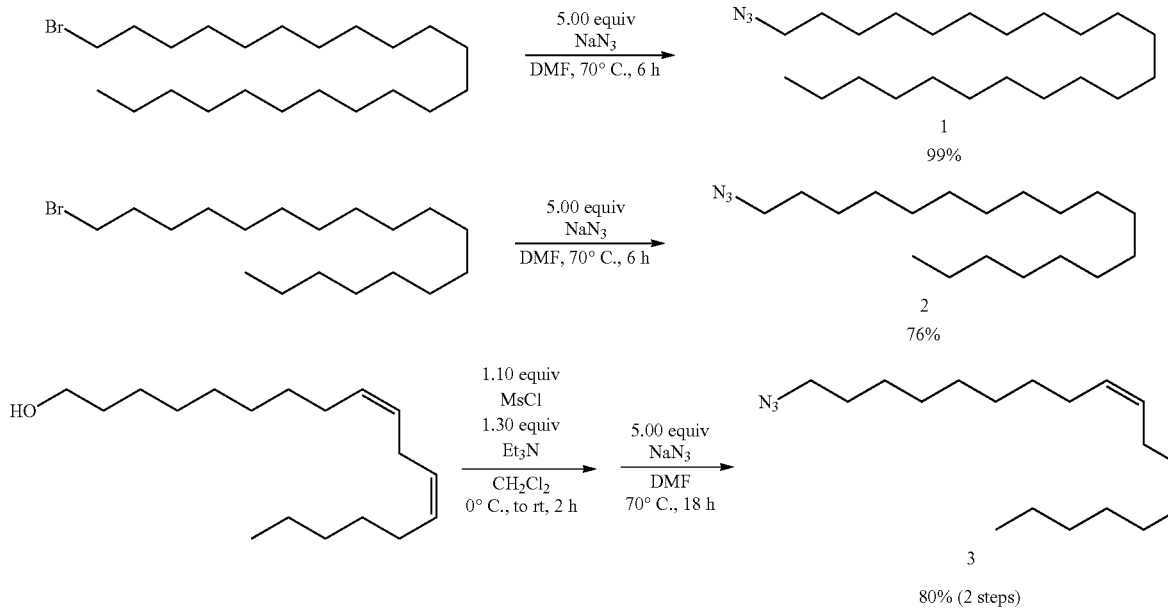

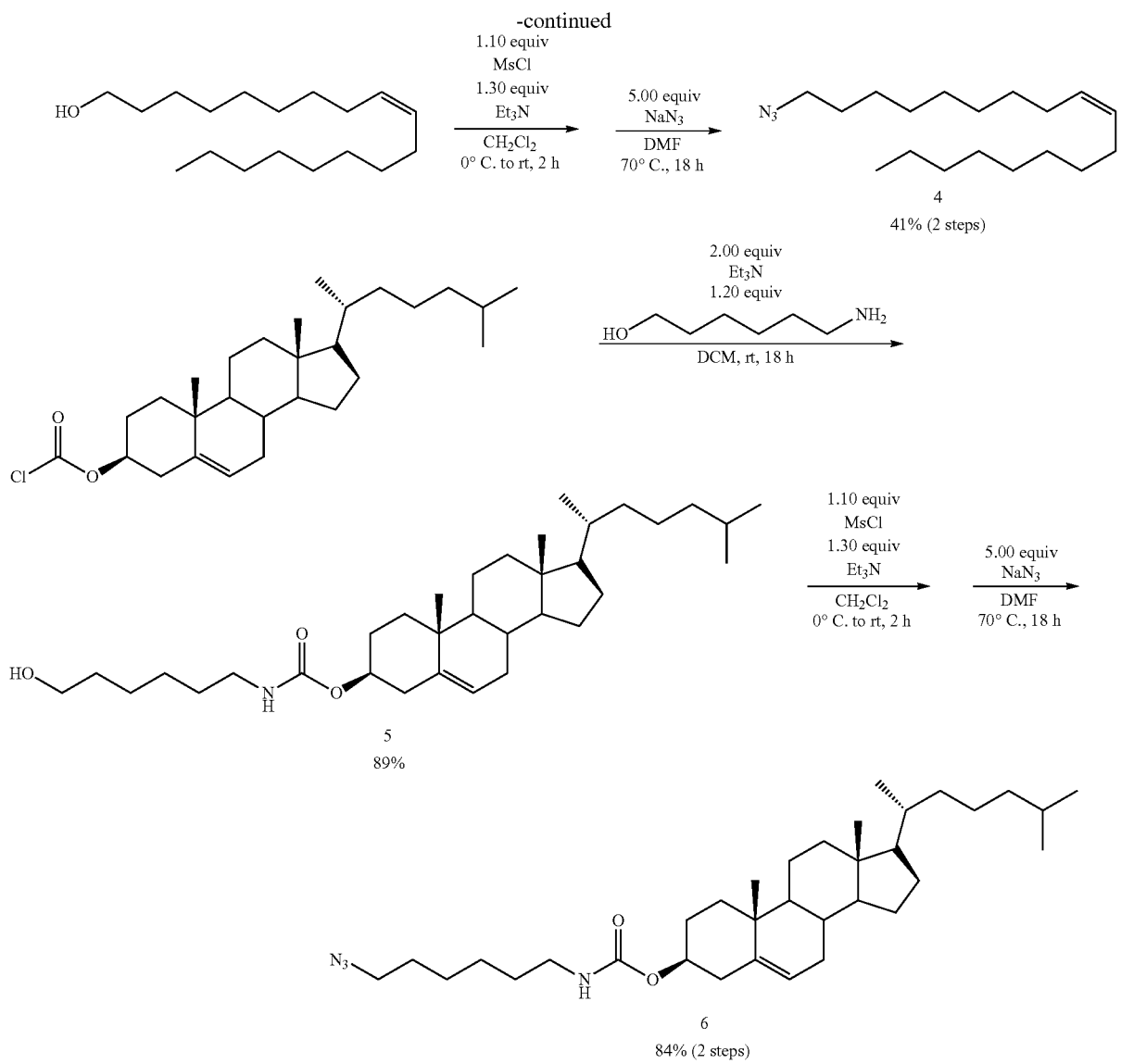

Docosyl Azide (1).

Docosyl bromide (10.0 g, 25.67 mmol) in anhydrous DMF (100 ml) was treated with sodium azide (8.35 g, 128.37 mmol) at 60° C. for 2 h. Then dilution of the reaction solution with ice water (1000 ml) gave white crystal. Filtration and drying on suction funnel and vacuum gave 1 as a white crystal (9.11 g, 25.90 mmol, quant). LC-MS calcd for [M+Na]$^+$ 621.2. found 621.2.

Stearyl Azide (2).

Bromooctadecane (10.0 g, 30.10 mmol) in anhydrous DMF (200 ml) was treated with sodium azide (9.78 g, 150.51 mmol) at 60° C. for 2 h. Then dilution of the reaction solution with ice water gave white crystal. Filtration and drying on suction funnel and then vacuum gave 2 as a white crystal. (6.82 g, 23.07 mmol, 76%)

Linoleyl Azide(3).

Linoleyl alcohol (10 ml, 32.3 mmol) in anhydrous DCM (80 ml) was treated with methanesulfonylchloride (2.75 ml, 35.5 mmol) and triethylamine (5.8 ml, 42.0 mmol) at room temperature for 2 h. Extraction with DCM/water, drying organic layer with sodium sulfate, and then evaporation gave crude mesylate. This crude was directly used for next step.

The crude in anhydrous DMF (300 ml) was treated with sodium azide (10.5 g, 161.50 mmol) at 60° C. for 18 h. Extraction with ethylacetate/water, drying organic layer with sodium sulfate, and then evaporation gave dark oil. The oil was chromatographed on silica gel. Eluent with Hexane gave 3 as clear oil (7.51 g, 25.67 mmol, 80% (2 steps)).

Oleyl Azide (4).

Oleyl alcohol (10 ml, 32.30 mmol) in anhydrous DCM (80 ml) was treated with methanesulfonylchloride (2.75 ml, 35.5 mmol) and triethylamine (5.8 ml, 42.0 mmol) at room temperature for 4 h. Extraction with DCM/water, drying organic layer with sodium sulfate, and then evaporation gave crude mesylate. This crude was directly used for next step.

The crude in anhydrous DMF (300 ml) was treated with sodium azide (10.5 g, 161.50 mmol) at 60° C. for 18 h. Extraction with ethylacetate/water, drying organic layer with sodium sulfate, and then evaporation gave dark oil. The oil was chromatographed on silica gel. Eluent with Hexane gave 3 as clear oil (4.00 g, 16.38 mmol, 44% (2 steps)).

Hydroxyhexylcarbamoylcholesterol (5).

1-amino-6-hexanol (5.00 g, 42.67 mmol) in anhydrous dichloromethane was treated with triethylamine (11.9 ml, 85.33 mmol) and cholesterol chloroformate (19.16 g, 42.67 mmol) at room temperature for 4 h. Extraction with DCM/brine, drying with sodium sulfate and evaporation gave yellow syrup. Then crystallized with DCM/Hexane gave 5 as white crystal (20.3 g, 38.31 mmol, 89%). LC-MS calcd for [M+Na]$^+$ 552.3. found 552.3.

Azidohexylcarbamoylcholesterol (6).

5 (15.0 g, 28.31 mmol) was treated with triethylamine (7.9 ml, 56.62 mmol) and methanesulfonylchloride (2.4 ml, 31.14 mmol) at room temperature for 4 h. Extraction with DCM/brine, drying, concentration in vacuo gave crude mesylate. This crude was directly used next step.

The crude in anhydrous DMF (300 ml) was treated with sodium azide (300 ml) at 60° C. for 18 h. Then Extraction with ethyl acetate/brine, drying organic layer with sodium sulfate and evaporation gave yellow syrup. The syrup was crystallized after the syrup was still stood for 18 h. The crystal was washed with water. Filtration and drying on a suction funnel and then vacuum gave 6 as a yellow crystal (13.24 g, 23.87 mmol, 84% (2 steps)).

Example 2

Lipid Alkyne Conjugate

Scheme 5

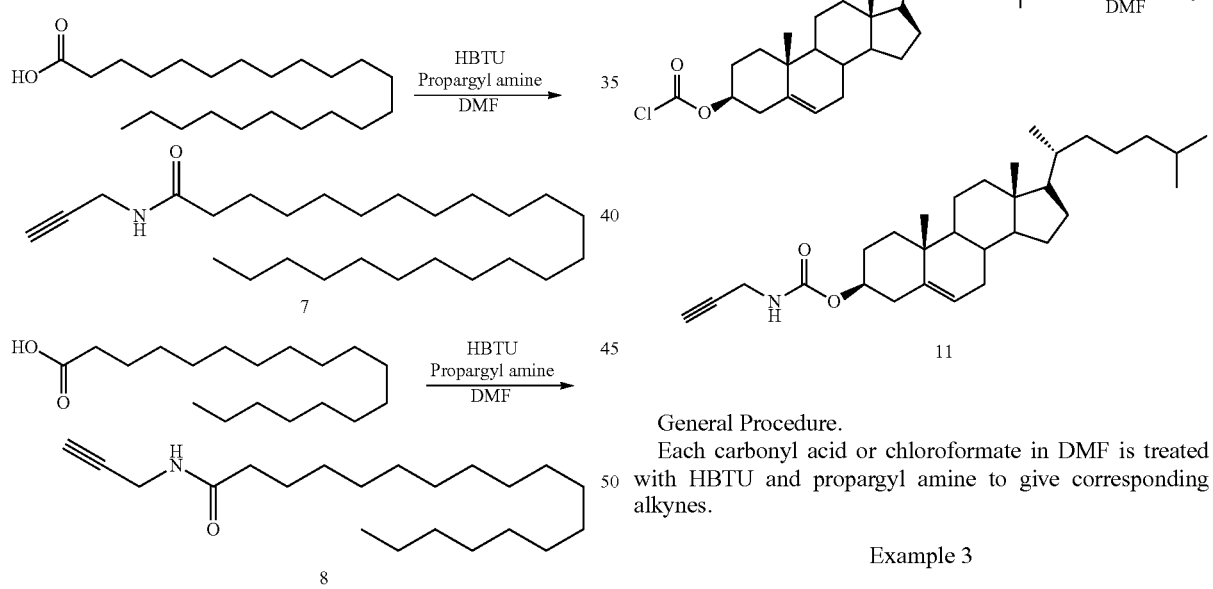

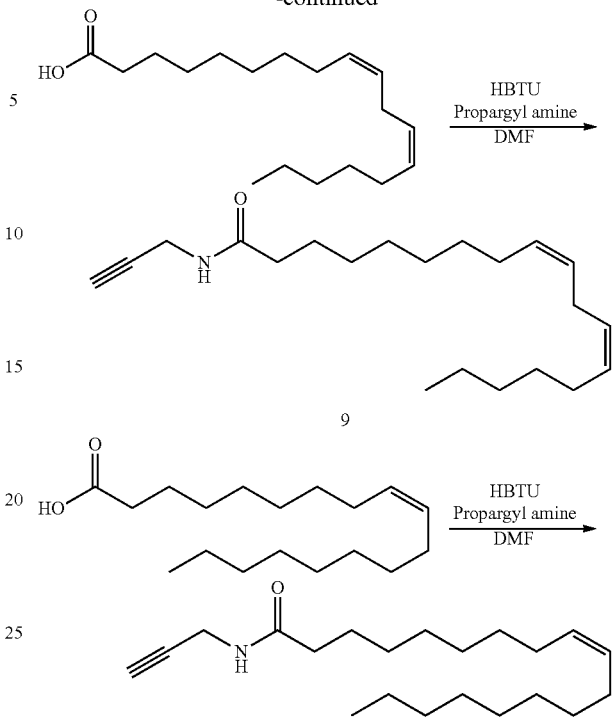

General Procedure.

Each carbonyl acid or chloroformate in DMF is treated with HBTU and propargyl amine to give corresponding alkynes.

Example 3

Lipid Azide Ester Conjugate

Scheme 6

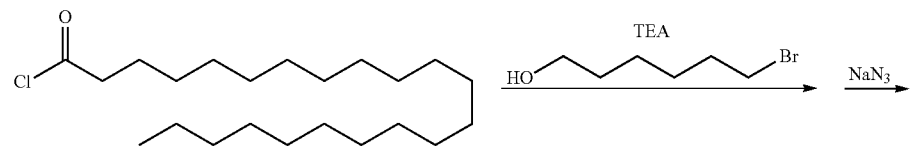

-continued
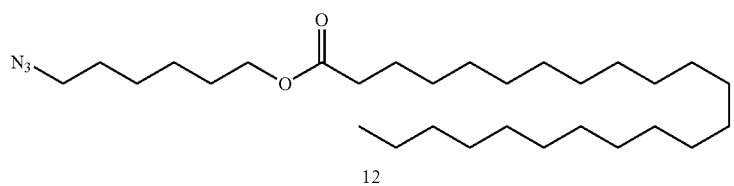
12
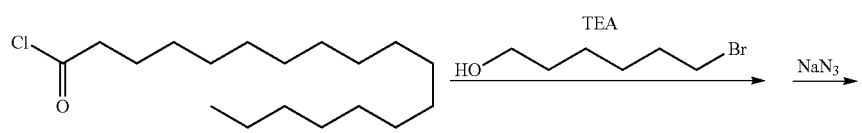
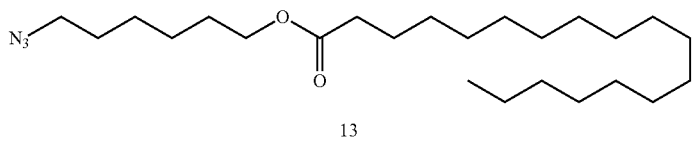
13
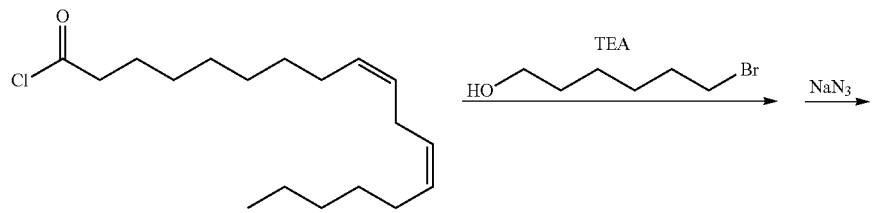
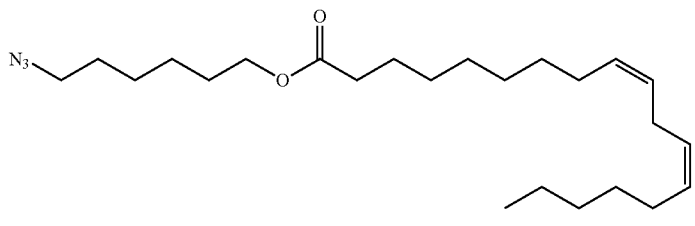
14
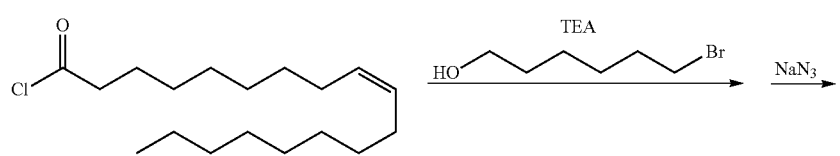
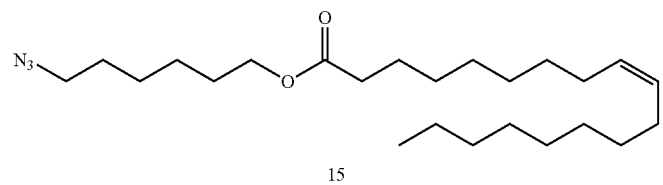
15
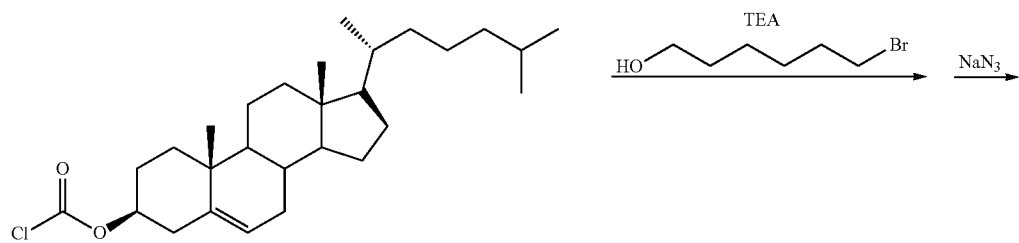

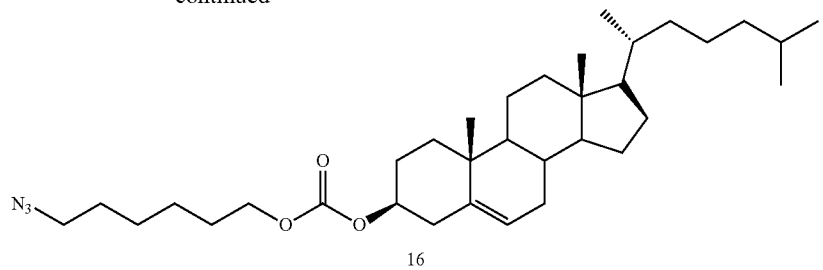

16

These azides will be used for post-synthesis after NH₄OH treatment.

Ester will be cleaved with esterase in a cell.

General Procedure.

Each Chloride or chloroformate in DCM are treated with TEA (2 equiv) and 1-bromohexanol (1.1 equiv) at room temperature. Aqueous work-up and concentration give crude bromide. The bromide in DMF is treated with sodium azide (5 equiv) at 60° C. Recrystallization gives corresponding azide.

Example 4

Synthesis of 2'/3'-O-Propargylnucleoside Derivatives

Scheme 7A

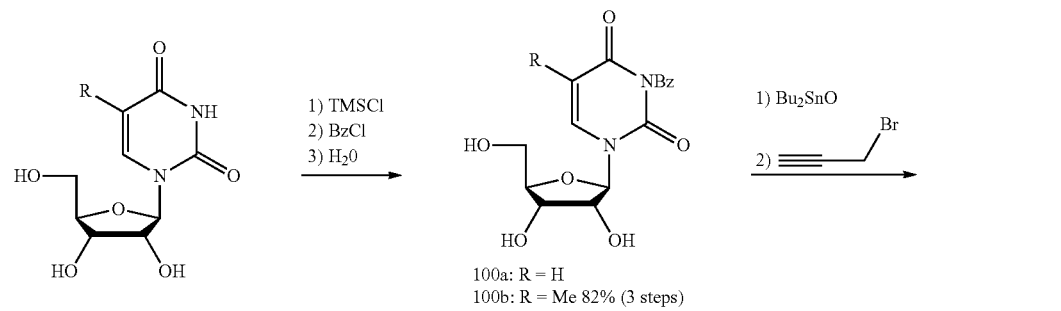

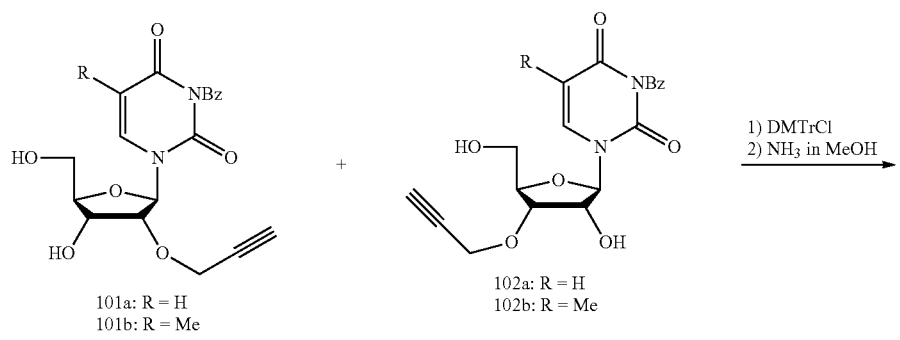

67% as mixture of 101b and 102b

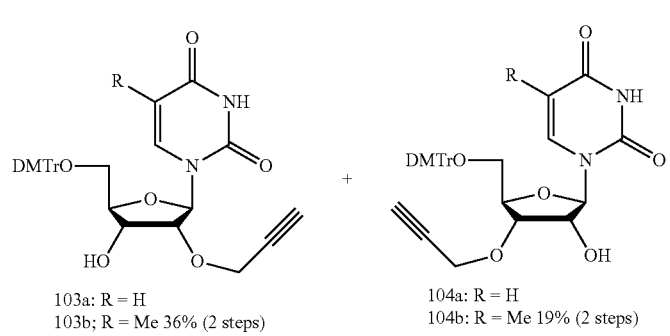

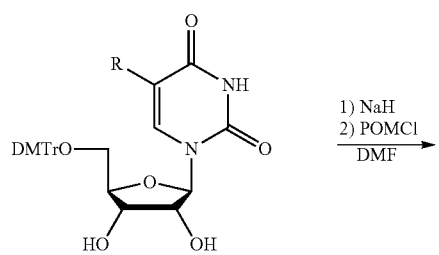
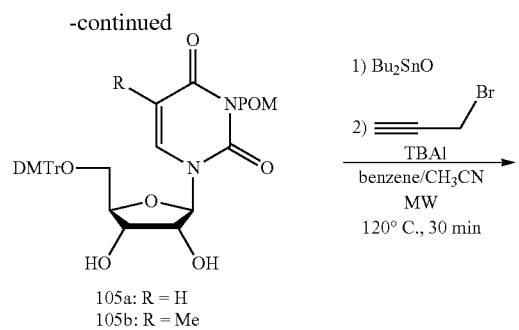

-continued

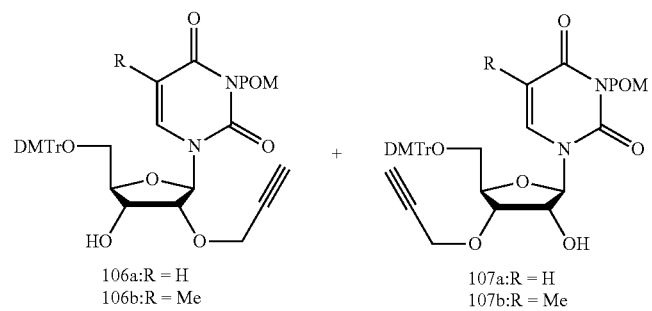

105a: R = H
105b: R = Me

106a: R = H
106b: R = Me

107a: R = H
107b: R = Me

Compound 100b.

5-methyluridine (20.0 g, 77.45 mmol) in pyridine (350 ml) was treated with chlorotrimethylsilane (49.4 ml, 42.07 mmol) for 30 min at room temperature. To the solution was added benzoyl chloride (9.90 ml, 11.98 mmol) in an ice bath. After 18 h, TLC monitoring and LC-MS analysis showed reaction completed. To the solution was added ice water (100 ml) in an ice bath. After 2 h, TLC monitoring and LC-MS analysis showed the cleavage of three trimethylsilyl ethers. The solution was directly extracted with ethyl acetate and brine. The organic layer was dried with sodium sulfate and then concentrated under reduced pressure. The residue was chromatographed on silica gel. Eluent with 5% MeOH in DCM gave 100a as white foam (23.5 g, 64.36 mmol, 82%). LC-MS calcd for [M+Na]$^+$ 385.1. found 385.1.

Compound 101b and 102b.

To the solution of 100a (330 mg, 0.91 mmol) in anhydrous DMF was added dibutyltinoxide (249 mg, 1.00 mmol) at 100° C. After 18 h, reaction was quenched with water. The reaction solution was concentrated under reduced pressure and then chromatographed on silica gel without aqueous work-up. Eluent with 10% MeOH in DCM gave mixture of 101b and 102b (140 mg, 0.34 mmol, 38%) as foam.

Compound 103b.

To the solution of 101b and 102b (5.00 g, 12.48 mmol) in anhydrous pyridine (200 ml) was added 4,4'-dimethoxytrityl-chloride (6.00 g, 17.71 mmol). After 4 h, TLC monitoring showed reaction completed. Then The solution was extracted with EtOAc and brine after quenched with water. The organic layer was concentrated under reduced pressure to give yellow residue. The residue was treated with 7 M ammonia in MeOH for 18 h at room temperature. Then the solution was evaporated to give yellow residue. The residue was chromatographed on silica gel. Eluent with EtOAc/Hexane (1:1 to 1:2) gave 103b as white foam (3.165 g, 5.41 mmol, 30%). LC-MS calcd for [M+Na]$^+$ 621.2. found 621.2.

Compound 104b.

104b was eluted after 103b was eluted. Yield was 770 mg (1.3 mmol, 8%). LC-MS calcd for [M+Na]$^+$ 621.2. found 621.2.

Compound 105a.

To the solution of 5'-O-DMTruridine (9.00 g, 36.75 mmol) in anhydrous DMF was added sodium hydride (1.94 g, 81.08 mmol) in an ice bath. After vigorous stirring for 1 h, chloromethyl pivalate (11.85 ml, 81.08 mmol) was added to the solution in an ice bath. After vigorous stirring for 24 h at 0° C. to room temperature, TLC monitoring showed reaction complete. The solution was partitioned with EtOAc and aqueous ammonium chloride solution. The organic layer was dried with sodium sulfate and concentrated under reduced pressure to give yellow residue. Chromatography gives 105a.

Compound 105b. Similar procedure to 105a gives 105b.

Compound 106a. To the solution of 105a in benzene/hexane (4:1, v/v) is added dibutyltinoxide (1.1 equiv). The mixture is irradiated by microwave at 120° C. for 20 min. After reaction, the mixture turns into clear solution. Then propargyl bromide (5 equiv) and tetrabutylammonium iodide (5 equiv) are added to the solution. The solution was irradiated by microwave at 120° C. for 2.5 h. Aqueous work-up and chromatography give 106a.

Compound 106b.
Similar procedure to 106a gives 106b.
Compound 107a.
107a is eluted after 106a.
Compound 107b.
Similar procedure to 107a gives 107b.

Scheme 7b. Preparation of 2′/3′-O-Propargyl-5-methyluridine Derivatives by microwave
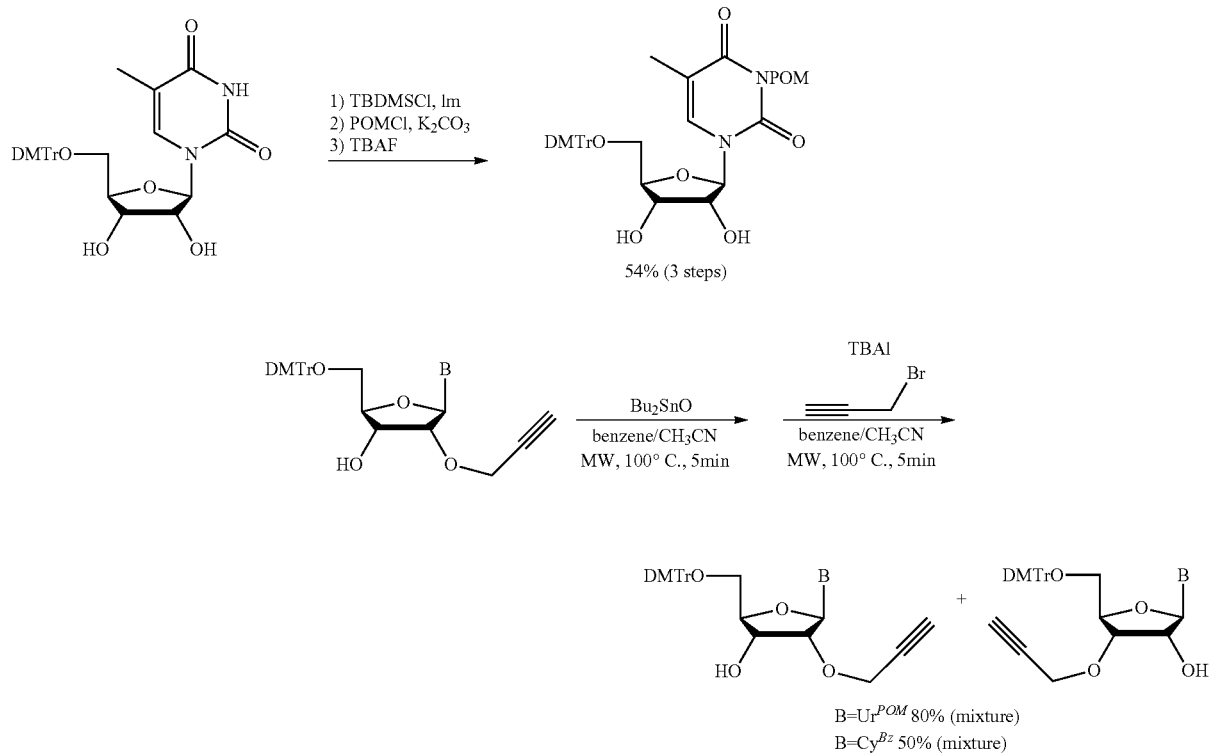
Example 5
Synthesis of 5′-O-Propargylcarbamoylnucleoside Derivatives
Scheme 8
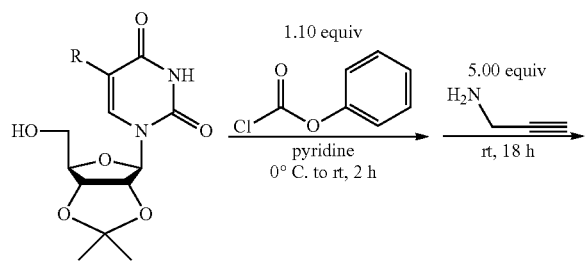
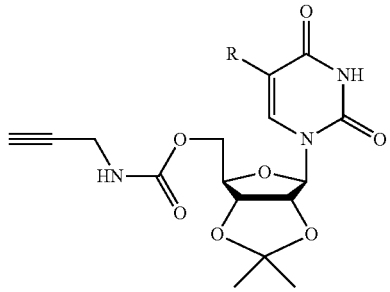
108a: R = H 96% (2 steps)
108b: R = Me
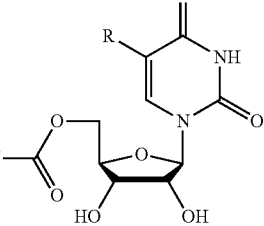
109a: R = H 99%
109b: R = Me
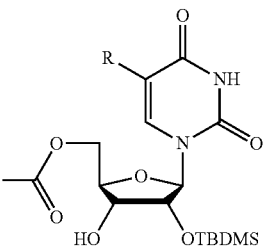
110a: R = H 20%
110b: R = Me

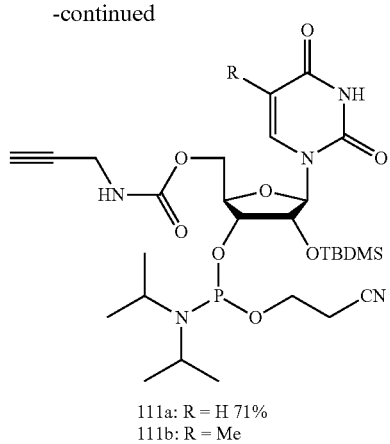

111a: R = H 71%
111b: R = Me

Compound 108a.

2'-3'-O-Isopropyrideneuridine (10.00 g, 35.18 mmol) in pyridine (350 ml) was treated with phenylchloroformate (4.8 ml, 38.70 mmol) at room temperature for 2 h. Then propargylamine (7.3 ml, 175.89 mmol) was added to the solution. After vigorous stirring 18 h at room temperature, TLC-monitoring showed reaction completed. The solution was directly partitioned with DCM and sat NaHCO₃aq. The organic layer was dried with sodium sulfate and concentrated under reduced pressure to give dark residue. The residue was chromatographed on silica gel. Eluent with 2% MeOH in DCM gave 108a as white foam (11.73 g, 32.10 mmol, 91% (2 steps). LC-MS calcd for [M+H]⁺ 366.0. found 366.0.

Compound 108b.

Similar procedure to 108a gives 108b.

Compound 109a.

108a (11.73 g, 32.10 mmol) in MeOH (20 ml) was refluxed with 80% AcOH (200 ml) for 18 h. Completion of the reaction was checked by LC-MS. The reaction solution was concentrated under reduced pressure to give yellow gummy syrup. The syrup was treated with MeOH (50 ml) and then sonicated for 30 min. Sonication gave white crystal. Filtration and drying on suction funnel and then vacuum gave 109a as white crystal (10.34 g, 31.78 mmol, 99%).

Compound 109b.

Similar procedure to 109a gives 109b.

Compound 110a.

109a (10.34 g, 28.30 mmol) in anhydrous THF (30 ml) was treated with silver nitrate (5.77 g, 34.00 mmol), pyridine (17.0 ml, 209.4 mmol) and tertiallybutyldimethylsilyl chloride (4.27 g, 28.30 mmol) at room temperature for 18 h. Then the solution was partitioned with DCM/water. The organic layer was dried with sodium sulfate and then concentrated under reduced pressure to give residue. The residue was chromatographed on silica gel. 110a and 3'-O-isomer (4.00 g, 32%) was eluted with Hexane/EtOAc (1:1) at the same time. Then the mixture was chromatographed on aluminum gel. Eluent with 2% MeOH in DCM gave pure 110a. LC-MS calcd for [M+Na]⁺ 462.1. found 462.1.

Compound 110b.

Similar procedure to 110a gives 110b.

Compound 111a.

110a (452 mg, 1.02 mmol) in anhydrous DCM (12 ml) was treated with diisopropylethylamine (612 µl, 3.41 mmol) and 2-cyanoethyl-N,N-diisopropylchlorophosphoramidite (380 ml, 1.71 mmol) at room temperature for 6 h. The solution was extracted with DCM/brine. Then the organic layer was dried with sodium sulfate and concentrated under reduced pressure to give yellow residue. The residue was chromatographed on silica gel. Eluent with TEA/Hexane/EtOAc (0.5:50:50) gave 111a (469 mg, 0.73 mmol, 71%) as white foam.

Compound 111b.

Similar procedure to 111a gives 111b.

Example 6

'Clicked' Compounds by Using of Propargylnulceosides and Azides

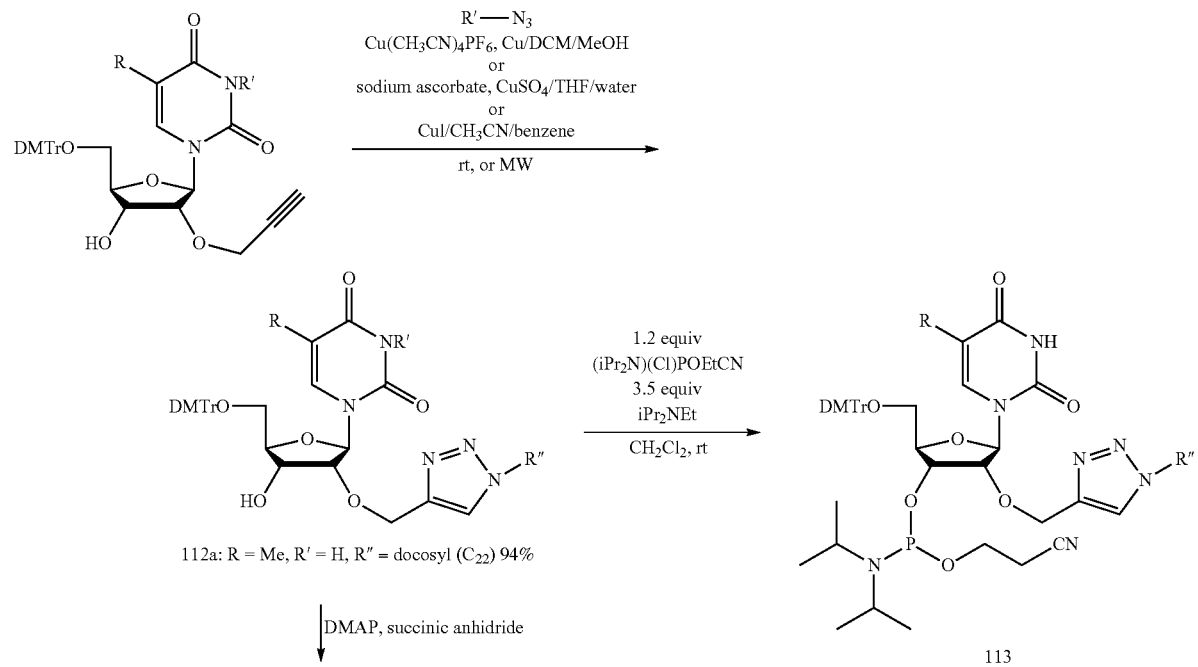

-continued
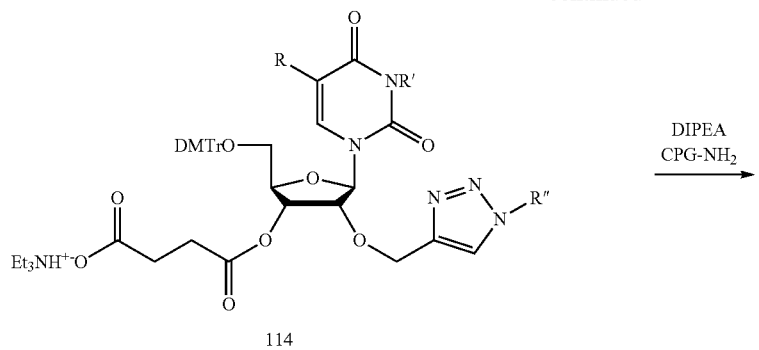
114
DIPEA
CPG-NH₂
→
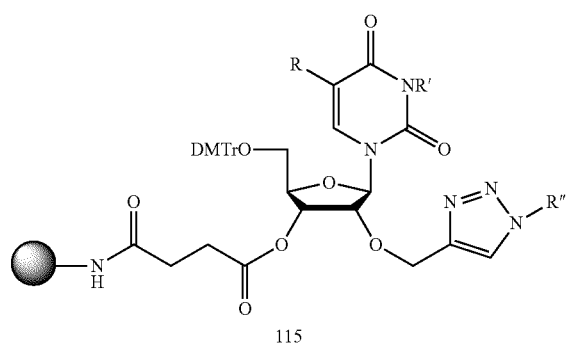
115
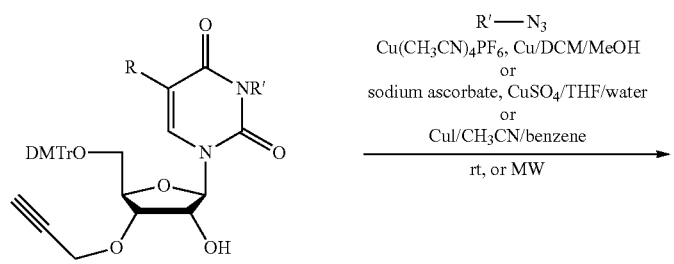
R'—N₃
Cu(CH₃CN)₄PF₆, Cu/DCM/MeOH
or
sodium ascorbate, CuSO₄/THF/water
or
CuI/CH₃CN/benzene
───────────→
rt, or MW
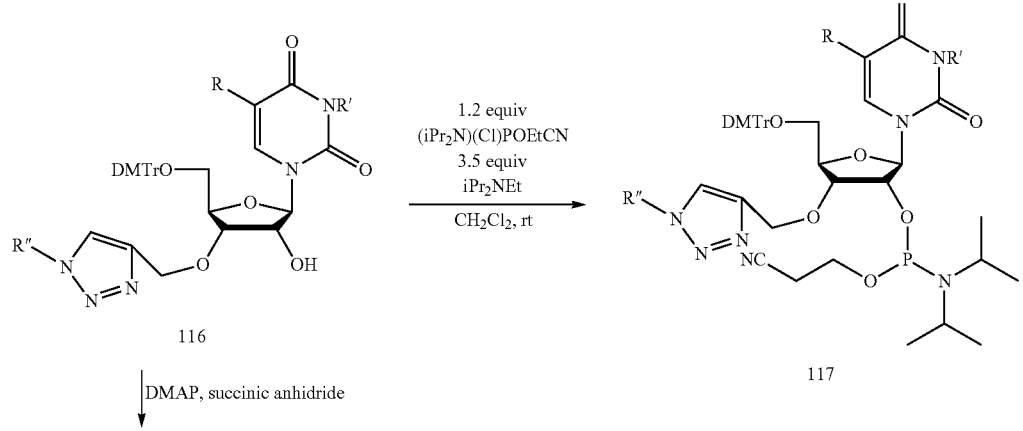
116
1.2 equiv
(iPr₂N)(Cl)POEtCN
3.5 equiv
iPr₂NEt
─────────→
CH₂Cl₂, rt
117
↓ DMAP, succinic anhidride -continued
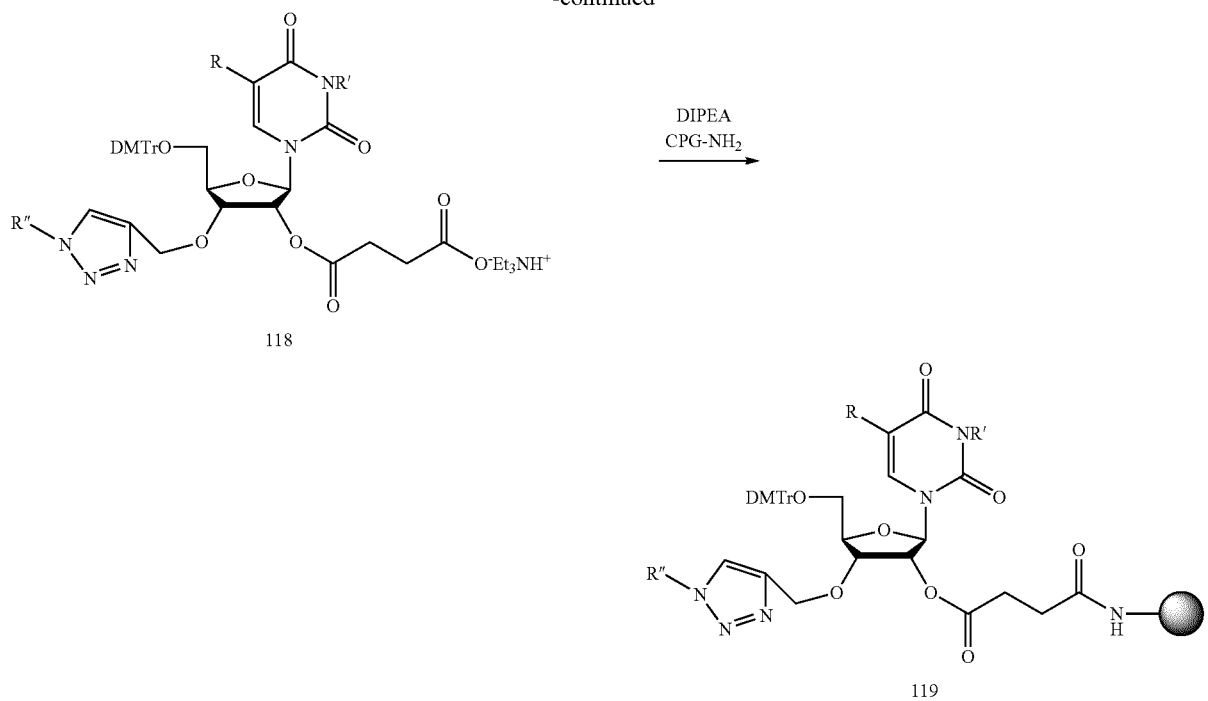
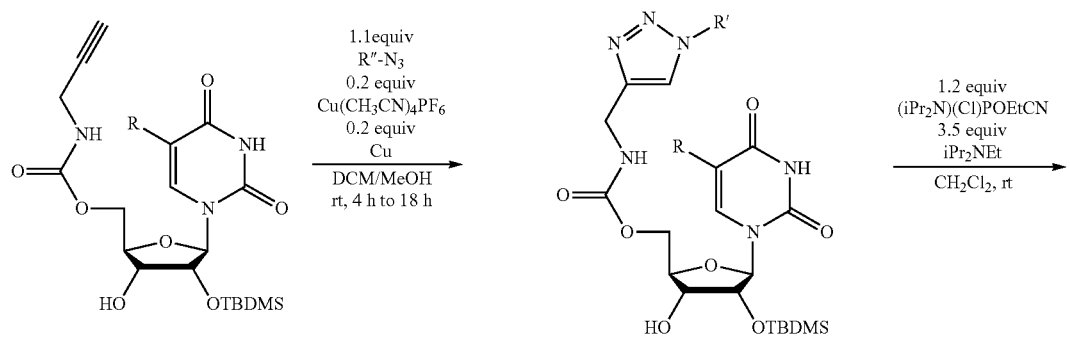
120a: R = H, R' = linoleyl (C18, w = 2) 88%
120b: R = H, R' = GalNAc-PEG 77%
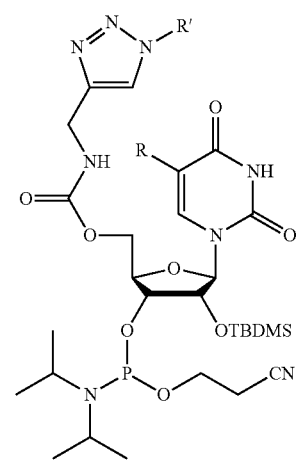
121a: R = H, R' = linoleyl (C18, w = 2) 50%
121b: R = H, R' = GalNAc-PEG 83%

Compound 112a.

103b (25 mg, 0.04 mmol) in DCM/MeOH (4:1, v/v) (0.5 ml) was treated with 1 (14 mg, 0.04 mmol), tetrakisacetonitrilecopper hexafluorophosphate (3 mg, 0.01 mmol) and copper (1 mg, 0.01 mmol). After 1 h, the solution was extracted with DCM/brine. The organic layer was concentrated under reduced pressure to give green residue. The residue was chromatographed on silica gel. Eluent with 1% MeOH in DCM gave 112a as white foam (36 mg, 0.037 mmol, 97%). LC-MS calcd for [M+Na]$^+$ 972.5. found 972.5.

Compound 113.

Typical phosphytilation gives 113.

Compound 114.

Typical succinilation gives 114.

Compound 115.

Typical immobilization to CPG gives 115.

Compound 116.

Similar procedure to 112a gives 116.

Compound 117.

Typical phosphytilation gives 117.

Compound 118.

Typical succinilation gives 118.

Compound 119.

Typical immobilization to CPG gives 119.

Compound 120a.

110a (100 mg, 0.17 mmol) in DCM/MeOH (4:1, v/v) (2 ml) was treated with 3 (59 mg, 0.17 mmol), tetrakisacetonitrilecopper hexafluorophosphate (13 mg, 0.03 mmol) and copper (2 mg, 0.03 mmol) at room temperature for 3 h. The solution was concentrated under reduced pressure and chromatographed on silica gel without aqueous work-up. Eluent with hexane/EtOAc (1:3) gave 120a as foam (122 mg, 0.16 mmol, 98%). LC-MS calcd for [M+H]$^+$ 731.2. found 731.2.

Compound 120b.

110a (500 mg, 1.14 mmol) in DCM/MeOH (4:1, v/v) was treated with 325 (460 mg, 1.14 mmol), tetrakisacetonitrilecopper hexafluorophosphate (42 mg, 0.11 mmol) and copper (7 mg, 0.11 mmol) at room temperature for 18 h. Then the solution was concentrated under reduced pressure and chromatographed on silica gel directly without aqueous work-up. Eluent with DCM/MeOH (10:1) gave 120b as white foam (800 mg, 0.88 mmol, 88%).

Compound 121a.

120a (730 mg, 1.00 mmol) in anhydrous DCM (10 ml) was treated with diisopropylethylamine (525 μl, 3.00 mmol) and 2-cyanoethyl-N,N-diisopropylethylphosphoramidite (335 μl, 1.50 mmol) at room temperature for 4 h. The solution was then extracted with DCM/brine. The organic layer was dried with sodium sulfate and then concentrated under reduced pressure to give dark residue. The residue was chromatographed on silica gel. Eluent with TEA/Hexane/EtOAc (0.5:60:30) gave 116a as white foam (463 mg, 0.50 mmol, 50%).

Compound 121b.

120b (400 g, 0.44 mmol) in anhydrous DCM (4 ml) was treated with diisopropylethylamine (230 μl, 1.33 mmol) and 2-cyanoethyl-N,N-diisopropylethylphosphoramidite (150 μl, 0.67 mmol) at room temperature for 6 h. The solution was partitioned with DCM/brine. The organic layer was dried with sodium sulfate and then concentrated under reduced pressure to give yellow residue. The residue was chromatographed on silica gel. Eluent with TEA/MeOH/EtOAc (0.5:2:100) gave 120b as white foam (403 mg, 0.36 mmol, 83%). LC-MS calcd for [M+Na]$^+$ 1123.3. found 1123.3.

Example 7

Sugar Ligands with Functionalized Alkynes or Azides

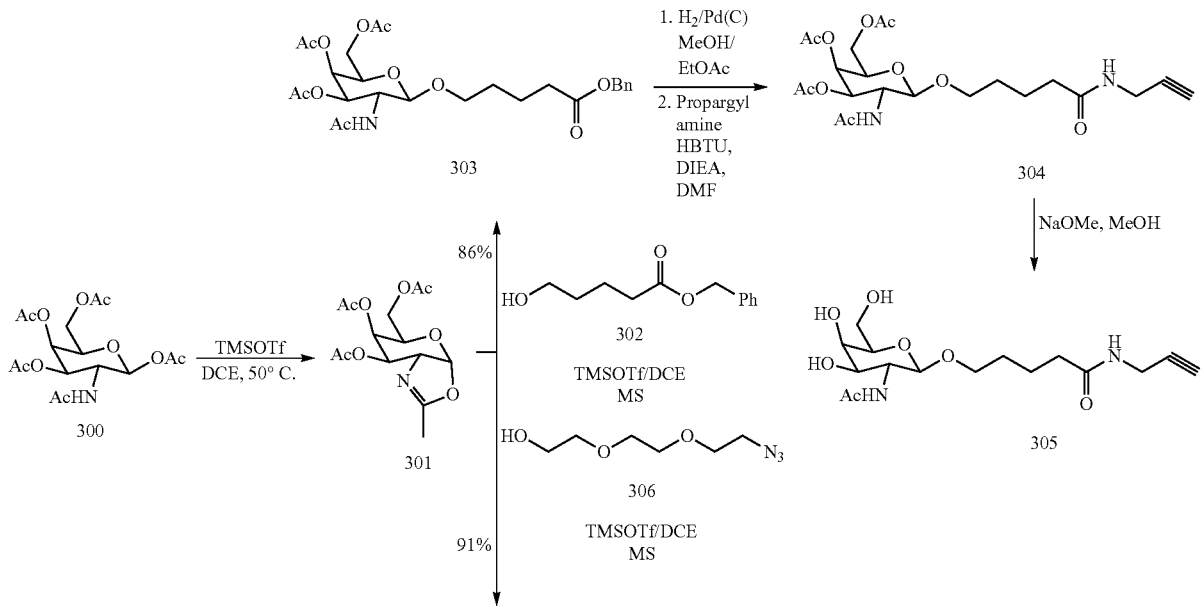

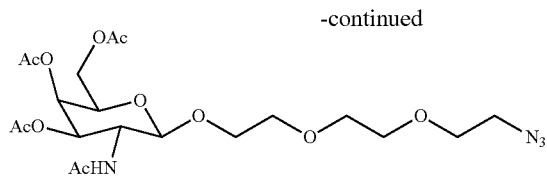

307

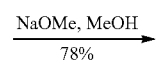

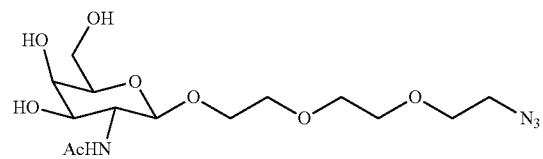

308

Preparation of 319:

Galactosamine pentaacetate 300 (52.00 g, 133.63 mmol) was taken in dichloroethane (300 mL) at ambient temperature. TMSOTf (44.55 g, 200.44 mmol) was added that and the mixture stirred at 50° C. for 90 minutes in a water bath, heating stopped and the mixture stirred overnight at room temperature. It was poured in to an ice cold sodium bicarbonate solution; extracted with dichloromethane, washed with water and dried over sodium sulfate. Solvents were removed in vacuo and the residue was dried under high vacuum overnight to get the compound 301 as a dark gum (TLC: 15% MeOH in CHCl$_3$, Rf Value: 0.5, 44.50 g, quantitative). It was used for next reaction with out further purification. $^1$H NMR and MALDI confirmed the product formation. $^1$H NMR (CDCl$_3$ 400 MHz) δ=6.01 (d, J=6.8 Hz, 1H), 5.46 (t, J=3.01 Hz, 1H), 4.91 (dd, J=3.29, 7.30 Hz, 1H), 4.26-3.93 (m, 4H), 2.12 (s, 3H), 2.07 (s, 6H), 2.05 (s, 3H). MS: MW calc. for C$_{14}$H$_{19}$NO$_8$: 329.11. Found 352.1 (M+Na).

Preparation of 303: Compound 301 (43.70 g, 133.56 mmol) and the benzyl ester 302 (41.71 g, 200.34 mmol) were dissolved in dichloroethane (300 mL), molecular sieves (50 g) was added to the solution and stirred for 30 minutes. TMSOTf (14.50 g, 66.78 mmol) was added and the mixture was stirred overnight at room temperature. It was poured into an ice cold solution of sodium bicarbonate and the product was extracted into dichloromethane, washed with water and dried over anhydrous sodium sulfate. Solvents were removed in vacuo and the residue was purified by silica gel column chromatography (gradient elution: 20-100% ethylacetate/hexanes) to get the required compound 303 as light brown gummy liquid (60.50 g, 86%). $^1$HNMR (DMSO-d$_6$ 400 MHz) δ=7.76 (d, J=9.03 Hz, 1H), 7.25-7.38 (m, 5H), 5.20 (d, J=3.17 Hz, 1H), 5.05 (s, 2H), 4.95 (dd, J=3.41, 11.23 Hz, 1H), 4.48 (d, J=8.30 Hz, 1H), 3.70-4.20 (m, 4H), 3.35-3.45 (m, 2H), 2.33 (t, J=7.32 Hz, 2H), 2.08 (s, 3H), 1.97 (s, 3H), 1.87 (s, 3H), 1.73 (s, 3H), 1.50-1.63 (m, 4H). MS: MW Calc. for C$_{26}$H$_{35}$NO$_{11}$: 537.22. Found 560.21 (M+Na).

Preparation 304:

Compound 303 (60.00 g, 111.68 mmol) was dissolved in a mixture of Methanol/ethylacetate and degassed with argon. Pd/C (6.00 g, 10 wt % Degussa, wet type) was added and hydrogenated under balloon pressure overnight. Filtered through a small pad of celite; washed with methanol and dried under high vacuum overnight to get the acid (48.85 g, 98%). $^1$HNMR (DMSO-d$_6$ 400 MHz) δ=11.97 (bs, 1H), 7.78 (d, J=9.20 Hz, 1H), 5.21 (d, J=3.16 Hz, 1H), 4.96 (dd, J=3.42, 11.30 Hz, 1H), 4.47 (d, J=8.26 Hz, 1H), 3.73-4.22 (m, 4H), 3.32-3.45 (m, 2H), 2.09 (s, 3H), 1.98 (s, 3H), 1.87 (s, 3H), 1.75 (s, 3H), 1.51-1.64 (m, 4H) MS: MW Calc. for C$_{19}$H$_{29}$NO$_{11}$: 447.17. Found 469.9 (M+Na). Part of the acid (5 g, 11.17 mmol), Propargyl amine (0.690 g, 12.29 mmol) and HBTU (4.23 g, 11.17 mmol) are dissolved in DMF (50 mL). DIEA is added to the reaction mixture and stir the reaction mixture overnight. Remove the solvent under reduced pressure and the residue extracted with dichloromethane, washed with water and dried over anhydrous sodium sulfate. Solvents are removed in vacuo and the residue purify by silica gel chromatography to get the product 304. MS: MW Calc. for C$_{22}$H$_{32}$NO$_{10}$: 484.21.

Preparation of 305:

Compound 304 (3.00 g, 6.19 mmol) is dissolved in a mixture of DCM/MeOH (1:2, 20 mL) and sodium methoxide solution (20 mL, 0.5 M in MeOH) is added to that and stir the mixture overnight. Neutralize the reaction mixture with AcOH and remove the solvents under reduced pressure. Residue is purified by silica gel chromatography to get the required product 305. MS: MW Calc. for C$_{16}$H$_{26}$NO$_7$: 358.39

Preparation of 307:

Compound 301 (42.30 g, 128.43 mmol) and the azido ethanol 306 (26 g, 192.45 mmol) were dissolved in dichloroethane (300 mL), molecular sieves (50 g) was added to the solution and stirred for 30 minutes. TMSOTf (14.29 g, 64.21 mmol) was added and the mixture was stirred overnight at room temperature. It was poured into an ice cold solution of sodium bicarbonate and the product was extracted into dichloromethane, washed with water and dried over anhydrous sodium sulfate. Solvents were removed in vacuo and the residue was purified by silica gel column chromatography (gradient elution: 20-100% ethyl acetate/hexanes, followed by 5-10% Methanol/ethyl acetate) to obtain the required compound 307 as light brown gummy liquid (59.23 g, 91.00%). $^1$HNMR (DMSO-d$_6$ 400 MHz) δ=7.77 (d, J=9.27 Hz, 1H), 5.20 (d, J=3.15 Hz, 1H), 4.97 (dd, J=3.39, 11.34 Hz, 1H), 4.55 (d, J=8.64 Hz, 1H), 3.72-4.22 (m, 5H), 3.30-3.63 (m, 11H), 2.09 (s, 3H), 1.98 (s, 3H), 1.88 (s, 3H), 1.76 (s, 3H), MS: MW Calc. for C$_{20}$H$_{32}$N$_4$O$_{11}$: 504.21. Found 527.1 (M+Na).

Preparation of 308:

Compound 307 (5.85 g, 11.59 mmol) was dissolved in a mixture of DCM/MeOH (1:2, 50 mL) and sodium methoxide solution (20 mL, 0.5 M in MeOH) was added to that and stir the mixture overnight. Neutralize the reaction mixture with AcOH and removed the solvents under reduced pressure. Residue was purified by silica gel chromatography (DCM, 20% MeOH/DCM) to get the required product 308. MS: MW Calc. for C$_{14}$H$_{26}$N$_4$O$_8$: 378.18. Found 401.19 (M+Na).

Scheme 11

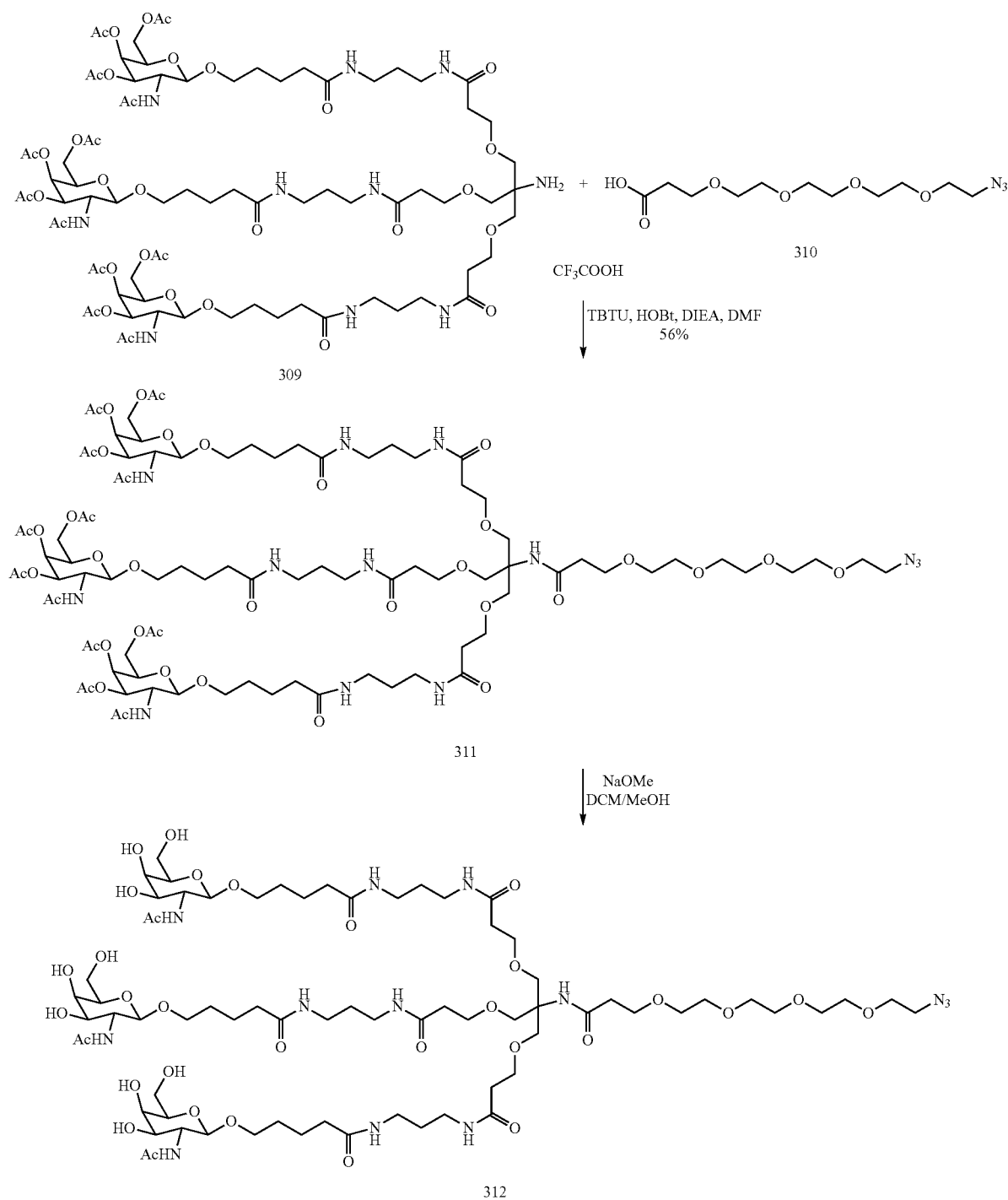

Preparation of 311:

PEG acid 310 (5.50 g, 2.908 mmol) was dissolved in DMF (50 mL); TBTU (1.23 g, 3.83 mmol), HOBt (0.520 g, 3.83 mmol) and DIEA (3.2 mL, 5 eq) were added to the mixture and stirred for 3-4 minutes. A solution of 309 (1.02 g, 1.2 eq) in DMF was added to the mixture and stirred the reaction mixture overnight. TLC was checked, solvents were removed under reduced pressure. The residue was dissolved in dichloromethane, washed with sodium bicarbonate solution (50 mL), water (50 mL) and dried over anhydrous sodium sulfate. Solvents were removed in vacuo and the residue was purified by silica gel column chromatography (ethyl acetate, followed by gradient elution 5-15% MeOH/DCM) to get the product 311 as an offwhite solid (3.30 g, 56%). MS: MW Calc. for $C_{90}H_{147}N_{13}O_{41}$: 2065.98. Found 2089.09 (M+Na).

Preparation of 312:

Compound 311 (0.92 g, 0.445 mmol) was dissolved in MeOH (10 mL) and sodium methoxide solution (10 mL, 0.5

M in MeOH) was added to that and stir the mixture overnight. Reaction was monitored by TLC and the mixture passed through a column of CM Sepharose resin. Washed with MeOH and removed the solvents in vacuo to get the product 312 (0.42 g, 57%). MS: MW Calc. for $C_{72}H_{129}N_{13}O_{32}$: 1687.89. Found 1710.90 (M+Na).

Preparation of 313:

Compound 311 (2.00 g, 0.967 mmol) is dissolved in THF (20 mL) to that $PPh_3$ (0.380 g, 1.45 mmol) is added and the mixture stir for 48 h. TLC is checked to see complete disappearance of starting material. Water (0.1 mL, 5 eq) is added to the reaction mixture and stir for another 24 h. TFA (0.140 g,

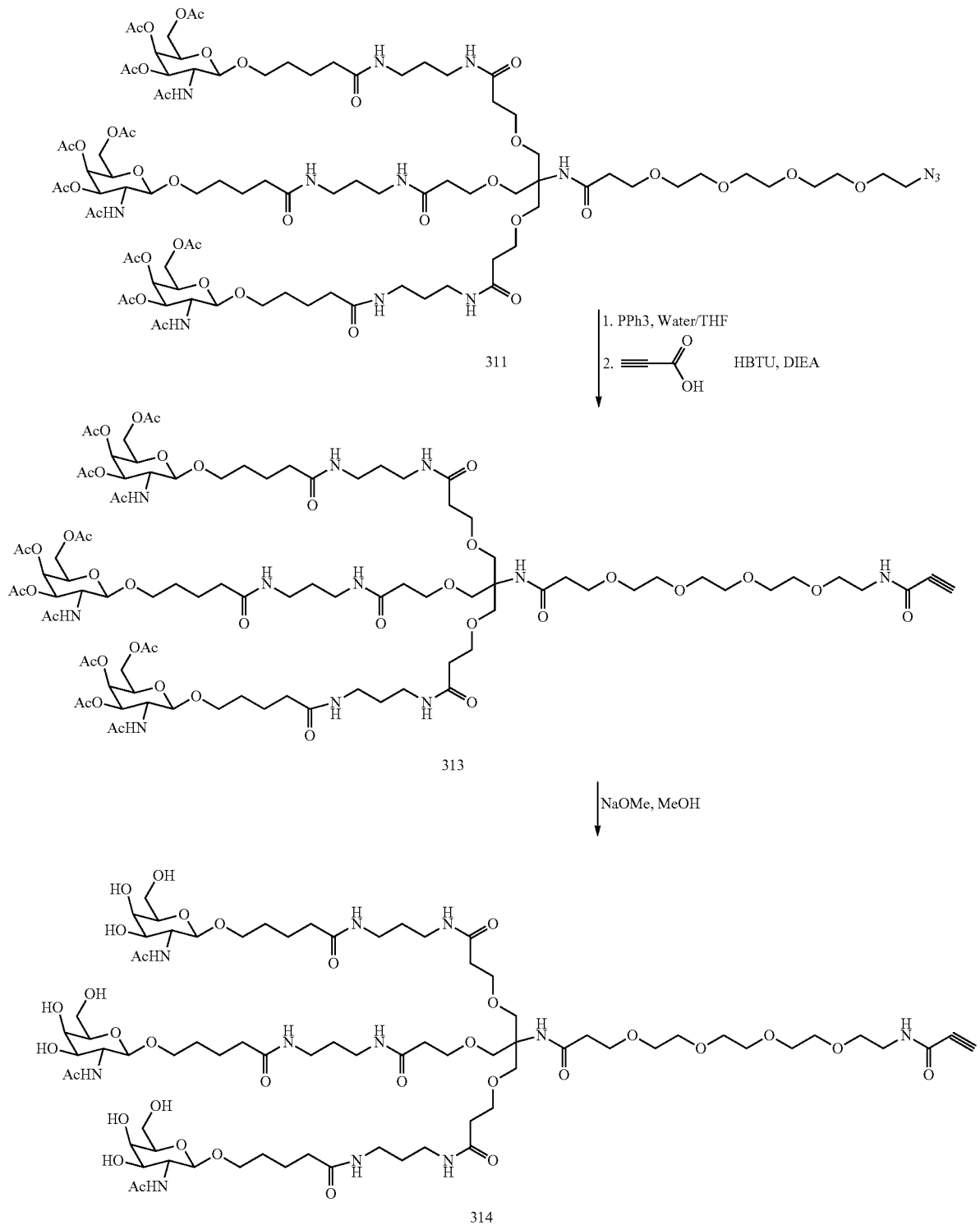

Scheme 12

1.20 mmol) and toluene (30 mL) are added and the concentrate under reduced pressure. The residue co-evaporates with toluene (2×30 mL) twice and dries under high vacuum. The product thus obtained can be used for the next reaction in the same day without further purification. MS: MW Calc. for $C_{90}H_{149}N_{11}O_{41}$: 2039.99. Compound from the above reaction and propynoic acid (0.081 g, 1.2 eq) are dissolved in DMF (20 mL). To that add HBTU (0.440 g, 1.16 mmol) and DIEA, stir the mixture overnight. Solvents are removed under reduced pressure. The residue is dissolved in dichloromethane, wash with sodium bicarbonate solution, water and dry over anhydrous sodium sulfate. Solvents are removed in vacuo and the residue is purified by silica gel column chromatography to get the product 313.

Preparation of 314:

Compound 311 (1.00 g, 0.447 mmol) is dissolved in MeOH (10 mL) and sodium methoxide solution (10 mL, 0.5 M in MeOH) is added to that and stir the mixture overnight. Reaction is monitored by TLC and the mixtures pass through a column of CM Sepharose resin. Wash with MeOH and remove the solvents in vacuo to get the product 314.

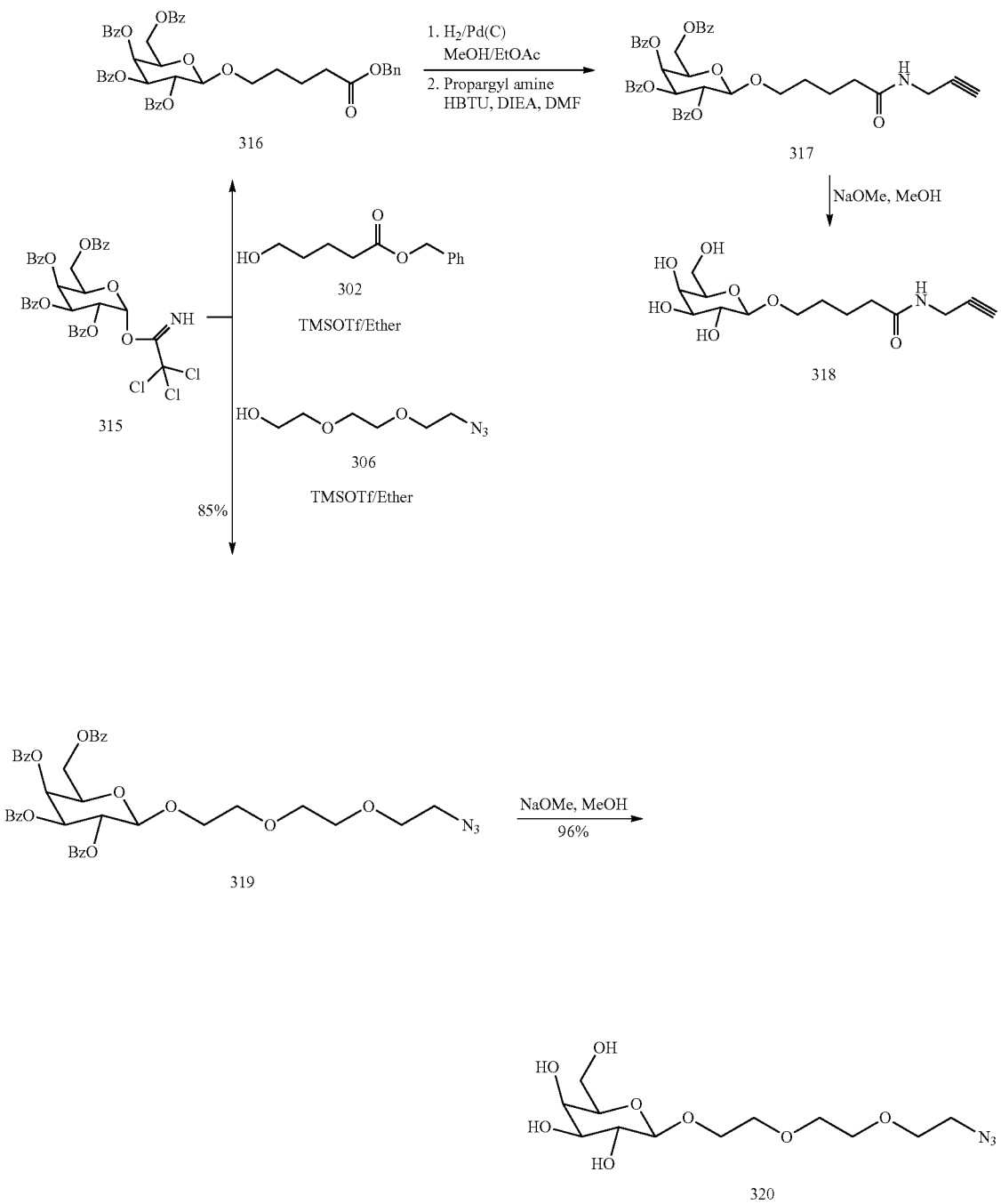

Scheme 13

Preparation of 316:

Galactose trichloroacetimidate 315 (10.00 g, 13.53 mmol) and the benzyl ester 302 (3.90 g, 14.88 mmol) are co evaporated with toluene (2×40 ml) two times and dried under high vacuum. Anhydrous ether (50 mL) and molecular sieves (20 g) are added to the solution and cool in an ice bath. TMSOTf (0.300 g, 1.349 mmol) is added and the mixtures stir for 15 minutes. Solvent is removed and purify the residue by silica gel column chromatography (gradient elution: 20-60% ethyl acetate/hexanes) to get the required compound 316.

Preparation of 317:

Compound 316 (5.00 g, 6.35 mmol) is taken in MeOH and hydrogenated under balloon pressure using Pd/C to get the acid. Crude acid and propargyl amine (0.384 g, 6.99 mmol) and HBTU (2.40 g, 6.35 mmol) are dissolved in DMF (50 mL). DIEA is added and stir the reaction mixture overnight. Solvent is removed and the residue is purified by silica gel chromatography to get the required product 317.

Preparation of 318:

Compound 317 (2.00 g, 2.72 mmol) is dissolved in a mixture of DCM/MeOH (1:2, 50 mL) and sodium methoxide solution (20 mL, 0.5 M in MeOH) is added to that and stir the mixture overnight. Neutralize the reaction mixture with AcOH and remove the solvents under reduced pressure. Purify the residue by silica gel chromatography (DCM, 20% MeOH/DCM) to get the required product 318.

Preparation of 319:

Galactose trichloroacetimidate 315 (10.00 g, 13.53 mmol) and the azido alcohol 306 (2.60 g, 14.88 mmol) were co evaporated with toluene (2×40 ml) two times and dried under high vacuum. Anhydrous ether (50 mL) and molecular sieves (20 g) were added to the solution and cooled in an ice bath. TMSOTf (0.300 g, 1.349 mmol) was added and the mixture was stirred for 15 minutes, TLC checked and quenched the reaction mixture with TEA. Solvent was removed and the residue purified by silica gel column chromatography (gradient elution: 20-60% ethylacetate/hexanes) to get the required compound 319 as a color less liquid (8.623 g, 85%). MS: MW Calc. for $C_{40}H_{39}N_3O_{12}$: 753.25. Found 776.30 (M+Na).

Preparation of 320:

Compound 319 (4.19 g, 5.55 mmol) was dissolved in a mixture of DCM/MeOH (1:2, 50 mL) and sodium methoxide solution (55 mL, 0.5 M in MeOH) was added to that and stir the mixture overnight. Neutralize the reaction mixture with AcOH and removed the solvents under reduced pressure. Residue was purified by silica gel chromatography (DCM, 20% MeOH/DCM) to get the required product 320 as a color less liquid (1.80 g, 96%). MS: MW Calc. for $C_{12}H_{23}N_3O_8$: 337.15. Found 360.15 (M+Na).

Scheme 14

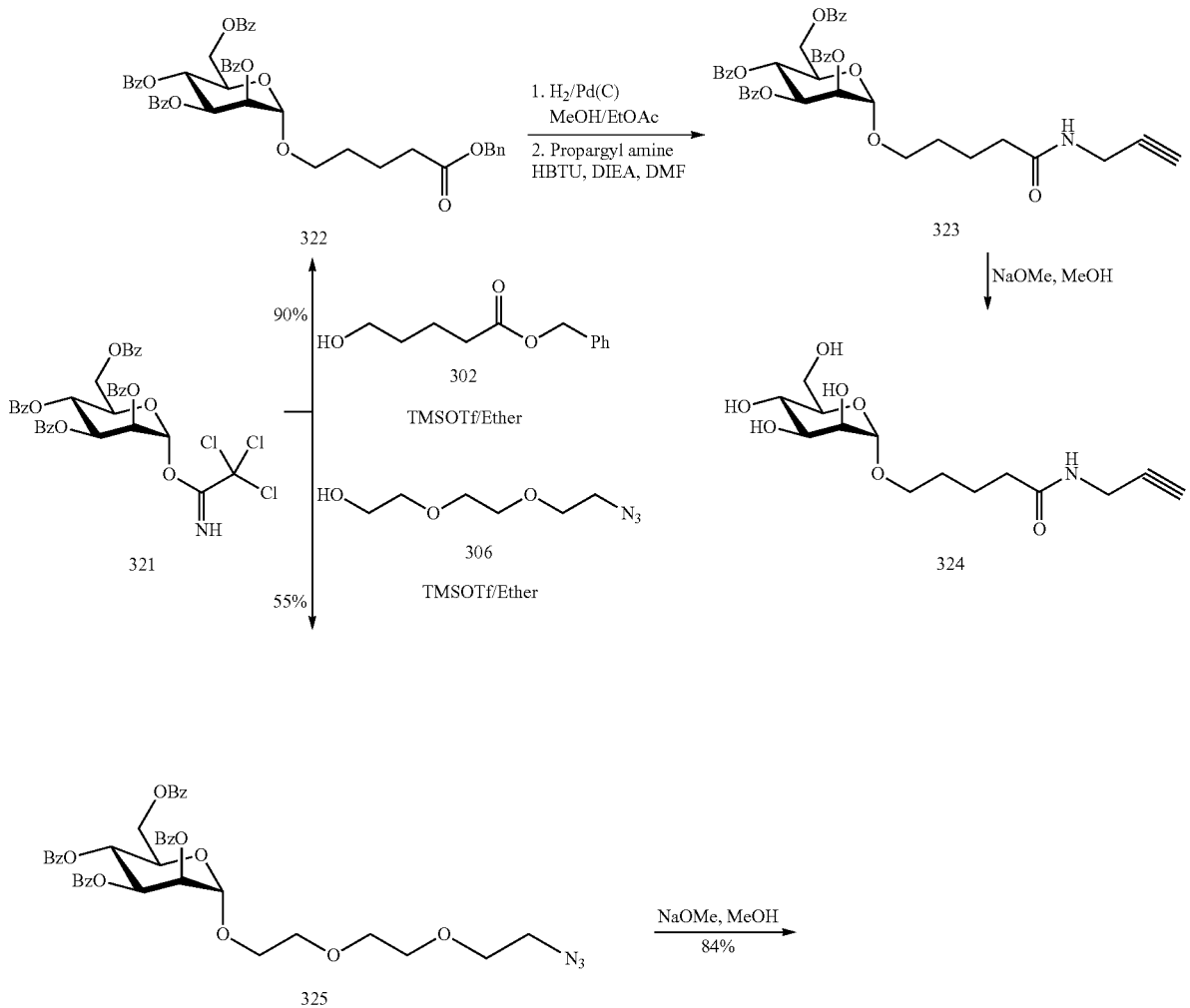

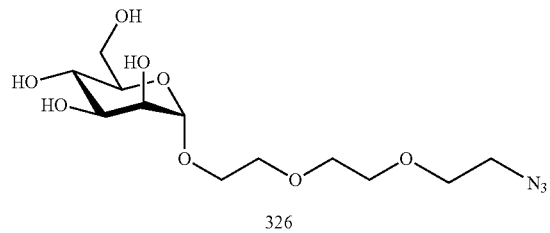

326

Preparation of 322:

Mannose trichloroacetimidate 321 (15.23 g, 20.55 mmol) and 302 (4.36 g, 1.02 eq.) were dissolved in Toluene and aziotroped two times. The residue dried under high vacuum overnight. Anhy diethyl ether (30 mL) and Molecular sieves (10 g) were added to that. Reaction mixture cooled in an ice-water bath. TMSOTf (0.5 mL, 0.1 eq) was added to that and stirred the mixture for 10 minutes. Reaction was monitored by TLC and quenched with TEA. Filtered of the molecular sieves and solvents were removed under reduced pressure. Residue was purified by chromatography (hexane, 15-25% EtOAc/Hexane) to get compound 322 as colorless liquid (14.52 g, 90%). MS: Calculated for $C_{46}H_{42}O_{12}$, 786.27. Found 809.25 ((M+Na).

Preparation of 323:

Mannose benzyl ester (14.30 g, 18.17 mmol) was dissolved in Ethyl acetate (100 mL) to that two drops of acetic acid was added. Degassed, Pd/C (1.50 g, 10 wt % Degussa wet type) was added and hydrogenated under balloon pressure for 24 hrs. Reaction was monitored by TLC and MALDI. It was filtered through a small pad of celite, washed with ethyl acetate. Solvent was removed and the residue dried under high vacuum to get the compound as color less oil (11.20 g, 90%). MS: Calculated for $C_{39}H_{36}O_{12}$, 696.22. Found 719.18 (M+Na). Crude acid (4.40 g, 6.35 mmol) and propargyl amine (0.384 g, 6.99 mmol) and HBTU (2.40 g, 6.35 mmol) are dissolved in DMF (50 mL). DIEA is added and stir the reaction mixture overnight. Solvent is removed and the residue is purified by silica gel chromatography to get the required product 323.

Preparation of 324:

Compound 323 (2.00 g, 2.72 mmol) is dissolved in a mixture of DCM/MeOH (1:2, 50 mL) and sodium methoxide solution (20 mL, 0.5 M in MeOH) is added to that and stir the mixture overnight. Neutralize the reaction mixture with AcOH and remove the solvents under reduced pressure. Purify the residue by silica gel chromatography to get the required product 324.

Preparation of 325:

Mannose trichloroacetimidate 321 (15.00 g, 20.24 mmol) and azido alcohol 306 (4.25 g, 1.2 eq) were dissolved in Toluene and aziotroped twice. The residue dried under high vacuum overnight Anhydrous diethyl ether (30 mL) and Molecular sieves (10 g) were added to mixture. Reaction mixture was cooled in an ice-water bath. TMSOTf (0.5 mL, 0.1 eq) was added and stirred the mixture for 10 minutes. Reaction was monitored by TLC and quenched with TEA. Filtered of the molecular sieves and solvents were removed under reduced pressure. Residue was purified by silica gel column chromatography (20-50% EtOAc/Hexane) to obtain compound 325 as colorless liquid (8.36 g, 55%). $^1$H NMR (DMSO-$d_6$, 400 MHz) δ=8.05 (d, J=7.2 Hz, 2H), 7.19-7.92 (m, 18H), 6.00 (t, J=10.4 Hz, 1H), 5.72 (dd, J=3.2, 10.4 Hz, 1H), 5.62 (dd, J=2, 3.2 Hz, 1H), 5.25 (d, J=1.6 Hz, 1H), 4.50-4.65 (m, 3H), 3.60-3.95 (m, 10H), 3.36 (t, J=4.8 Hz, 2H). MS: MW Calc. for $C_{40}H_{39}N_3O_{12}$: 753.25. Found 776.23 (M+Na).

Preparation of 326:

Compound 319 (5.30 g, 7.03 mmol) was dissolved in a mixture of DCM/MeOH (1:2, 50 mL) and sodium methoxide solution (70 mL, 0.5 M in MeOH) was added to that and stir the mixture overnight. Neutralize the reaction mixture with AcOH and removed the solvents under reduced pressure. Residue was purified by silica gel chromatography (DCM, 20% MeOH/DCM) to get the required product 320 as a color less liquid (1.98 g, 84%). MS: MW Calc. for $C_{12}H_{23}N_3O_8$: 337.15. Found 360.15 (M+Na)

Scheme 15

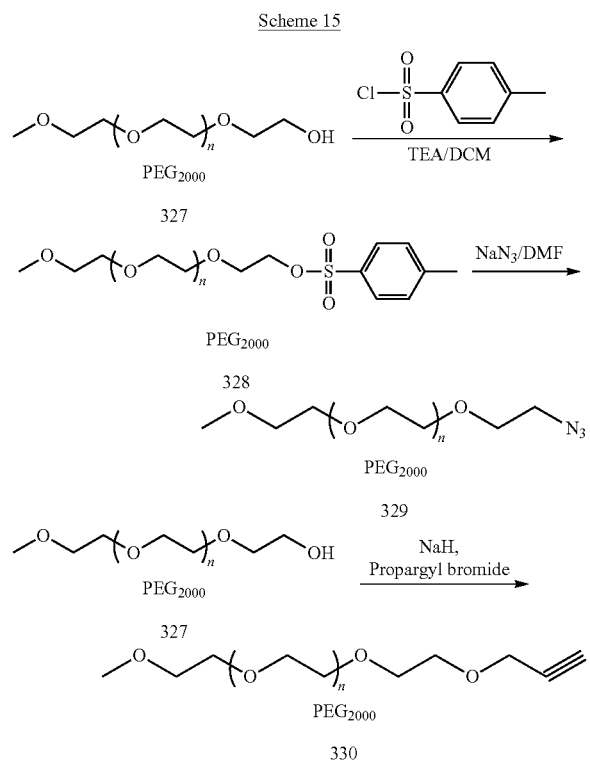

Preparation of 329:

mPEG$_{2000}$ (20.00 g, 10.00 mmol) and TEA (4.08 mL, 3 eq) were dissolved in DCM (100 mL) and cooled in an ice bath. To that a solution of tosyl chloride (3.00 g, 1.45 eq) in DCM (20 mL) was added drop wise and stirred the mixture overnight. Diluted with DCM, washed with water and saturated sodium bicarbonate solution. Dried over sodium sulfate and removed the solvent in vacuo to get the required tosylate 328. Tosylate and NaN$_3$ (25 g) were taken in DMF and heated at 100° C. in pressure bottle overnight. Transferred to an RB flask and removed the solvent under reduced pressure. Triturated with DCM and filtered through sintered funnel washed with DCM. Crude product was purified by silica gel chromatography to get the required product as a white powder (18.10 g, 82%).

Preparation of 330:

mPEG$_{2000}$ 327 (20.00 g, 10.00 mmol) was dissolved in DMF (100 ml) and cooled in ice bath. NaH (1.00 g, excess, 60%) was added and stirred the mixture for 30 minutes. Propargyl bromide (3.00 g, 1.5 eq) and TBAI (2.00 g) were added and stirred mixture overnight. Quenched with ice cold water and removed the solvents under reduced pressure. Dissolved the residue in DCM and washed with water and dried over sodium sulfate. Crude product was purified by silica gel chromatography to get the required product 330 (18.20 g, 81%) as pale brown solid.

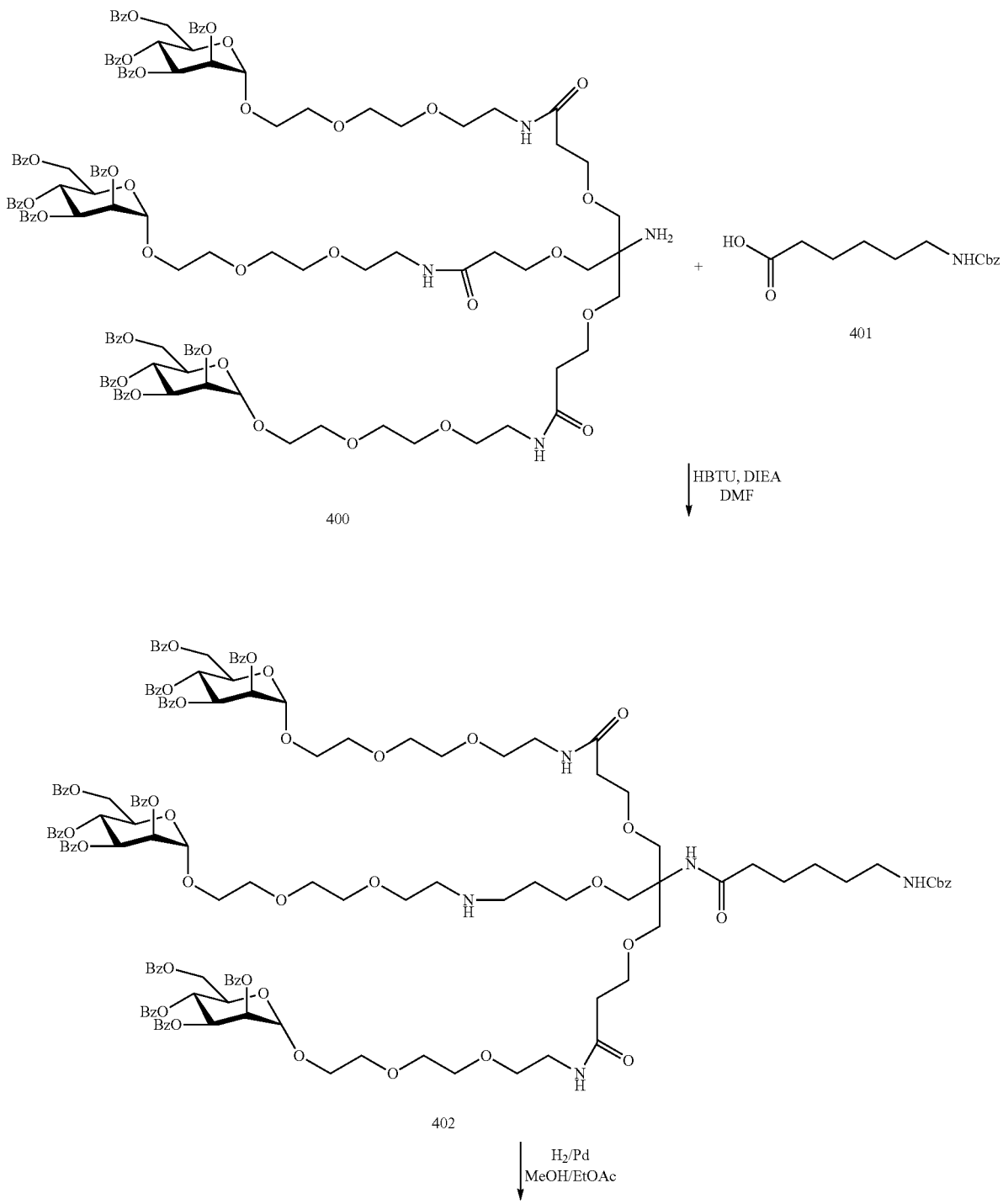

Scheme 16

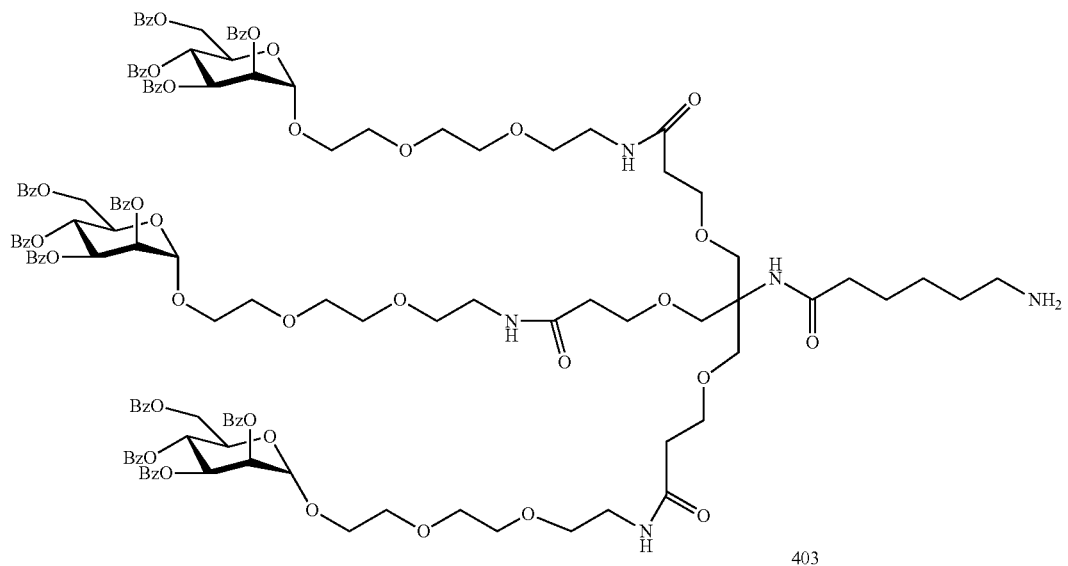
403
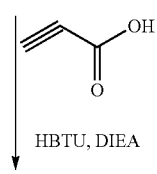
HBTU, DIEA

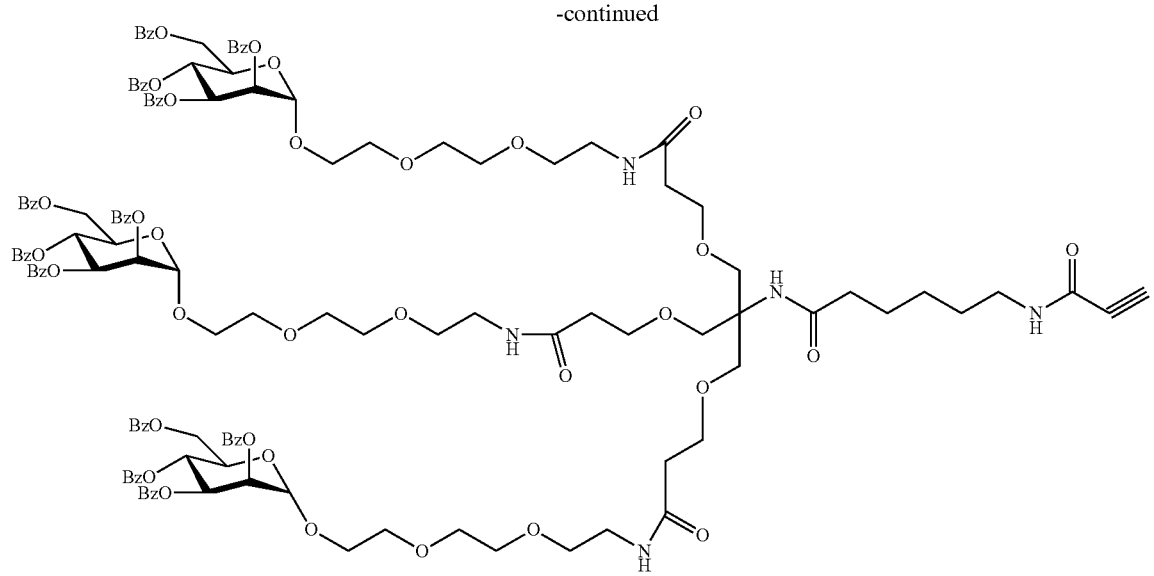
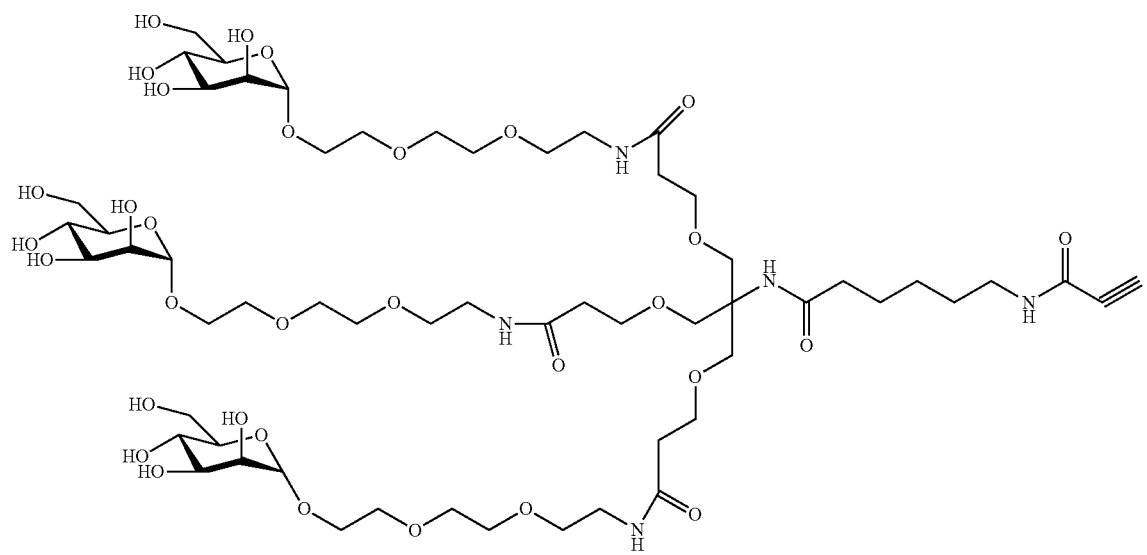

Preparation of 402:

Z-amino caproic acid 401 (1.00 g, 3.76 mmol) is dissolved in DMF (50 mL). To that HBTU (1.43 g, 3.76 mmol) and DIEA (3.26 mL, 5.00 eq.) is added and stir the mixture for few minutes. Dissolve mannose amine 400 (7.41 g, 3.00 mmol) in 50 ml of DMF and add that to the reaction mixture, stir for 48 hrs. Solvents are removed in vacuo and the residue dissolve in DCM, wash with NaHCO$_3$ solution and water. Dry over anhydrous sodium sulfate and the solvents are removed under reduced pressure. Purify the compound by silica gel chromatography to get the required compound 402.

Preparation of 403:

Took compound 402 (3.00 g, 1.10 mmol) in methanol (50 mL), to that 1 mL of acetic acid is added. Hydrogenate under balloon pressure using Pd/C (0.300 g, 10 wt % Degussa wet type) to get the compound 403.

Preparation of 404:

Compound 403 (2.00 g, 0.776 mmol) reacts with propynoic acid under peptide coupling conditions to get the compound 404.

Preparation of 405:

Compound 404 (1.00 g, 0.380 mmol) is dissolved in MeOH (10 mL) and sodium methoxide solution (10 mL, 0.5 M in MeOH) is added to that and stir the mixture overnight. Reaction is monitored by TLC and the mixtures pass through a column of CM Sepharose resin. Wash with MeOH and remove the solvents in vacuo to get the product 405.

Scheme 17

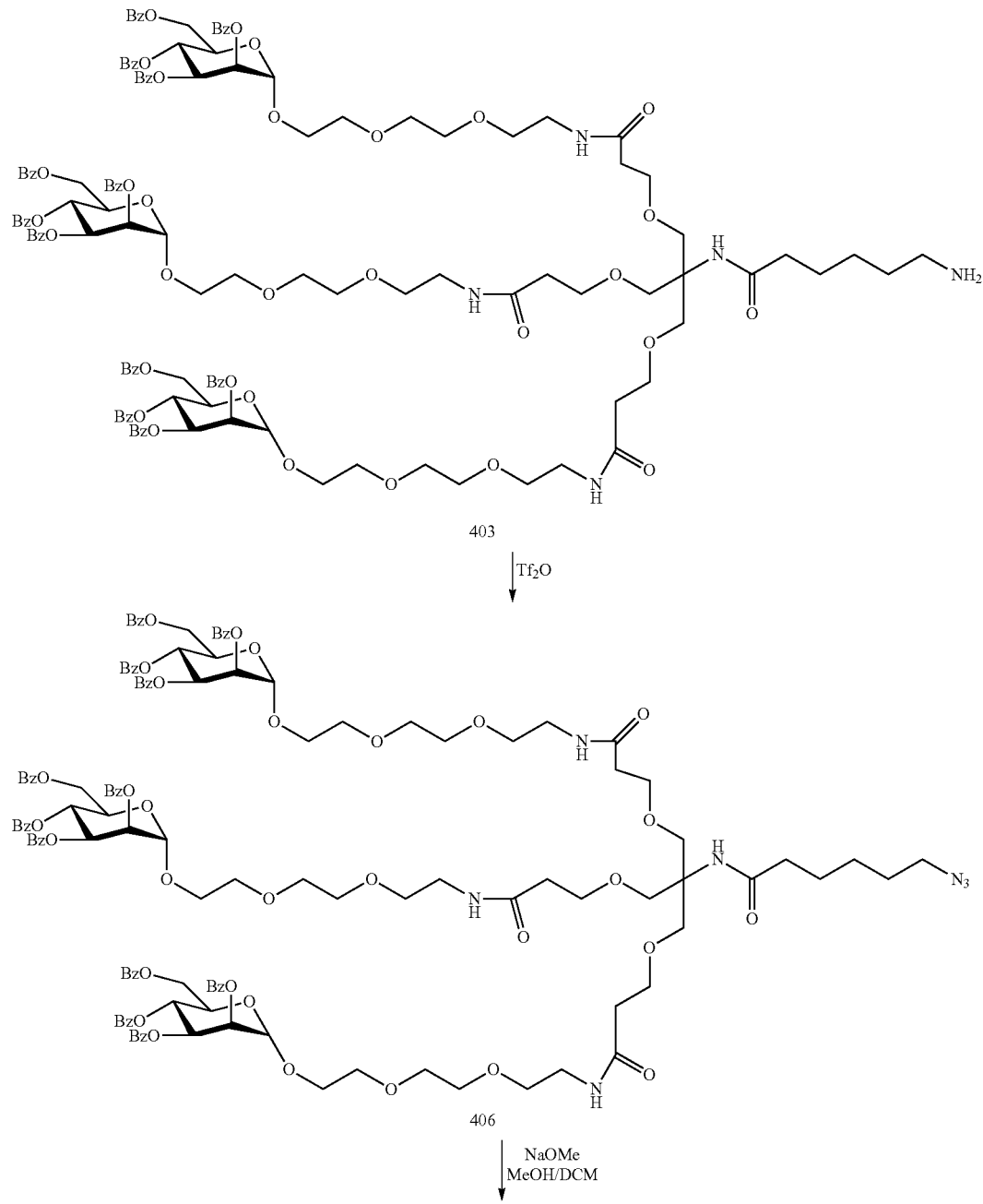

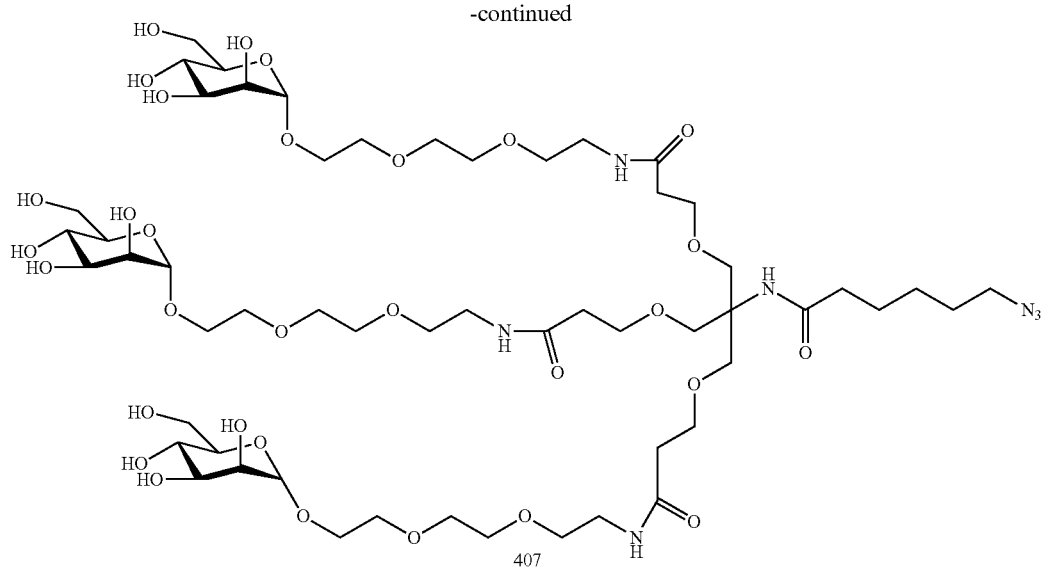

407

Preparation of 406:
Compound 403 (2.00 g, 0.776 mmol) reacts with Triflic anhydride and sodium azide to get the compound 406.

Preparation of 407:
Compound 406 (1.00 g, 0.384 mmol) is dissolved in MeOH (10 mL) and sodium methoxide solution (10 mL, 0.5 M in MeOH) is added to that and stir the mixture overnight. Reaction is monitored by TLC and the mixtures pass through a column of CM Sepharose resin. Wash with MeOH and remove the solvents in vacuo to get the product 407

Scheme 18

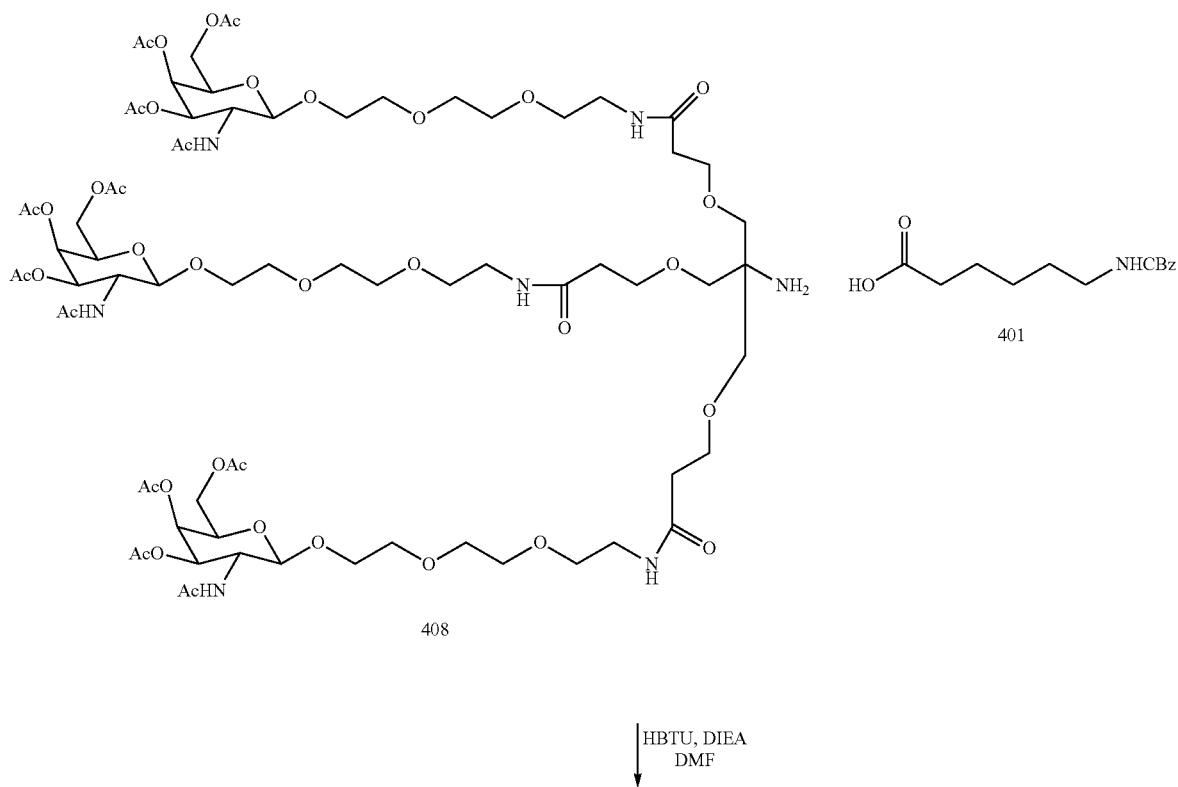

408

401

HBTU, DIEA
DMF

123
124
-continued
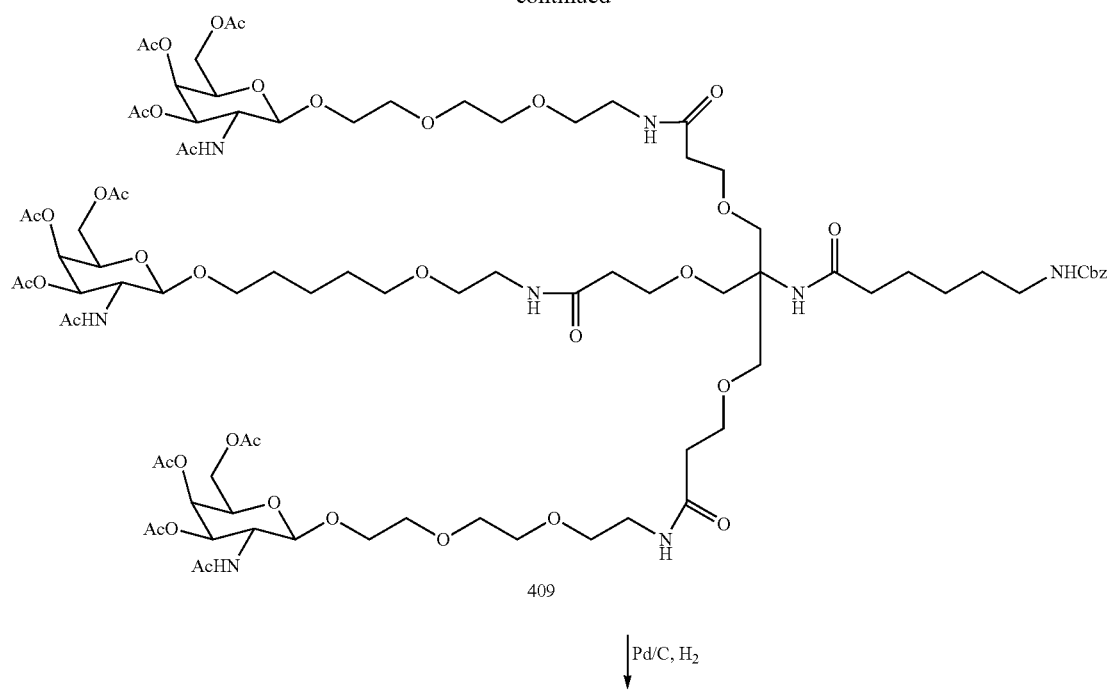
409
↓ Pd/C, H₂
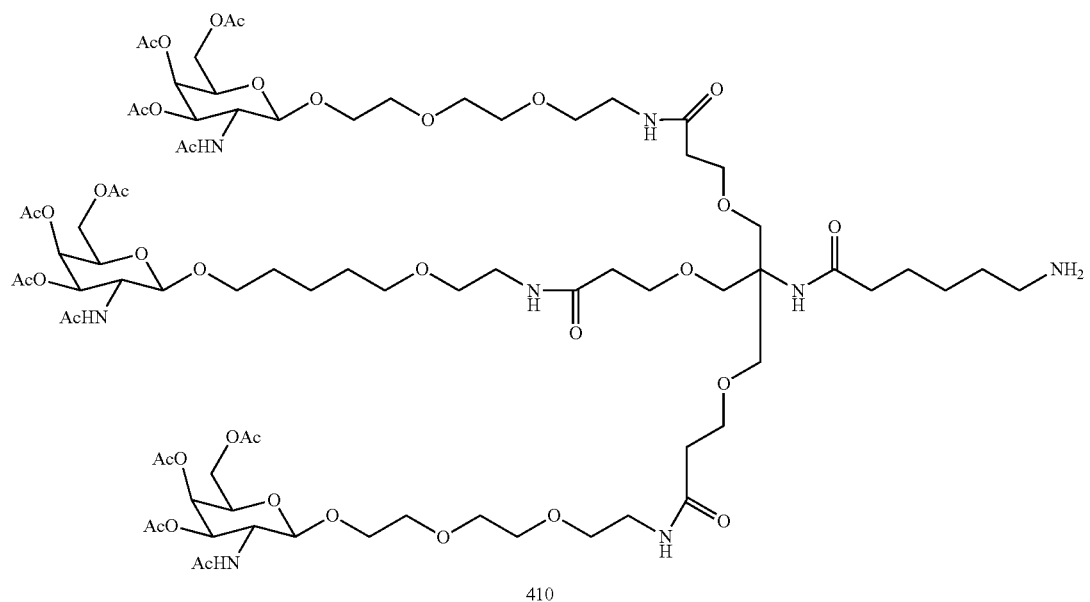
410
↓ Tf₂O, NaN₃

-continued

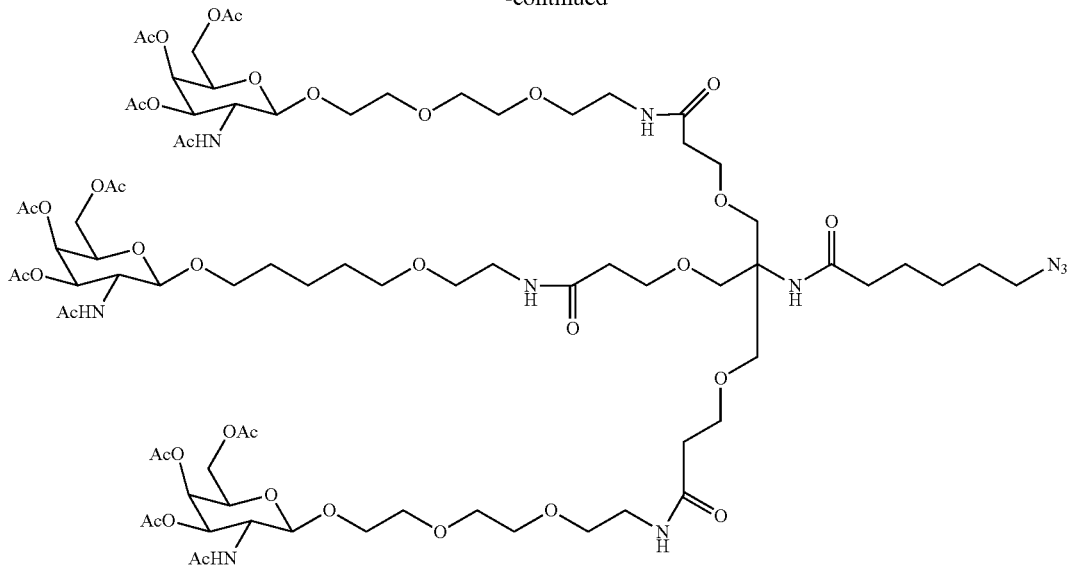

411

↓ NaOMe, MeOH

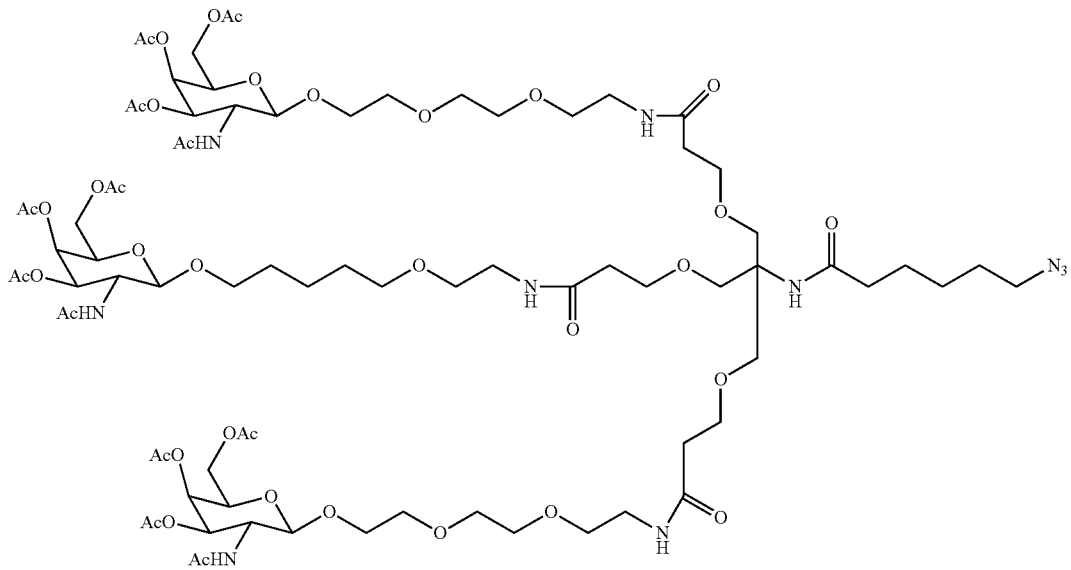

412

Preparation of 409:

Z-amino caproic acid 401 (2.19 g, 8.25 mmol) was dissolved in DMF (50 mL). To that HBTU (3.13 g, 8.25 mmol) and DIEA (7.19 mL, 5.00 eq.) was added and stirred the mixture for few minutes. GalNAc amine 408 (10.10 g, 5.52 mmol) was dissolved in 50 ml of DMF and was added to reaction mixture, stirred for 48 hrs. TLC and MALDI were checked for product formation. Solvents were removed in vacuo and the residue was dissolved in DCM, washed with NaHCO$_3$ solution and water. Dried over anhydrous sodium sulfate and the solvents were removed under reduced pressure. Residue was purified by silica gel column chromatography (eluted with ethyl acetate, followed by gradient elution of 5-15% MeOH/DCM) to get the required compound 409 as off white solid (6.20 g, 57%). $^1$HNMR (DMSO-d$_6$ 400 MHz) δ=7.89 (t, J=5.12 Hz, 3H), 7.80 (d, J=9.27 Hz, 3H), 7.15-7.40 (m, 7H), 5.20 (d, J=3.41 Hz, 3H), 4.98 (s, 2H), 4.95 (dd, J=3.40, 11.30 Hz, 3H), 4.54 (d, J=8.64 Hz, 3H), 3.72-4.10 (m, 12H), 3.10-3.65 (m, 52H), 2.28 (t, J=6.20 Hz, 6H), 2.09 (s, 9H), 1.98 (s, 9H), 1.88 (s, 9H), 1.76 (s, 9H), 1.09-1.30 (m, 6H). MS: MW Calc. for $C_{87}H_{136}N_8O_{42}$: 1964.88. Found 1987.75 (M+Na).

Preparation of 410:

Compound 409 (6.10 g, 3.10 mmol) was dissolved in methanol (50 mL), to that 1 mL of acetic acid was added. Degassed the reaction mixture, Pd/C (0.700 g, 10 wt %

Degussa wet type) was added to the solution and hydrogenated under balloon pressure for 36 hrs. Reaction mixture was filtered through a small pad of celite, washed with MeOH. To the filtrate, 1.25 eq of TFA and toluene (50 mL) were added and solvents removed under reduced pressure. The residue was co-evaporated with toluene two times and dried under high vacuum overnight night to get the required compound 410 as an off white solid (6.10 g, quantitative). This compound used as such for the next reaction with out any further purification. MS: MW Calc. for $C_{79}H_{130}N_8O_{40}$: 1830.84. Found 1853.81 (M+Na).

Preparation of 411:

Compound 410 (2.00 g, 1.09 mmol) reacts with $Tf_2O$ and sodium azide to get compound 411.

Preparation of 412:

Compound 411 (1.00 g, 0.539 mmol) is dissolved in MeOH (10 mL) and sodium methoxide solution (10 mL, 0.5 M in MeOH) is added to that and stir the mixture overnight. Reaction is monitored by TLC and the mixtures pass through a column of CM Sepharose resin. Wash with MeOH and remove the solvents in vacuo to get the product 412.

Scheme 19
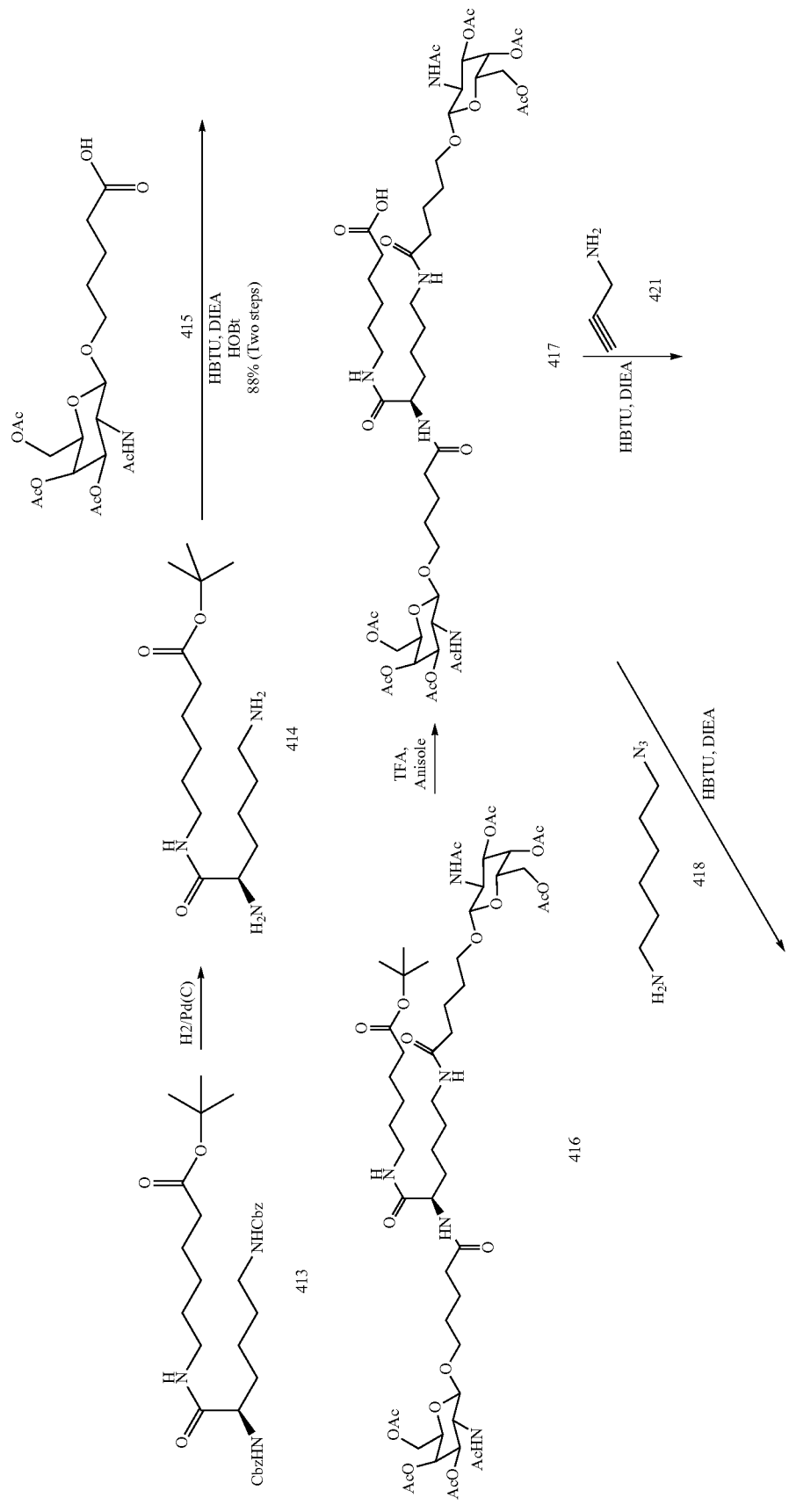

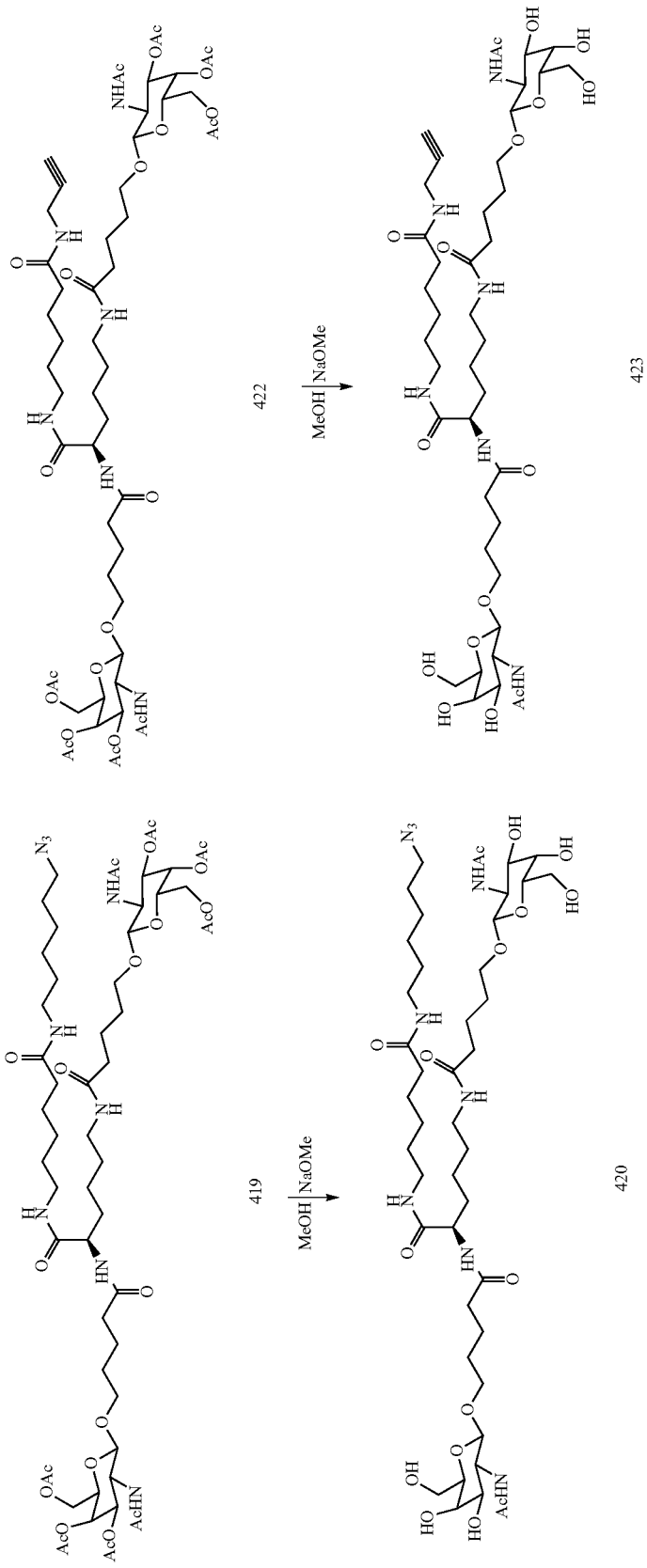

Preparation of 414:

Compound 413 (3.30 g, 5.65 mmol) was dissolved in a mixture of MeOH/EtOAc (60 mL, 1:2); Pd/C (500 mg, Degussa wet type) was added and hydrogenated under balloon pressure over night. Filtered the reaction mixture through a small pad of celite and removed the solvents to get the required product 414. The crude product used for the next reaction with out further purification. MS: MW Calc. for $C_{16}H_{33}N_3O_3$: 315.25. Found 316.22 (M+H)

Preparation of 416:

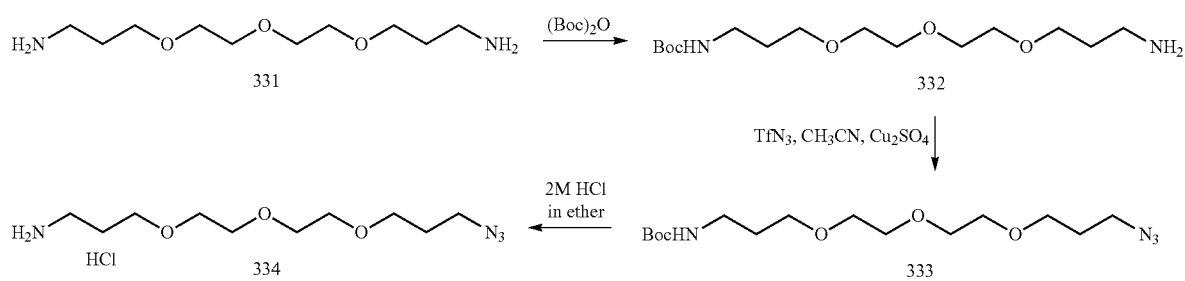

Scheme 20

GalNAc acid 415 (5.81 g, 12.99 mmol) and HBTU (4.976 g, 13.02 mmol) were dissolved in DMF (50 mL) to that DIEA (6.79 mL, 5 eq) was added and stirred the mixture for few minutes. To that a solution of compound 414 in DMF was added and stirred overnight at room temperature. Solvents were removed in vacuo and the residue was dissolved in DCM, washed with $NaHCO_3$ solution and water. Dried over anhydrous sodium sulfate and the solvents were removed under reduced pressure. Residue was purified by silica gel column chromatography (eluted with ethyl acetate, followed by gradient elution of 3-10% MeOH/DCM) to get the required compound 416 as off white solid (5.25 g, 79%). MS: MW Calc. for $C_{54}H_{87}N_5O_{23}$: 1173.58. Found 1196.60 (M+Na).

Preparation of 417:

Compound 416 (5.15 g, 4.40 mmol) was dissolved in DCM (30 mL) to that TFA (30 ml in 20 mL of DCM) was added and stirred for 2 hr's at room temperature. TLC checked and removed the solvents. Co-evaporated with toluene two times and dried under high vacuum. Crude product used for the next reaction. MS: MW Calc. for $C_{50}H_{79}N_5O_{23}$: 1117.52. Found 1140.55 (M+Na).

Preparation of 419:

Compound 419 is prepared from 418 and 417 using HBTU mediated peptide coupling.

Preparation of 420:

Compound 419 (1.00 g, 0.805 mmol) is dissolved in MeOH (10 mL) and sodium methoxide solution (10 mL, 0.5 M in MeOH) is added to that and stir the mixture overnight. Reaction is monitored by TLC and the mixtures pass through a column of CM Sepharose resin. Wash with MeOH and remove the solvents in vacuo to get the product 420.

Preparation of 422:

Compound 422 is prepared from 421 and 417 using HBTU mediated peptide coupling.

Preparation of 423:

Compound 422 (1.00 g, 0.866 mmol) is dissolved in MeOH (10 mL) and sodium methoxide solution (10 mL, 0.5 M in MeOH) is added to that and stir the mixture overnight. Reaction is monitored by TLC and the mixtures pass through a column of CM Sepharose resin. Wash with MeOH and remove the solvents in vacuo to get the product 423.

Example 8

Folate Building Blocks for Click-Chemistry

In order to synthesize azido functional group containing folate conjugates the following strategy was used. The azido amine tether 334 was synthesized starting from the commercially available diamine 331 as shown in Scheme 10.

Synthesis of Amine 332:

A solution of $(Boc)_2O$ (66 g, 0.303 mol) in dioxane (1 L) was added in a dropwise fashion over 4 h to a cooled (0° C.) solution of the diamine (400 g, 1.82 mol) in dioxane (1 L), and the mixture was stirred at room temperature overnight. Aqueous workup then column chromatography provided the pure mono Boc amine 332 (83 g, 86%). MS: MW Calc. for $C_{15}H_{32}N_2O_5$: 320.42. Found 321.41 (MH$^+$).

Synthesis of Azide 333:

The triflic azide stock solution was prepared as reported in *Tetrahedron Letters* 47 (2006) 2382-2385. The amine (0.96 g, 3 mmol), sodium bicarbonate (0.85 mg, 10 mmol) and copper (II) sulfate pentahydrate (22 mg, 0.1 mmol) were dissolved in water (3 mL). Triflic azide stock solution (5 mL) was added, followed by the addition of methanol (20 mL) to yield a homogeneous system. The blue mixture was stirred for 30 min after which the TLC and MS showed the complete disappearance of starting amine. The reaction mixture was concentrated in a rotary evaporator and the residue was purified by chromatography on silica gel (eluent: dichloromethane-methanol) to obtain the pure azide 333 (1 g, 96%) as an oil. MS: MW Calc. for $C_{15}H_{30}N_4O_5$: 346.42. Found 347.41 (MH$^+$). $^1$HNMR (CDCl$_3$, 400 MHz) δ=4.68 (bs, 1H), 3.40-3.30 (m, 12H), 3.16 (t, J=6.4 Hz, 2H), 3.00-2.95 (m, 2H), 1.68-1.54 (m, 4H), 1.04 (s, 9H).

Synthesis of 334:

The azide 333 (1 g, 2.88 mmol) was dissolved in ethanol (10 mL) and to this a 2M solution of HCl in ether was added and the mixture was stirred at room temperature overnight. The MS showed the absence of starting material. The reaction mixture was concentrated and the thus obtained oil was used as such for the next reaction without further purification. MS: MW Calc. for $C_{10}H_{23}ClN_4O_3$: 246.17. Found 247.17 (WH$^+$). $^1$HNMR (DMSO-d$_6$ 400 MHz) δ=8.96 (bs, 1H), 7.92 (bs, 2H), 3.52-3.40 (m, 12H), 3.37 (t, J=6.8 Hz, 2H), 2.85-2.77 (m, 2H), 1.81-1.70 (m, 4H).

The commercially available pteroic acid 335 was transiently protected with t-butyldiphenyl silyl group and treated with isobutyric anhydride followed by acidic workup provided the exocyclic amine protected pteroic acid 336 which on coupling with methyl t-butyl ester of glutamic acid provided the fully protected folic acid 338. Hydrolysis of the t-butyl ester with TFA provided the acid 339 which was coupled with the azido amine tether 334 to give the couple product 340 as an oil. Treatment of this compound with lithium hydroxide followed by methylamine provided the azido compound 341.

Synthesis of 336:

To a suspension of pteroic acid (25 g, 61.2 mmol) and DMAP (11.25 g, 92 mmol) in anhydrous pyridine (400 mL), TBDPS chloride (42 g, 153 mmol) was added. The reaction mixture was stirred at room temperature for 30 h after which isobutric anhydride (14.6 g, 92 mmol) was added and the mixture was slightly warmed. An additional 60 mL of pyridine was also added and the reaction mixture was stirred at room temperature overnight. The reaction mixture became homogenous after which pyridine and other volatiles were concentrated in a rotary evaporator. The residue was stirred with EtOAc (1 L) and acetic acid (100 mL) and water (500 mL) for 24 h. The thus obtained slurry was filtered, the residue was washed with water (500 mL), EtOAc (1 L) and dried to obtain the pure product as a white solid (26.1 g, 89%). $^1$H NMR (DMSO-d$_6$, 400 MHz) δ=8.87 (s, 1H), 7.95 (d, J=8.6 Hz, 2H), 7.67 (d, J=8.6 Hz, 2H), 5.21 (s, 2H), 2.79-2.74 (m, 1H), 1.12 (d, J=6.83 Hz, 6H), $^{13}$C NMR (DMSO-d$_6$) δ=180.72, 166.49, 159.25, 149.87, 147.68, 142.69, 136.34, 134.45, 130.54, 129.16, 128.86, 127.49, 34.96, 33.09, 26.52, 18.88, 18.74. $^{19}$F NMR (DMSO-d$_6$) δ—64.32. MS. Molecular weight calculated for $C_{20}H_{17}F_3N_6O_5$, Cal. 478.12. Found 479.12 (MH$^+$).

Synthesis of 338:

In a representative procedure, the pteroic acid precursor 336 (2.4 g, 5 mmol) was dissolved in anhydrous DMF (20 mL), HBTU (1.9 g, 1 eq.) followed by DIEA (1 mL, 5 eq.) were added and stirred for 20 minutes. To this reaction mixture the amine hydrochloride 337 (1.2 g, 1 eq) was added as a solution in DMF (6 mL). Reaction was monitored by TLC (8% MeOH/DCM, PMA stain). TLC of the reaction mixture showed completion of the reaction. The reaction mixture was slowly poured in ice with vigorous stirring. The precipitated product was filtered to get the product 338 as a white solid (Yield=2.85 g, 86%). $^1$H NMR (DMSO-d$_6$, 400 MHz) δ=12.33 (s, 1H), 11.94 (s, 1H), 8.88 (s, 1H), 8.82 (d, J=7.3 Hz, 1H), 7.90 (d, J=8.6 Hz, 2H), 7.68 (d, J=8.4 Hz, 2H), 5.22 (s, 2H), 4.46-4.40 (m, 1H), 3.62 (s, 3H), 2.86-2.73 (m, 1H), 2.32 (t, J=7.4 Hz, 2H) 2.05-1.90 (m, 2H), 1.35 (m, 9H), 1.12 (d, J=6.8 Hz, 6H). $^{13}$C NMR DMSO-d$_6$) δ=180.75, 172.13, 171.45, 165.64, 159.10, 154.80, 149.97, 149.79, 147.72, 141.75, 134.15, 130.53, 128.70, 128.49, 117.50, 114.64, 79.79, 51.96, 51.91, 34.96, 31.22, 27.68, 25.71, 18.72. MS. Molecular weight calculated for $C_{30}H_{34}F_3N_7O_8$, Cal. 677.63. Found 676.72 (M−H).

Synthesis of 339:

The ester 338 (2 g, 2.9 mmol) was dissolved in 20 mL of 50% TFA in dichloromethane and the solution was stirred at room temperature for 30 min. after which the TLC showed the complete disappearance of the starting ester. The reaction mixture was concentrated and the residue was crystallized from CH$_2$Cl$_2$:Hexanes (2:3) and crystallized product was filtered off and dried to obtain the pure product 339 (1.76 g, 96%) as off white powder. $^1$H NMR (DMSO-d$_6$, 400 MHz) δ=12.32 (bs, 1H), 11.94 (s, 1H), 8.88 (s, 1H), 8.84 (d, J=7.4 Hz, 1H), 7.90 (d, J=8.3 Hz, 2H), 7.69 (d, J=8.3 Hz, 2H), 5.22 (s, 2H), 4.45-4.41 (m, 1H), 3.62 (s, 3H), 2.78-2.75 (m, 1H), 2.35 (t, J=7.4 Hz, 2H) 2.07-1.92 (m, 2H), 1.12 (d, J=6.8 Hz, 6H). $^{13}$C NMR DMSO-d$_6$) δ=180.77, 173.70, 172.19, 165.70, 159.21, 155.54, 149.93, 149.84, 147.75, 141.78, 134.18, 130.53, 128.71, 128.49, 117.51, 114.64, 53.98, 52.06, 51.93, 34.97, 30.11, 25.68, 18.73. MS. Molecular weight calculated for $C_{26}H_{26}F_3N_7O_8$, Cal. 621.18. Found 620.18 (M−H$^−$).

Synthesis of 340:

Coupling of the amine 334 (0.6 g) with the acid 339 (1.2 g) using a similar procedure to that used for the synthesis of 338 provided the coupled azide 340 (1.68 g, 93%) as a light yellow foam. $^1$H NMR (DMSO-d$_6$, 400 MHz) δ=12.34 (s, 1H), 11.95 (s, 1H), 8.89 (s, 2H), 7.92 (d, J=8.4 Hz, 2H), 7.81 (m, 1H), 7.70 (d, J=8.4 Hz, 2H), 5.22 (s, 2H), 4.40-4.34 (m, 1H), 3.62 (s, 3H), 3.50-3.31 (m, 15H), 3.09-3.00 (m, 2H), 2.80-2.72 (m, 1H), 2.20 (t, J=7.4 Hz, 2H) 2.10-1.89 (m, 2H), 1.76-1.54 (m, 4H), 1.12 (d, J=6.8 Hz, 6H). MS. Molecular weight calculated for $C_{36}H_{46}F_3N_{11}O_{10}$, Cal. 849.81. Found 850.2 (MH$^+$).

Synthesis of 341:

The azide 340 (1 g) was dissolved in THF (20 mL) and to it an aqueous solution of lithium hydroxide (100 mg in 2 mL of water) was added and the solution was stirred at room temperature for 4 h after which the MS showed the complete disappearance of SM. The reaction mixture was acidified to pH 5 using acetic acid and the RM was diluted with ethyl acetate (100 mL). The precipitated product was filtered off and washed with water and ethyl acetate and dried under vacuo at 40° C. overnight to get the pure azide 341 (0.455 g 55%) as an orange solid. $^1$H NMR (DMSO-d$_6$, 400 MHz) δ=8.59 (s, 1H), 7.85 (bs, 1H), 7.72 (bs, 1H), 7.56 (d, J=8.4 Hz, 2H), 6.88 (bs, 1H), 6.65 (d, J=8.4 Hz, 2H), 4.45 (s, 2H), 4.00-4.02 (m, 1H), 3.50-3.33 (m, 14H), 3.04-3.00 (m, 2H), 2.07-1.83 (m, 4H), 1.76-1.54 (m, 4H). MS. Molecular weight calculated for $C_{29}H_{39}N_{11}O_8$, Cal. 669.69. Found 668.2 (M−H).

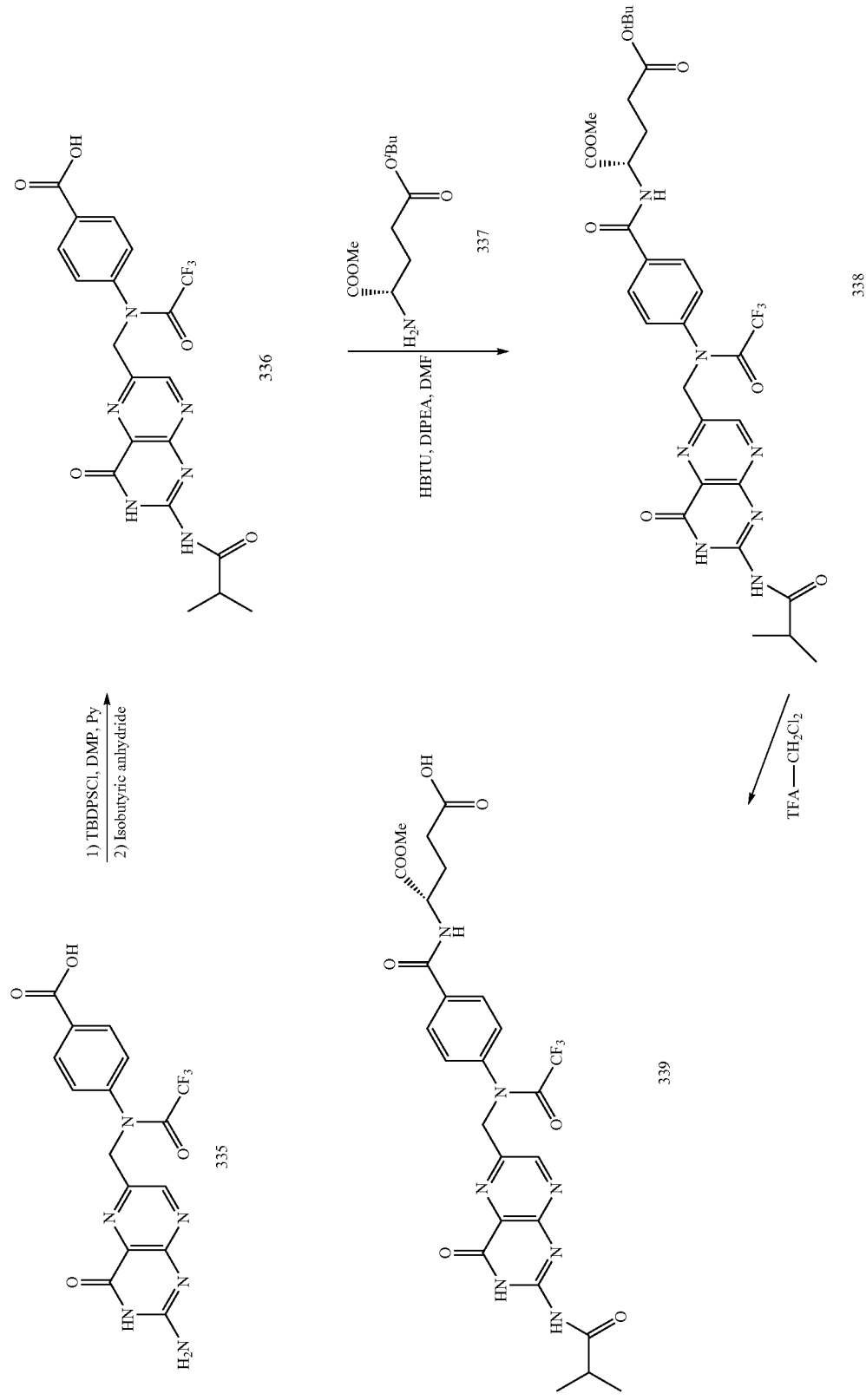
Scheme 21

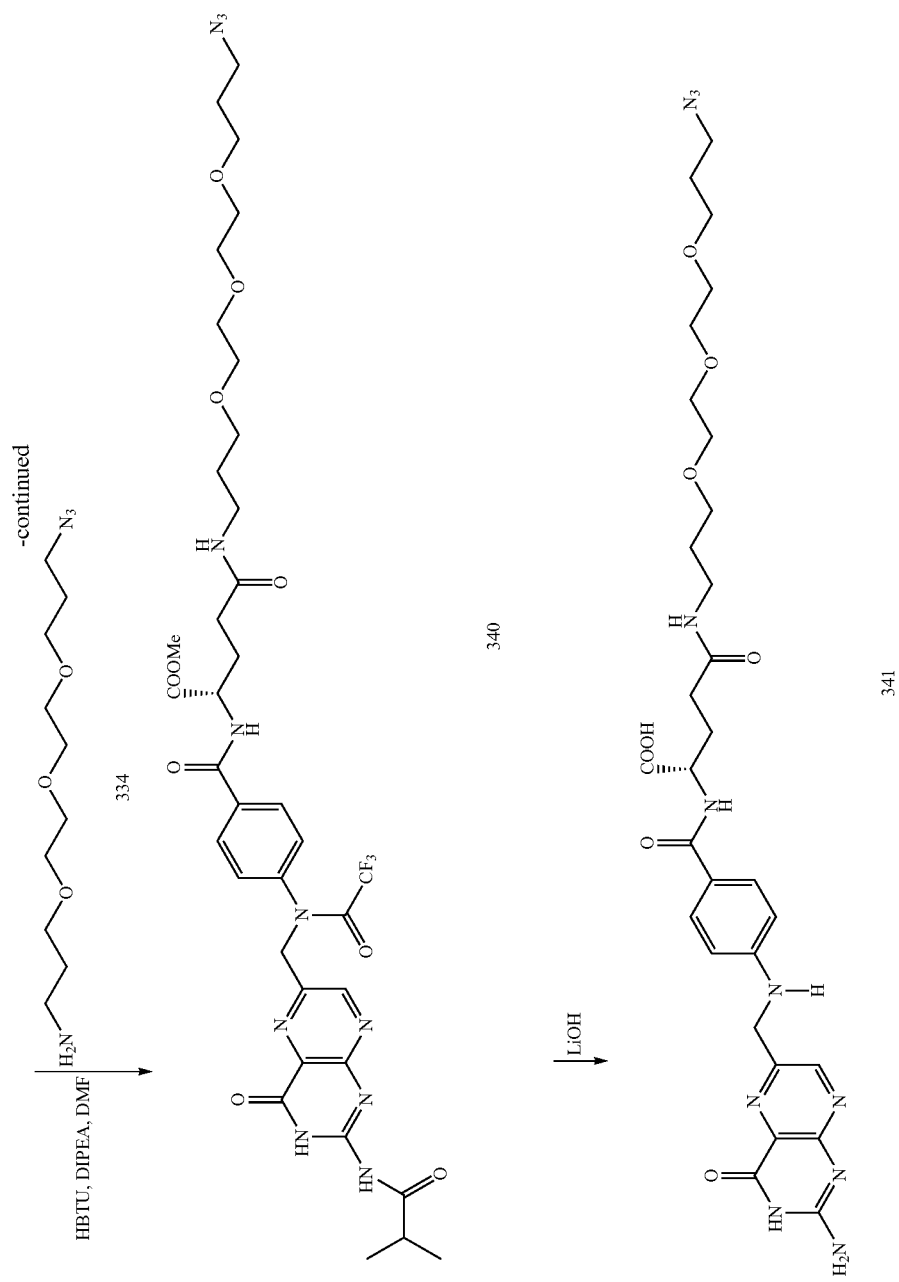

In another embodiment, we have synthesized the alkyne containing folic acid is synthesized as follows. In this case the protected pteroic acid 335 was coupled with the protected lysine 342 to get the coupled product 343 which on Cbz deprotection provided the amine 344. Coupling of the amine 344 with the acid 350 provided the coupled product 345 which after purification and deprotection provided the product 346 as described below.

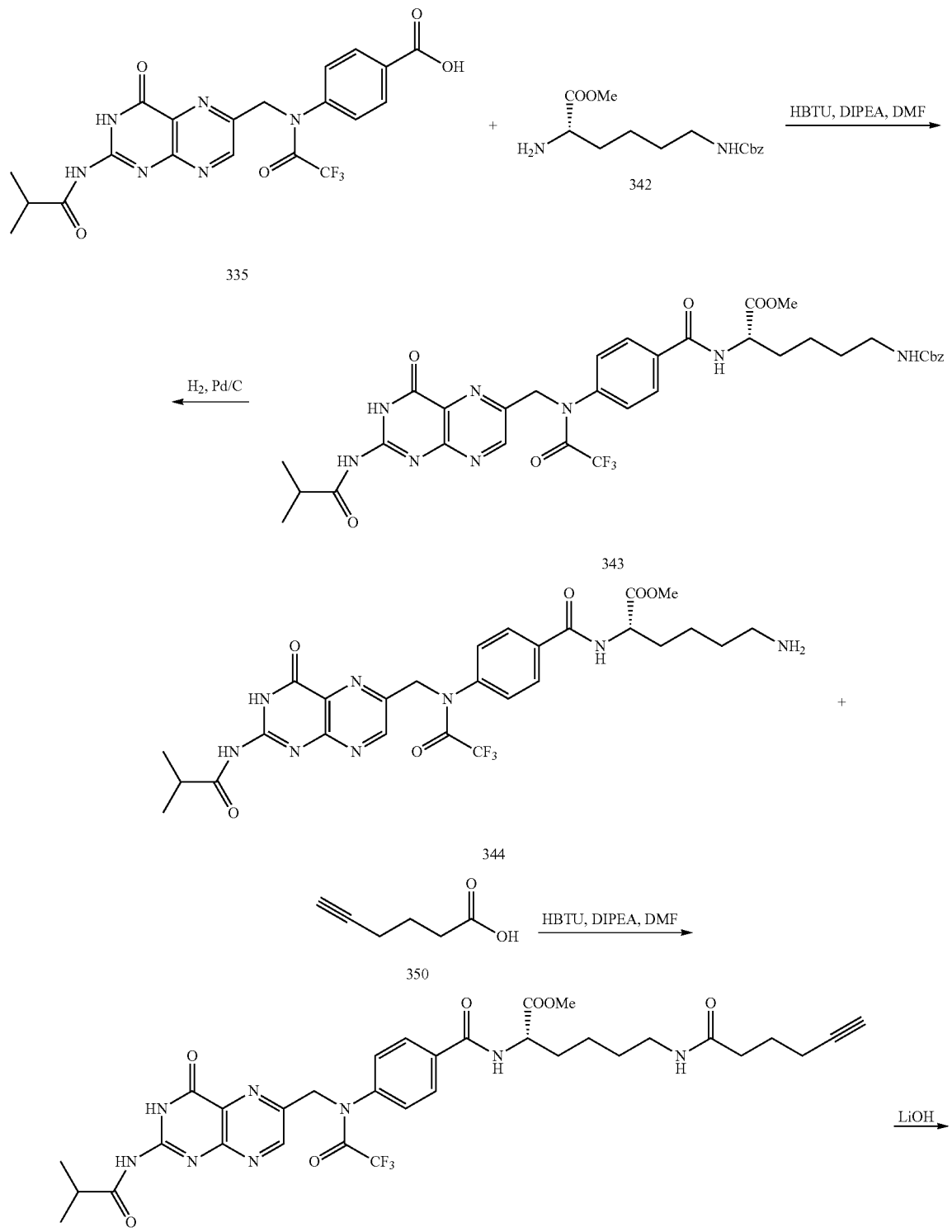

Scheme 22

-continued

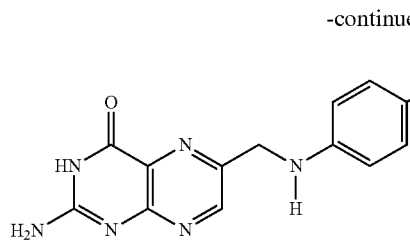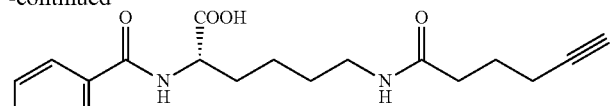

346

Synthesis of 343:
Using a similar procedure to that used for the synthesis of 338, coupling of the acid 335 with the lysine derivative 342 provided the coupling product 343 as a white solid in 95% yield.

Synthesis of 344:
The compound 343 on hydrogenation with Pd/C provided the deprotected amine 344 as a yellow solid.

Synthesis of 345:
Coupling of the amine 344 with the acid 350 using a procedure to that used for the synthesis of 338 provided the couple product 345 in high yields.

Synthesis of 346:

The deprotection of the protecting groups is achieved using a similar procedure as described for the synthesis of 341 to isolate the fully deprotected alkyne 346.

In another embodiment the folate conjugated oligo building block is synthesized as follows. The synthesis of the building block 362 is carried out using a similar procedure to that of 115 and the synthesis of the amidite is carried out as described for the synthesis of 121.

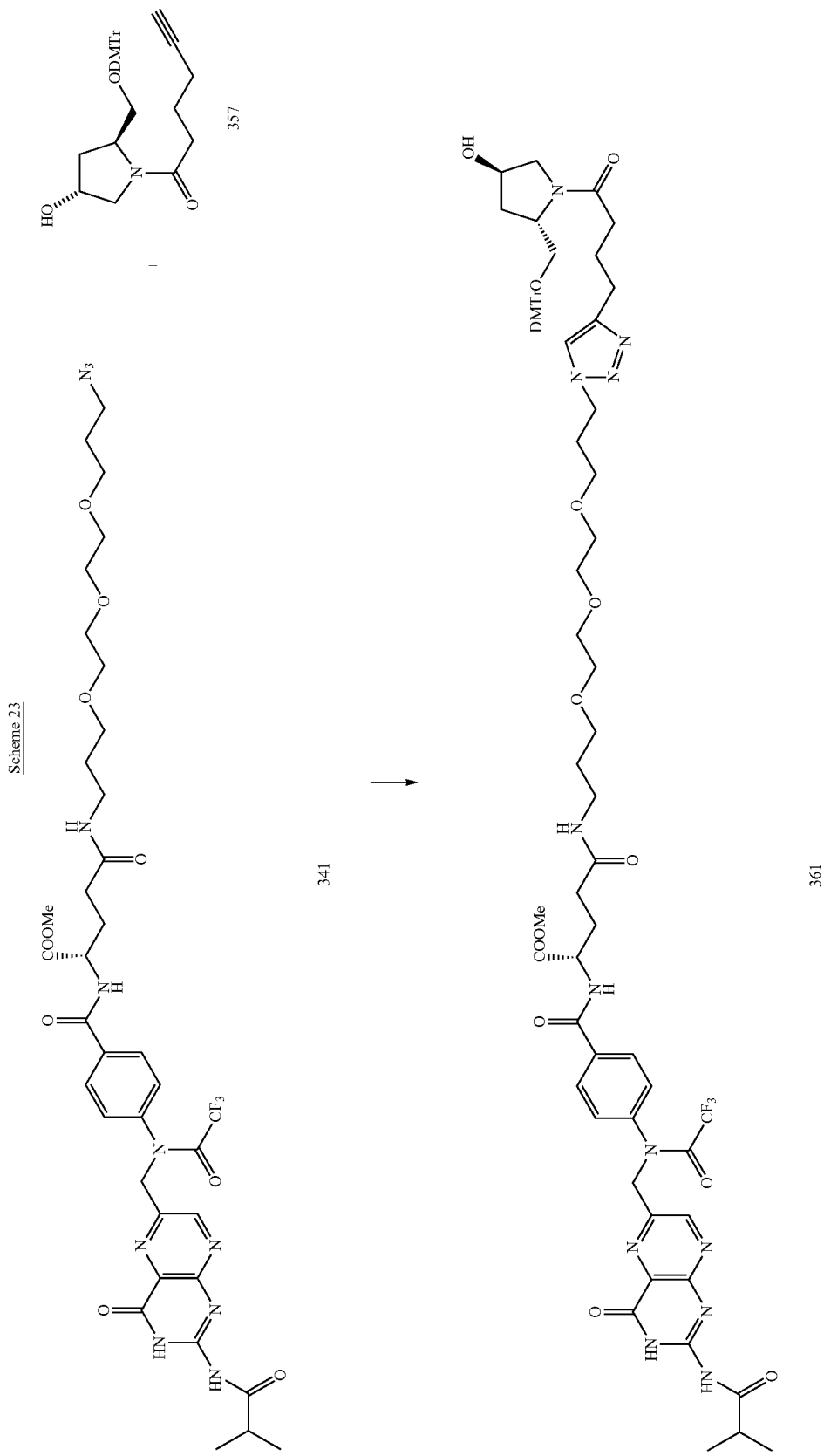

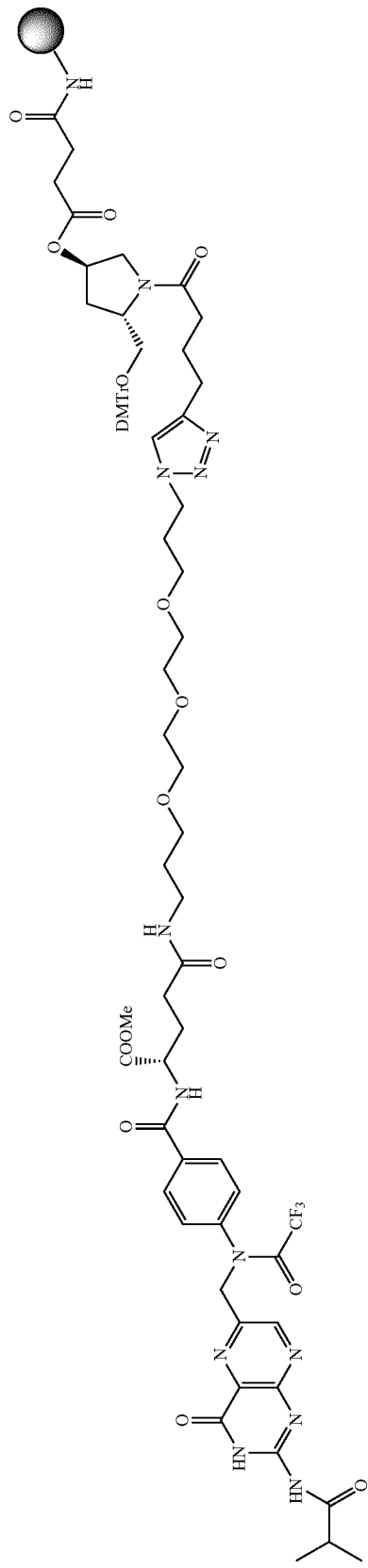

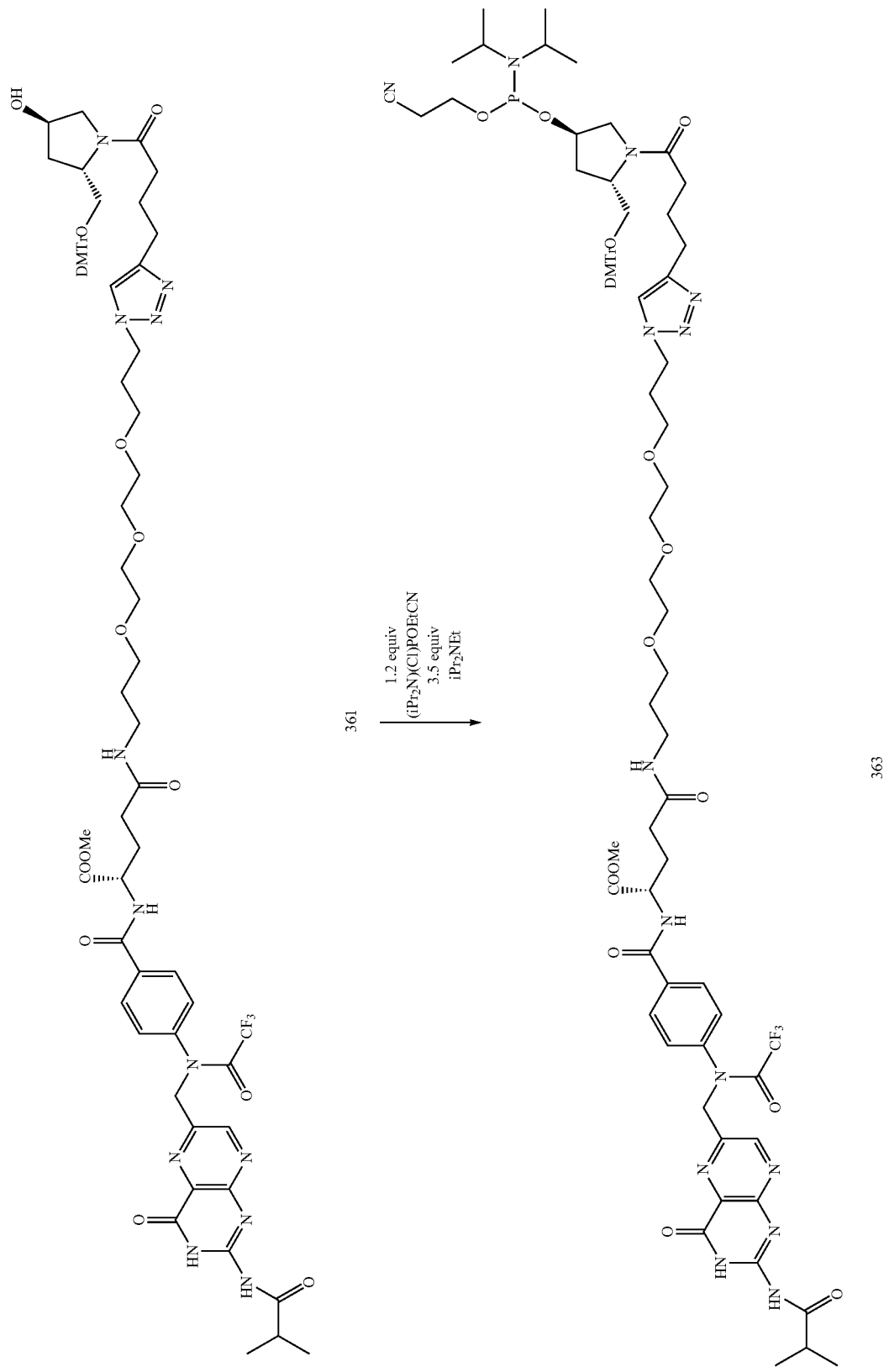

Example 9
Lipid Building Blocks for Click Chemistry
The following acetylinic CPG supports and phosphoramidites were prepared in the usual way.
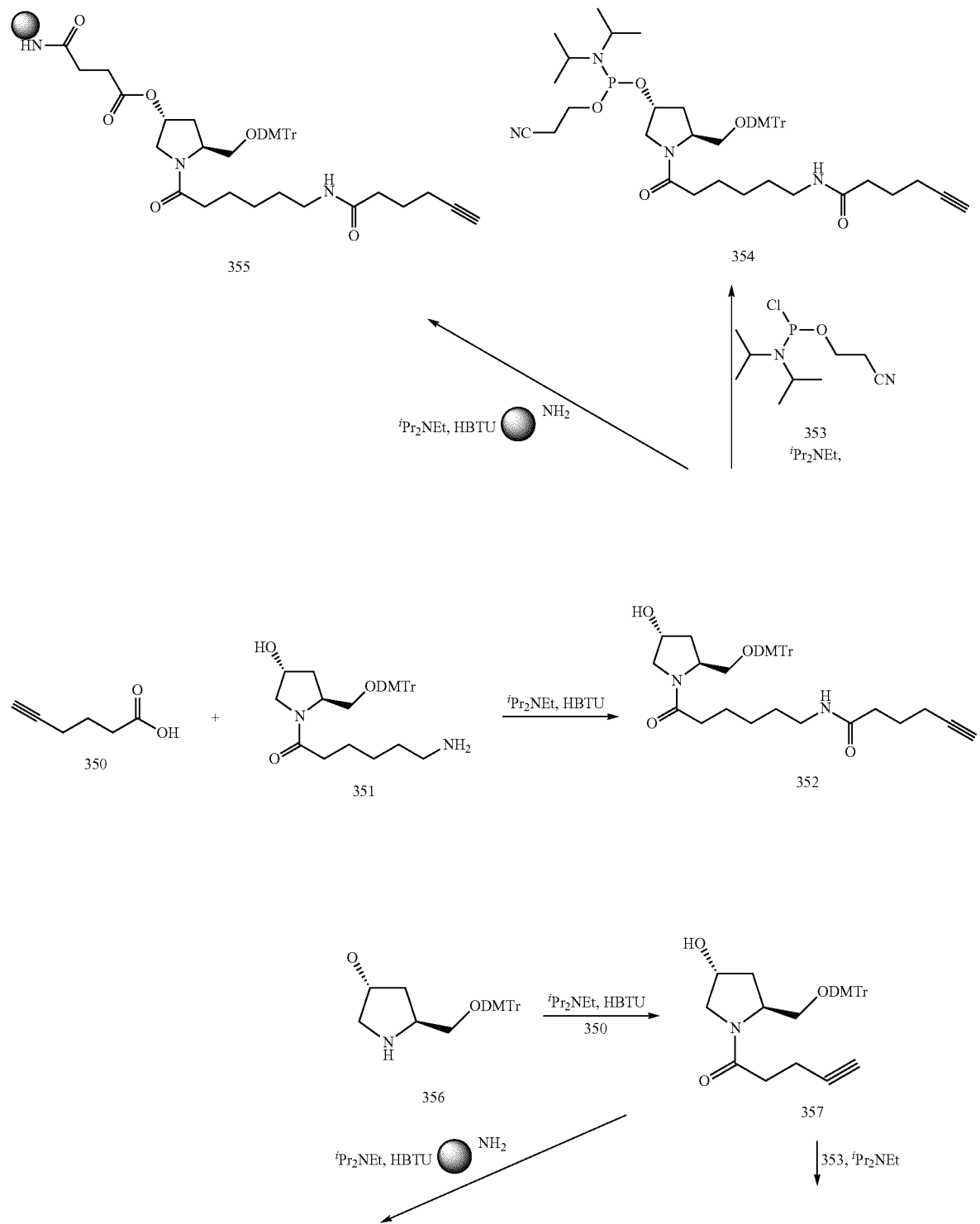
Scheme 25

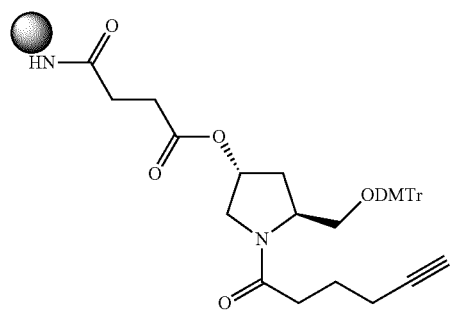

359

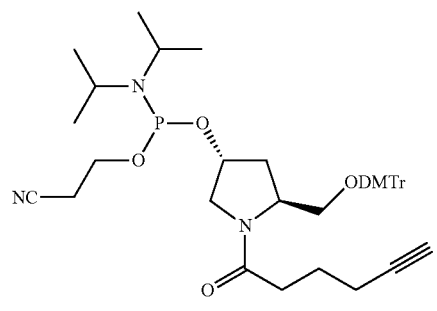

358

Preparation of Compound 352

A solution of compound 351 (8 g, 15 mmol) in DCM (300 mL) was treated successively with Hünig's base (2.5 eq), 350 (1.1 eq) and HBTU (1.05 eq). The solution was stirred at r.t. overnight. Aqueous workup then column chromatography gave pure compound 352. Yield 7.3 g, 78%.

Preparation of Compound 357

Compound 357 was prepared using a procedure analogous to that described for compound 352.

Preparation of Compound 354

Compound 354 was prepared using a procedure analogous to that described for compound 358. Yield 5.7 g, 84%.

Preparation of Compound 358

A solution of Hünig's base (2 eq) and compound 357 (5.0 g, 9.7 mmol) in DCM (50 mL) was treated with amidite reagent (1.5 eq). After stirring for 10 min, TLC showed complete reaction. Aqueous workup then column chromatography gave pure compound 358 (6.1 g, 88%).

Preparation of Compound 359

A solution of compound 357 (2.07 g, 4.03 mmol) in DCM (150 mL) was treated with DMAP (3 eq) then succinic anhydride (2 eq) and stirred at r.t. overnight. Column chromatography gave the intermediate succinate (2.5 g g, 87%) as a $^+$HNEt$_3$ salt. A solution of this intermediate (2.49 g, 4.07 mmol) in DMF (200 mL) was treated successively with Hünig's base (5 eq), HBTU (1 eq) then 500 Å, 140 μmol/g CPG-NH$_2$ (29.1 g, 1 eq). After shaking for 1 h, the support was collected by filtration then subjected to capping with Ac$_2$O/py (4:1, 200 mL) by shaking for 1 h. After collection by filtration and drying in vacuo, 22.4 g of 359 was obtained. Loading calculated to be 90 μmol/g.

Preparation of Compound 355

Compound 354 was prepared using a procedure analogous to that described for compound 359. Obtained 22.4 g with loading 91 μmol/g.

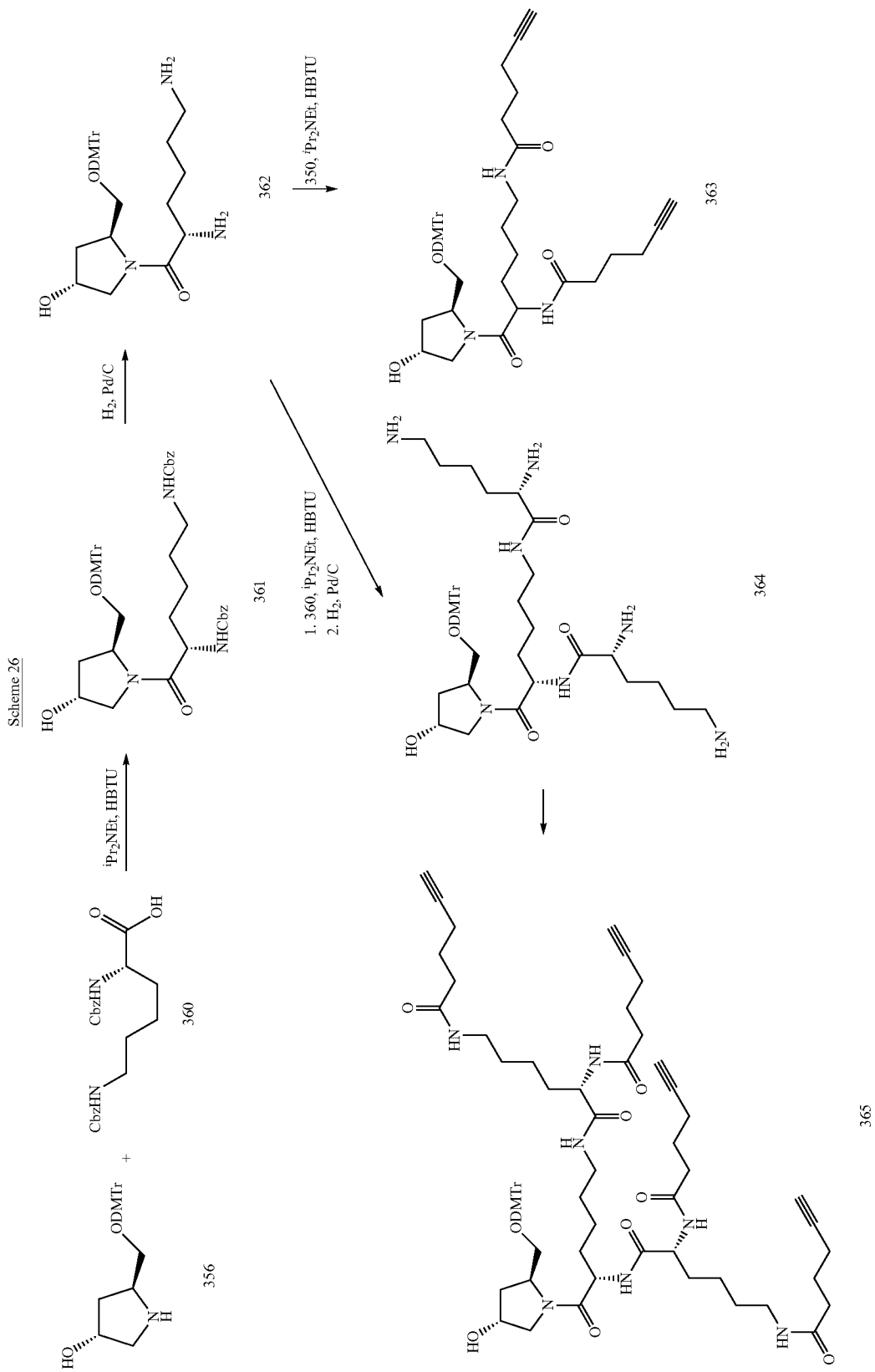

Preparation of Compound 361

Compound 361 was prepared using a procedure analogous to that described for compound 352.

Scheme 27

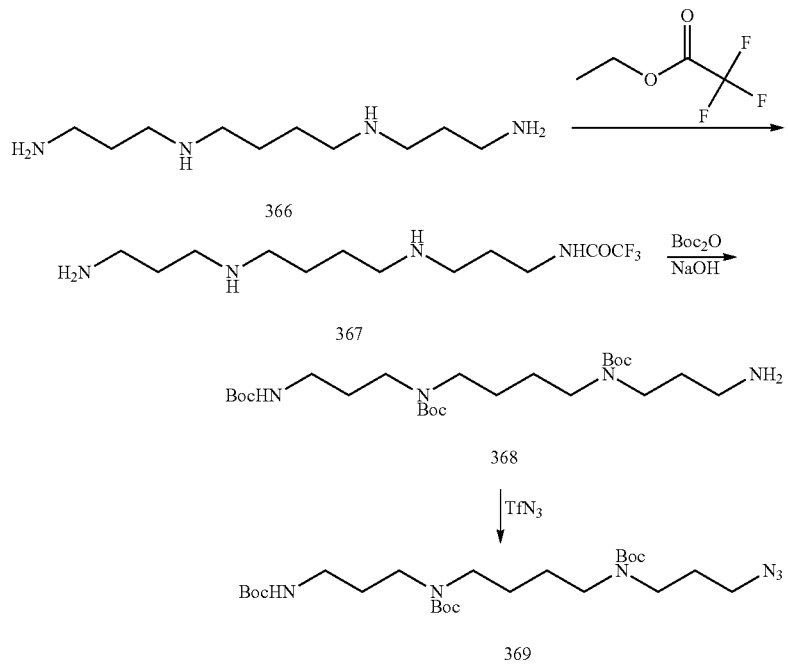

Preparation of compound 368

Spermine 366 (6.0 g, 30 mmol) was dissolved in MeOH (350 mL), cooled at −78° C. and ethyltrifluoro acetate (4.1 mL, 35 mmol) was added. The solution was warmed to r.t. and stirred for 1 h whereon a solution of Boc₂O (30.5 g, 410 mmol) in MeOH (30 mL) was added dropwise to the crude intermediate 367. After 16 h at r.t., the mixture was hydrolyzed by addition of aqueous NaOH. Extraction into EA then column chromatography gave pure compound 3 (5.7 g, 38%).

Example 10

Glycolipid Building Blocks for Click Chemistry

Acetylene unit was coupled with the lithocholic derivative 500 via a peptide linkage to give 501. After hydrolysis, Gal-NAc unit will be coupled with 502 to give 503.

Scheme 28
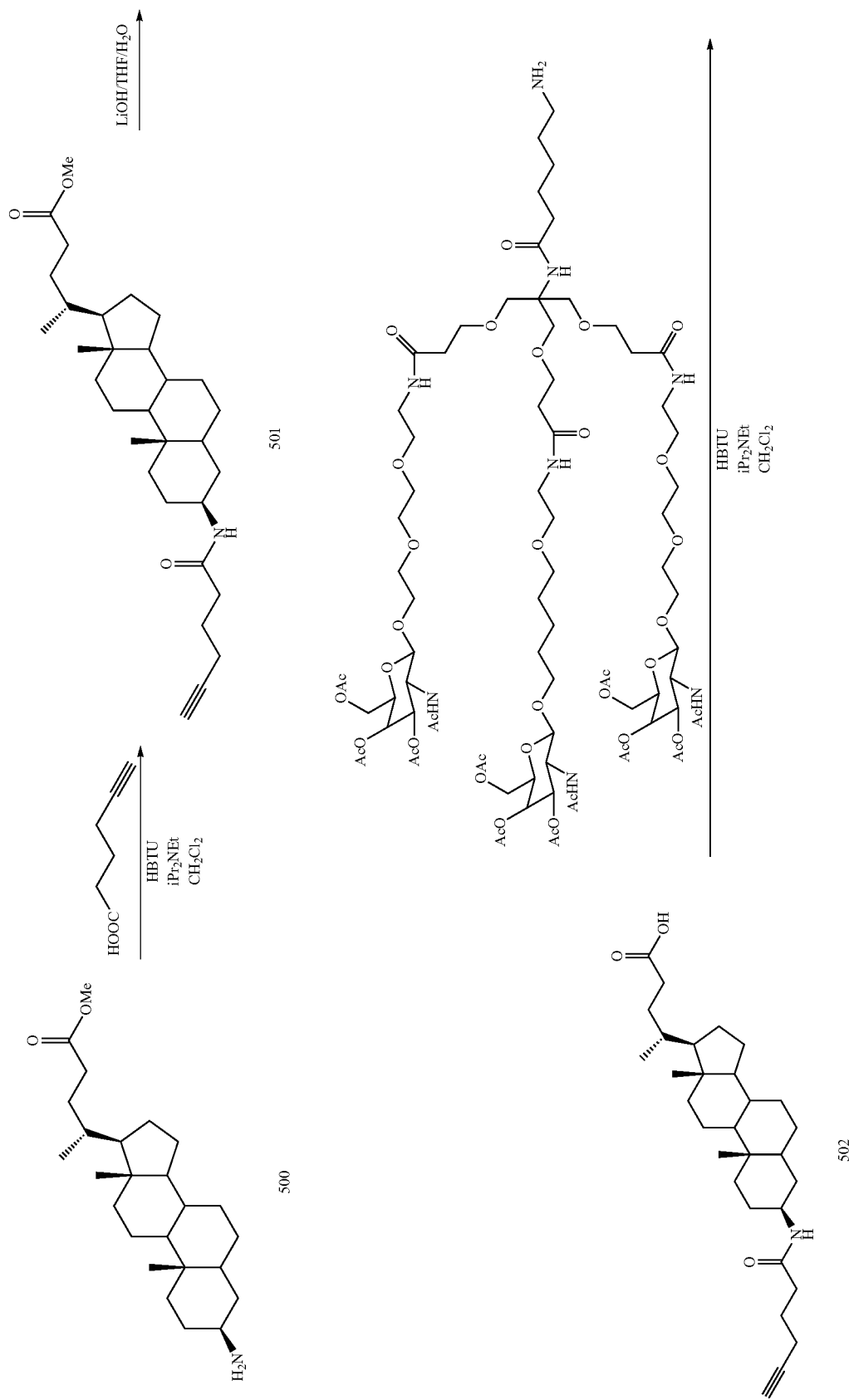

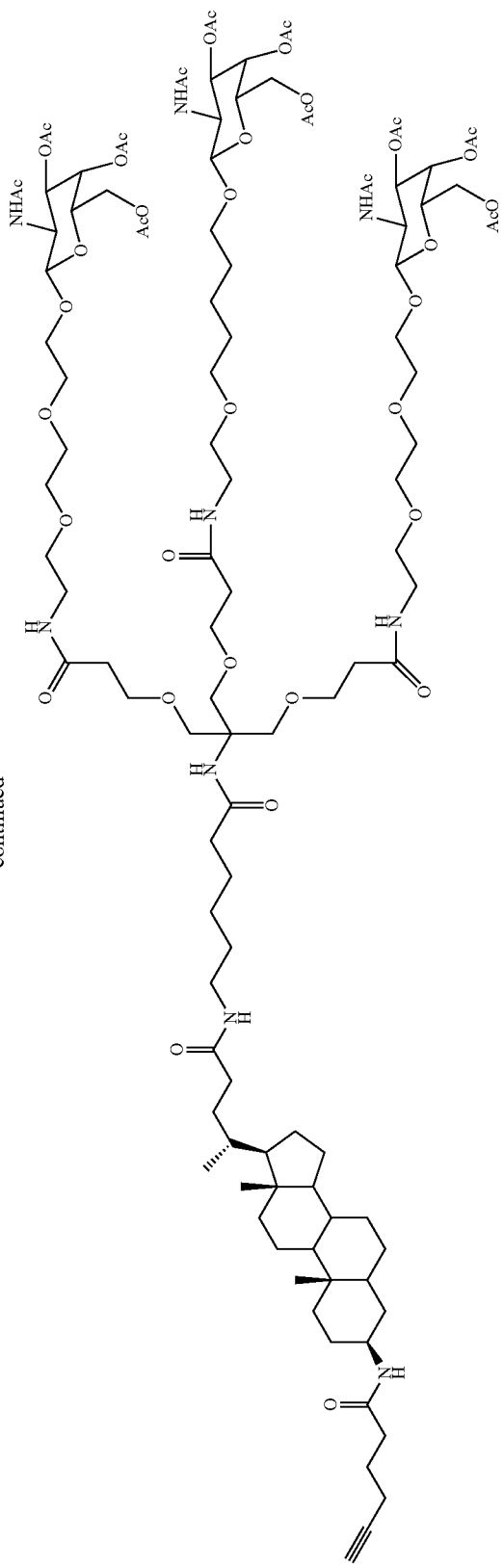

Compound 501: To a solution of 5-hexynoic acid (907 mg, 8.09 mmol) in DMF (50 mL), HBTU (3.07 g, 8.09 mmol) and iPr$_2$NEt (6.71 mL, 38.5 mmol) were added. After 5 minute, compound 500 (3.0 g, 7.7 mmol) was added to the solution. The reaction mixture was stirred for 14 hours at room temperature. After extraction with Et$_2$O (300 mL) and NaHCO$_3$ aq. (150 mL), purification by silica gel column chromatography (Hexane:EtOAc=2:1, R$_f$=0.37) gave compound 501 (3.63 g, 7.50 mmol, 98%). $^1$H NMR (DMSO-d$_6$, 400 MHz) δ 7.70 (d, J=7.2 Hz, 1H), 3.95-3.97 (m, 1H), 3.57 (s, 3H), 2.78 (t, J=2.6 Hz, 1H), 0.86-2.34 (m, 40H), 0.61 (s, 3H). $^{13}$C NMR (DMSO-d$_6$, 100 MHz) δ 173.6, 170.7, 84.1, 71.2, 55.9, 55.4, 51.1, 44.2, 42.2, 39.1, 36.3, 35.1, 34.7, 34.5, 34.1, 30.5, 30.3, 27.6, 26.3, 25.7, 24.5, 24.4, 23.7, 23.4, 20.6, 18.0, 17.4. Molecular weight for C$_{31}$H$_{50}$NO$_3$ (M+H)$^+$ Calc. 484.38. Found 484.3.

Commercially available azide unit 504 was coupled with the lithocholic derivative 500 to give 505. After hydrolysis, 506 will be coupled with the GalNAc unit to give a glycolipid molecule containing azide group 507.

Scheme 29
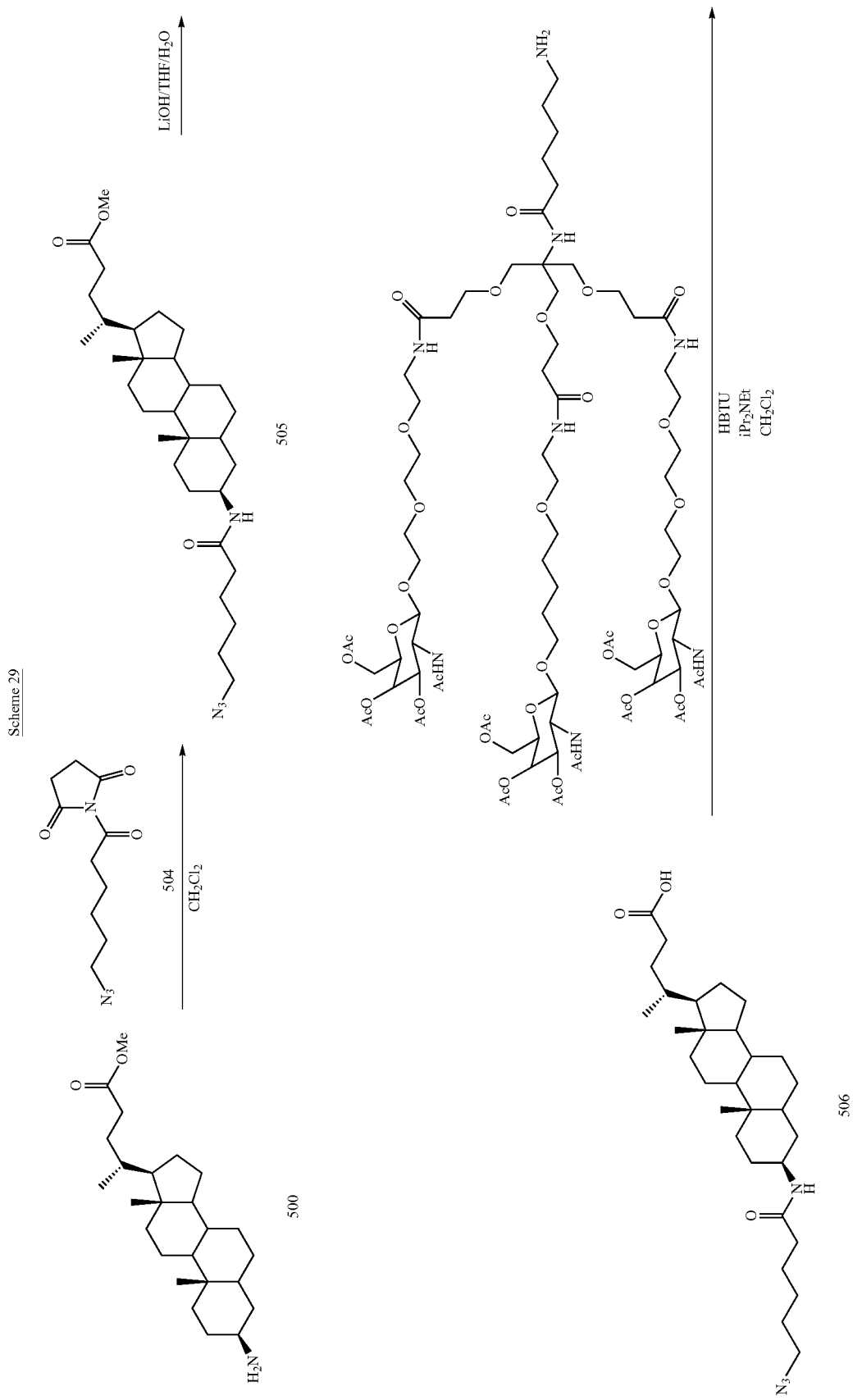

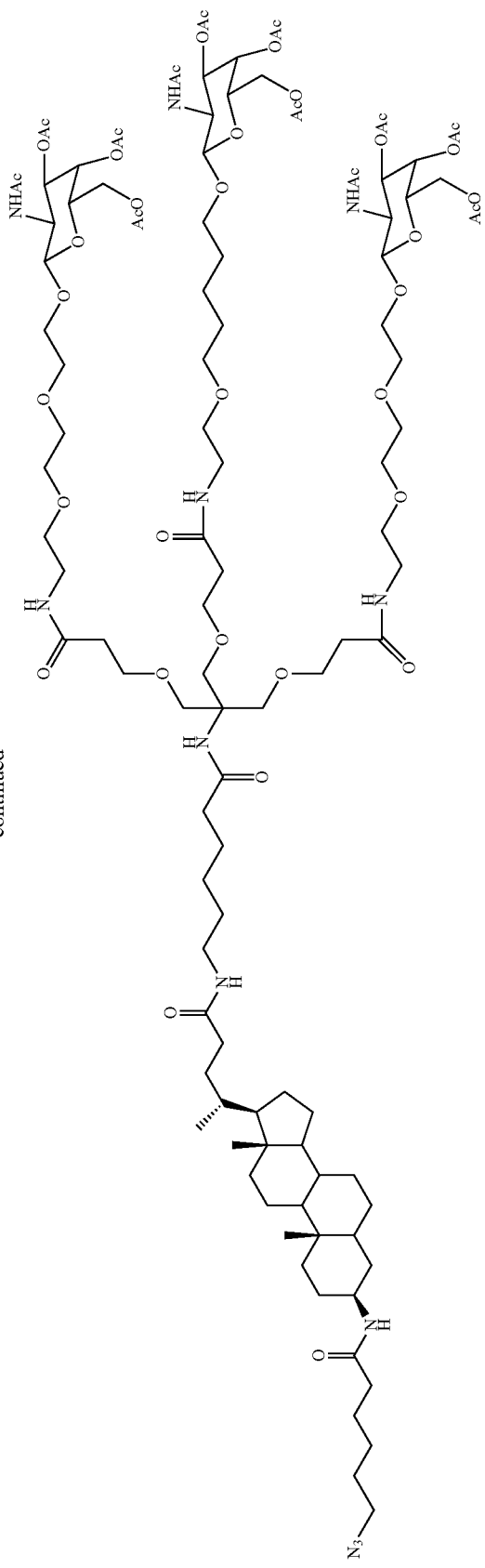
507

Olyel-lithocholic acetylene derivative 509 will be prepared from 508 by standard peptide coupling using propargylamine. Commercially available diamine will be protected and converted to the corresponding azide derivative 512. The azide will be coupled with 508 to generate oleyl-lithocholic azide derivative 513.
Scheme 30
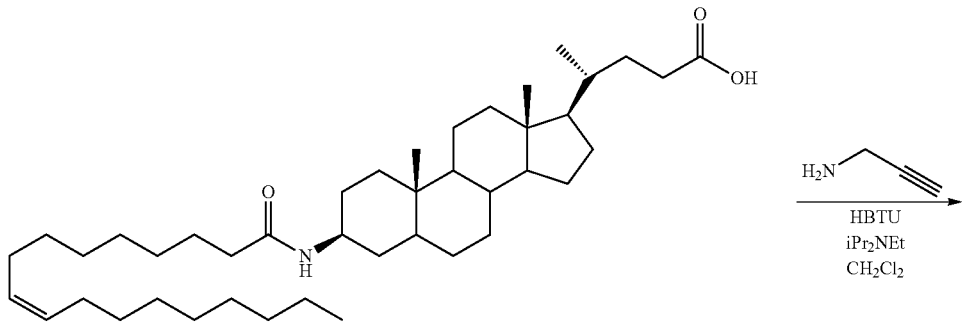
508
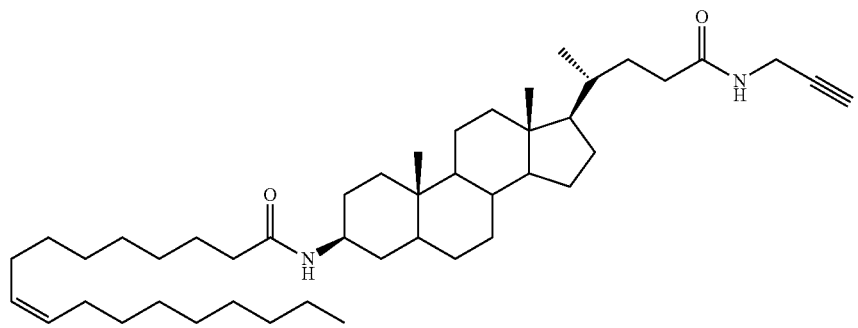
509
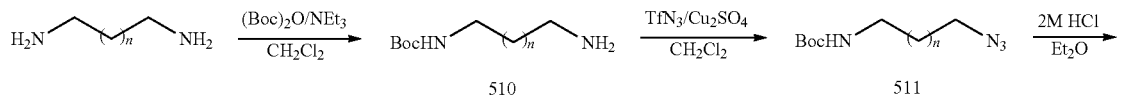
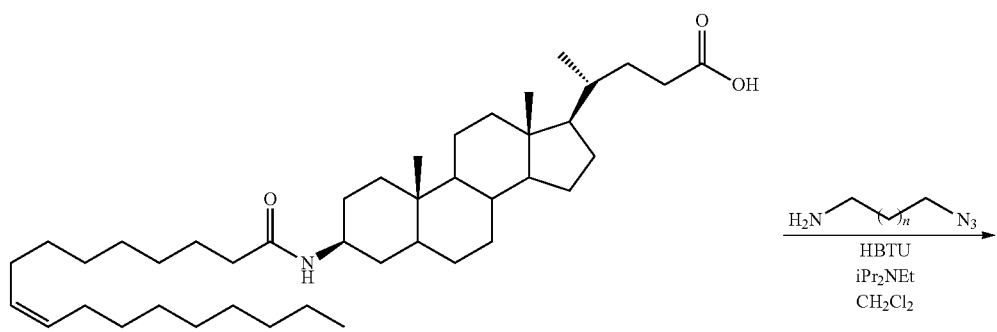
508

-continued
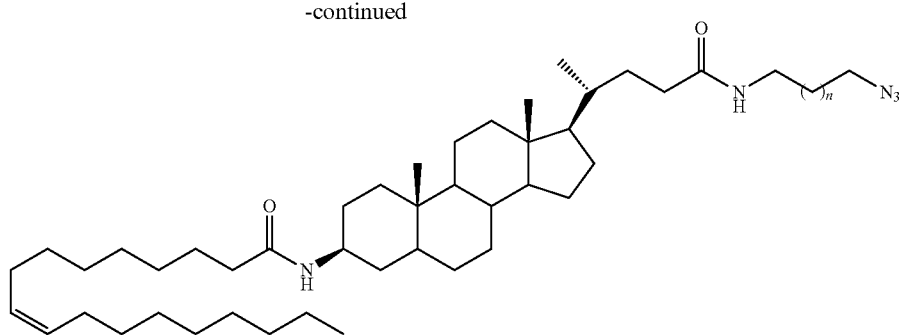
513
Another oleyl-lithocholic derivative 514 will be functionalized with propargylamine and azide compound 512 to give 515 and 516, respectively.
Scheme 31
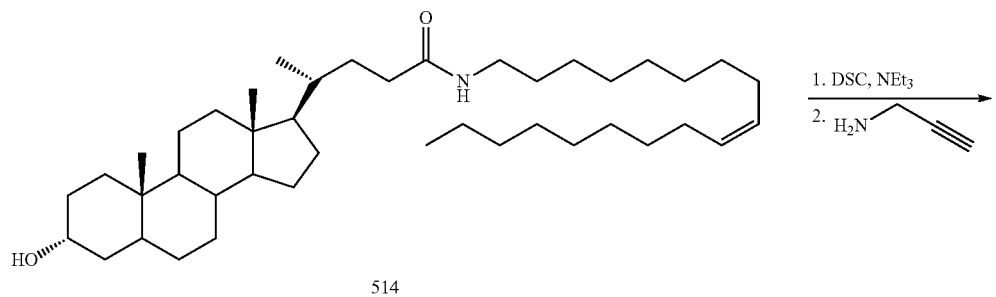
514
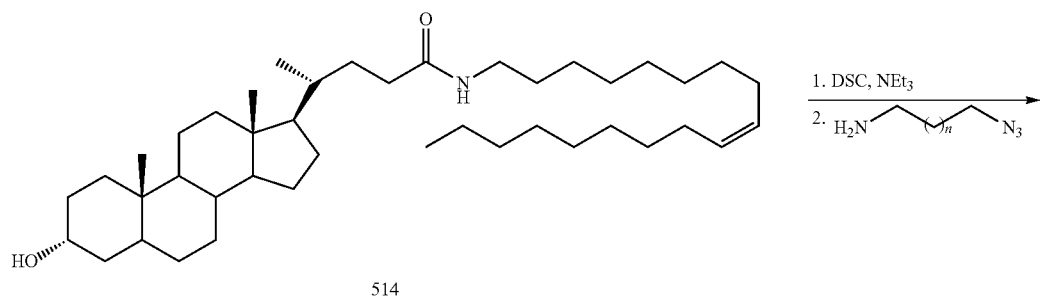
514

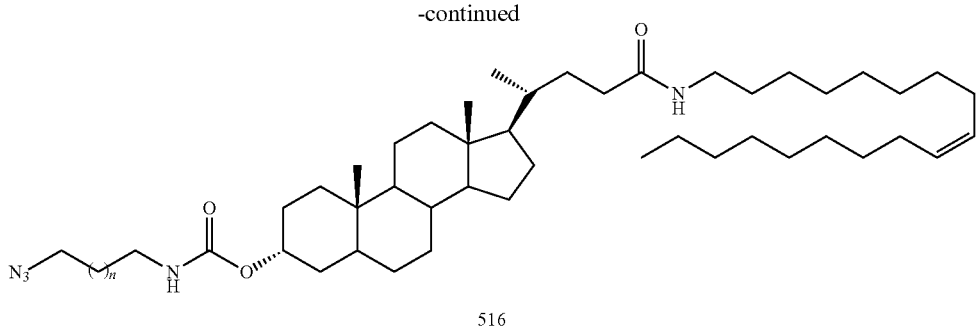
516
The lithocholic ester 517 was coupled with propargyamine to affor compound 518. Conjugation of 517 with azide compound 512 via a carbamate linkage to give 519.
Scheme 32
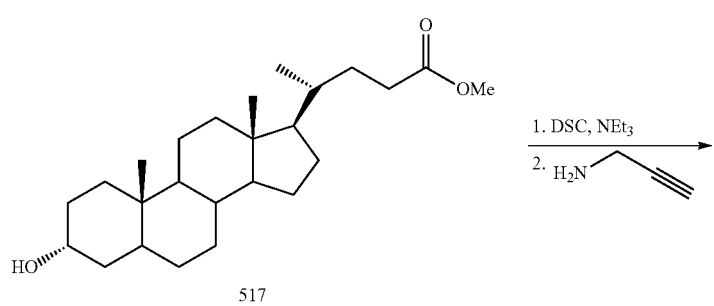
517
1. DSC, NEt₃
2. H₂N—CH₂—C≡CH
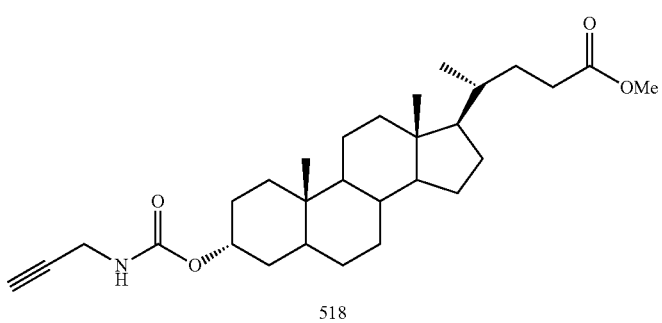
518
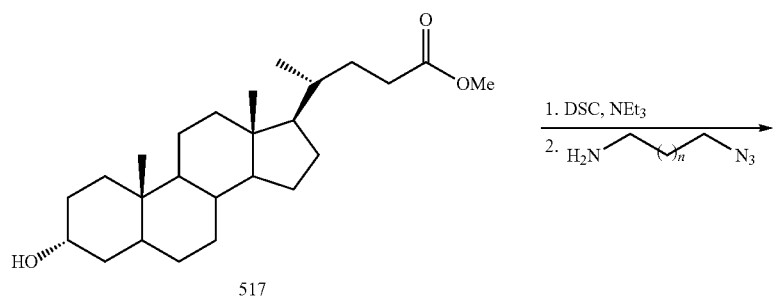
517
1. DSC, NEt₃
2. $H_2N(\ )_n N_3$

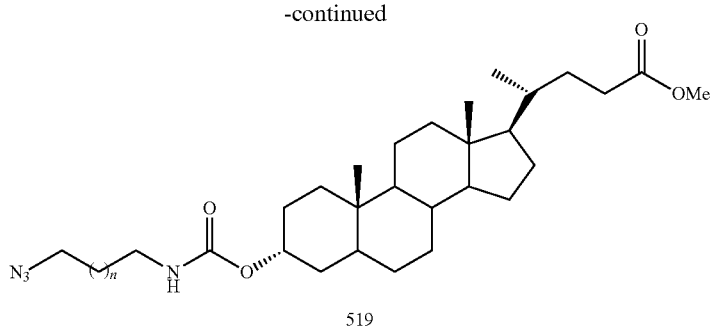

519

Compound 518: The activation of the hydroxyl group of compound 517 was carried out using N,N'-disuccinimidyl carbonate and triethylamine in $CH_2Cl_2$. After aqueous work-up, the crude material (3.03 g, 5.88 mmol) was dissolved in $CH_2Cl_2$ (60 mL). Then, triethylamine (1.64 mL, 11.76 mmol) and propargylamine (0.524 mL, 7.64 mmol) were added to the solution. The reaction mixture was stirred for 14 hours at room temperature. Aqueous work-up and purification by column chromatography (Hexane:EtOAc=5:1 to 2:1) gave compound 518 (2.25 g, 4.77 mmol, 81%). $^1$H NMR (DMSO-$d_6$, 400 MHz) δ 7.44 (t, J=5.5 Hz, 1H), 4.43-4.51 (m, 1H), 3.73-3.75 (m, 2H), 3.57 (s, 3H), 3.08 (t, J=2.2 Hz, 1H), 2.16-2.36 (m, 2H), 0.86-1.93 (m, 32H), 0.61 (s, 3H). $^{13}$C NMR (DMSO-$d_6$, 100 MHz) δ 173.6, 155.5, 81.5, 73.6, 72.7, 55.9, 55.4, 51.1, 42.2, 41.2, 39.9, 35.3, 34.7, 34.5, 34.1, 32.3, 30.5, 30.3, 29.6, 27.6, 26.6, 26.5, 25.9, 23.7, 23.0, 20.3, 18.0, 11.8. Molecular weight for $C_{29}H_{45}NNaO_4$ $(M+Na)^+$ Calc. 494.32. Found 494.2.

Oleyl-lithocholic GalNAc building block will be synthesized according to Scheme 19. Compound 523 was prepared from compound 508 (Rensen, P. C. N. et al., J. Med. Chem., 2004, 47, 5798-5808). Briefly, standard peptide coupling of 508 with ethyl iminodiacetate gave 520. The ester hydrolysis generated the corresponding di-acid 521. The di-acid was coupled with GalNAc via anhydro intermediate 522 to give 523. 523 will be functionalized with propargylamine and azide compound 512 to give 524 and 525, respectively.

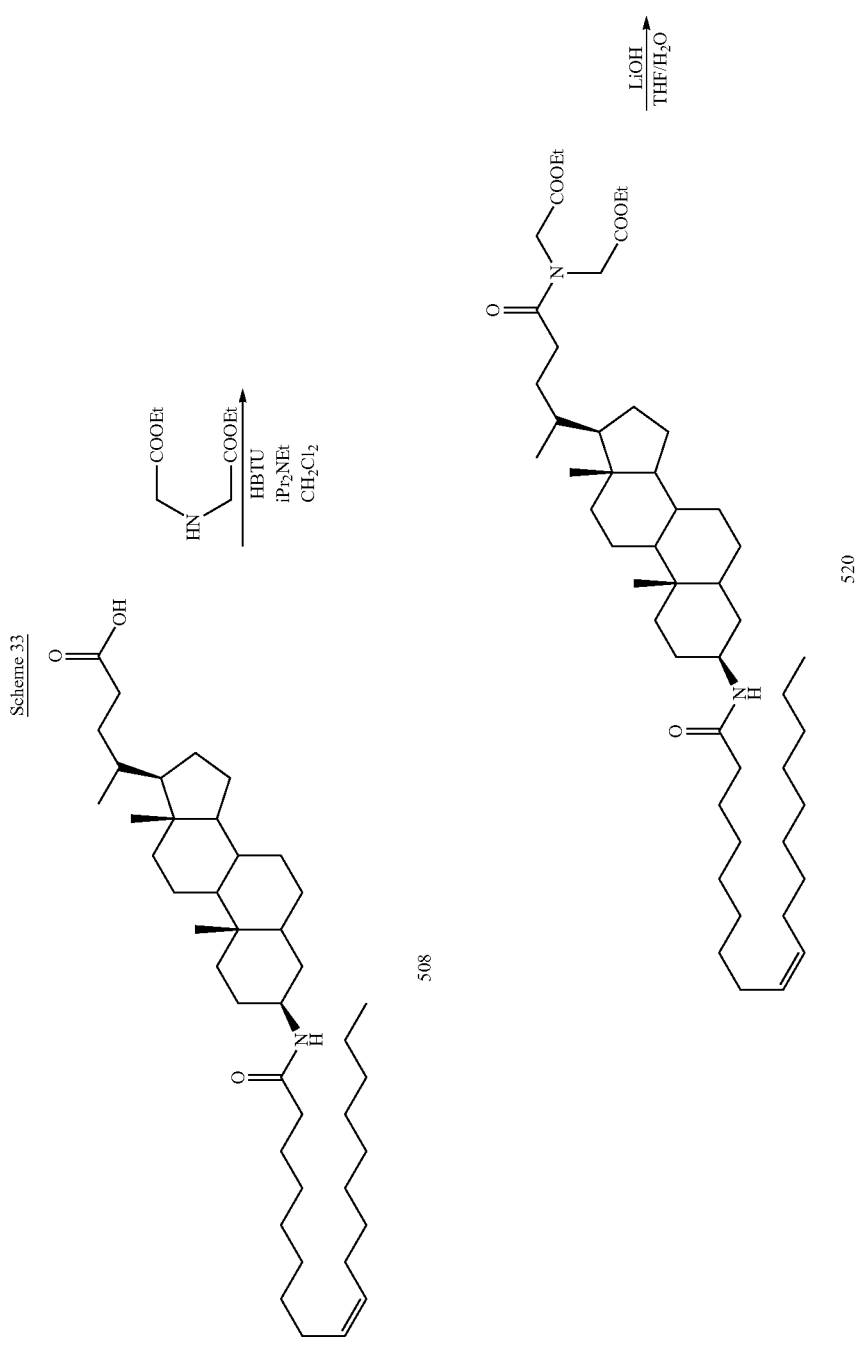

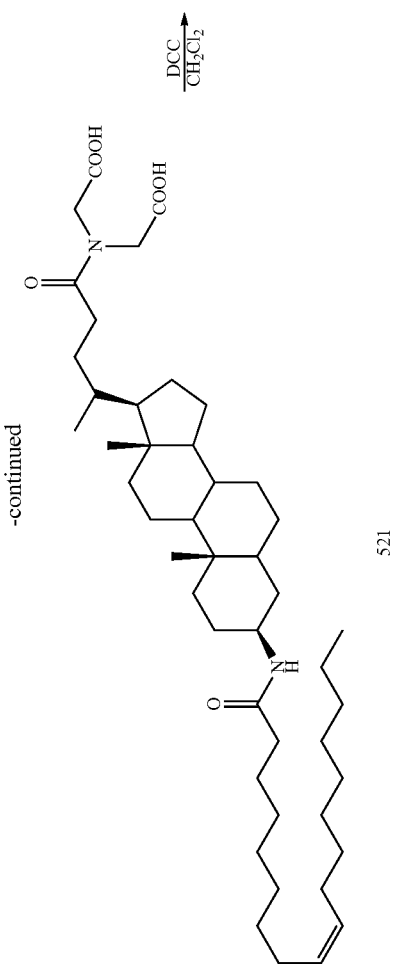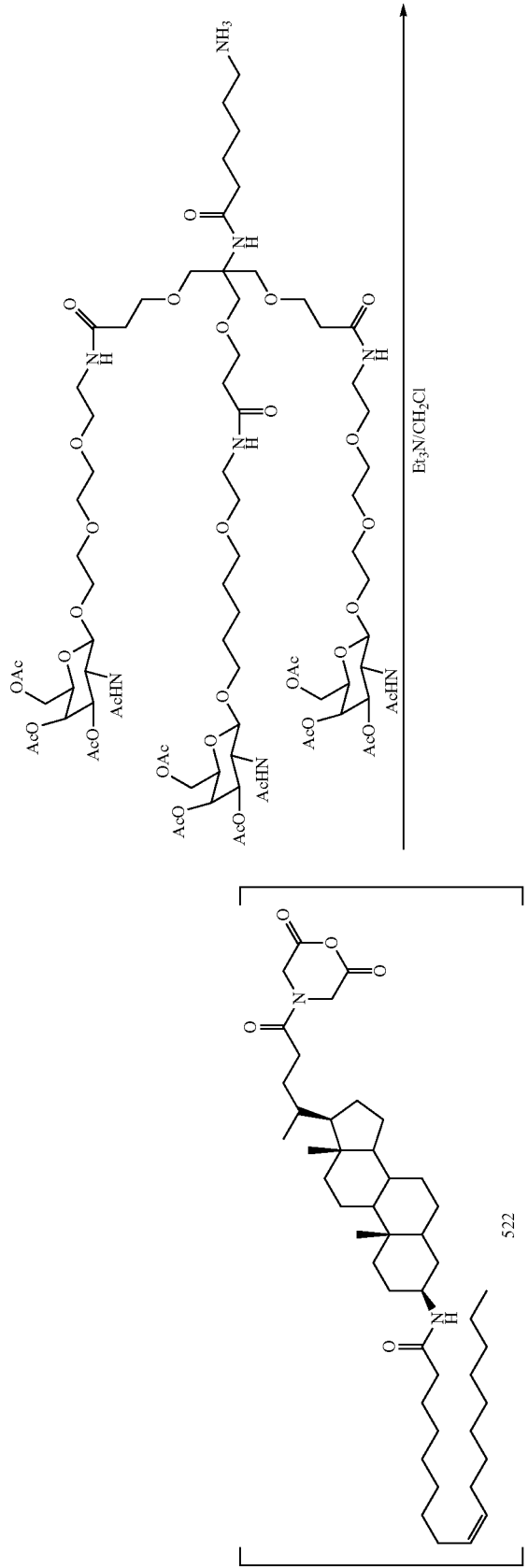

-continued
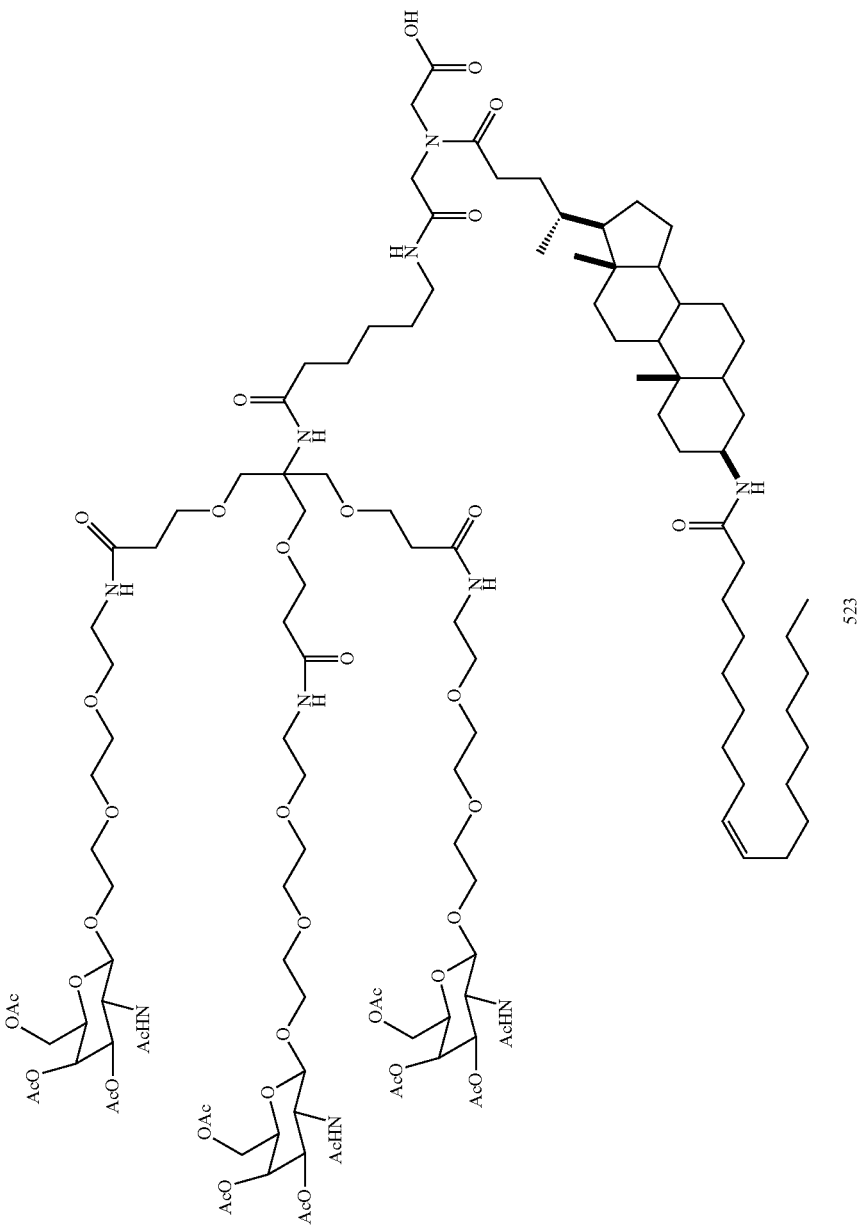
523

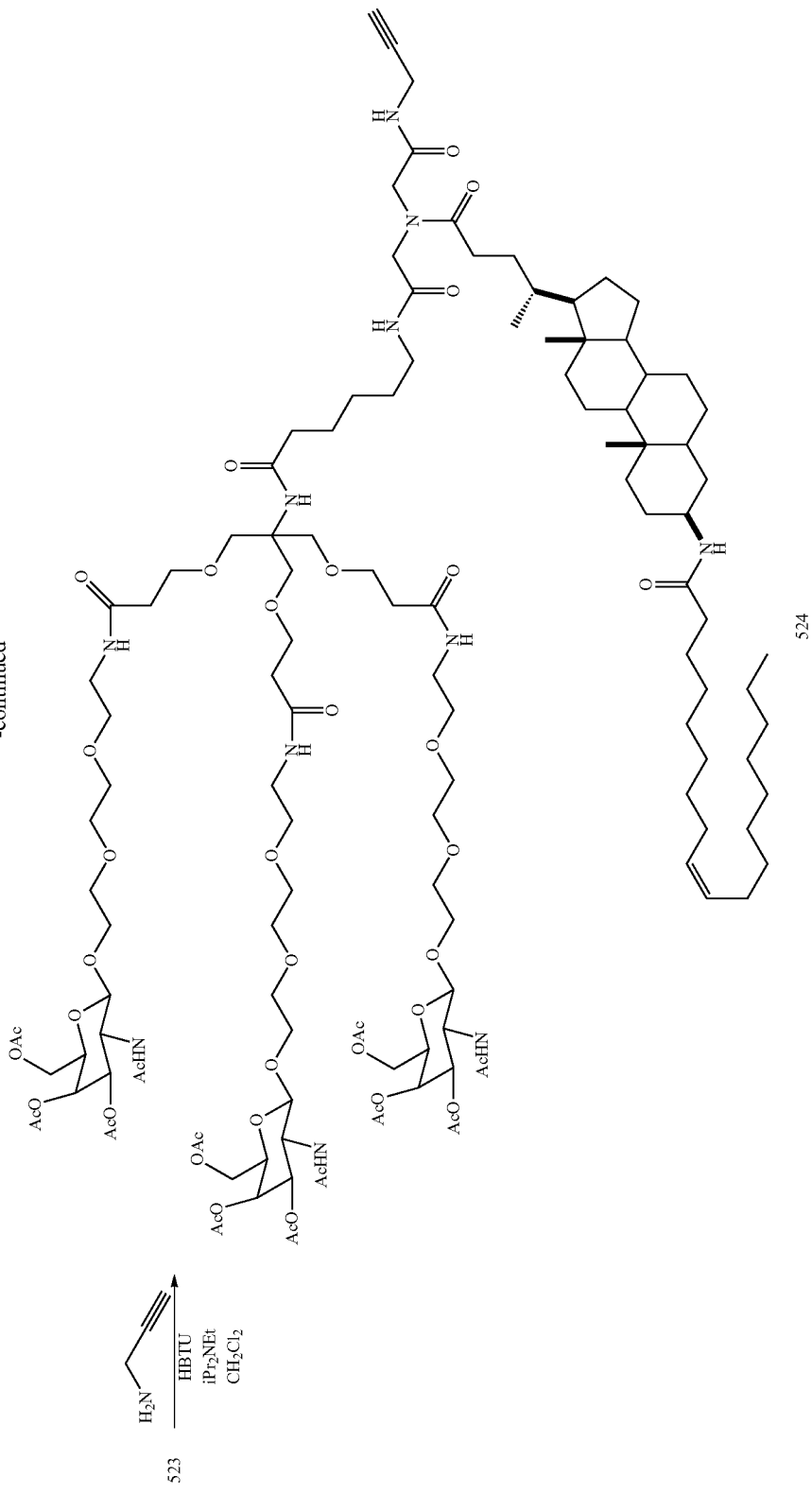

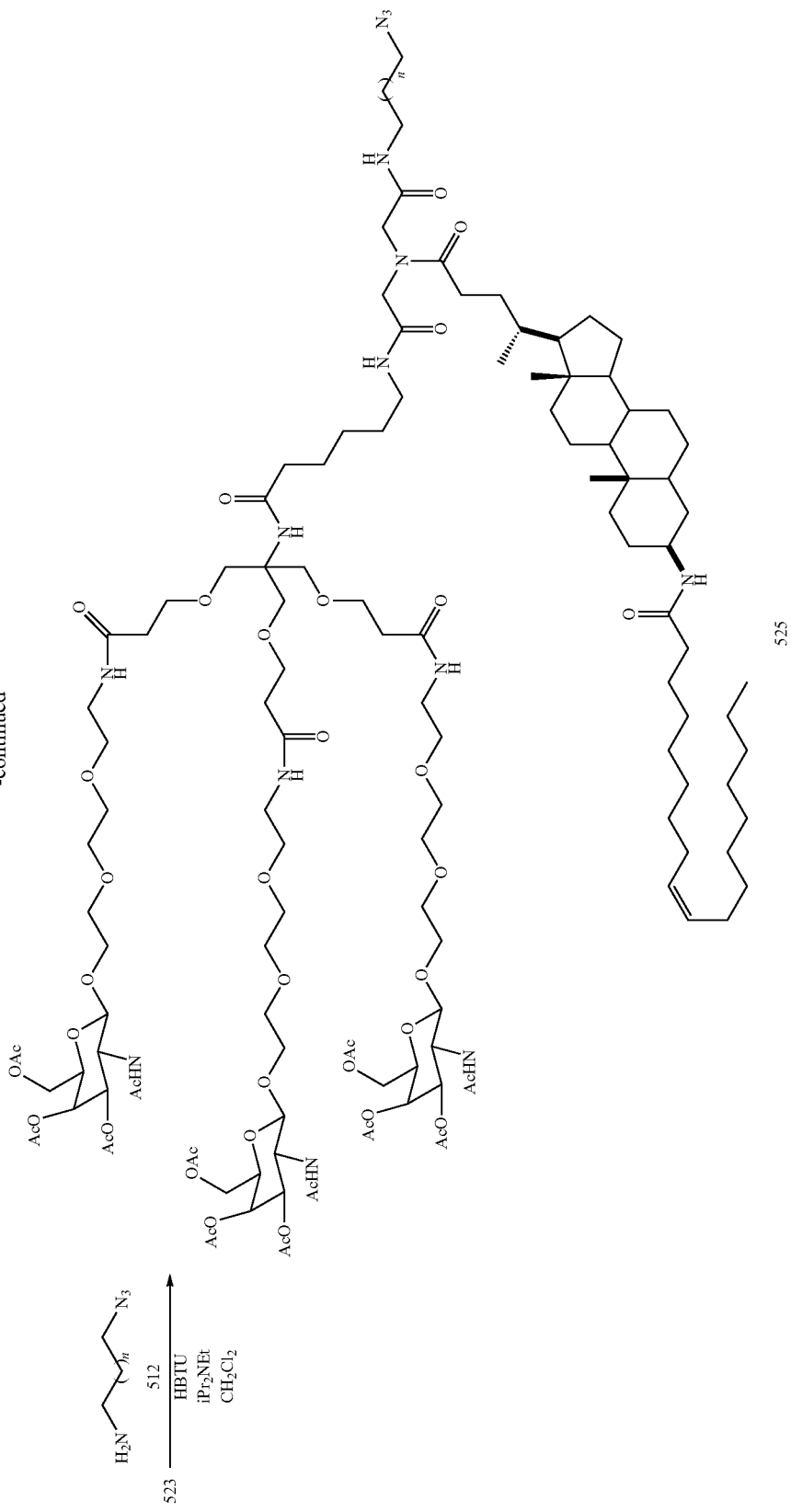

Preparation of Compound 520:

A solution of compound 508 (10.5 g, 16.4 mmol, Rensen, P. C. N. et al., *J. Med. Chem.*, 2004, 47, 5798-5808) and HBTU (6.54 g, 17.2 mmol) in $CH_2Cl_2$ (170 mL) was treated successively with $iPr_2NEt$ (14.3 mL, 82.1 mmol) and diethyl iminodiacetate (3.26 g, 17.2 mmol) then allowed to stir for 69 hours at room temperature. Aqueous work-up then silica gel column chromatography (hexane:ethyl acetate=1:1, $R_f$=0.47) gave compound 520.

Yield: 11.1 g, 83%. $^1H$ NMR ($CDCl_3$, 400 MHz) δ 5.66 (d, J=8.0 Hz, 1H), 5.33-5.36 (m, 2H), 4.14-4.26 (m, 9H), 0.86-2.38 (m, 71H), 0.64 (s, 3H). $^{13}C$ NMR ($CDCl_3$, 100 MHz) δ 174.0, 172.1, 169.4, 169.0, 129.9, 129.7, 61.6, 61.2, 60.8, 56.4, 56.1, 50.2, 47.9, 44.9, 42.7, 40.1, 39.7, 38.1, 37.1, 35.6, 35.3, 35.0, 31.9, 31.4, 30.9, 30.6, 29.7, 29.67, 29.60, 29.5, 29.3, 29.24, 29.22, 29.1, 28.1, 27.2, 27.1, 26.7, 26.1, 25.9, 24.8, 24.1, 22.6, 21.0, 18.4, 14.18, 14.16, 14.11, 14.09, 12.0. Molecular weight for $C_{50}H_{87}N_2O_6$ $(M+H)^+$ Calc. 811.66. Found 811.6.

Preparation of Compound 521:

Compound 520 (6.05 g, 7.46 mmol) was treated with lithium hydroxide monohydrate (1.25 g, 29.8 mmol) in THF (110 mL) and $H_2O$ (22 mL). After 4 hours, 70 mL of Amberlite IR-120 (plus) ion exchange resin was added then stirred for 10 minutes. The resulting clear solution was filtered, washed with $THF/H_2O$ and evaporated. Co-evaporation with toluene gave the compound 521 as a white solid.

Yield: 4.81 g, 85%. $^1H$ NMR ($CDCl_3$, 400 MHz) δ 5.99 (d, J=7.2 Hz, 1H), 5.32-5.36 (m, 2H), 4.13-4.24 (m, 5H), 0.86-2.37 (m, 65H), 0.64 (s, 3H). $^{13}C$ NMR ($CDCl_3$, 100 MHz) δ 175.3, 173.7, 173.0, 171.5, 130.0, 129.7, 107.9, 67.7, 56.4, 55.9, 45.6, 42.7, 40.1, 39.8, 38.1, 36.9, 35.6, 35.3, 35.0, 31.9, 30.9, 30.4, 29.8, 29.75, 29.70, 29.6, 29.5, 29.4, 29.3, 29.2, 29.1, 28.2, 27.3, 27.2, 26.7, 26.1, 26.0, 25.9, 24.2, 24.1, 23.9, 22.7, 21.0, 18.4, 14.1, 12.0. Molecular weight for $C_{46}H_{77}N_2O_6$ $(M-H)^-$ Calc. 753.58. Found 753.5.

Preparation of Compound 523:

To a solution of compound 521 (583 mg, 0.772 mmol) in $CH_2Cl_2$ (25 mL), 1M DCC solution of $CH_2Cl_2$ (0.772 mL, 0.772 mmol) was added at room temperature and the reaction mixture was stirred for 1.5 hours to form the intermediate 522. Then, a solution of compound 5 (1.50 g, 0.772 mmol) and $Et_3N$ (0.377 mL, 2.70 mmol) in $CH_2Cl_2$ (5 mL) was added. The reaction mixture was stirred overnight. The crude was purified by silica gel column chromatography (5% MeOH in $CH_2Cl_2$ with 2% $Et_3N$, $R_f$=0.24) to yield the compound 523. Yield: 1.62 g, 79% as the triethylammonium salt. $^1H$ NMR ($CDCl_3$, 400 MHz) δ 5.68 (d, J=7.2 Hz, 1H), 5.29-5.34 (m, 5H), 5.15-5.18 (m, 3H), 4.77-4.79 (m, 3H), 3.41-4.16 (m, 59H), 2.93-3.24 (m, 6H), 0.85-2.56 (m, 117H), 0.61 (s, 3H). $^{13}C$ NMR ($CDCl_3$, 100 MHz) δ 174.9, 173.5, 172.2, 171.6, 170.8, 170.43, 170.36, 129.9, 129.7, 101.63, 101.58, 70.63, 70.60, 70.5, 70.3, 69.8, 69.69.29, 69.26, 69.22, 69.1, 68.75, 68.67, 67.3, 66.80, 66.75, 62.9, 61.6, 59.6, 56.43, 56.37, 56.1, 56.0, 53.4, 52.7, 50.63, 50.56, 45.6, 44.9, 42.7, 40.11, 40.07, 40.05, 39.8, 39.7, 39.30, 39.27, 39.1, 38.1, 37.1, 36.5, 35.6, 35.44, 35.38, 35.0, 31.9, 31.4, 30.6, 29.72, 29.67, 29.5, 29.3, 29.2, 29.1, 28.2, 27.2, 27.1, 26.7, 26.1, 25.9, 25.3, 24.8, 24.15, 24.11, 23.2, 22.6, 21.0, 20.9, 20.7, 18.5, 14.1, 12.0, 8.5, 7.7. MALDI-TOF MS calcd for $C_{125}H_{205}N_{10}O_{45}Na$ $(M+Na)^+$ 2589.40. Found 2588.76.

Pseudouridine Building Blocks for Click Chemistry

N1 at pseudouridine was alkylated with methyl acrylate to give 526. This ester was hydrolyzed to give the corresponding acide derivative 527. A standard peptide coupling of 527 with propargylamine and azide compound will give 528 and 529 for conjugation via click chemistry, respectively.

Scheme 34

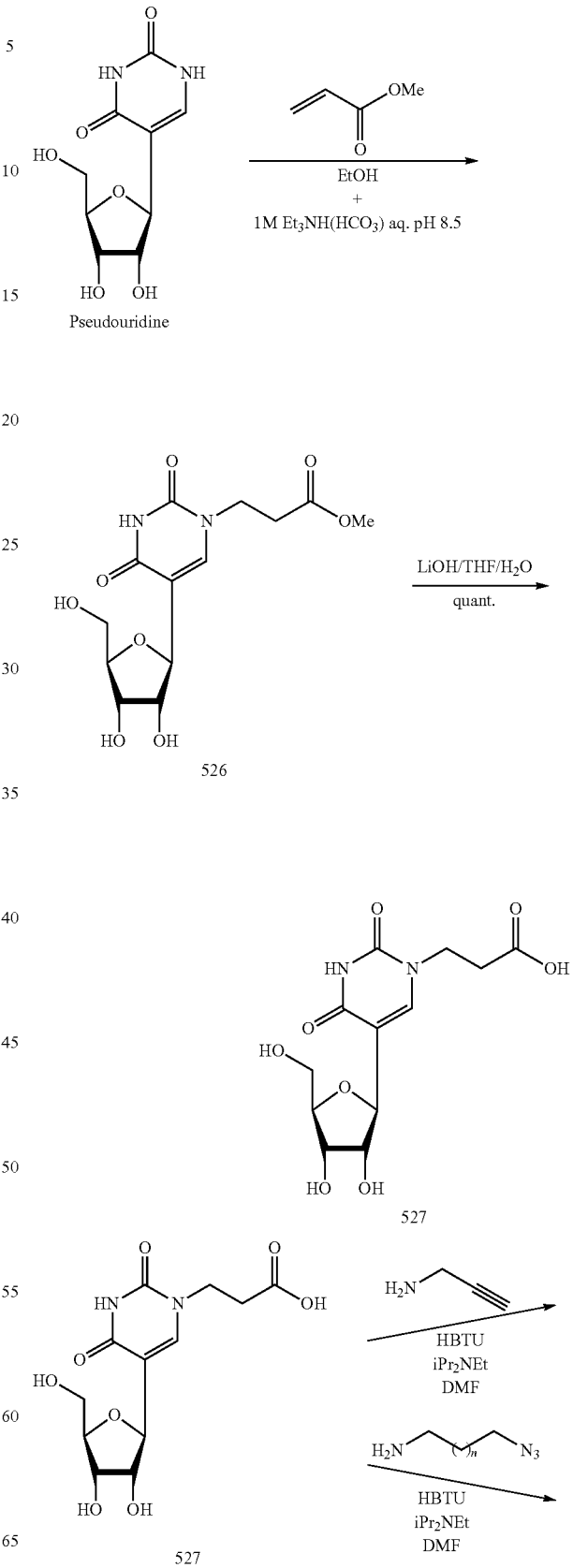

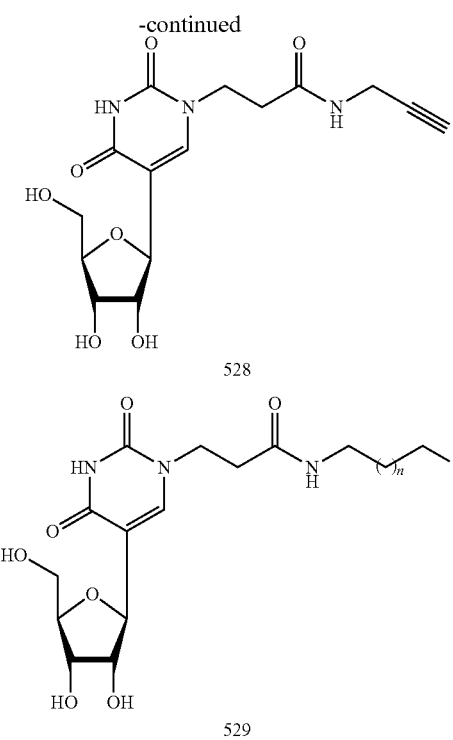

528

529

Example 11

Synthesis of Spermine Azide for Conjugation to Oligonucleotides

For bioconjugation using click chemistry, azide-containing spermine derivatives were synthesized.

Scheme 35

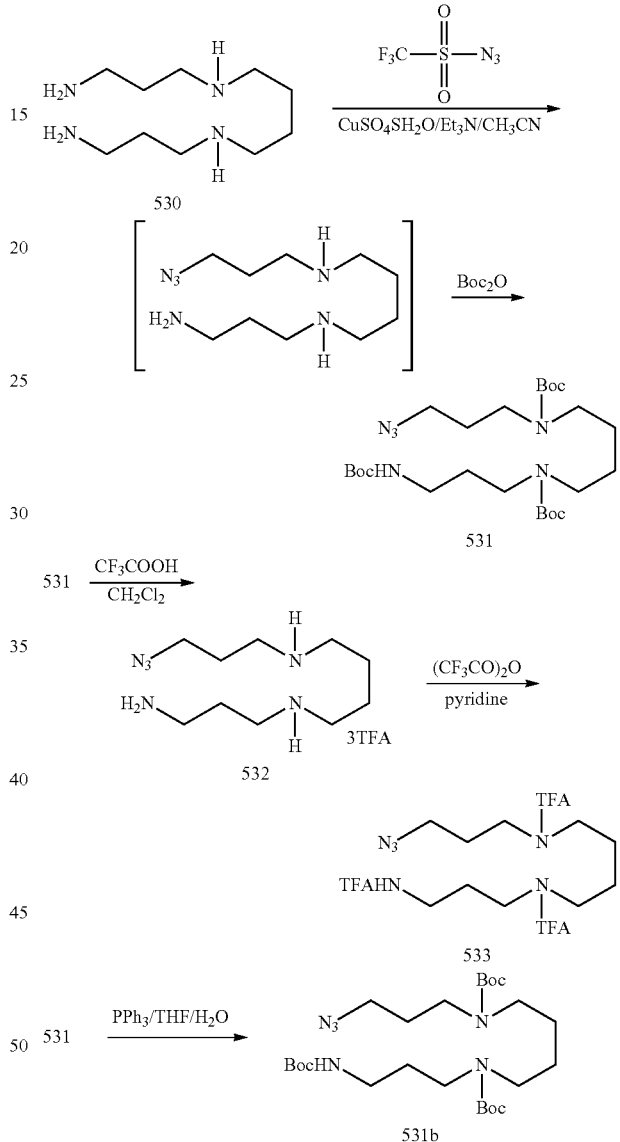

Compound 526:

To a solution of pseudouridine (20 g, 81.9 mmol) in 1M triethylammoniumbicarbonate buffer (pH 8.5, 780 mL) and EtOH (940 mL), methyl acrylate was dropwisely added. The reaction mixture was stirred overnight. After 16 hours, TLC showed a complete reaction. The solvent was removed and dried in vacuo to give a white foam. The crude material was purified by silica gel column chromatography (10% MeOH in $CH_2Cl_2$, $R_f$=0.23) to give 526 (26.6 g, 80.5 mmol, 98%). $^1H$ NMR (MeOH-$d_4$, 400 MHz) δ 7.77 (d, J=0.8 Hz, 1H), 4.58 (d, J=4.8 Hz, 1H), 4.15 (t, J=5.2 Hz, 1H), 4.05 (t, J=5.0 Hz, 1H), 3.98-4.02 (m, 2H), 3.91-3.94 (m, 1H), 3.80 (dd, J=12.0 Hz, 3.3 Hz, 1H), 3.67 (s, 3H), 3.66 (dd, J=12.0 Hz, 3.3 Hz, 1H), 2.73-2.77 (m, 2H). $^{13}C$ NMR (CDCl$_3$, 100 MHz) δ 173.1, 165.4, 152.5, 145.8, 112.9, 85.6, 81.5, 75.6, 72.6, 63.3, 52.5, 46.2, 33.7. Molecular weight for $C_{13}H_{19}N_2O_8$ $(M+H)^+$ Calc. 330.11. Found 331.0.

Compound 527:

To a solution of compound 526 (5.00 g, 15.1 mmol) in THF (100 mL) and $H_2O$ (20 mL), lithium hydroxide monohydrate (1.03 g, 25.5 mmol) was added. The reaction mixture was stirred overnight. Additional lithium hydroxide monohydrate (500 mg, 11.9 mmol) was added. After 2 hours, the reaction mixture was treated with Amberlite IR-120 (plus) ion exchange resin. The resin was filtered off and washed with THF/$H_2O$. The filtrate was evaporated to give compound 527 as a white solid (4.78 g, quantitatively). $^1H$ NMR (DMSO-$d_6$, 400 MHz) δ 11.34 (s, 1H), 7.75 (s, 1H), 4.92-4.93 (m, 1H), 4.70-4.72 (m, 1H), 4.45 (d, J=4.0 Hz, 1H), 3.80-3.93 (m, 4H), 3.68-3.72 (m, 1H), 3.61 (dd, J=12.0 Hz, 3.2 Hz, 1H), 3.47 (dd, J=12.0 Hz, 4.0 Hz, 1H), 3.17 (d, J=3.2 Hz, 1H), 2.59 (t, J=7.0 Hz, 2H). $^{13}C$ NMR (DMSO-$d_6$, 100 MHz) δ 172.1, 163.0, 150.4, 143.6, 111.4, 83.2, 79.0, 73.7, 70.4, 61.3, 44.1, 32.7. Molecular weight for $C_{12}H_{15}N_2O_8$ $(M-H)^-$ Calc. 315.08. Found 315.1.

Compound 531: A suspension of sodium azide (4.36 g, 67 mmol) in acetonitrile (80 mL) was cooled in an ice bath. Then, trifluoromethanesulfonic anhydride (15.7 g, 9.4 mL, 55.6 mmol) was dropwisely added to the mixture using a dropping funnel over 10 minute. After the reaction was run for 2 hours in an ice bath, the reaction mixture was filtered to remove the precipitation. The precipitation was washed with 20 mL of acetonitrile. The combined acetonitrile solution containing triflic azide was directly used for the subsequent azidotransfer reaction.

Spermine (530, 11.25 g, 55.6 mmol) was dissolved in acetonitrile (50 mL). Then, copper sulfate pentahydrate (139 mg, 0.556 mmol) and triethylamine (15.5 mL, 111.2 mmol) were added to the solution while stirring. The mixture was cooled in an ice bath, then, the triflic azide solution prepared above was added to the mixture slowly. The reaction mixture was allowed to warm to room temperature and run overnight. Di-tert-butyl dicarbonate (60.7 g, 278 mmol) was slowly added to the solution and the reaction mixture was stirred for 2 hours. After evaporation, the crude was extracted with EtOAc and $H_2O$, dried over anhydrous $Na_2SO_4$, and purified by silica gel column chromatography (Hexane:EtOAc=2:1, $R_f$=0.46) to give 531 (13.12 g, 24.8 mmol, 45%).

$^1$H NMR (DMSO-$d_6$, 400 MHz) δ 6.77 (brs, 1H), 3.30-3.34 (m, 2H), 3.11-3.19 (m, 8H), 2.86-2.90 (m, 2H), 1.71-1.72 (m, 2H), 1.54-1.56 (m, 2H), 1.37-1.39 (m, 29H). Molecular weight for $C_{25}H_{48}N_6NaO_6$ (M+Na)$^+$ Calc. 551.35. Found 551.2.

Compound 533:

To a solution of compound 532 (324 mg, 0.568 mmol) in pyridine (5 mL), trifluoroacetic anhydride (0.316 mL, 2.27 mmol) was added dropwise at 0° C. The reaction mixture was stirred for 14 hours at room temperature. After extraction with $CH_2Cl_2$ and $NaHCO_3$ aq., the crude was purified by silica gel column chromatography (Hexane:EtOAc=1:1, $R_f$=0.34) to give compound 533 (214 mg, 0.414 mmol, 73%). $^1$H NMR (DMSO-$d_6$, 400 MHz) δ 9.48-9.53 (m, 1H), 3.18-3.43 (m, 12H), 1.75-1.80 (m, 4H), 1.51-1.54 (m, 4H). $^{19}$F NMR (376 MHz, DMSO-$d_6$) δ —70.91, −70.95, −70.97, −71.01, −71.04, −71.15, −71.17, −77.23, −77.25, −77.38. Molecular weight for $C_{16}H_{21}F_9N_6NaO_3$ (M+Na)$^+$ Calc. 539.14. Found 539.0.

The extended spermine analogs containing azide group were also synthesized.

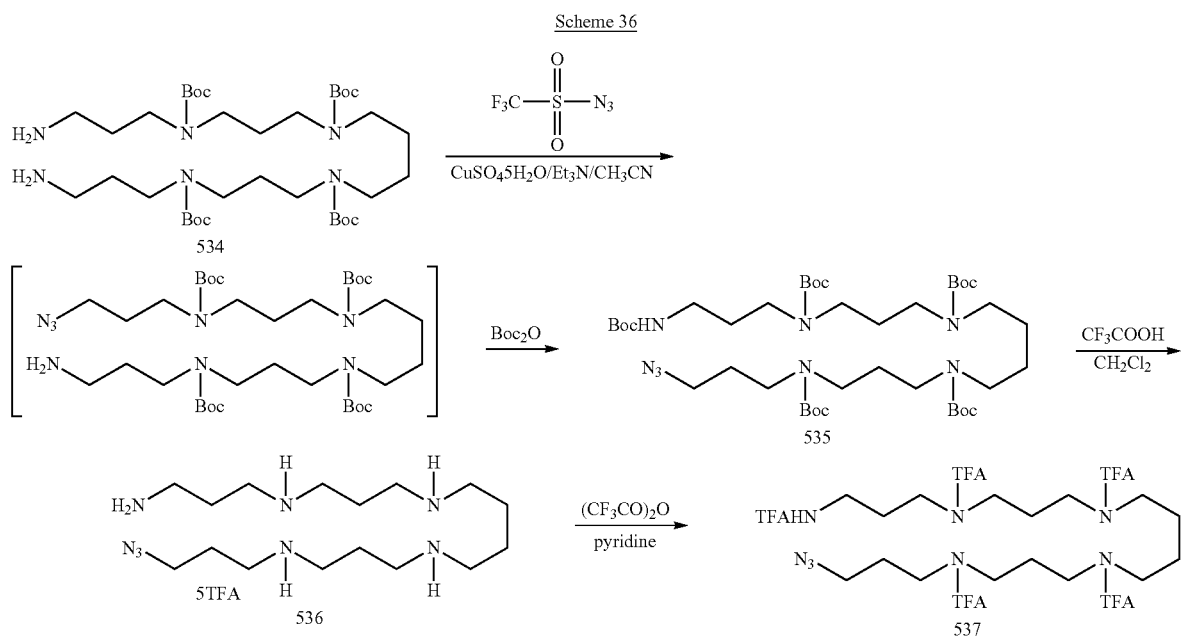

Scheme 36

Compound 531b:

To a solution of compound 531 (1.5 g, 2.84 mmol) in THF (20 mL) and $H_2O$ (1 mL), triphenylphosphine (1.49 g, 5.68 mmol) was added. The reaction mixture was stirred at room temperature overnight. After evaporation, the crude was purified by silica gel column chromatography ($CH_2Cl_2$:MeOH=4:1, $R_f$=0.70) to give 531b (1.13 g, 2.25 mmol, 79%). $^1$H NMR (DMSO-$d_6$, 400 MHz) δ 6.78 (brs, 1H), 3.10-3.15 (m, 8H), 2.87-2.89 (m, 2H), 2.48-2.51 (m, 2H), 1.37-1.55 (m, 35H). Molecular weight for $C_{25}H_{51}N_4O_6$ (M+H)$^+$ Calc. 503.38. Found 503.2.

Compound 532:

To a solution of compound 531 (1.37 g, 2.59 mmol) in $CH_2Cl_2$ (36 mL), trifluoroacetic acid (4 mL) was slowly added at 0° C. The reaction mixture was stirred for 5 hours at room temperature. After removing the solvent, the crude was precipitated in $Et_2O$ to give compound 532 (950 mg, 1.67 mmol, 64%) as the TFA salt. $^1$H NMR (DMSO-$d_6$, 400 MHz) δ 8.78 (brs, 2H), 8.68 (brs, 2H), 7.93 (brs, 3H), 3.48 (t, J=6.4 Hz, 2H), 2.94-2.95 (m, 10H), 1.82-1.93 (m, 4H), 1.62 (brs, 4H). Molecular weight for $C_{10}H_{25}N_6$ (M+H)$^+$ Calc. 229.21. Found 229.3.

Compound 535:

A suspension of sodium azide (436 mg, 6.70 mmol) in acetonitrile (8 mL) was cooled in an ice bath. Then, trifluoromethanesulfonic anhydride (0.94 mL, 5.56 mmol) was slowly added to the mixture. After the reaction was run for 2 hours in an ice bath, the reaction mixture was filtered to remove the precipitation. The precipitation was washed with 20 mL of acetonitrile. The combined acetonitrile solution containing triflic azide was directly used for the subsequent diazotransfer reaction.

Compound 534 (J. Med. Chem. 2005, 48, 2589-2599; 5 g, 6.97 mmol) was dissolved in acetonitrile (30 mL). Then, copper sulfate pentahydrate (28 mg, 0.112 mmol) and triethylamine (7.75 mL, 55.6 mmol) were added to the solution. The mixture was cooled in an ice bath, then, the triflic azide solution prepared above was added to the mixture slowly. The reaction mixture was allowed to warm to room temperature and run overnight. After transferred half of this solution (~32 mL) into a different flask, di-tert-butyl dicarbonate (1.52 g, 6.98 mmol) was slowly added and the reaction mixture was stirred for 2 hours. After evaporation, the residue was extracted with EtOAc and H$_2$O, dried over anhydrous Na$_2$SO$_4$, filtered, and concentrated in vacuo. The crude was purified by silica gel column chromatography (Hexane:EtOAc=1:1, R$_f$=0.35) to give 535 (281 mg, 0.333 mmol, 5%). $^1$H NMR (DMSO-d$_6$, 400 MHz) δ 6.73 (brs, 1H), 3.05-3.33 (m, 18H), 2.86-2.88 (m, 2H), 1.36-1.70 (m, 57H). Molecular weight for C$_{41}$H$_{78}$N$_8$NaO$_{10}$ (M+Na)$^+$ Calc. 865.57. Found 865.5.

Compound 536:

To a solution of compound 535 (275 mg, 0.326 mmol) in CH$_2$Cl$_2$ (8 mL), trifluoroacetic acid (2 mL) was added dropwise at 0° C. The reaction mixture was stirred for 30 min at 0° C. and then for 90 min at room temperature. After removing the solvent, the crude was precipitated in Et$_2$O to give compound 536 (235 mg, 0.257 mmol, 79%) as the TFA salt. $^1$H NMR (D$_2$O, 400 MHz) δ 3.50 (t, J=6.0 Hz, 2H), 3.09-3.15 (m, 18H), 2.06-2.10 (m, 6H), 1.94-1.97 (m, 2H), 1.76 (brs, 4H). Molecular weight for C$_{16}$H$_{39}$N$_8$ (M+H)$^+$ Calc. 343.33. Found 343.2.

Compound 537:

To a solution of compound 536 (200 mg, 0.219 mmol) in pyridine (3 mL), trifluoroacetic anhydride (0.245 mL, 1.75 mmol) was added dropwise at 0° C. The reaction mixture was stirred for 14 hours at room temperature. After removing solvent, the crude was purified by silica gel column chromatography (Hexane:EtOAc=1:2, R$_f$=0.34) to give compound 537 (127 mg, 0.154 mmol, 70%). $^1$H NMR (DMSO-d$_6$, 400 MHz) δ 9.45-9.53 (m, 1H), 3.30-3.44 (m, 12H), 3.22 (t, J=6.0 Hz, 2H), 1.80-1.89 (m, 8H), 1.55 (brs, 4H). $^{19}$F NMR (376 MHz, DMSO-d$_6$) δ —70.90, −70.92, −70.96, −70.98, −71.06, −71.11, −71.13, −71.16, −71.20, −71.34, −77.26, −77.28, −77.41. Molecular weight for C$_{26}$H$_{33}$F$_{15}$N$_8$NaO$_5$ (M+Na)$^+$ Calc. 845.22. Found 845.3.

The oligoamine derivatives with azide functionality were synthesized as follows.

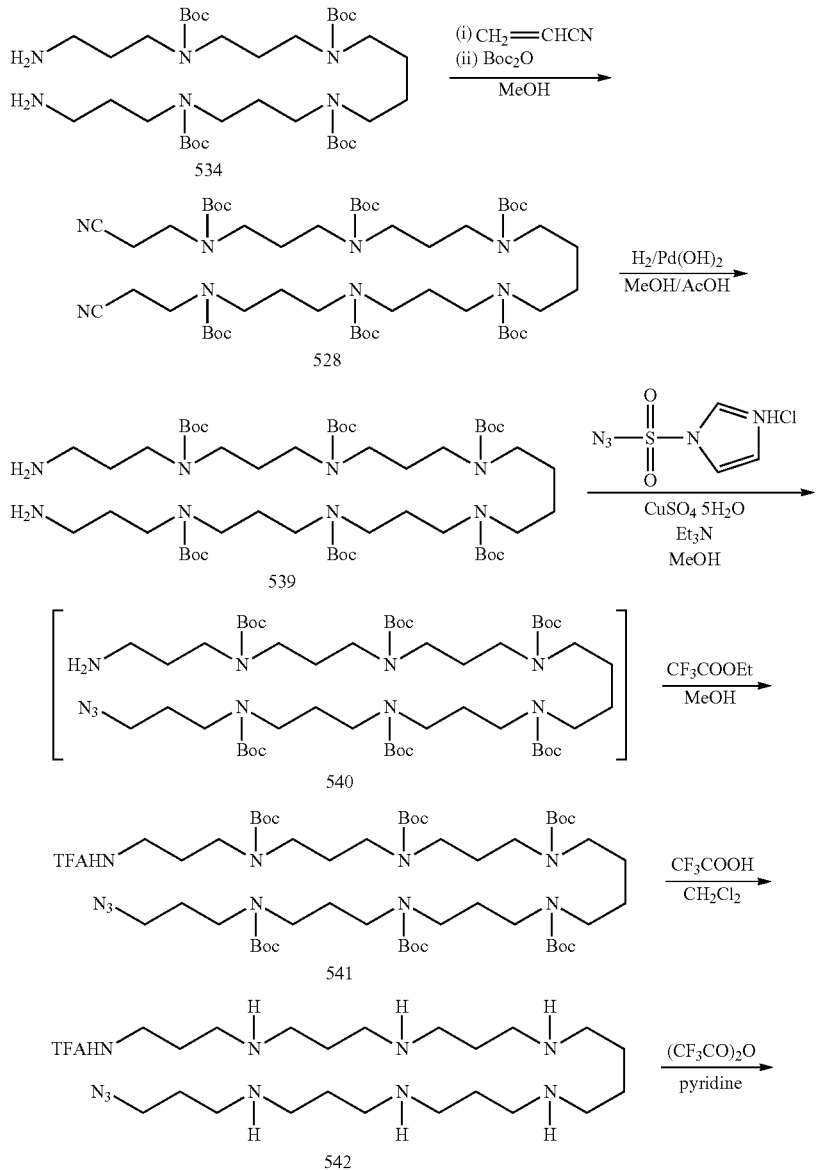

Scheme 37

-continued

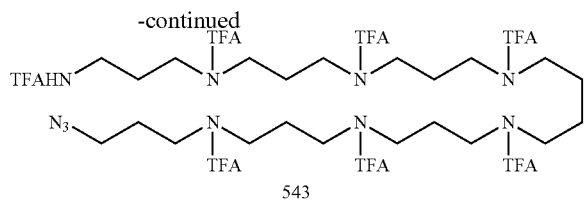

543

Compound 538:

To a solution of compound 534 (40 g, 55.8 mmol) in methanol (300 mL), triethylamine (64 mL) and acrylonitrile (7.35 mL, 111.6 mmol) were added. The reaction was stirred for 14 hours at room temperature. Then, di-tert-butyl dicarbonate (37.1 g, 170 mmol) was slowly added at ° C. and the mixture was stirred for 14 hour at room temperature. After aqueous work-up, the crude was purified by silica gel column chromatography (Hexane:EtOAc=1:4, $R_f$=0.72) to give 538 (23.9 g, 23.4 mmol, 42%). $^1$H NMR (DMSO-$d_6$, 400 MHz) δ 3.40 (t, J=6.4 Hz, 4H), 3.09-3.15 (m, 20H), 2.69 (t, J=6.4 Hz, 4H), 1.36-1.65 (m, 66H). $^{13}$C NMR (DMSO-$d_6$, 100 MHz) δ 170.3, 154.5, 119.0, 79.1, 78.3, 78.2, 59.7, 45.0, 44.1, 42.4, 28.0, 27.9, 20.7, 14.1. Molecular weight for $C_{52}H_{94}N_8NaO_{12}$ (M+Na)$^+$ Calc. 1045.69. Found 1045.5.

Compound 539:

A solution of compound 538 (7.88 g, 7.70 mmol) in methanol (80 mL) and acetic acid (10 mL) was hydrogenated over Pd(OH)$_2$/C (8.0 g) at 50 psi hydrogen pressure for 14 hours. After filtration through Celite, the filtrate was concentrated in vacuo. The residue was extracted with CHCl$_3$ (300 mL) and 1M NaOH (40 mL). The organic layer was separated, dried over anhydrous MgSO$_4$, filtered and concentrated to afford compound 539 (7.90 g, 7.66 mmol, 99%) as a viscous oil. $^1$H NMR (DMSO-$d_6$, 400 MHz) δ 3.62 (brs, 4H), 3.08-3.14 (m, 24H), 1.36-1.63 (m, 70H). $^{13}$C NMR (DMSO-$d_6$, 100 MHz) δ 154.6, 154.5, 154.4, 79.1, 78.3, 78.2, 46.3, 44.3, 38.5, 30.8, 28.0, 27.2, 25.1. Molecular weight for $C_{52}H_{103}N_8O_{12}$ (M+H)$^+$ Calc. 1031.77. Found 1031.5.

Compound 541:

To a solution of compound 539 (7.40 g, 7.18 mmol) in methanol (72 mL), triethylamine (2.5 mL, 18.0 mmol), copper sulfate pentahydrate (18 mg, 0.072 mmol) and imidazole-1-sulfonyl azide hydrochloride (903 mg, 4.31 mmol) were added. The reaction mixture was stirred for 2 hours at room temperature (540; Molecular weight for $C_{52}H_{101}N_{10}O_{12}$ (M+H)$^+$ Calc. 1057.76. Found 1057.5). Then, ethyl trifluoroacetate (2.60 mL, 21.5 mmol) was added and the mixture was stirred for 2 hours at room temperature. After aqueous work-up, the crude was purified by silica gel column chromatography (Hexane:EtOAc=1:1, $R_f$=0.38) to give 541 (1.75 g, 1.52 mmol, 21%). $^1$H NMR (DMSO-$d_6$, 400 MHz) δ 9.38 (brs, 1H), 3.10-3.33 (m, 28H), 1.31-1.71 (m, 70H). $^{19}$F NMR (376 MHz, DMSO-$d_6$) δ—77.27. $^{13}$C NMR (DMSO-$d_6$, 100 MHz) δ 156.3, 155.9, 154.5, 154.4, 120.2, 117.3, 114.5, 78.4, 78.3, 78.2, 63.4, 48.4, 46.3, 44.2, 37.0, 27.9, 27.3, 25.1. Molecular weight for $C_{54}H_{99}F_3N_{10}NaO_{13}$ (M+Na)$^+$ Calc. 1175.72. Found 1175.3.

Compound 542:

To a solution of compound 541 (1.75 g, 1.52 mmol) in CH$_2$Cl$_2$ (40 mL), trifluoroacetic acid (10 mL) was slowly added at 0° C. The reaction mixture was stirred for 1 hour at 0° C. and then for 6 hours at room temperature. Removal of the solvent in vacuo afforded compound 542 as a white foam. This material was used for the next reaction without further purification. Molecular weight for $C_{24}H_{52}F_3N_{10}O$ (M+H)$^+$ Calc. 553.43. Found 553.3.

Compound 543:

To a solution of compound 542 (1.52 mmol) in pyridine (20 mL), trifluoroacetic anhydride (2.11 mL, 15.2 mmol) was added dropwise at 0° C. The reaction mixture was stirred for 14 hours at room temperature. After removing solvent, the crude was extracted with CH$_2$Cl$_2$ and H$_2$O. The organic layer was dried over anhydrous Na$_2$SO$_4$, then filtered and concentrated in vacuo. The crude was purified by silica gel column chromatography (EtOAc) to give compound 543 (1.45 g, 1.28 mmol, 85%). $^1$H NMR (DMSO-$d_6$, 400 MHz) δ 9.43-9.51 (m, 1H), 3.32-3.38 (m, 26H), 3.21-3.23 (m, 2H), 1.80-1.87 (m, 12H), 1.55 (brs, 4H). $^{19}$F NMR (376 MHz, DMSO-$d_6$) δ—71.00, −71.05, −71.13, −71.21, −71.26, −71.32, −71.35, −71.40, −77.32, −77.35, −77.47. $^{13}$C NMR (DMSO-$d_6$, 100 MHz) δ 156.5, 155.8, 155.6, 155.5, 155.3, 120.5, 117.7, 114.8, 114.4, 111.9, 48.3, 47.9, 46.7, 45.9, 44.6, 44.2, 44.0, 43.7, 36.9, 36.4, 27.7, 27.4, 25.9, 25.7, 25.3, 25.0, 24.0, 23.5, 23.3. Molecular weight for $C_{36}H_{44}F_{21}N_{10}O_7$ (M−H)$^-$ Calc. 1127.31. Found 1127.0.

Example 12

Preparation of 1'-Triazoylribofuranose Derivatives

Scheme 38

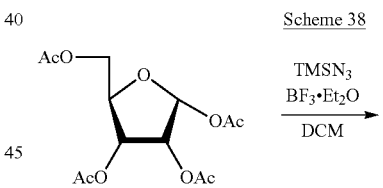

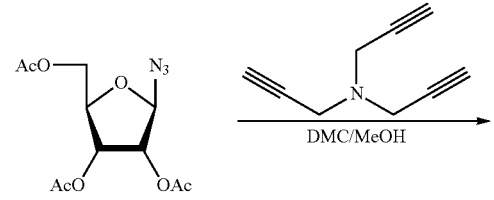

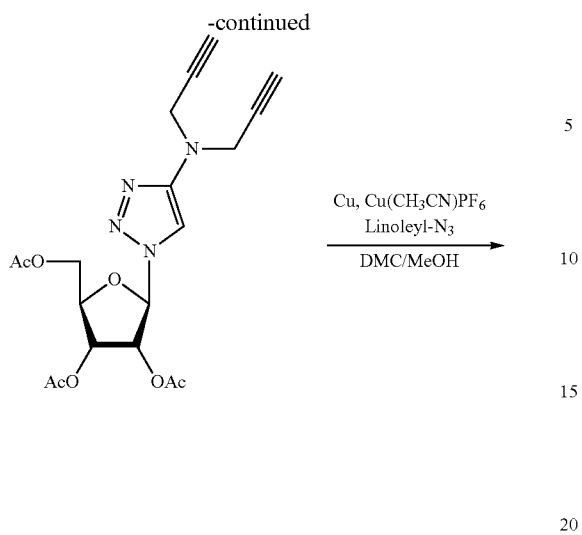

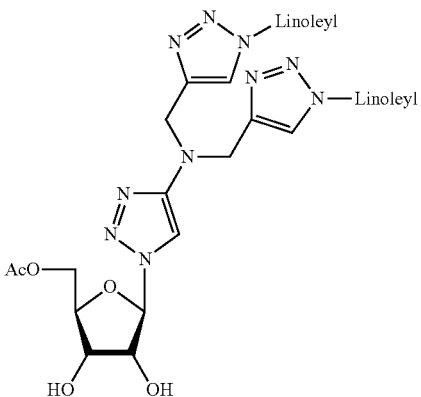

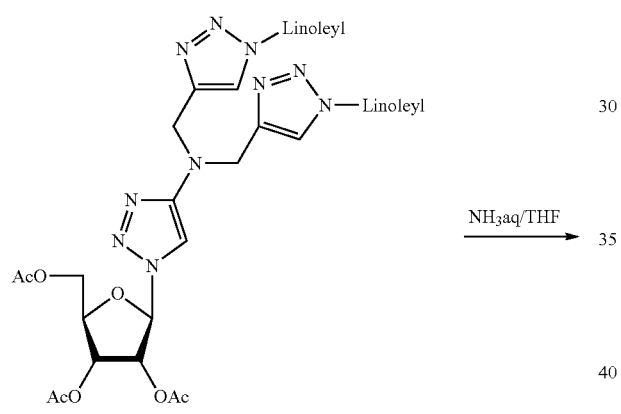

Example 13

Functionalized Peptides for Conjugation to Oligonucleotides

The peptides shown in Table 5 are synthesized by following solid phase Fmoc chemistry for conjugation to oligonucleotides via the click chemistry approach. Peptides P1-P3 contains a azido moiety and peptides P4-P6 contain terminal alkynes to conjugate to oligonucleotides or a carrier molecules with complementary function group.

TABLE 5

| | Functionalized peptide for conjugation | |
|---|---|---|
| Peptide | | Functional group for conjugation |
| P1 | $N_3-(CH_2)_{15}-CO$-Tyr-Gly-Arg-Lys-Lys-Arg-Arg-Gln-Arg-Arg-Arg-Pro-Pro-Gln-$NH_2$ | Azide |
| P2 | cyclo-[Phe-Arg-Gly-Asp-Lys($N_3-(CH_2)_{15}-COOH$)] | Azide |
| P3 | $N_3-(CH_2)_{15}-CO$-Arg-Arg-Arg-Arg-Arg-Arg-Arg-Arg-$NH_2$ | Azide |
| P4 | $C{\equiv}C-(CH_2)_3-CO$-Tyr-Gly-Arg-Lys-Lys-Arg-Arg-Gln-Arg-Arg-Pro-Pro-Gln-$NH_2$ | Alkyne |
| P5 | cyclo-[Phe-Arg-Gly-Asp-Lys($C{\equiv}C-(CH_2)_3-COOH$)] | Alkyne |
| P6 | $C{\equiv}C-(CH_2)_3-CO$-Arg-Arg-Arg-Arg-Arg-Arg-Arg-Arg-$NH_2$ | Alkyne |

Example 14

On Support Post Synthetic Click Chemistry after Oligonucleotide Synthesis

Figure 12:
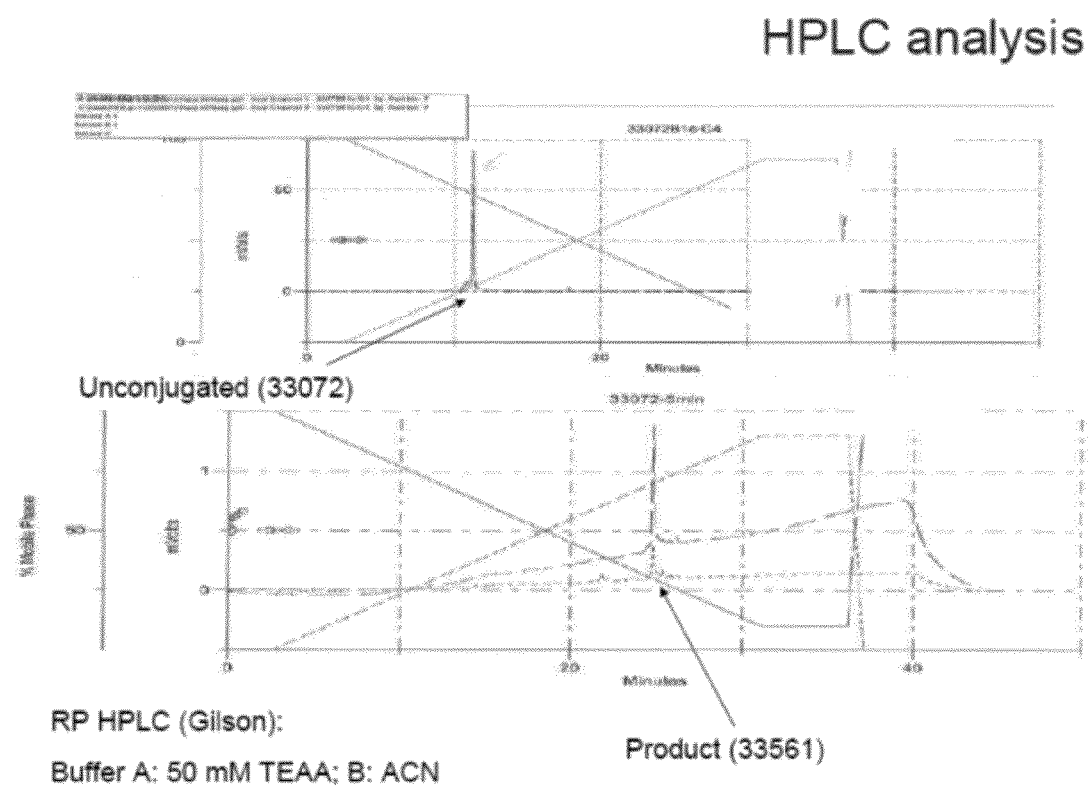
FIG. 12: HPLC analysis of ligand conjugation by Click chemistry.
Figure 13:
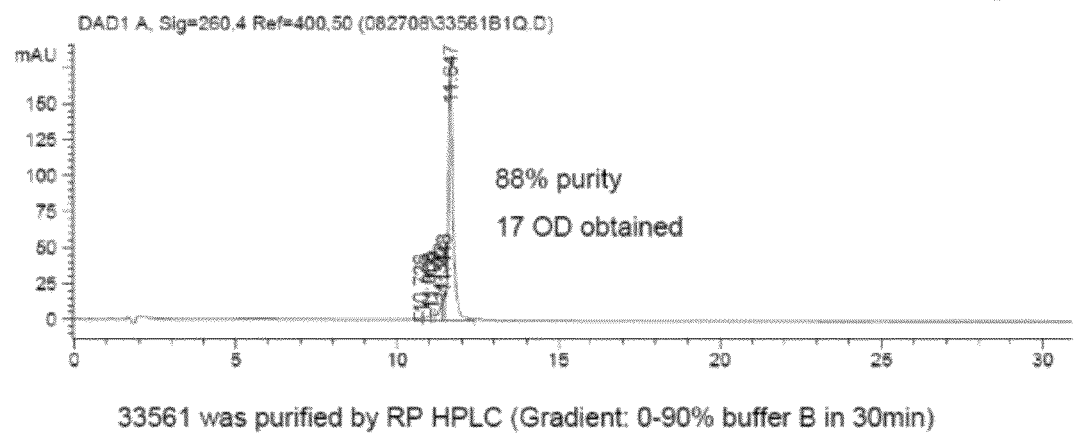
FIG. 13: HPLC analysis of purified Click chemistry conjugation.

Scheme 39 shows exemplary on support conjugation of ligands to oligonucleotide by click chemistry. One equivalent of oligonucleotide-alkyne (1 µmole scale synthesis0 was reacted with 10 equivalent of C22-azide (MeOH/THF 1:1 v/v) in the presence of 0.25 equivalent $CuSO_4$ and 2 equivalents of sodium ascorbate. The resulting conjugated oligonucleotide (33561) was analyzed by HPLC and results are shown in FIG. 12. Conjugated oligonucleotide was purified by RP-HPLC to with 88% purity as determined by HPLC analysis, FIG. 13.

Scheme 39

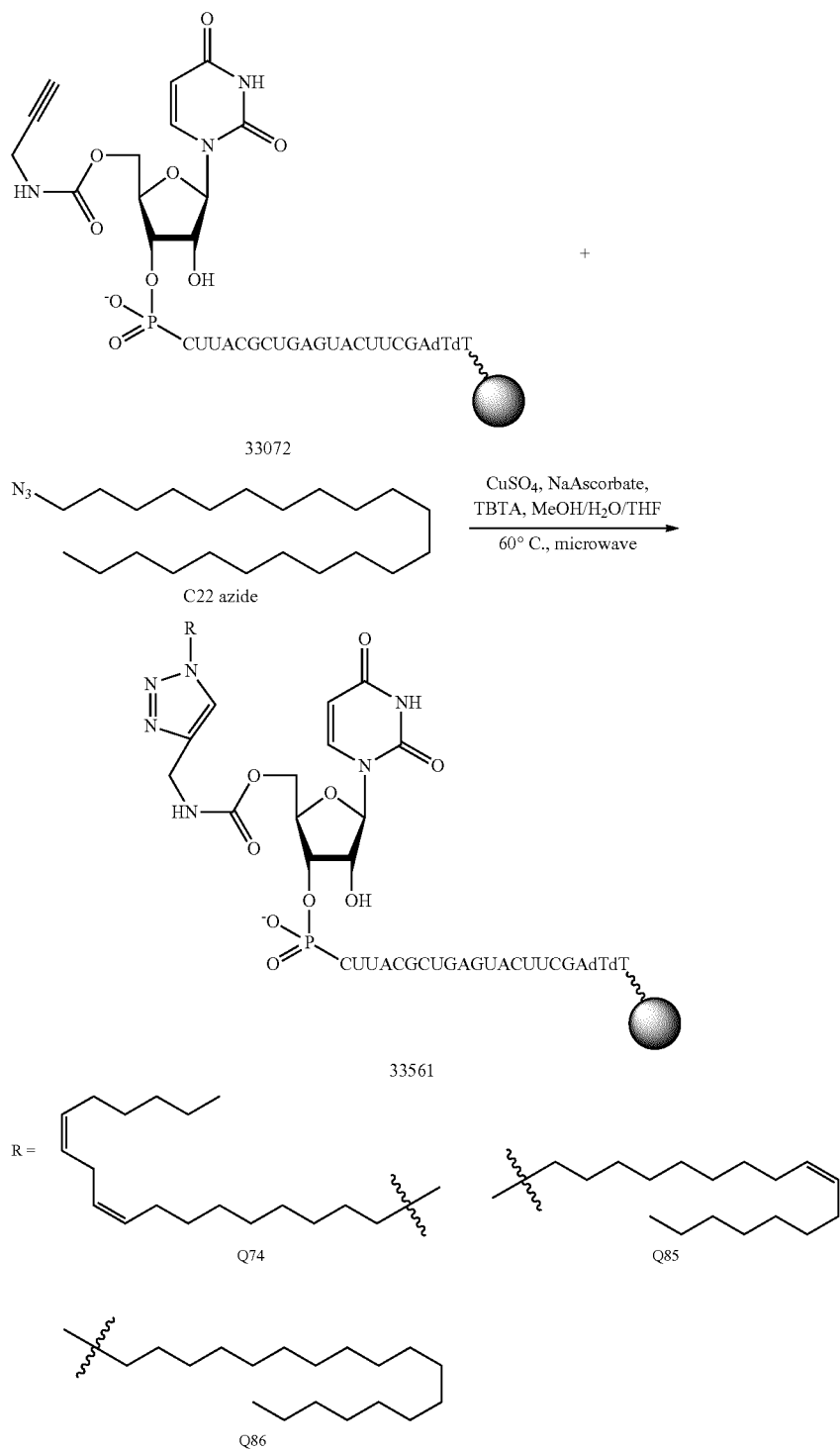

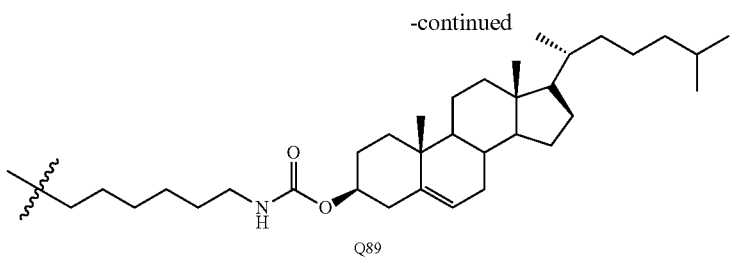

Q89

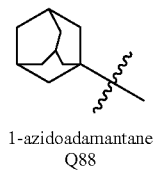

1-azidoadamantane
Q88

Example 15

Post Synthetic Labeling of Oligonucleotides with 6-Carboxyfluorescein by Click Chemistry a. Synthesis of 6-Carboxyfluorescein-Propargylamide (Alkynyl FAM)

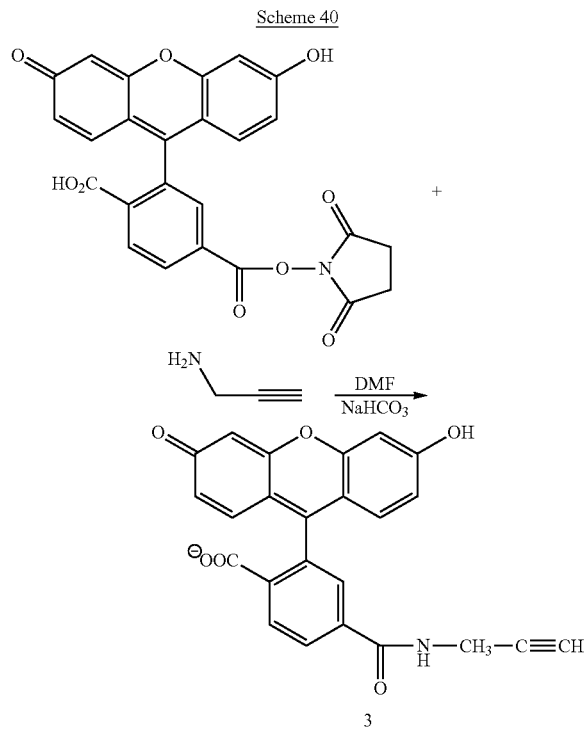

A solution of 6.8 ul (0.1 mmol) of propargylamine in DMF (1.0 ml) was added to a solution of 22 mg (0.046 mmol) of 6-carboxyfluorescein NHS ester in DMF (1.0 ml) and 0.1M NaHCO3 (0.2 ml) buffer. After overnight stirring at room temperature, the solvent was removed under vacuum. A small amount of reaction mixture was submitted for LC-MS analysis. The crude mixture was purified by Silica gel column chromatography. (DCM: MeOH 9:1). LC-MS analysis confirms that alkenyl FAM is formed. Cal Mass: 414.09. Found Mass: 414.0.

b. Synthesis of Azio-Labeled Oligonucleotide

Figure 14:
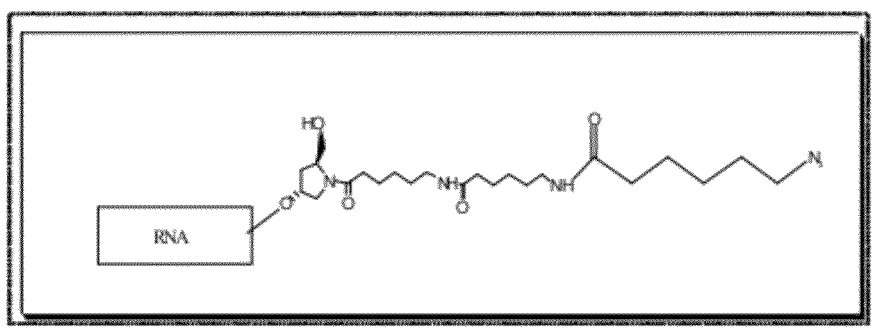
FIG. 14: Schematic representation of an Azido-labeled oligonucleotide.

A schematic representation of an azido-labeled oligonucleotide is shown in FIG. 14. To incorporate the azido group at the 3'-end of siRNA, 100 nmole of Amino modified siRNA (Al-3991) in 100 ul of 0.2 M NaHCO₃ buffer (pH 9.0) incubated for 15 h at room temperature with 2.0 umole of azido ester in 25 ul DMF. After 15 h sample was analyze by IEX analysis. Leave the sample at room temperature for 9 h to complete the reaction. After 24 h sample was analyzed by LC-MS and it confirms the integrity of the compound. Cal Mass: 7269.35. Found Mass: 7268.56.

c. Click Chemistry

Figure 15:
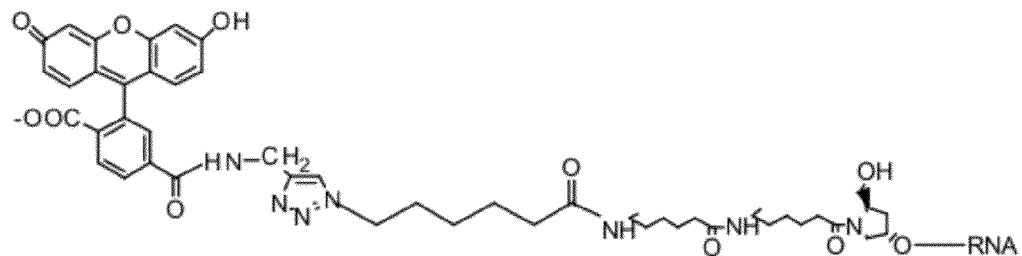
FIG. 15: Schematic representation 6-Carboxyfluorescein-propargylamide conjugated with an azido-labeled oligonucleotide by Click chemistry.
Figure 16:
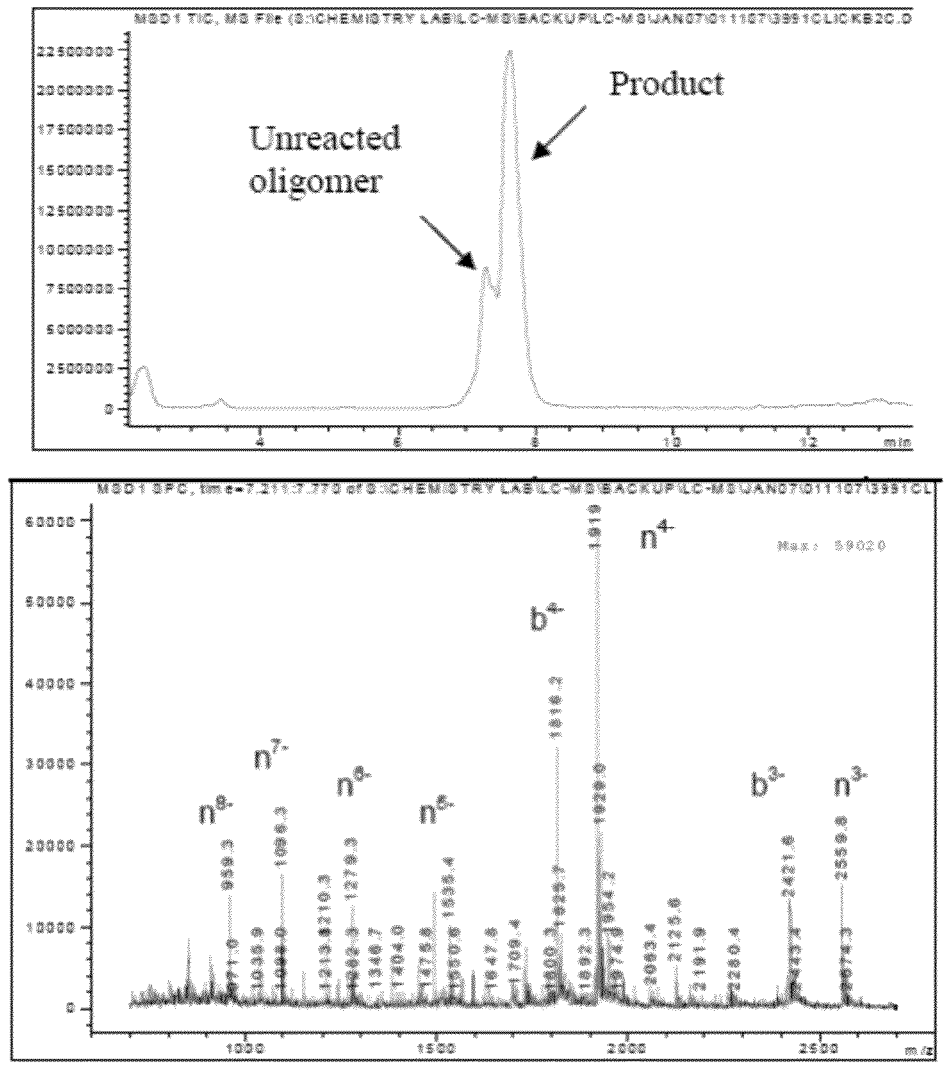
FIG. 16: LC-MS analysis of crude product of Click chemistry reaction between 6-Carboxyfluorescein-propargylamide and azide-labeled oligonucleotide.

FIG. 15 shows 6-Carboxyfluorescein-propargylamide conjugated with an azido-labeled oligonucleotide by Click chemistry. Azido-oligonucleotide (5.0 nmol) in 100 ul of water was reacted with a 150-fold excess of alkynyl FAM in 25 ul of dry DMSO at 80° C. for 72 h. Unreacted dye was removed by size-exclusion chromatography on a PD-10 column. LC-MS data shows that 1,3-dipolar cycloaddition between alkynyl 6-carboxyfluorescein (FAM) and azido-labeled single-stranded RNA was carried out under aqueous conditions to produce FAM-labeled siRNA, FIG. 16. Fluorescein-conjugated oligomer (n): Cal Mass: 7684. Found Mass 7682.3, unconjugated starting material (b): Cal Mass: 7269. Found Mass 7277.

Example 16

Azide Modified C6-Aminohydroxyprolinol

The DMTr-protected C6-aminoprolinol were converted to the corresponding azide derivative as follows.

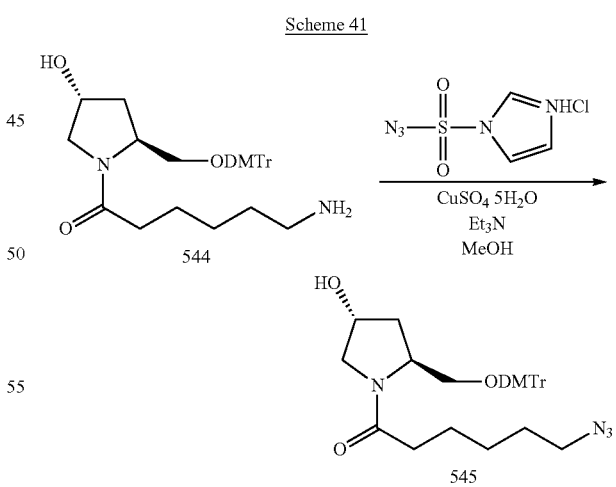

Compound 545:

To a solution of compound 544 (200 mg, 0.375 mmol) in methanol (5 mL), triethylamine (0.157 mL, 1.13 mmol), copper sulfate pentahydrate (1 mg, 0.00375 mmol), and imidazole-1-sulfonyl azide hydrochloride (94 mg, 0.45 mmol) were added. The reaction mixture was stirred for 1 hour at room temperature. The product formation was confirmed by mass analysis. Molecular weight for $C_{32}H_{38}N_4NaO_5$ $(M+Na)^+$ Calc. 581.27. Found 581.0; $C_{32}H_{39}N_4O_5$ $(M+H)^+$ Calc. 559.29. Found 559.0.
Example 17
Triazole-Linked Nucleoside Building Block
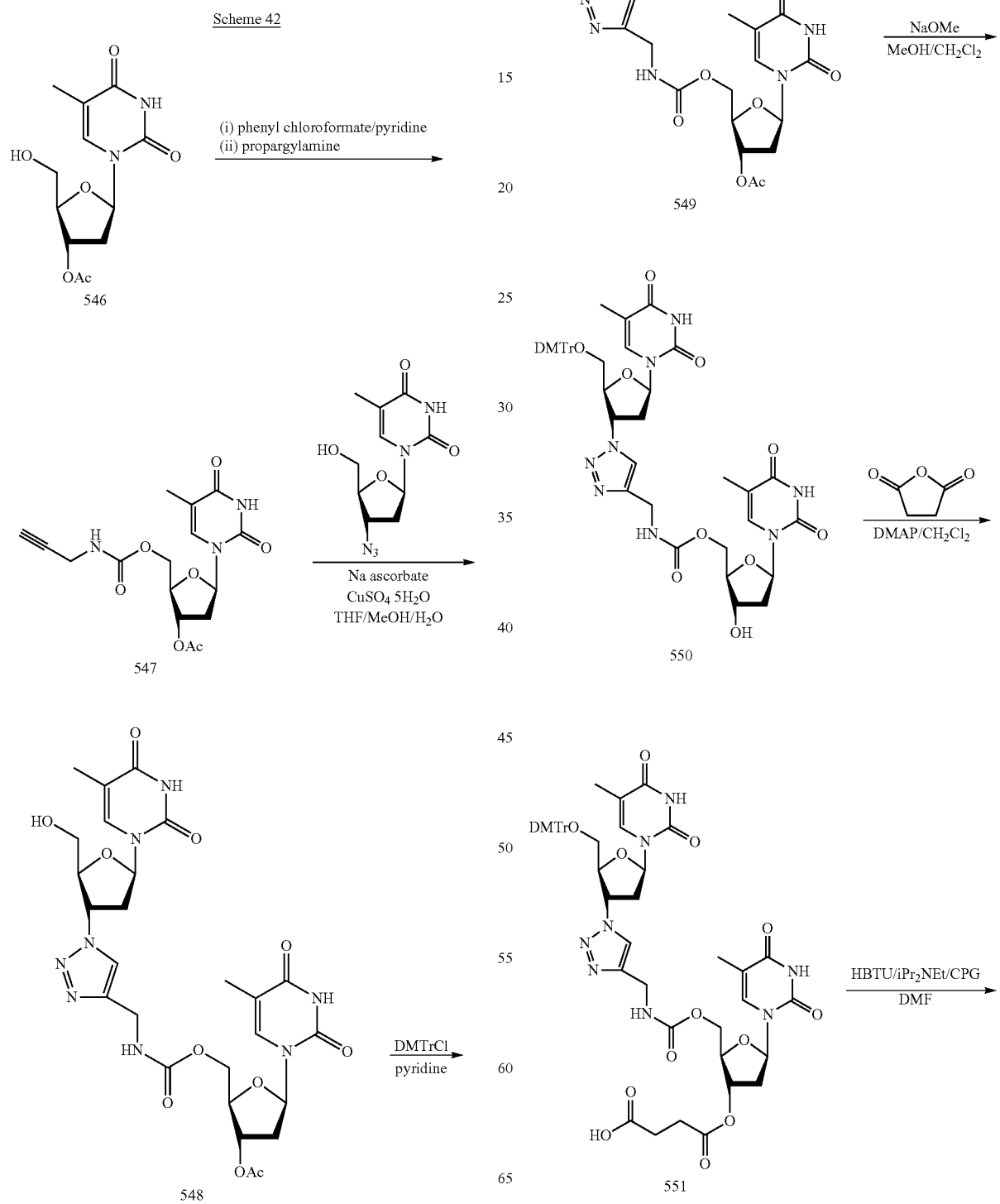

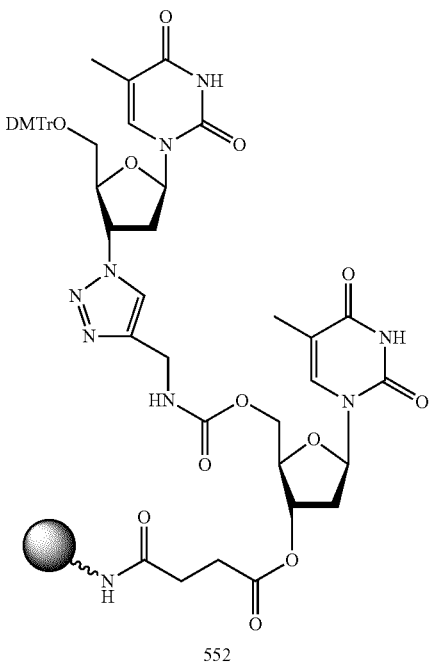

552

Compound 547:

To a solution of compound 546 (Prime organics, 2.13 g, 7.49 mmol) in pyridine (30 mL), phenylchloroformate (1.04 mL, 8.24 mmol) was added at 0° C. After stirring for 2 hours at room temperature, propargylamine was added at 0° C. The mixture was stirred for 14 hours at room temperature. After removal of the solvent, aqueous work-up and purification by silica gel column chromatography (Hexane:EtOAc=1:2, $R_f$=0.19) to give 547 (2.73 g, 7.47 mmol, 99%). $^1$H NMR (DMSO-d$_6$, 400 MHz) δ 11.37 (s, 1H), 7.88 (t, J=5.6 Hz, 1H), 7.46 (s, 1H), 6.19 (dd, J=5.8 Hz, 9.0 Hz, 1H), 5.17-5.18 (m, 1H), 4.23-4.26 (m, 1H), 4.10-4.15 (m, 2H), 3.81 (dd, J=2.4 Hz, 5.6 Hz, 2H), 3.13 (t, J=2.4 Hz, 1H), 2.43-2.47 (m, 1H), 2.24 (dd, J=5.8 Hz, 13.8 Hz, 1H), 2.07 (s, 3H), 1.79 (s, 3H). $^{13}$C NMR (DMSO-d$_6$, 100 MHz) δ 170.0, 163.6, 155.5, 150.5, 135.6, 109.9, 83.7, 81.4, 81.1, 74.3, 73.2, 64.2, 35.6, 29.8, 12.2. Molecular weight for $C_{16}H_{19}N_3NaO_7$ (M+Na)$^+$ Calc. 388.11. Found 388.0.

Compound 548:

To a solution of compound 547 (2.59 g, 7.09 mmol) and 3'-azidothymidine (1.89 g, 7.09 mmol) in THF (50 mL) and MeOH (50 mL), H$_2$O (25 mL), (+)-sodium L-ascorbate (140 mg, 0.709 mmol), and copper sulfate pentahydrate (35 mg, 0.142 mmol) were added. The reaction mixture was heated at 70° C. for 2 hours. After removal of the solvent, co-evaporation with pyridine twice gave pale-yellow foam (quantitative yield). The material was used for the next reaction. Analytical samples were obtained by silica gel column chromatography (10% MeOH in CH$_2$Cl$_2$, $R_f$=0.36). $^1$H NMR (DMSO-d$_6$, 400 MHz) δ 11.38 (s, 1H), 11.37 (s, 1H), 8.16 (s, 1H), 7.97 (t, J=5.6 Hz, 1H), 7.81 (d, J=0.8 Hz, 1H), 7.46 (d, J=1.2 Hz, 1H), 6.41 (t, J=6.6 Hz, 1H), 6.19 (dd, J=6.0 Hz, 8.8 Hz, 1H), 5.33-5.37 (m, 1H), 5.29 (t, J=5.2 Hz, 1H), 5.18 (d, J=6.8 Hz, 1H), 4.09-4.29 (m, 6H), 3.66-3.71 (m, 1H), 3.57-3.62 (m, 1H), 2.61-2.73 (m, 2H), 2.44-2.46 (m, 1H), 2.20-2.25 (m, 1H), 2.07 (s, 3H), 1.81 (s, 3H), 1.72 (s, 3H). $^{13}$C NMR (DMSO-d$_6$, 100 MHz) δ 170.1, 163.7, 163.6, 155.9, 149.6, 145.2, 136.3, 135.9, 124.0, 122.7, 110.0, 109.8, 84.7, 84.0, 83.9, 81.6, 74.6, 64.2, 60.7, 59.4, 47.6, 37.2, 35.9, 35.6, 20.8, 12.2, 12.1. Molecular weight for $C_{26}H_{32}N_8NaO_{11}$ (M+Na)$^+$ Calc. 655.21. Found 655.0.

Compound 549:

To a solution of compound 548 (~7.09 mmol) in pyridine (70 mL), DMTrCl (2.76 g, 8.15 mmol) was added. The reaction mixture was stirred at room temperature for 14 hours. After removal of the solvent, aqueous work-up and purification by silica gel column chromatography (5% MeOH in CH$_2$Cl$_2$, $R_f$=0.26) to give 549 (5.69 g, 6.09 mmol, 86%). $^1$H NMR (DMSO-d$_6$, 400 MHz) δ 11.38 (s, 2H), 8.17 (s, 1H), 7.97 (t, J=5.8 Hz, 1H), 7.66 (s, 1H), 7.46 (s, 1H), 7.21-7.35 (m, 9H), 6.86-6.87 (m, 4H), 6.42 (t, J=6.4 Hz, 1H), 6.20 (dd, J=6.0 Hz, 8.8 Hz, 1H), 5.54 (dd, J=7.2 Hz, 14.4 Hz, 1H), 5.19 (d, J=6.0 Hz, 1H), 4.10-4.35 (m, 6H), 3.73 (s, 6H), 3.26-3.34 (m, 2H), 2.73-2.77 (m, 2H), 2.44-2.46 (m, 1H), 2.21-2.26 (m, 1H), 2.06 (s, 3H), 1.71 (s, 3H), 1.59 (s, 3H). $^{13}$C NMR (DMSO-d$_6$, 100 MHz) δ 170.0, 163.6, 155.8, 150.4, 145.2, 144.5, 135.7, 135.1, 126.7, 122.2, 113.2, 109.9, 109.8, 85.9, 83.8, 83.8, 82.2, 81.4, 74.4, 64.1, 63.0, 59.2, 55.0, 37.2, 35.9, 35.5, 20.8, 12.1, 11.8. Molecular weight for $C_{47}H_{49}N_8O_{13}$ (M−H)$^−$ Calc. 933.34. Found 933.0.

Compound 550:

To a solution of compound 549 (5.48 g, 5.86 mmol) in CH$_2$Cl$_2$ (90 mL) and MeOH (10 mL), 0.5 M NaOMe in MeOH (22.8 mL, 11.4 mmol) was added. The reaction mixture was stirred at room temperature for 14 hours. After removal of the solvent, the crude was purified by silica gel column chromatography (10% MeOH in CH$_2$Cl$_2$, $R_f$=0.46) to give 550 (4.59 g, 5.14 mmol, 88%). $^1$H NMR (DMSO-d$_6$, 400 MHz) δ 11.39 (s, 1H), 11.30 (s, 1H), 8.15 (s, 1H), 7.87 (t, J=5.8 Hz, 1H), 7.65 (s, 1H), 7.42 (s, 1H), 7.20-7.34 (m, 9H), 6.85-6.87 (m, 4H), 6.40 (t, J=6.6 Hz, 1H), 6.18-6.21 (m, 1H), 5.52 (dd, J=7.2 Hz, 14.4 Hz, 1H), 5.37 (d, J=4.4 Hz, 1H), 4.20-4.32 (m, 6H), 4.03-4.06 (m, 1H), 3.91-3.93 (m, 1H), 3.73 (s, 6H), 3.06-3.27 (m, 1H), 2.72-2.76 (m, 2H), 2.19-2.26 (m, 1H), 2.03-2.07 (m, 1H), 1.71 (s, 3H), 1.59 (s, 3H). $^{13}$C NMR (DMSO-d$_6$, 100 MHz) δ 163.7, 163.6, 156.0, 150.4, 145.3, 144.5, 135.9, 135.1, 126.8, 122.2, 113.2, 109.8, 109.7, 85.9, 84.2, 83.8, 82.2, 70.4, 63.0, 59.2, 55.0, 38.6, 37.2, 35.9, 12.1, 11.8. Molecular weight for $C_{45}H_{47}N_8O_{12}$ (M–H)⁻ Calc. 891.33. Found 891.0.

Compound 551:

To a solution of compound 550 (3.56 g, 3.99 mmol) in $CH_2Cl_2$ (75 mL), DMAP (1.46 g, 12.0 mmol) and succinic anhydride (799 mg, 7.98 mmol) were added. The reaction mixture was stirred overnight at room temperature. Purification by silica gel column chromatography (5% MeOH/5% $Et_3N$ in $CH_2Cl_2$, $R_f$=0.11) of the crude mixture gave the compound 551 as the corresponding triethylammonium salt (4.29 g, 3.92 mmol, 98%). ¹H NMR (DMSO-d₆, 400 MHz) δ 11.34 (brs, 2H), 8.17 (s, 1H), 7.98 (t, J=5.8 Hz, 1H), 7.65 (s, 1H), 7.45 (s, 1H), 7.20-7.34 (m, 9H), 6.84-6.86 (m, 4H), 6.40 (t, J=6.4 Hz, 1H), 6.19 (dd, J=6.0 Hz, 8.8 Hz, 1H), 5.53 (dd, J=7.0 Hz, 14.6 Hz, 1H), 5.18 (d, J=6.0 Hz, 1H), 4.08-4.32 (m, 6H), 3.72 (s, 6H), 3.23-3.39 (m, 2H), 2.72-2.76 (m, 2H), 2.41-2.54 (m, 5H), 2.19-2.24 (m, 1H), 1.70 (s, 3H), 1.58 (s, 3H). ¹³C NMR (DMSO-d₆, 100 MHz) δ 173.7, 172.1, 163.7, 163.6, 155.8, 150.4, 145.2, 144.5, 135.7, 135.1, 126.7, 122.2, 113.2, 109.8, 85.9, 83.8, 82.2, 81.4, 74.4, 64.2, 63.0, 62.5, 59.2, 52.0, 37.2, 35.8, 35.5, 29.4, 29.2, 12.1, 11.8. Molecular weight for $C_{49}H_{51}N_8O_{15}$ (M–H)⁻ Calc. 991.35. Found 991.0.

Compound 552:

Compound 551 (4.21 g, 3.85 mmol) was dissolved in DMF (250 mL). HBTU (1.53 g, 4.04 mmol) then $iPr_2NEt$ (3.35 mL, 19.3 mmol) and finally CPG-$NH_2$ (Prime Synthesis CPG-585 angstrom, $NH_2$ loading=124 mmol/g) (34.2 g, 4.24 mmol) were added in succession. The mixture was shaken for 4 h at room temperature, then the solid was collected by filtration, washed with $CH_2Cl_2$ (500 mL), then 50% MeOH/$CH_2Cl_2$ (500 mL) and dried in vacuo. The residual amino groups were capped by shaking for 1 h with $Ac_2O$/Pyridine/$Et_3N$ (80 mL/240 mL/16 mL). Filtration and washing with $CH_2Cl_2$ (500 mL) and 50% MeOH/$CH_2Cl_2$ (500 mL) then drying overnight in vacuo gave compound 552 (~36 g, 64 mmol/g).

Example 18

Figure 17:
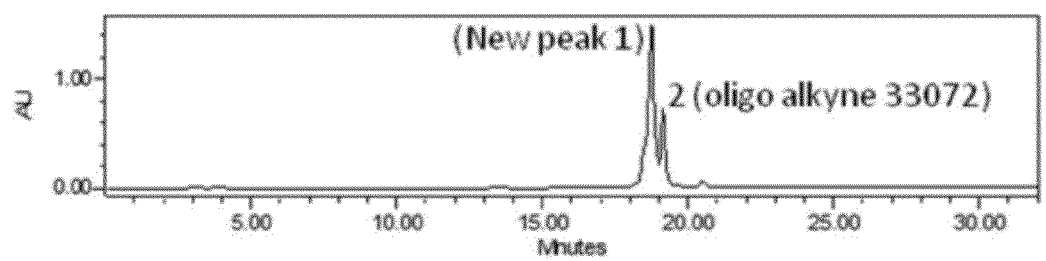
FIG. 17: Reverse-phase HPLC analysis of click reaction of free spermine azide with RNA alkyne.

Conjugation of Free Spermine Molecule to RNA on the Solid Support Via Click Chemistry Compound 554: (1) RNA alkyne on the solid support, A-33072.1, (11 mg, 0.62 mmol) was treated with spermine azide (553, 3.53 mg, 6.18 μmol) in the presence of $CuSO_4 \cdot 5H_2O$ (0.62 μmol) and sodium ascorbate (3.1 μmole), and the mixture was kept on a heating block at 65° C. for 2 h. The solvent volume of the reaction was maintained as a 1:1 ratio of t-BuOH/$H_2O$ (v/v) (1 ml). After reaction the beads were subsequently washed with water, methanol and acetonitrile and allowed to dry at room temperature. (2) Deprotection: The reacted beads were treated with aqueous methylamine (125 μl) for 20 min at 65° C., then cooled to –20° C. for 20 min. The filtrate was collected, and the beads were washed with DMSO (100 μl×3) and combined them with the filtrate, then cooled at –20° C. for 10 min. Triethylamine trihydrofluoride (175 μl) was added to the combined filtrate and the mixture was kept at 65° C. for 20 min. After dialysis, the crude reaction mixture was analyzed by reverse-phase HPLC and LC-MS, FIG. 17. (3) RP-HPLC and LC-MS: The material was loaded to an analytical RP-HPLC on a gradient using two buffer systems (0.1M TEAA, pH 7.0 and acetonitrile), % B=0-40%/20 min, ~100%/30 min, 1 ml/min, linear gradient, UV: 260 nm; Column: XTerra RP-18, 4.6×250 mm. The crude materials also analyzed by LC-MS (calcd mass 7220. found 7219 and 7260).

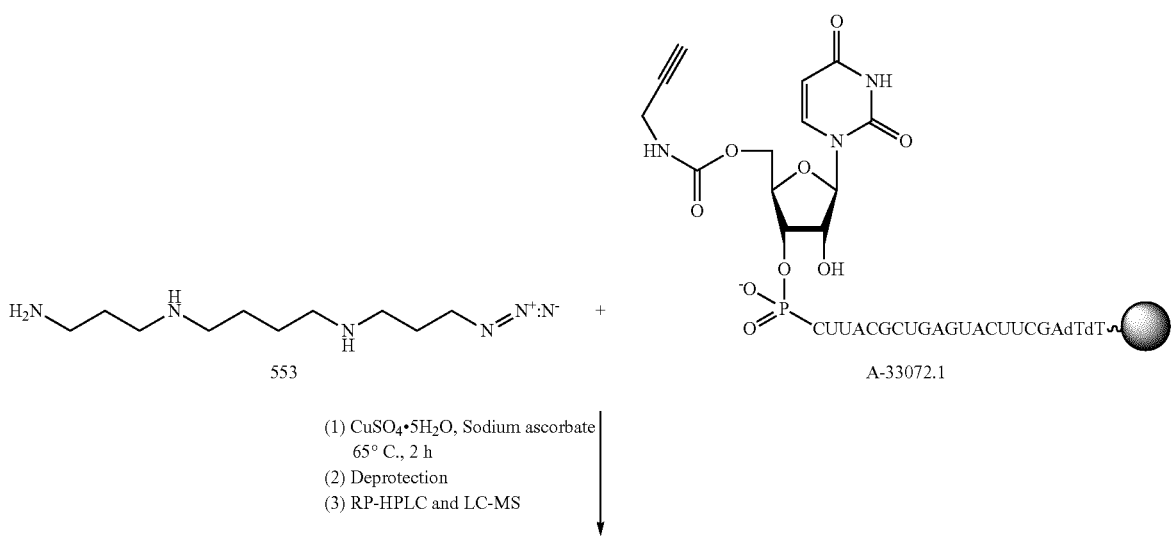

Scheme 43

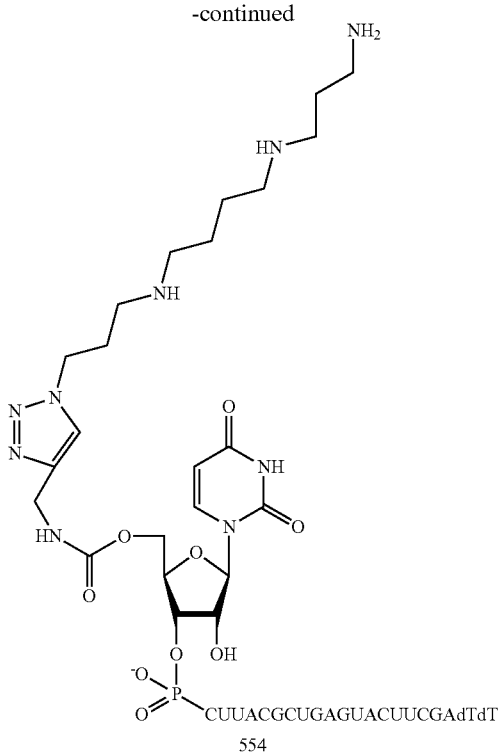
554
Example 19
Conjugation of Boc-Protected Spermine Molecule to RNA on the Solid Support Via Click Chemistry
Compound 555: The reaction between boc-protected spermine azide 531a and RNA alkyne A-33072.1 on the solid support was described below. Boc-protected spermine azide was used to establish a model reaction for click chemistry with the RNA alkyne.
Scheme 44
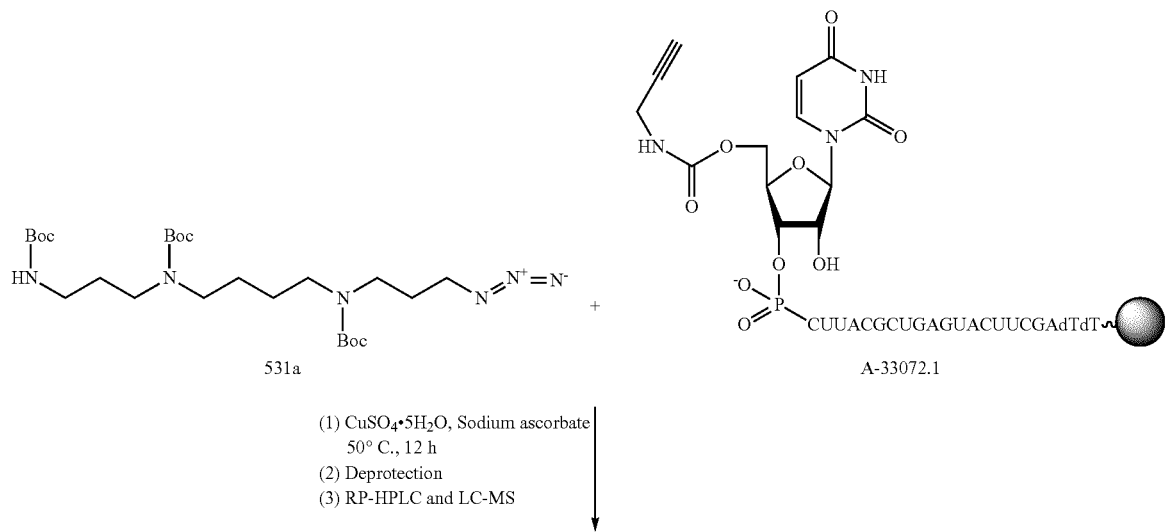

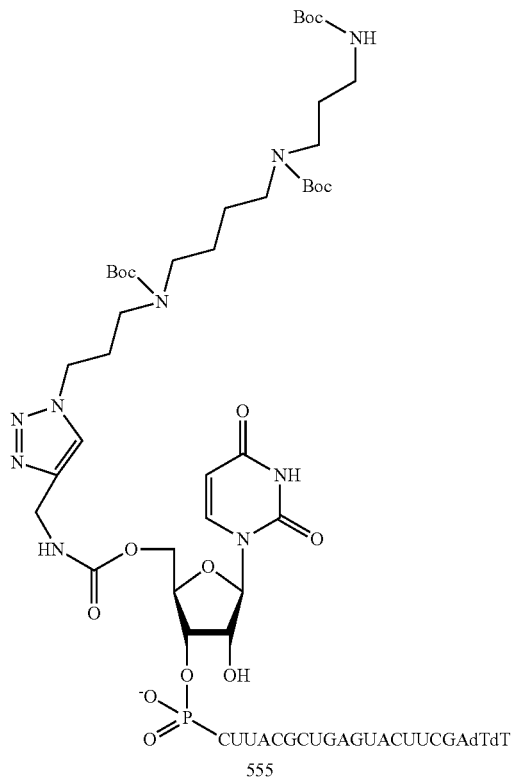

555

(1) RNA alkyne on the solid support, A-33072.1, (11 mg, 0.62 μmol) was treated with boc-protected spermine azide (531a, excess) in the presence of $CuSO_4.5H_2O$ (0.93 mmol) and sodium ascorbate (3.1 μmole), and the mixture was kept on a heating block at 50° C. for 12 h. The volume of the solvent for the reaction was maintained as a 1:1 ratio of t-BuOH/$H_2O$ (v/v) (1 ml). After reaction the beads were subsequently washed with water, methanol and acetonitrile and allowed to dry at room temperature.

(2) Deprotection: The reacted beads were treated with aqueous methylamine (125 μl) for 20 min at 65° C., then cooled to −20° C. for 20 min. The filtrate was collected, and the beads were washed with DMSO (100 μl×3) and combined them with the filtrate, then cooled at −20° C. for 10 min. Triethylamine trihydrofluoride (175 μl) was added to the combined filtrate and the mixture was kept at 65° C. for 20 min. After dialysis, the crude reaction mixture was analyzed by reverse-phase HPLC and LC-MS.

(3) RP-HPLC and LC-MS: The material was loaded to an analytical RP-HPLC on a gradient using two buffer systems (0.1M TEAA, pH 7.0 and acetonitrile), % B=0-60%/20 min, ~100%/30 min, 1 ml/min, linear gradient, UV: 260 nm; Column: XTerra RP-18, 4.6×250 mm. The crude materials also analyzed by LC-MS (calcd mass 7520. found 7519), FIG. 18.

Example 20

Conjugation of TFA-Protected Spermine Molecule to RNA on the Solid Support Via Click Chemistry Compound 556: The reaction between TFA-protected spermine azide 533 and RNA alkyne A-37068.1 on the solid support was described below.

Scheme 45

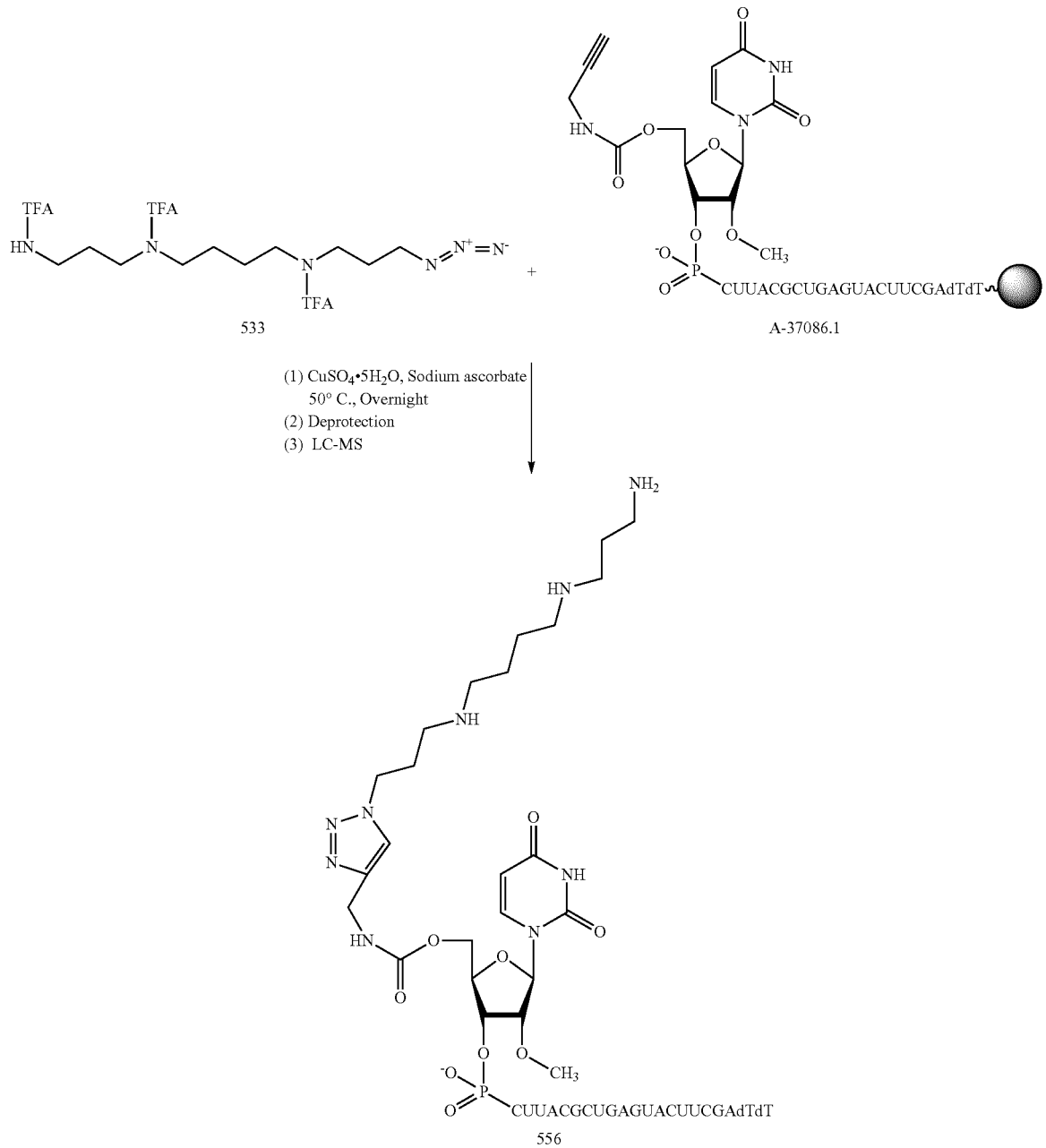

(1) RNA alkyne on the solid support, A-37086.1, (11 mg, 1 μmol) was treated with TFA-protected spermine azide (533, excess) in the presence of CuSO$_4$·5H$_2$O (1.5 μmol) and sodium ascorbate (5 μmole), and the mixture was kept on a heating block at 50 C for overnight. The volume of the reaction solvent was maintained as a 1:1 ratio of t-BuOH/H$_2$O (v/v) (1 ml). After reaction the beads were subsequently washed with water, methanol and acetonitrile and allowed to dry at room temperature.

(2) Deprotection: The reacted beads were treated with aqueous methylamine (125 μl) for 20 min at 65° C., then cooled to −20° C. for 20 min. The filtrate was collected, and the beads were washed with DMSO (100 μl×3) and combined them with the filtrate, then cooled at −20° C. for 10 min. Triethylamine trihydrofluoride (175 μl) was added to the combined filtrate and the mixture was kept at 65° C. for 20 min.

(3) LC-MS: After dialysis, the crude reaction mixture was analyzed by LC-MS (calcd mass 7235. found 7234).

Example 21

Conjugation of TFA-Protected Spermine (Seven Amines) to RNA on the Solid Support Via Click Chemistry Compound 557 can be synthesized by a procedure similar to that of example 19 or 20 and utilizing the extended spermine 543.

Scheme 46

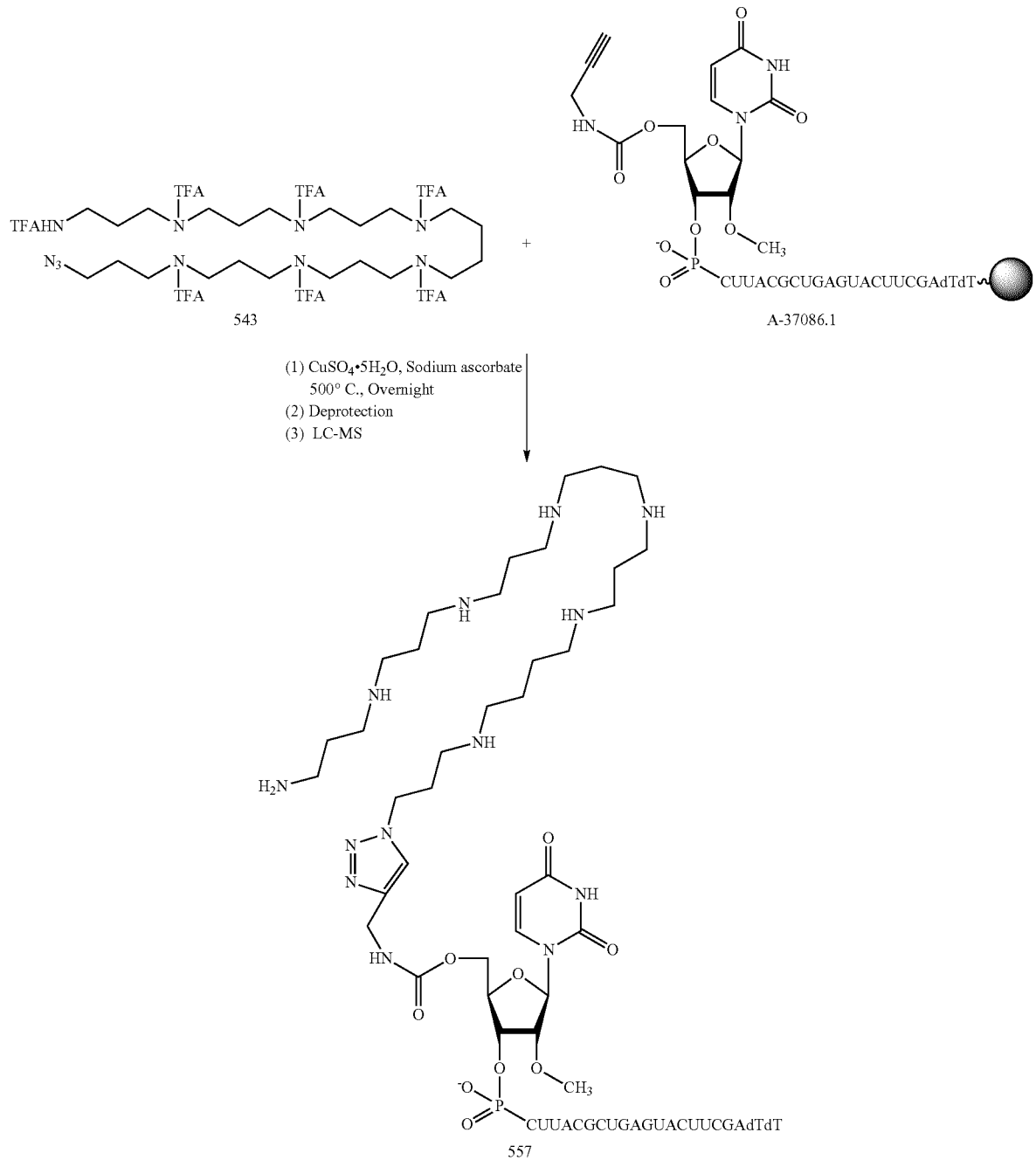

Example 22

Oligonucleotides

1. Synthesis of Single-Stranded RNA by Solid Phase Method

Figure 19:
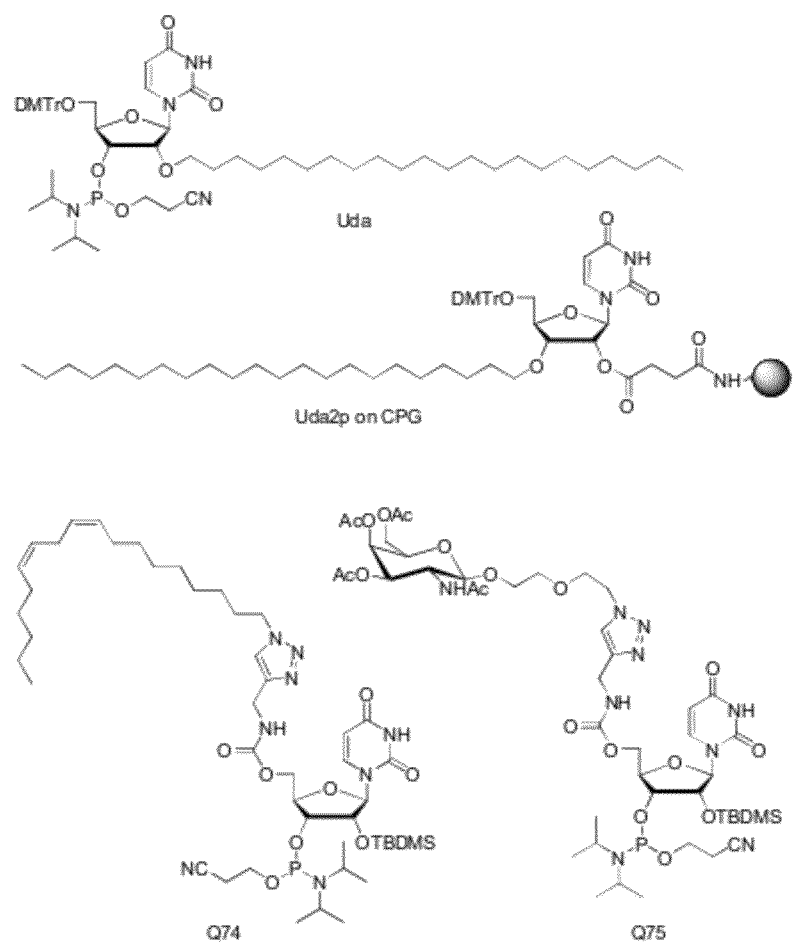
FIG. 19: Schematic representation of special amidites and CPGs used to make the modified RNA sequences of Table 6.
Figure 20:
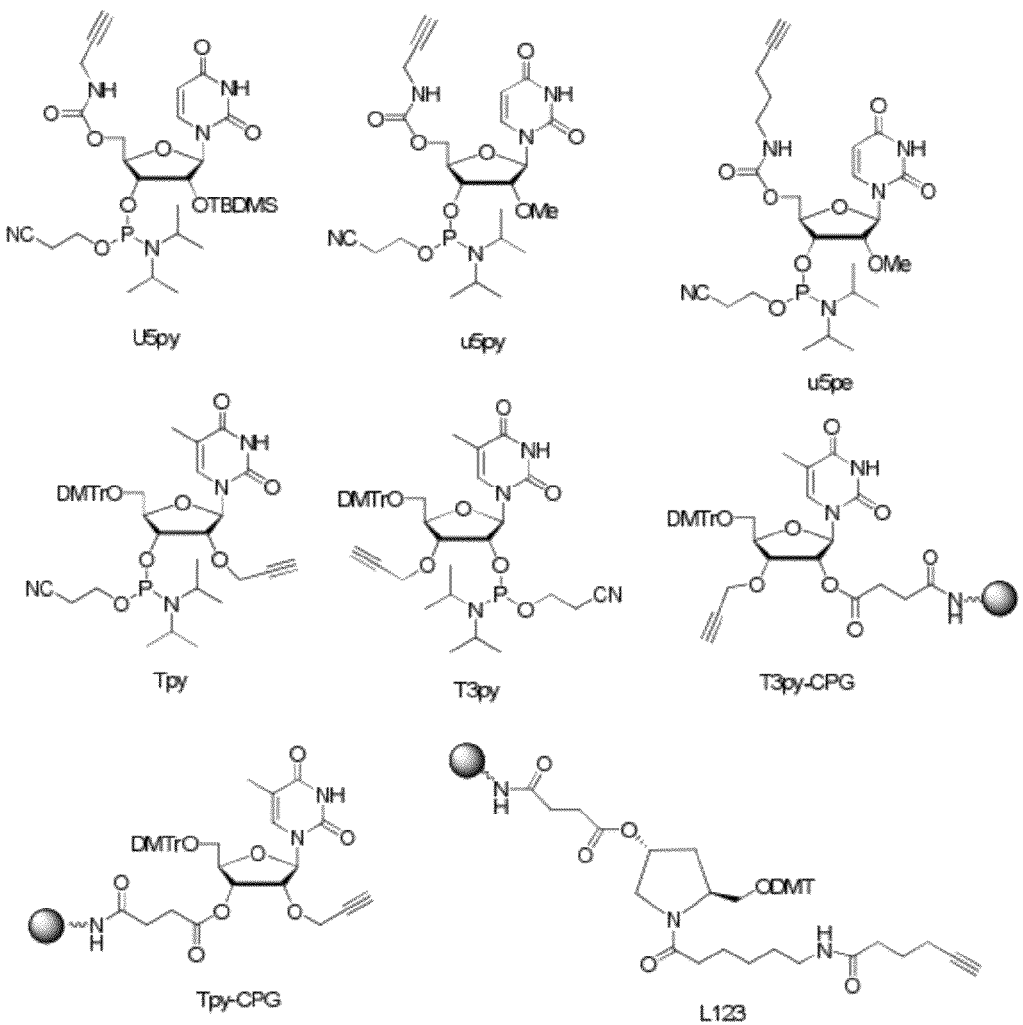
FIG. 20: Schematic representation of special amidites and CPGs used to make the RNA-alkyne scaffold. Sequences incorporating these monomers are shown in Table 7.

RNA oligonucleotides (Table 6) were synthesized on a DNA synthesizer ABI 394 using standard phosphoramidite chemistry with commercially available 5'-O-(4,4'-dimethoxytrityl)-3'-O-(2-cyanoethyl-N,N-diisopropyl)phosphoramidite monomers of uridine (U), 4-N-benzoylcytidine ($C^{Bz}$), 6-N-benzoyladenosine ($A^{Bz}$) and 2-Nisobutyrylguanosine ($G^{iBu}$) with 2'-O-t-butyldimethylsilyl protected phosphoramidites, and 5'-O-(4,4'-dimethoxytrityl)-2'-deoxythymidine-3'-O-(2-cyanoethyl-N,N-diisopropyl)phosphoramidite (T). Modified RNA phosphoramidites and CPG used in this study are shown in FIGS. 19 and 20. After cleavage and de-protection, RNA oligonucleotides were purified by anion-exchange or reverse phase high-performance liquid chromatography (AX-HPLC or RP-HPLC) and characterized by LC-MS.

2. Synthesis of RNA-Alkyne Scaffolds

The solid-supported phosphotriester alkyne scaffolds (3', 5' terminal positions and internal position in Table 7) were synthesized in the same way as what is mentioned in the previous section except for extended nucleotide coupling time (30 min) wherever alkyne monomer was involved. After synthesis, a small portion of CPG was deprotected and analyzed by AX-HPLC and LC-MS.

3. Cu(I)-Catalyzed 1,3-Dipolar Cycloaddition Reaction Optimization

Click reaction conditions were optimized using a 5'-alknye modified RNA on CPG (seq. #33072, Table 8). The effects of equivalence of stating materials, temperature and solvent were investigated in the click reaction of seq. #33072 with 1-azido-docosane (C22-azide) (Scheme 39). The optimization results were synthesized in Table 9. It would found that TBTA can facilitate the click reaction in the conditions used in this study. The click did not happen without TBTA (reaction No. 1 and 2). $Cu^{2+}$ level should maintain at a certain level (0.4 eqv. of alkyne in reaction No. 5) and too low $Cu^{2+}$ level negatively affect the click reaction (reaction No. 9). It was also found that DMF, DMSO could be used as a co-solvent but they did not show as good as THF (reaction No. 5, 7, 8). Microwave aided reaction was much faster. The reaction was completed after two days. This mild condition may be useful for some thermally unstable RNA sequences (reaction No. 12-13). In summary, the optimal conditions we found in the click reactions of RNA-alkyne with C22-azide include the molar ratio of RNA-alkyne:azide:Cu:TBTA:NaAsc (1:2.9: 0.4:2.8:3.2), microwave-aided heating at 60° C. for 45 min in $H_2O$/MeOH/THF (8/8/5 v/v/v).

After reaction optimization, different azides (FIG. 21) were tested for 1,3-dipolar cycloaddition with this RNA-alkyne in the optimized conditions. It was shown that all click reactions gave excellent reaction completion rate except for 1-azido-adamantane with only 50% completion, Table 9. Its steric environment was expected to account for this slow click reaction. Extended reaction to 90 min did not improve the reaction completion rate (data not shown).

4. General Procedure for Cu(I)-Catalyzed 1,3-Dipolar Cycloaddition

To a solid-supported oligoalkyne phosphotriester seq. #33072-37088 in Table 8 (0.62 µmol) was added a mixture of an azide (FIG. 21) (3 equiv by alkyne, 1.8 µmol, 36 µL of a 50 mM solution in THF), $CuSO_4$ (0.4 equiv, 0.25 µmol, 5 µL of a 50 mM solution in $H_2O$), freshly prepared sodium ascorbate (3.2 equiv, 2.0 µmol, 12 µL of a 50 mM solution in H2O), TBTA (2.8 equiv, 1.7 µmol, 35 µL of a 50 mM solution in THF). Water, MeOH and THF were added to obtain a total volume of 1200 µL (around 8:8:5 v/v/v). The resulting preparation was heated in a sealed glass tube with Explorer-48 (CEM) microwave synthesizer at a 100 W and a 30 s premixing time. The temperature was monitored with an internal infrared probe to 60° C. during 45 min. The solution was removed, and the CPG supports were washed with THF and MeOH then dried. After cleavage and de-protection, the click reaction progress was analyzed by RP-HPLC and the products were characterized by LC-MS.

Figure 23:
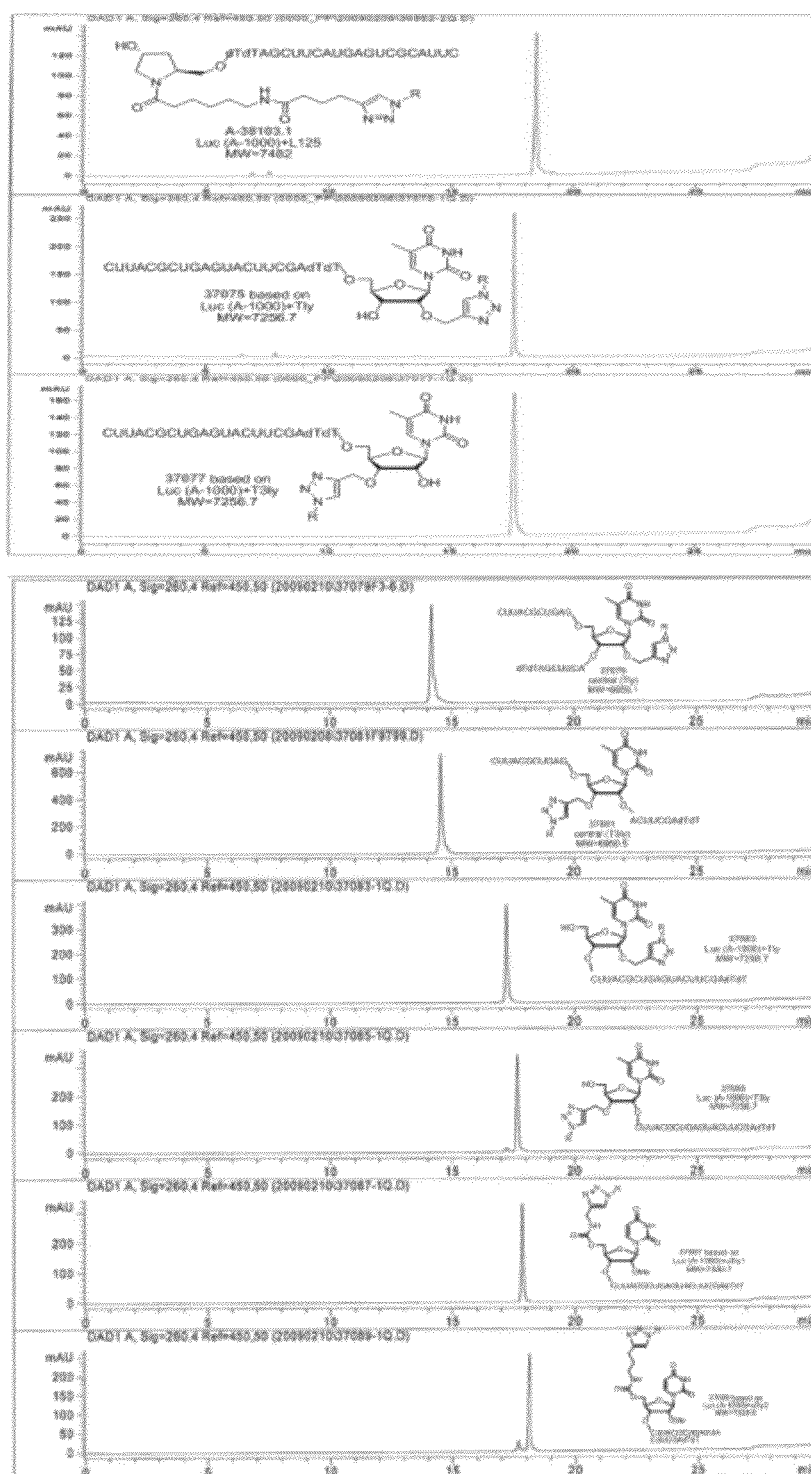
FIG. 23: (a) Schematic representation of modified RNA. (b) and (c) RP-HPLC analysis of purified click products (refer to Table 11) (analysis condition: [1]Reaction completion was measured by RP-HPLC (DeltaPak C4 column, 150×3.9 mm I.D., 5 μm, 300 Å; buffer A: 50 mM TEAA, pH 7.0; buffer B: ACN; gradient: 0-70% buffer B in 24 min; 30° C., 1 mL/min)

The click reaction mixtures were purified by RP-HPCL using semi-preparative DeltaPak C4 column (Waters) with 0-90% ACN (buffer B) gradient in 40 min. The purified RNAs were analyzed by RP-HPCL and LC-MS. The HPLC profiles of purified click product were shown in FIG. 23.

Table 11 summarizes the click modified oligonucleotides that were synthesized.

TABLE 6

| RNA and modified RNA sequences made by solid phase sequences ||||||
|---|---|---|---|---|---|
| Strand No. | Strand (S/AS) | Sequence (5'-3') | Calc. mass | Obs. mass | Yield (OD) | Purity |
| 1000 | S | CUUACGCUGAGUACUUCGATT | 6607.0 | — | stock | — |
| 1001 | AS | UCGAAGUACUCAGCGUAAGTT | 6693.1 | — | stock | — |
| 33024.1 | S | C(Uda)UACGCUGAGUACUUCGATT | 6915.6 | 6914 | 53.0 | 93% |
| 33025.1 | S | CU(Uda)ACGCUGAGUACUUCGATT | 6915.6 | | 108.0 | 92% |
| 33026.1 | S | CUUACGC(Uda)GAGUACUUCGATT | 6915.6 | | 229.0 | 91% |
| 33027.1 | S | CUUACGCUGAG(Uda)ACUUCGATT | 6915.6 | | 110.0 | 95% |
| 33028.1 | S | CUUACGCUGAGUAC(Uda)UCGATT | 6915.6 | | 200.0 | 97% |
| 33029.1 | S | CUUACGCUGAGUACU(Uda)CGATT | 6915.6 | | 213.0 | 96% |
| 33031.1 | S | CUUACGCUGAGUACUUCGAT(Uda2p) | 6917.5 | | 72.0 | 93% |
| 33032.1 | S | CUUACGCUGAG(Uda)ACUUCGAT(Uda2p) | 7226.1 | | 68.0 | 88% |
| 33033.1 | S | C(Uda)UACGCUGAGUACUUCGAT(Uda2p) | 7226.1 | | 79.0 | 86% |
| 33035.1 | AS | UCGAAGUACUCAGCGUAAGT(Uda2p) | 7003.6 | | 36.0 | 86% |
| 33034.1s | S | Q74CUUACGCUGAGUACUUCGATT | 7285.7 | | 59.0 | 93% |
| 33071.1 | S | Q75CUUACGCUGAGUACUUCGATT | 7328.5 | | 37.0 | 92% |

Note:
(Uda): 2'-docosanoyl-uridine-3'-phosphate
(Uda2p): 3'-docosanoyl-uridine-2'-phosphate (amidite and CPG)
Q74: uridine-5'-(N1-linolyl-4-methylaminocarbony1-1,2,3 triazol)-3'-phosphate
Q75: uridine-5'-[N1-(GalNAc-1-ethyloxyethyl)-1,2,3 triazol] -3'-phosphate

TABLE 7

RNA-alkyne scaffolds made for click reactions in this study

| Strand No. | Sequence (5'-3') | Calc. mass | Obs. mass | Crude purity[1] |
|---|---|---|---|---|
| 33072.1 | Q83CUUACGCUGAGUACUUCGAdTdT | 6994.2 | 6992 | 62.3% |
| 36594.1 | AAcGcuGGGcGuuAAucAAdTdTL123 | 7191.7 | 7190 | 68.8% |
| 37074.1 | CUUACGCUGAGUACUUCGAdTdT(Tpy) | 6965.2 | 6964 | 61.2% |
| 37076.1 | CUUACGCUGAGUACUUCGAdTdT(T3py) | 6965.2 | 6964 | 58.7% |
| 37078.1 | CUUACGCUGAG(Tpy)ACUUCGAdTdT | 6659.1 | 6657 | 46.9% |
| 37080.1 | CUUACGCUGAG(T3py)ACUUCGAdTdT | 6659.1 | 6658 | 58.9% |
| 37082.1 | (Tpy)CUUACGCUGAGUACUUCGAdTdT | 6965.23 | 6964 | 43.5% |
| 37084.1 | (T3py)CUUACGCUGAGUACUUCGAdTdT | 6965.23 | 6963 | 68.0% |
| 37086.1 | (u5py)CUUACGCUGAGUACUUCGAdTdT | 7009.26 | 7006 | 68.0% |
| 37088.1 | (u5pe)CUUACGCUGAGUACUUCGAdTdT | 7037.32 | 7034 | 67.3% |

[1]Purity was measured by RP-HPLC (DeltaPak C4 column, 150 × 3.9 mm I.D., 5 μm, 300 Å; buffer A: 50 mM TEAA, pH 7.0; buffer B: ACN; gradient: 0-70% buffer B in 24 min; 30° C., 1 mL/min)

TABLE 8

Cu(I)-Catalyzed 1,3-Dipolar Cycloaddition Reaction Optimization (RNA-alkyne seq#33072 clicks with C22 azide in Scheme 39)

| Rxn No. | Starting material (molar ratio of alkyne:azide:Cu:TBTA:NaAsc) | Solvent | Temp. (° C.) Time (min) | Reaction completion (%) | Right mass? |
|---|---|---|---|---|---|
| 1 | 1:16:0.4:0:3.2 | H₂O/MeOH/THF | 60° C.; 45 min | No rxn | No |
| 2 | 1:16:0.4:2.8:3.2 | H₂O/MeOH/THF | 60° C.; 45 min | 70.8%[1] | Yes |
| 3 | 1:8.6:0.4:2.8:3.2 | H₂O/MeOH/THF | 60° C.; 45 min | 98.1% | Yes |
| 4 | 1:5.7:0.4:2.8:3.2 | H₂O/MeOH/THF | 60° C.; 45 min | ~100% | Yes |
| 5 | 1:2.9:0.4:2.8:3.2 | H₂O/MeOH/THF | 60° C.; 45 min | 98.9% | Yes |
| 6 | 1:2.9:0.1:2.8:3.2 | H₂O/MeOH/THF | 60° C.; 45 min | 49.4% | Yes |
| 7 | 1:2.9:0.4:2.8:3.2 | H₂O/MeOH/DMSO | 60° C.; 45 min | 88.3% | Yes |
| 8 | 1:2.9:0.4:2.8:3.2 | H₂O/MeOH/DMF | 60° C.; 45 min | 78.5% | Yes |
| 9[2] | 1:2.9:0.4:2.8:3.2 (10x dilution) | H₂O/MeOH/DMF | 60° C.; 45 min | 56.5% | Yes |
| 10[3] | 1:2.9:0.4:2.8:3.2 (10x concentration) | H₂O/MeOH/DMF | 60° C.; 45 min | 59.7% | Yes |
| 11 | 1:2.9:0.4:2.8:3.2 | H₂O/MeOH/THF | 60° C.; 5 min | 57.0% | Yes |
| 12 | 1:2.9:0.4:2.8:3.2 | H₂O/MeOH/THF | r.t., 17 hr | 88.4% | Yes |
| 13 | 1:2.9:0.4:2.8:3.2 | H₂O/MeOH/THF | r.t., 48 hr | ~100%% | Yes |

[1]Reaction completion was measured by RP-HPLC (DeltaPak C4 column, 150 × 3.9 mm I.D., 5 μm, 300 Å; buffer A: 50 mM TEAA, pH 7.0; buffer B: ACN; gradient: 0-70% in 24 min; 30° C., 1 mL/min);
[2]azide concentration in reaction solution was 14.9 mM;
[3]azide concentration in reaction solution was 0.5 mM;

TABLE 9

Cu(I)-Catalyzed 1,3-Dipolar Cycloaddition with Different Azides

| Azides | Strand No. | Sequences | Reaction completion (%)[1] | Calc. mass | Obs. mass |
|---|---|---|---|---|---|
| 1-azido-docosane (C22-azide) | 33561.1 | Q87CUUACGCUGAGUACUUCGAdTdT | 98.1% | 7345.8 | 7344 |
| 1-azido-octadeca-6,9-diene (C18(ω = 2)-azide) | 33034.1c | Q74CUUACGCUGAGUACUUCGAdTdT | 93.4% | 7285.7 | 7284 |

TABLE 9-continued

Cu(I)-Catalyzed 1,3-Dipolar Cycloaddition with Different Azides

| Azides | Strand No. | Sequences | Reaction completion (%)[1] | Calc. mass | Obs. mass |
|---|---|---|---|---|---|
| 1-azido-octadec-9-diene (C18(ω = 1)-azide) | 33559.1 | Q85CUUACGCUGAGUACUUCGAdTdT | 88.9% | 7287.7 | 7285 |
| 1-azido-octadecane (C18-azide) | 33560.1 | Q86CUUACGCUGAGUACUUCGAdTdT | 95.3% | 7289.7 | 7288 |
| 1-azido-adamantane | 33562.1 | Q88CUUACGCUGAGUACUUCGAdTdT | 50.6% | 7171.5 | 7169 |
| Cholesterol-azide | 33563.1 | Q89CUUACGCUGAGUACUUCGAdTdT | 95.7% | 7549.1 | 7547 |

[1]Reaction completion was measured by RP-HPLC (DeltaPak C4 column, 150 × 3.9 mm I.D., 5 μm, 300 Å; buffer A: 50 mM TEAA, pH 7.0; buffer B: ACN; gradient: 0-70% buffer B in 24 min; 30° C., 1 mL/min);

TABLE 10

Figure 22:
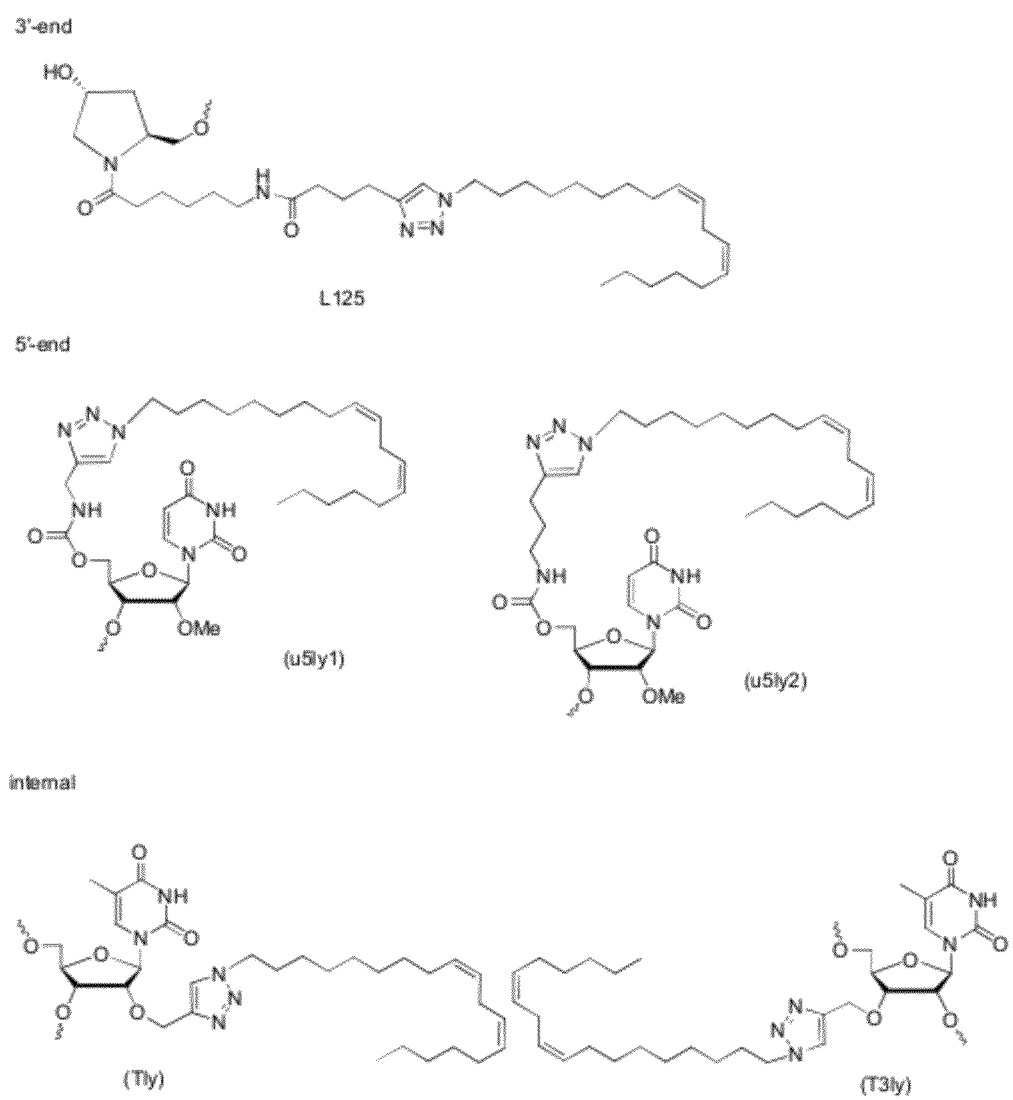
FIG. 22: Schematic representation of modified monomers after incorporation into oligonucleotides. Sequences incorporating these monomers are shown in Table 10.

Cu(I)-Catalyzed 1,3-Dipolar Cycloaddition Reaction of Different RNA-alkynes with 1-Azido-octadeca-6,9-diene (C18(ω = 2)-azide (FIG. 22)

| RNA-alkyne position | Strand No. | Sequences (5'-3') | Reaction completion (%) | Calc. mass | Obs. mass |
|---|---|---|---|---|---|
| 3'-terminal | 38103.1 | AAcGcuGGGcGuuAAucAAdTdTL125 | 51.7%[1] | 7483.2 | 7482 |
|  | 37075.1 | CUUACGCUGAGUACUUCGAdTdT(T1y) | ~100% | 7256.7 | 7255 |
|  | 37077.1 | CUUACGCUGAGUACUUCGAdTdT(T31y) | 90.3% | 7256.7 | 7255 |
| 5'-terminal | 33561.1 | Q87CUUACGCUGAGUACUUCGAdTdT | 98.1% | 7345.8 | 7344 |
|  | 37083.1 | (T1y)CUUACGCUGAGUACUUCGAdTdT | ~100% | 7256.7 | 7255 |
|  | 37085.1 | (T31y)CUUACGCUGAGUACUUCGAdTdT | 96.6% | 7256.7 | 7256 |
|  | 37087.1 | (u51y1)CUUACGCUGAGUACUUCGAdTdT | 91.0% | 7300.7 | 7299 |
|  | 37089.1 | (u51y2)CUUACGCUGAGUACUUCGAdTdT | 84.0% | 7328.8 | 7326 |
| Internal | 37079.1 | CUUACGCUGAG(T1y)ACUUCGAdTdT | ~100% | 6950.5 | 6949 |
|  | 37081.1 | CUUACGCUGAG(T31y)ACUUCGAdTdT | 91.5% | 6950.5 | 6949 |

[1]The reaction completion reached ~100% if the molar ratio of alkyne:azide:Cu:TBTA:NaAsc was 1:5.8:0.8:5.6:6.4 with other conditions unchanged.

TABLE 11

Overall purified click products obtained in this study

| Strand No. | Sequence (5'-3') | Calc. mass | Obs. mass | Yield (OD) | Purity |
|---|---|---|---|---|---|
| 33034.1c[1] | Q74CUUACGCUGAGUACUUCGAdTdT | 7285.7 | 7284 | 9.4 | 94% |
| 33559.1 | Q85CUUACGCUGAGUACUUCGAdTdT | 7287.7 | 7285 | 10.6 | 94% |
| 33560.1 | Q86CUUACGCUGAGUACUUCGAdTdT | 7289.7 | 7288 | 8.1 | 94% |
| 33561.1 | Q87CUUACGCUGAGUACUUCGAdTdT | 7345.8 | 7344 | 15.5 | 89% |
| 33562.1 | Q88CUUACGCUGAGUACUUCGAdTdT | 7171.5 | 7169 | 4.04 | 97% |
| 33563.1 | Q89CUUACGCUGAGUACUUCGAdTdT | 7549.1 | 7547 | 24.1 | 95% |
| 38103.1 | AAcGcuGGGcGuuAAucAAdTdTL125 | 7483.2 | 7482 | 45.4 | 87% |
| 37075.1 | CUUACGCUGAGUACUUCGAdTdT(T1y) | 7256.7 | 7255 | 46.2 | 96% |
| 37077.1 | CUUACGCUGAGUACUUCGAdTdT(T31y) | 7256.7 | 7255 | 71.0 | 90% |
| 37079.1 | CUUACGCUGAG(T1y)ACUUCGAdTdT | 6950.5 | 6949 | 6.3 | 80% |
| 37081.1 | CUUACGCUGAG(T31y)ACUUCGAdTdT | 6950.5 | 6949 | 35.5 | 84% |

TABLE 11-continued

Overall purified click products obtained in this study

| Strand No. | Sequence (5'-3') | Calc. mass | Obs. mass | Yield (OD) | Purity |
|---|---|---|---|---|---|
| 37083.1 | (T1y)CUUACGCUGAGUACUUCGAdTdT | 7256.7 | 7255 | 20.0 | 79% |
| 37085.1 | (T31y)CUUACGCUGAGUACUUCGAdTdT | 7256.7 | 7256 | 44.0 | 89% |
| 37087.1 | (u51y1)CUUACGCUGAGUACUUCGAdTdT | 7300.7 | 7299 | 36.0 | 89% |
| 37089.1 | (u51y2)CUUACGCUGAGUACUUCGAdTdT | 7328.8 | 7326 | 11.7 | 90% |

[1]33034.1c was obtained by click reaction with exact sequence as 33034-1s which was obtained by solid phase synthesis (see Table 1);

5. 3'-Exo Nuclease Stability Assays

Nuclease stability of the oligonucleotides can be determined easily using methods and protocols known in the art and available to one of skill in the art.

Example 23

RNA Interference Activity of Oligonucleotides

1. Dual-Luciferase Assay for RNA Interfering Evaluation

Modified RNAs obtained by solid-phase synthesis and click reactions were evaluated in RNA interfering in dual-luciferase assays. Duplexes were prepared by heating at 95° C. for 2 min and cooling to room temperature for 2 hours in 1X Phosphate buffered saline. (Table 12-14).

The ability of modified siRNAs to suppress gene expression was studied by a dual-luciferase assay using a pGL4 vector (Promega), which contained the Renilla and firefly luciferase genes. The siRNA sequences were designed to target the firefly luciferase gene. Stably transfected HeLa cells were then transfected with the indicated amounts of siRNAs, and the signals of firefly luciferase were normalized to those of renilla luciferase. HeLa SS6 cells were stably transfected with plasmids encoding firefly (target) and Renilla (control) luciferases.

Figure 24:
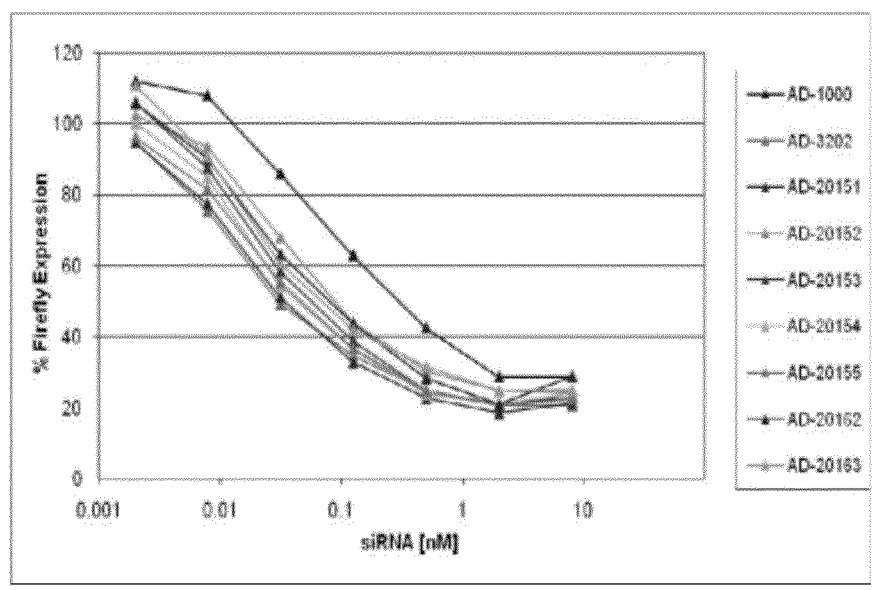
FIG. 24: Dose response curves of selected modified siRNAs.

RNA interference methods: Hela cells were grown at 37° C., 5% $CO_2$ in Dulbecco's modified Eagles's medium (DMEM, GIBCO) supplemented with 10% fetal bovine serum (FBS) and 1% antibiotic. The cells were maintained in the exponential growth phase. The cells were then plated in 96-well plates (0.1 mL medium per well) to reach about 90% confluence at transfection. Transfection was allowed to proceed for 24 hr at 37° C. and on day 2 the culture medium was changed to OPTIMEM 1, a reduced serum media (GIBCO). Two luciferase plasmids, Renilla luciferase (pRL-CMV) and firefly luciferase (pGL3) from Promega, were used as control and reporter, respectively. Transfection of siRNAs was carried out with Lipofectamine 2000 (Invitrogen) as described by the manufacturer for adherent cell lines. The final volume was 150 uL per well. On day 2 cells are transfected with, firefly luciferase targeting, siRNA of varying concentrations ranging from 2 pM to 8 nM mediated by Lipofectamine 2000 reagent (Invitrogen). After 24 h, cells were analyzed for both firefly and renilla luciferase expression using a plate luminometer with a delay time of 2 s and an integrate time of 10 s. (VICTOR2, PerkinElmer, Boston, Mass.) and the Dual-Glo Luciferase Assay kit (Promega), FIG. 24. Firefly/renilla luciferase expression ratios were used to determine percent gene silencing relative to untreated (no siRNA) controls. Values generated represent the mean of triplicates.

The screening process began with a primary screen where all the compounds were screened against the parent unmodified duplex as a comparison. Some of the potent duplexes from this screen which showed IC 50 values several fold lower than that of the parent were then selected for a secondary screen or head to head comparison. All compounds were seen to be more potent than the parent duplex. However, the ones that showed at least 5 fold improved potency were the duplexes with Uda (C22 linker) at position 2, 15 and 16 on the sense strand (Table 15). The final set of compounds was compared to one of our best modifications AD3202 and it can be seen that these compounds match up to AD 3202 in potency, however the exact mechanism by which the Uda modification contributes to improved activity is to be determined through further studies.

Materials and Methods
Cells and Reagents
Dual HeLa (HeLa cells transfected with PGL4 plasmid for luciferase expression)
Tissue culture medium, trypsin and Lipofectamine-2000—purchased from Invitrogen (Carlsbad, Calif.).
DMEM supplemented with 10% fetal bovine serum, 1% antibiotic solution.
siRNA treatment was performed using Opti-MEM (Invitrogen) containing 1 mg/ml Lipofectamine2000
DMEM without phenol red, Promega Dual Glo Luciferase Assay kit, 0.25% Trypsin (Invitrogen).

TABLE 12

Duplex information and IC50 values (Part I)

| Duplex | Strand No. | S/AS | Sequence 5' to 3' | Modifications | IC 50 Values (nM) |
|---|---|---|---|---|---|
| AD-1000 | 1000 | S | CUUACGCUGAGUACUUCGAdTdT | None | Artifact, 0.906 |
|  | 1001 | AS | UCGAAGUACUCAGCGUAAGdTdT | None | range 0.2-0.3 |
| AD-20271 | 37079 | S | CUUACGCUGAG(T1y)ACUUCGAdTdT | U12-->(T1y) | 0.22 |
|  | 1001 | AS | UCGAAGUACUCAGCGUAAGdTdT | none |  |

TABLE 12-continued

Duplex information and IC50 values (Part I)

| Duplex | Strand No. | S/AS | Sequence 5' to 3' | Modifications | IC 50 Values (nM) |
|---|---|---|---|---|---|
| AD-20272 | 37081 | S | CUUACGCUGAG(T31y)ACUUCGAdTdT | U12-->(T31y) | 0.228 |
|  | 1001 | AS | UCGAAGUACUCAGCGUAAGdTdT | none |  |
| AD-20273 | 37083 | S | (T1y)CUUACGCUGAGUACUUCGAdTdT | 5' (T1y) | 0.348 |
|  | 1001 | AS | UCGAAGUACUCAGCGUAAGdTdT | none |  |
| AD-20274 | 37085 | S | (T31y)CUUACGCUGAGUACUUCGAdTdT | 5' (T31y) | 0.324 |
|  | 1001 | AS | UCGAAGUACUCAGCGUAAGdTdT | none |  |
| AD-20275 | 37087 | S | (u51y1)CUUACGCUGAGUACUUCGAdTdT | 5' (u51y1) | 0.263 |
|  | 1001 | AS | UCGAAGUACUCAGCGUAAGdTdT | none |  |
| AD-20276 | 37089 | S | (u51y2)CUUACGCUGAGUACUUCGAdTdT | 5' (u51y2) | 0.376 |
|  | 1001 | AS | UCGAAGUACUCAGCGUAAGdTdT | none |  |
| AD-20201 | 36862 | S | CUUACGCUGAGUACUUCGAdTdTL125 | 3' L125 | 0.922 |
|  | 1001 | AS | UCGAAGUACUCAGCGUAAGdTdT | none |  |
| AD-20202 | 37075 | S | CUUACGCUGAGUACUUCGAdTdT(T1y) | 3' (T1y) | 1.12 |
|  | 1001 | AS | UCGAAGUACUCAGCGUAAGdTdT | none |  |
| AD-20203 | 37077 | S | CUUACGCUGAGUACUUCGAdTdT(T31y) | 3' (T31y) | 1.41 |
|  | 1001 | AS | UCGAAGUACUCAGCGUAAGdTdT | none |  |
| AD-20321 | 38103.1 | S | AAcGcuGGGcGuuAAucAAdTdTL125 | 2'OMe-all Py and 3' L125 | out of range |
|  | 24599 | AS | UUGAUuAACGCCcAGCGUUdTsdT | none |  |

TABLE 13

Duplex information and IC50 values (Part II)

| Duplex | Strand No. | S/AS | Sequence 5' to 3' | Modifications | IC 50 Values (nM) | Fold Increase in activity as compared to parent |
|---|---|---|---|---|---|---|
| AD-1000 | 1000 | S | CUUACGCUGAGUACUUCGAdTdT | None | 0.38 | Parent |
|  | 1001 | AS | UCGAAGUACUCAGCGUAAGdTdT | None |  |  |
| AD-20151 | 33024.1 | S | C(Uda)UACGCUGAGUACUUCGAdTdT | U2-->Uda | 0.07 | 5 fold |
|  | 1001 | AS | UCGAAGUACUCAGCGUAAGdTdT | none |  |  |
| AD-20152 | 33026.1 | S | CUUACGC(Uda)GAGUACUUCGAdTdT | U8-->Uda | 0.176 | 2 fold |
|  | 1001 | AS | UCGAAGUACUCAGCGUAAGdTdT | none |  |  |
| AD-20153 | 33027.1 | S | CUUACGCUGAG(Uda)ACUUCGAdTdT | U12-->Uda | 0.044 | 8 fold |
|  | 1001 | AS | UCGAAGUACUCAGCGUAAGdTdT | none |  |  |
| AD-20154 | 33028.1 | S | CUUACGCUGAGUAC(Uda)UCGAdTdT | U15-->Uda | 0.092 | 4 fold |
|  | 1001 | AS | UCGAAGUACUCAGCGUAAGdTdT | none |  |  |
| AD-20155 | 33029.1 | S | CUUACGCUGAGUACU(Uda)CGAdTdT | U16-->Uda | 0.073 | 5 fold |
|  | 1001 | AS | UCGAAGUACUCAGCGUAAGdTdT | none |  |  |
| AD-20156 | 33031.1 | S | CUUACGCUGAGUACUUCGAdT(Uda2p) | Uda2p-3'end | 1.18 |  |
|  | 1001 | AS | UCGAAGUACUCAGCGUAAGdTdT | none |  |  |
| AD-20157 | 33032.1 | S | CUUACGCUGAG(Uda)ACUUCGAdT(Uda2p) | U12-->Uda, Uda2p -3'end | NA—out of range |  |
|  | 1001 | AS | UCGAAGUACUCAGCGUAAGdTdT | none |  |  |
| AD-20158 | 33033.1 | S | C(Uda)UACGCUGAGUACUUCGAdT(Uda2p) | U2-->Uda, Uda2p-3'end | 1.5 | 2 fold |
|  | 1001 | AS | UCGAAGUACUCAGCGUAAGdTdT | none |  |  |
| AD-20159 | 33034.1 | S | Q74CUUACGCUGAGUACUUCGAdTdT | Q 74 - 5'end | 0.154 | 2 fold |
|  | 1001 | AS | UCGAAGUACUCAGCGUAAGdTdT | none |  |  |

TABLE 13-continued

Duplex information and IC50 values (Part II)

| Duplex | Strand No. | S/AS | Sequence 5' to 3' | Modifications | IC 50 Values (nM) | Fold Increase in activity as compared to parent |
|---|---|---|---|---|---|---|
| AD-20160 | 1000 | S | CUUACGCUGAGUACUUCGAdTdT | none | 2.03 | |
| | 33035.1 | AS | UCGAAGUACUCAGCGUAAGdT(Uda2p) | Uda2p-3'end -AS | | |
| AD-20161 | 33071.1 | S | Q75CUUACGCUGAGUACUUCGAdTdT | Q75 -5'end | 0.43 | |
| | 1001 | AS | UCGAAGUACUCAGCGUAAGdTdT | none | | |

TABLE 14

Duplex information and IC50 values (Part III)

| Duplex | Single Strand # | S/AS | Sequence 5' to 3' | Modifications | IC 50 Values (nM) | Fold Increase in activity as compared to parent |
|---|---|---|---|---|---|---|
| AD-1000 | 1000 | S | CUUACGCUGAGUACUUCGAdTdT | None | 0.326 | Parent |
| | 1001 | AS | UCGAAGUACUCAGCGUAAGdTdT | None | | |
| AD-20162 | 33558.1 | S | Q84CUUACGCUGAGUACUUCGAdTdT | Q84 5'end | 0.125 | 2.6 fold |
| | 1001 | AS | UCGAAGUACUCAGCGUAAGdTdT | none | | |
| AD-20163 | 33559.1 | S | Q85CUUACGCUGAGUACUUCGAdTdT | Q85 5'end | 0.126 | 2.6 fold |
| | 1001 | AS | UCGAAGUACUCAGCGUAAGdTdT | none | | |
| AD-20164 | 33560.1 | S | Q86CUUACGCUGAGUACUUCGAdTdT | Q86 5'end | 0.206 | 1.6 fold |
| | 1001 | AS | UCGAAGUACUCAGCGUAAGdTdT | none | | |
| AD-20165 | 33561.1 | S | Q87CUUACGCUGAGUACUUCGAdTdT | Q87 5'end | 0.35 | |
| | 1001 | AS | UCGAAGUACUCAGCGUAAGdTdT | none | | |
| AD-20166 | 33562.1 | S | Q88CUUACGCUGAGUACUUCGAdTdT | Q88 5'end | 0.318 | |
| | 1001 | AS | UCGAAGUACUCAGCGUAAGdTdT | none | | |
| AD-20167 | 33563.1a | S | Q89CUUACGCUGAGUACUUCGAdTdT | Q89 5'end | 0.771 | |
| | 1001 | AS | UCGAAGUACUCAGCGUAAGdTdT | none | | |
| AD-20168 | 33563.1b | S | Q89CUUACGCUGAGUACUUCGAdTdT | Q89 5'end | 0.953 | |
| | 1001 | AS | UCGAAGUACUCAGCGUAAGdTdT | none | | |

TABLE 15

Duplex information and IC50 values (Part IV)

| Duplex | Single strand # | S/AS | Sequence 5' to 3' | Modifications | IC 50 Values (nM) | Fold Increas in activity as compared to parent |
|---|---|---|---|---|---|---|
| AD-1000 | 1000 | S | CUUACGCUGAGUACUUCGAdTdT | None | 0.242 | |
| | 1001 | AS | UCGAAGUACUCAGCGUAAGdTdT | None | | |
| AD-20151 | 33024.1 | S | C(Uda)UACGCUGAGUACUUCGAdTdT | U2-->Uda | 0.036 | 6.5 fold |
| | 1001 | AS | UCGAAGUACUCAGCGUAAGdTdT | none | | |
| AD-20152 | 33026.1 | S | CUUACGC(Uda)GAGUACUUCGAdTdT | U8-->Uda | 0.083 | 3 fold |
| | 1001 | AS | UCGAAGUACUCAGCGUAAGdTdT | none | | |
| AD-20153 | 33027.1 | S | CUUACGCUGAG(Uda)ACUUCGAdTdT | U12-->Uda | 0.052 | 4 fold |
| | 1001 | AS | UCGAAGUACUCAGCGUAAGdTdT | none | | |
| AD-20154 | 33028.1 | S | CUUACGCUGAGUAC(Uda)UCGAdTdT | U15-->Uda | 0.044 | 5 fold |
| | 1001 | AS | UCGAAGUACUCAGCGUAAGdTdT | none | | |

TABLE 15-continued

Duplex information and IC50 values (Part IV)

| Duplex | Single strand # | S/AS | Sequence 5' to 3' | Modifications | IC 50 Values (nM) | Fold Increas in activity as compared to parent |
|---|---|---|---|---|---|---|
| AD-20155 | 33029.1 | S | CUUACGCUGAGUACU(Uda)CGAdTdT | U16-->Uda | 0.046 | 6 fold |
|  | 1001 | AS | UCGAAGUACUCAGCGUAAGdTdT | none |  |  |
| AD-20162 | 33558.1 | S | Q84CUUACGCUGAGUACUUCGAdTdT | Q84 5'end | 0.074 | 3 fold |
|  | 1001 | AS | UCGAAGUACUCAGCGUAAGdTdT | none |  |  |
| AD-20163 | 33559.1 | S | Q85CUUACGCUGAGUACUUCGAdTdT | Q85 5'end | 0.062 | 4 fold |
|  | 1001 | AS | UCGAAGUACUCAGCGUAAGdTdT | none |  |  |

We claim:

1. A compound of formula (II), or pharmaceutically acceptable salts thereof:

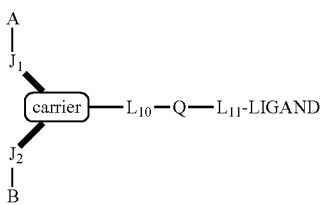

(II)

wherein A and B are each independently hydrogen, a protecting group, optionally substituted aliphatic, optionally substituted aryl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)—O-nucleoside, or —P($Z^1$)($Z^2$)—O-oligonucleotide; wherein $Z^1$ and $Z^2$ are each independently for each occurrence O, S or optionally substituted alkyl, provided that either one or both of A and B is independently —P($Z^1$)($Z^2$)—O-nucleoside, or —P($Z^1$)($Z^2$)—O-oligonucleotide;

$J_1$ and $J_2$ are each independently O, S, $NR^N$, optionally substituted alkyl, OC(O)NH, NHC(O)O, C(O)NH, NHC(O), OC(O), C(O)O, OC(O)O, NHC(O)NH, NHC(S)NH, OC(S)NH, OP(N($R^P$)$_2$)O, or OP(N($R^P$)$_2$);

carrier is a cyclic group selected from the group consisting of pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, thiazolidinyl, isothiazolidinyl, quinoxalinyl, pyridazinonyl, and decalin; or carrier is an acyclic group containing a serinol backbone or a diethanolamine backbone;

$R^N$ is H, optionally substituted alkyl, optionally substituted alkenyl, optionally substituted alkynyl, optionally substituted aryl, optionally substituted cycloalkyl, optionally substituted aralkyl, optionally substituted heteroaryl, or an amino protecting group;

$R^P$ is independently H, optionally substituted alkyl, optionally substituted alkenyl, optionally substituted alkynyl, optionally substituted aryl, optionally substituted cycloalkyl, or optionally substituted heteroaryl;

Q is

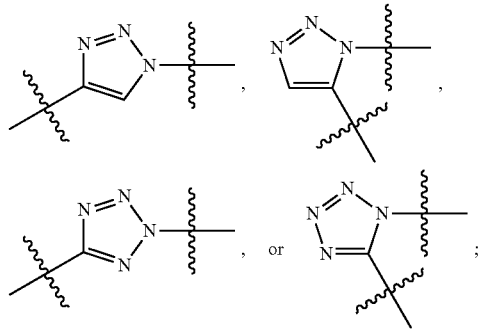

$L_{10}$ and $L_{11}$ are independently absent or a linker; and the ligand is selected from the group consisting of thyrotropin, melanotropin, lectin, glycoprotein, surfactant protein A, Mucin carbohydrate, multivalent lactose, multivalent galactose, multivalent N-acetyl-galactosamine, multivalent N-acetyl-glucosamine, multivalent mannose, multivalent fucose, glycosylated polyaminoacids, transferrin, bisphosphonate, polyglutamate, polyaspartate, a lipid, cholesterol, a steroid, bile acid, folate, vitamin B12, biotin, and an RGD peptide.

2. The compound of claim 1, wherein carrier is a cyclic group selected from the group consisting of pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, thiazolidinyl, isothiazolidinyl, quinoxalinyl, pyridazinonyl, and decalin.

3. The compound of claim 1, wherein either one or both of A and B is independently —P($Z^1$)($Z^2$)—O-oligonucleotide.

4. The compound of claim 3, wherein the oligonucleotide is a single-stranded oligonucleotide.

5. The compound of claim 4, wherein the single-stranded oligonucleotide is a single-stranded siRNA.

6. The compound of claim 4, wherein the single-stranded oligonucleotide is a micro RNA.

7. The compound of claim 3, wherein the oligonucleotide is a double-stranded oligonucleotide.

8. The compound of claim 7, wherein the double-stranded oligonucleotide is a double-stranded siRNA.

9. A pharmaceutical composition comprising a compound of claim 1 and a pharmaceutically acceptable excipient.

10. A compound of claim 1, wherein the linker is represented by structure

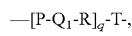

wherein:
P, R and T are each independently absent, CO, NH, O, S, OC(O), NHC(O), $CH_2$, $CH_2NH$, $CH_2O$; $NHCH(R^a)C(O)$, —C(O)—$CH(R^a)$—NH—, —C(O)-(optionally substituted alkyl)-NH—, CH=N—O,

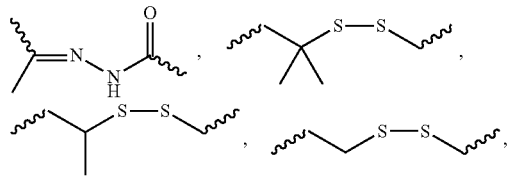

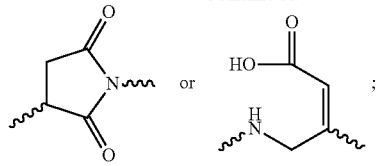

$Q_1$ is absent, —$(CH_2)_n$—, —$C(R^{100})(R^{200})(CH_2)_n$—, —$(CH_2)_nC(R^{100})(R^{200})$—, —$(CH_2CH_2O)_mCH_2CH_2$—, or —$(CH_2CH_2O)_mCH_2CH_2NH$—;

$R^a$ is H or an amino acid side chain;

$R^{100}$ and $R^{200}$ are each independently H, $CH_3$, OH, SH or $N(R^X)_2$;

$R^X$ is independently H, methyl, ethyl, propyl, isopropyl, butyl or benzyl;

q is an integer from 0-20;

n is an integer from 1-20; and m is an integer from 0-50;

provided that at least one of P, R, T, and $Q_1$ is present in the linker.

11. The compound of claim 1, wherein

[carrier]

is an acyclic group containing a serinol backbone or a diethanolamine backbone.

* * * * *